United States Patent
Vo-Dinh et al.

(10) Patent No.: US 10,493,296 B2
(45) Date of Patent: *Dec. 3, 2019

(54) NON-INVASIVE ENERGY UPCONVERSION METHODS AND SYSTEMS FOR IN-SITU PHOTOBIOMODULATION

(71) Applicants: IMMUNOLIGHT, LLC, Detroit, MI (US); DUKE UNIVERSITY, Durham, NC (US)

(72) Inventors: Tuan Vo-Dinh, Chapel Hill, NC (US); Jonathan P. Scaffidi, Durham, NC (US); Venkata Gopal Reddy Chada, Durham, NC (US); Benoit Lauly, Durham, NC (US); Yan Zhang, Durham, NC (US); Molly K. Gregas, Durham, NC (US); Ian Nicholas Stanton, Durham, NC (US); Joshua T. Stecher, Durham, NC (US); Michael J. Therien, Durham, NC (US); Frederic A. Bourke, Jr., Aspen, CO (US); Harold Walder, Belville, NC (US); Zak Fathi, Raleigh, NC (US); Jennifer A. Ayres, Raleigh, NC (US); Zhenyuan Zhang, Durham, NC (US); Joseph H. Simmons, Tucson, AZ (US); Stephen John Norton, Cary, NC (US)

(73) Assignees: IMMUNOLIGHT, LLC, Detroit, MI (US); DUKE UNIVERSITY, Durham, NC (US)

(*) Notice: Subject to any disclaimer, the term of this patent is extended or adjusted under 35 U.S.C. 154(b) by 510 days.

This patent is subject to a terminal disclaimer.

(21) Appl. No.: 15/045,524

(22) Filed: Feb. 17, 2016

(65) Prior Publication Data

US 2016/0263393 A1 Sep. 15, 2016

Related U.S. Application Data

(63) Continuation of application No. 12/764,184, filed on Apr. 21, 2010, now Pat. No. 9,302,116.

(Continued)

(51) Int. Cl.
*A61N 5/06* (2006.01)
*A61K 49/00* (2006.01)
(Continued)

(52) U.S. Cl.
CPC ............ *A61N 5/062* (2013.01); *A61B 5/0059* (2013.01); *A61B 5/0071* (2013.01); *A61B 5/055* (2013.01);
(Continued)

(58) Field of Classification Search
CPC ............ A61L 2202/21; A61L 2202/22; A61L 2/0047; A61L 2/08; A61M 5/007;
(Continued)

(56) References Cited

U.S. PATENT DOCUMENTS 6,087,141 A   7/2000 Margolis-Nunno et al.
6,180,415 B1  1/2001 Schultz et al.
(Continued)

FOREIGN PATENT DOCUMENTS

JP   2003-522149 A      7/2003
JP   WO 2007129682 A1 * 11/2007 ......... G01N 21/6428
(Continued)

OTHER PUBLICATIONS

Office Action dated Mar. 13, 2017 in Japanese Patent Application No. 2016-058097 (with English language translation).
(Continued)

*Primary Examiner* — Brandy S Lee
(74) *Attorney, Agent, or Firm* — Oblon, McClelland, Maier & Neustadt, L.L.P.

(57) ABSTRACT

Products, compositions, systems, and methods for modifying a target structure which mediates or is associated with a biological activity, including treatment of conditions, disorders, or diseases mediated by or associated with a target structure, such as a virus, cell, subcellular structure or extracellular structure. The methods may be performed in situ in a non-invasive manner by placing a nanoparticle (Continued)

having a metallic shell on at least a fraction of a surface in a vicinity of a target structure in a subject and applying an initiation energy to a subject thus producing an effect on or change to the target structure directly or via a modulation agent. The nanoparticle is configured, upon exposure to a first wavelength $\lambda_1$, to generate a second wavelength $\lambda_2$ of radiation having a higher energy than the first wavelength $\lambda_1$. The methods may further be performed by application of an initiation energy to a subject in situ to activate a pharmaceutical agent directly or via an energy modulation agent, optionally in the presence of one or more plasmonics active agents, thus producing an effect on or change to the target structure. Kits containing products or compositions formulated or configured and systems for use in practicing these methods.

188 Claims, 52 Drawing Sheets

Related U.S. Application Data

(60) Provisional application No. 61/171,152, filed on Apr. 21, 2009.

(51) Int. Cl.
| | | |
|---|---|---|
| *A61N 1/40* | (2006.01) | |
| *A61N 5/02* | (2006.01) | |
| *A61B 5/00* | (2006.01) | |
| *A61B 5/055* | (2006.01) | |
| *A61B 6/00* | (2006.01) | |
| *A61K 41/00* | (2006.01) | |
| *A61M 5/00* | (2006.01) | |
| *A61L 2/00* | (2006.01) | |
| A61L 2/08 | (2006.01) | |
| A61N 5/10 | (2006.01) | |
| A61N 5/067 | (2006.01) | |

(52) U.S. Cl.
CPC ............ *A61B 5/4848* (2013.01); *A61B 6/481* (2013.01); *A61K 41/0042* (2013.01); *A61K 41/0052* (2013.01); *A61K 41/0061* (2013.01); *A61K 49/0039* (2013.01); *A61L 2/0047* (2013.01); *A61M 5/007* (2013.01); *A61N 1/406* (2013.01); *A61N 5/02* (2013.01); *A61N 5/0601* (2013.01); *A61L 2/08* (2013.01); *A61L 2202/21* (2013.01); *A61L 2202/22* (2013.01); *A61N 5/0618* (2013.01); *A61N 5/0622* (2013.01); *A61N 5/0624* (2013.01); *A61N 5/10* (2013.01); *A61N 2005/063* (2013.01); *A61N 2005/067* (2013.01); *A61N 2005/0656* (2013.01); *A61N 2005/0659* (2013.01); *A61N 2005/0662* (2013.01); *A61N 2005/1098* (2013.01)

(58) Field of Classification Search
CPC .............. A61N 1/406; A61N 2005/063; A61N 2005/0656; A61N 2005/0659; A61N 2005/0662; A61N 2005/067; A61N 2005/1098; A61N 5/02; A61N 5/0601; A61N 5/0618; A61N 5/062; A61N 5/0622; A61N 5/0624; A61N 5/10; A61B 5/0059; A61B 5/0071; A61B 5/055; A61B 5/4848; A61B 6/481; A61B 2562/12; A61B 5/0476; A61B 5/082; A61B 5/14517; A61B 5/1477; A61B 5/4266; A61B 5/7267; A61B 2560/0412; A61B 2562/0295; A61K 41/0042; A61K 41/0052; A61K 41/0061; A61K 49/0039; B33Y 80/00; G06K 9/00536; G06N 3/02
See application file for complete search history.

(56) References Cited

U.S. PATENT DOCUMENTS

| | | | |
|---|---|---|---|
| 6,530,944 B2 | 3/2003 | West et al. | |
| 6,719,778 B1 | 4/2004 | Van Tassel et al. | |
| 7,123,359 B2 | 10/2006 | Armstrong et al. | |
| 7,368,086 B2* | 5/2008 | Naasani ............... | B82Y 15/00 422/82.05 |
| 7,927,791 B2 | 4/2011 | Welch et al. | |
| 9,302,116 B2* | 4/2016 | Vo-Dinh ............ | A61K 49/0039 |
| 2002/0103517 A1* | 8/2002 | West ................... | A61K 41/0042 607/88 |
| 2002/0127224 A1* | 9/2002 | Chen .................... | A61K 39/44 424/130.1 |
| 2004/0014060 A1 | 1/2004 | Hoheisel et al. | |
| 2004/0150818 A1 | 8/2004 | Armstrong et al. | |
| 2006/0160134 A1 | 7/2006 | Melker et al. | |
| 2006/0247866 A1 | 11/2006 | Welch et al. | |
| 2008/0091249 A1* | 4/2008 | Wang ................... | A61N 5/0613 607/88 |
| 2008/0132886 A1 | 6/2008 | Cohen et al. | |
| 2008/0214988 A1 | 9/2008 | Altshuler et al. | |
| 2008/0241262 A1 | 10/2008 | Lee et al. | |
| 2008/0248001 A1 | 10/2008 | Bourke | |
| 2009/0023736 A1 | 1/2009 | Koya et al. | |
| 2009/0032781 A1* | 2/2009 | Wang ..................... | B82B 1/00 252/521.2 |
| 2009/0263485 A1 | 10/2009 | Li et al. | |
| 2009/0294692 A1 | 12/2009 | Bourke, Jr. et al. | |
| 2010/0003316 A1 | 1/2010 | Vo-Dinh et al. | |
| 2010/0016783 A1 | 1/2010 | Bourke, Jr. et al. | |
| 2011/0021970 A1 | 1/2011 | Vo-Dinh et al. | |
| 2011/0149292 A1 | 6/2011 | Himmelhaus | |
| 2011/0253909 A1 | 10/2011 | Himmelhaus et al. | |
| 2011/0256577 A1 | 10/2011 | Himmelhaus et al. | |
| 2012/0126143 A1 | 5/2012 | Himmelhaus | |
| 2013/0102054 A1 | 4/2013 | Bourke, Jr. et al. | |
| 2013/0156905 A1 | 6/2013 | Bourke, Jr. et al. | |
| 2013/0240758 A1 | 9/2013 | Bourke, Jr. et al. | |
| 2014/0134307 A1 | 5/2014 | Bourke, Jr. | |
| 2014/0163303 A1 | 6/2014 | Bourke, Jr. et al. | |
| 2014/0222117 A1 | 8/2014 | Bourke, Jr. et al. | |
| 2015/0182934 A1 | 7/2015 | Bourke, Jr. | |
| 2015/0290614 A1 | 10/2015 | Bourke, Jr. | |
| 2016/0005503 A1 | 1/2016 | Bourke, Jr. et al. | |
| 2016/0067524 A1 | 3/2016 | Bourke, Jr. | |

FOREIGN PATENT DOCUMENTS

| | | | |
|---|---|---|---|
| JP | 2007-536356 A | 12/2007 | |
| JP | 2009-24115 A | 2/2009 | |
| JP | 2009-544584 A | 12/2009 | |
| JP | 2010-523557 A | 7/2010 | |
| JP | 2010-523690 A | 7/2010 | |
| JP | 2012-524795 A | 10/2012 | |
| JP | 5908396 B2 | 4/2016 | |
| JP | 6300854 B2 | 3/2018 | |
| WO | WO 2006/033766 A2 | 3/2006 | |
| WO | WO 2006033766 A2 * | 3/2006 | ......... A61K 49/0041 |
| WO | WO 2007/115291 A2 | 10/2007 | |
| WO | WO 2007/129682 A1 | 11/2007 | |
| WO | WO 2008/006588 A1 | 1/2008 | |
| WO | WO 2008/007290 | 1/2008 | |
| WO | WO 2008006588 A1 * | 1/2008 | ....... G01N 33/54346 |
| WO | WO 2008/121077 | 10/2008 | |
| WO | WO 2009/114567 A1 | 9/2009 | |
| WO | WO 2009/124189 A1 | 10/2009 | |
| WO | WO 2010/123993 A1 | 10/2010 | |

OTHER PUBLICATIONS

Japanese Office Action dated Feb. 9, 2018 in Japanese Patent Application No. 2017-236041 (with English translation), citing documents AO through AT, and AX therein, 8 pages.

(56) References Cited

OTHER PUBLICATIONS

Prashant K. Jain, et al., "Noble Metals on the Nanoscale: Optical and Photothermal Properties and Some Applications in Imaging, Sensing, Biology, and Medicine", Accounts of Chemical Research, vol. 41 No. 12, Dec. 2008, pp. 1578-1586.
Japanese Office Action dated May 28, 2018 in Patent Application No. 2017-236041, 3 pages.
Stephen J. Norton, et al., "Plasmon Resonances of Nanoshells of Spheroidal Shape" IEEE Transactions on Nanotechnology, vol. 6, No. 6, XP011196366, Nov. 2007, pp. 627-638.
L. R. Hirsch, et al., "Nanoshell-mediated near-infrared thermal therapy of tumors under magnetic resonance guidance" Proceedings of the National Academy of Sciences, vol. 100, No. 23, XP002993017, Nov. 11, 2003, pp. 13549-13554.
Wensha Yang, et al., "Novel FRET-Based Radiosensitization Using Quantum Dot-Photosensitizer Conjugates" IEEE, Conference Record of the Forty-First Asilomar Conference on Signals, Systems & Computers, XP031242401, Nov. 2007, pp. 1861-1865.
Weibo Cai, et al., "Applications of gold nanoparticles in cancer nanotechnology" Nanotechnology, Science and Applications, vol. 2008, No. 1, XP55092975, 2008, pp. 17-32.
Office Action dated Dec. 15, 2015, in European patent application No. 10 767 701.5.
Office Action dated Aug. 3, 2015, in Japanese patent application No. 2012-507351 (w/English translation).
Thermal Radiation—Wikipedia. At http.//en.wikipeda.org/wiki/Themal_radiation accessed Feb. 11, 2015 (7 pp.).
Black-body radiation—Wkipedia At http://en.wikipedia.org/wiki/Black-body_radiation accessed Feb. 11, 2015 (10 pp.).
Electromagnetic Spectrum at http://www2.lbl.gov./MicroWorlds/ALSTool/EMSpec/EMSpec2.html accessed Feb. 11, 2015 (1p.).
Office Action and Search Report dated Jan. 16, 2015, in Taiwan patent application No. 099112582 (w/ English translation of Search Report).
Young et al, "Photochemical hammerhead ribozyme activation", Bioorganic & Medicinal Chemistry Letters, (2006), vol. 16(10), pp. 2658-2661.
Office Action dated Nov. 25, 2014 in Japanese patent application No. 2012,507351 (w/English translation).
Office Action dated May 26, 2014 in Japanese Patent Application No. 2012-507351 (with English language translation).
Examination Report dated Nov. 17, 2011, in Pakistani patent application No. 327/2010.
First Substantive Examination Report dated Apr. 21, 2010, in Saudi patent application No. 110310317. (English translation only).
Jones, "Heat Energy" at http://physics.about.com/od/glossary/g/heat.htm accessed Oct. 8, 2013 1 p.
"Black-body radiation" at http:en.wikipedia.org/wiki-black-body_radiation accessed Oct. 8, 2013 18 pp.
"Heat Energy" at http://www.sciencelearn.org.nz/Contexts/Fire/Science-Ideas-and-Concepts/Heat-energy accessed Oct. 8, 2013 3 pp.
"Energy and Heat" at http://www4_uswsp.edu/geo/faclty/ritter/geog101/textbook/energy_and_heat_html accessed Oct. 8, 2013 2 pp.
European Office Action dated Feb. 14, 2018 in Patent Application No. 10 767 701.5, 5 pages.
Japanese Office Action dated Sep. 11, 2017 in Japanese Patent Application No. 2016-058097 (with English translation).
Office Action dated Jul. 19, 2018 in Argentinian Patent Application No. 20100101318.
Examination Report dated Oct. 4, 2018, in Indian patent application No. 9081/DELNP/2011 (17 pages).
Office Action dated May 7, 2019, in Japanese patent application No. 2018-120683, with English translation 6 pages.
Communication pursuant to Rules 70(2) and 70a(2) EPC dated Apr. 22, 2016 in European Patent Application No. 10767701.5.
Extended European Search Report dated Mar. 29, 2018 in Patent Application No. 10767701.5.
Examination Report dated Jun. 19, 2019, in Pakistan patent application No. 343/2016, (2 pages).
Examination Report dated Jun. 19, 2019, in Pakistan patent application No. 327/2010 (2 pages).
Communication dated Jun. 14, 2019, in European patent application No. 10 767 701.5 (3 pages).

* cited by examiner

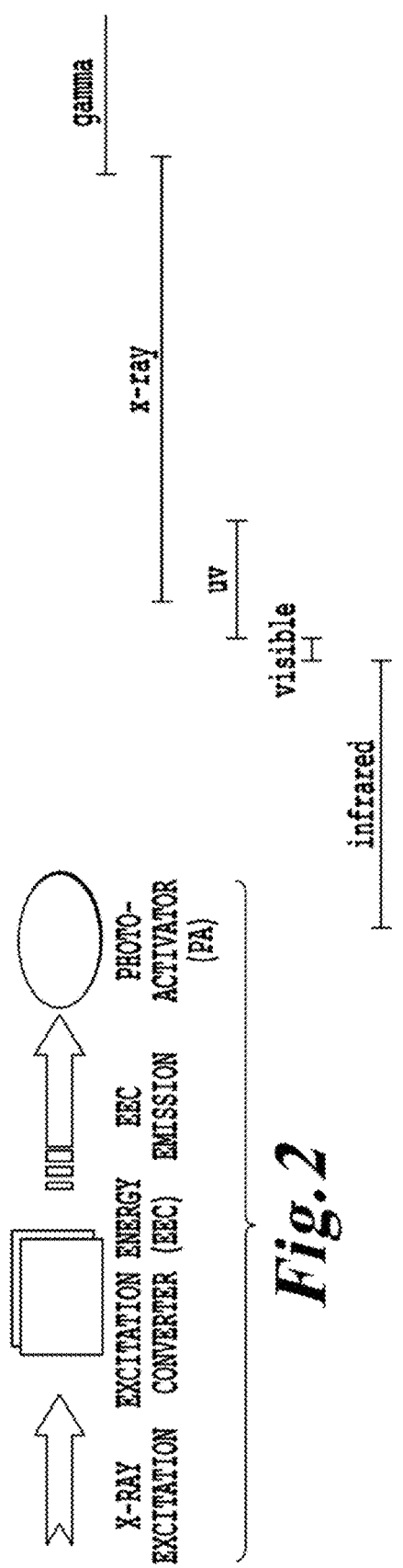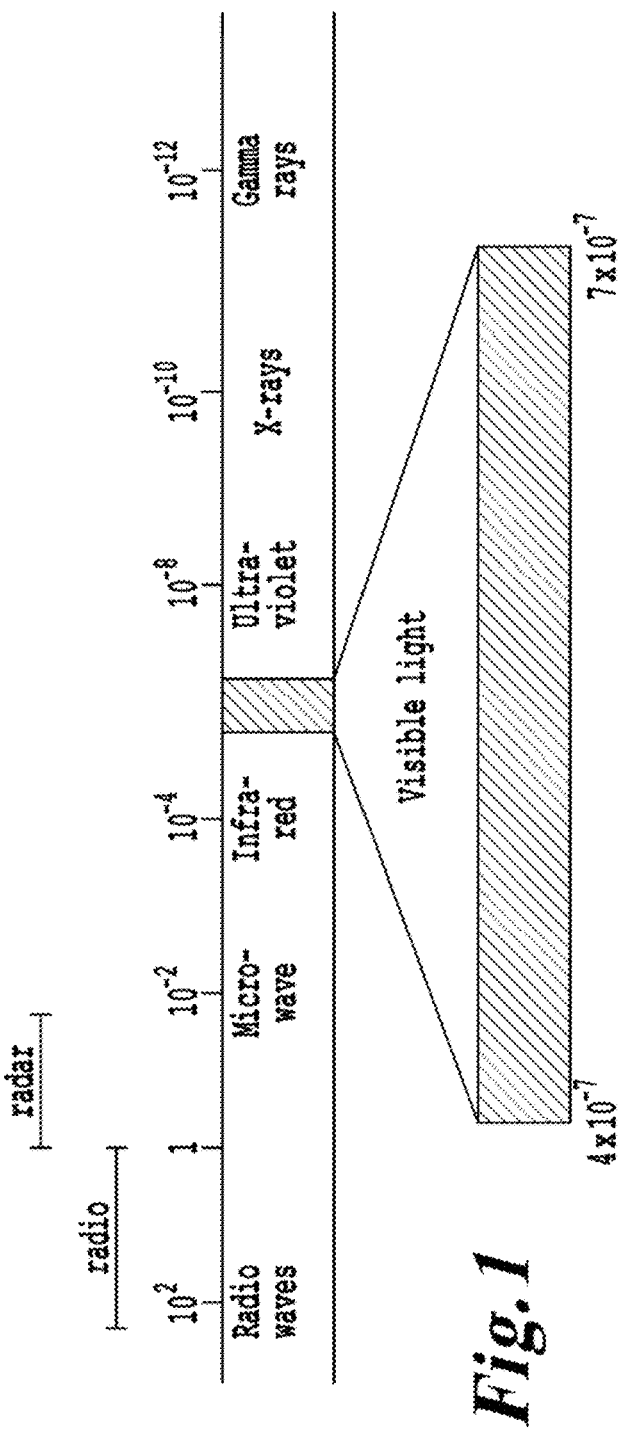
Fig. 2
Fig. 1

PLASMONICS PHOTO-ACTIVE PROBES

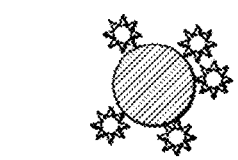
PA MOLECULES BOUND TO METAL NANOPARTICLE
*Fig. 8A-1*

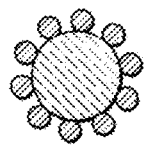
PA-CONTAINING NANO-PARTICLE COVERED WITH METAL NANOPARTICLES
*Fig. 8A-2*

 PHOTO-ACTIVE (PA) MOLECULE (PHOTOSENSITIZER)

 METAL (e.g. Au, Ag)

 MATERIAL CONTAINING PA

 PROTECTIVE COATING

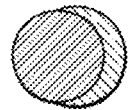
METAL NANOPARTICLE COVERED WITH PA NANOCAP
*Fig. 8A-3*

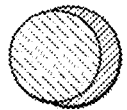
PA-CONTAINING NANO-PARTICLE COVERED WITH METAL NANOCAP
*Fig. 8A-4*

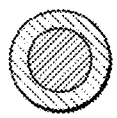
METAL NANOPARTICLE COVERED WITH PA NANOSHELL
*Fig. 8A-5*

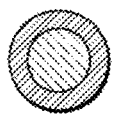
PA-CONTAINING NANO-PARTICLE COVERED WITH METAL NANOSHELL
*Fig. 8A-6*

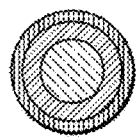
PA-CONTAINING NANO-PARTICLE COVERED WITH METAL NANOSHELL WITH PROTECTIVE COATING LAYER
*Fig. 8A-7*

$Y_2O_3=Y_2O_3$, $Y_2O_3$: Ln; sub 5-nm.
Au(Ag,Pt)shell=monolayer to x nm

PLASMONICS PHOTO-ACTIVE PROBES

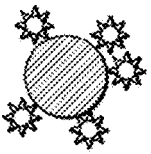 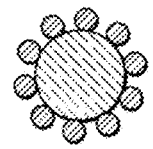

☆ PHOTO-ACTIVE (PA) MOLECULE (PHOTOSENSITIZER)

▨ METAL (e.g. Au,Ag)

▨ UPCONVERTING MATERIAL (UCm)

▨ PROTECTIVE COATING

PA MOLECULES BOUND TO METAL NANOPARTICLE

UCm-CONTAINING NANO-PARTICLE COVERED WITH METAL NANOPARTICLES

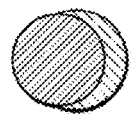   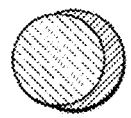

METAL NANOPARTICLE COVERED WITH UCm NANOCAP

UCm-CONTAINING NANO-PARTICLE COVERED WITH METAL NANOCAP

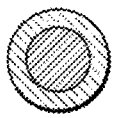 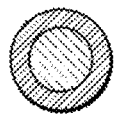 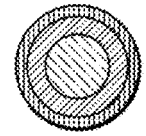

METAL NANOPARTICLE COVERED WITH UCm NANOSHELL

UCm-CONTAINING NANO-PARTICLE COVERED WITH METAL NANOSHELL

UCm-CONTAINING NANO-PARTICLE COVERED WITH METAL NANOSHELL WITH PROTECTIVE COATING LAYER

UC PLASMONICS PHOTO-ACTIVE PROBES
WITH DIELECTRIC LAYER

PHOTO-ACTIVE (PA) MOLECULE (PHOTOSENSITIZER)

METAL (e.g. Au, Ag)

UPCONVERTING MATERIAL (UCm)

DIELECTRIC LAYER (e.g. SILICA)

PROTECTIVE COATING

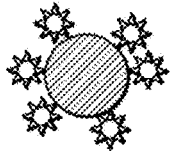

PA MOLECULES BOND TO METAL NANOPARTICLE

*Fig. 10B-1*

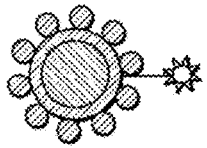

UNm-NANOPARTICLE COVERED WITH DIELECTRIC LAYER AND METAL NANOPARTICLES

*Fig. 10B-2*

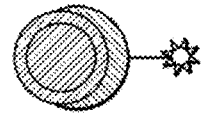

METAL NANOPARTICLE COVERED WITH DIELECTRIC LAYER AND UCm NANOCAP

*Fig. 10B-3*

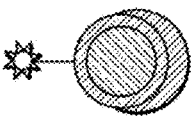

UCm NANOPARTICLE COVERED WITH DIELECTRIC LAYER AND METAL NANOCAP

*Fig. 10B-4*

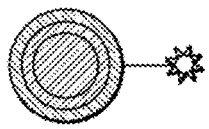

METAL NANOPARTICLE COVERED WITH DIELECTRIC LAYER AND UCm NANOSHELL

*Fig. 10B-5*

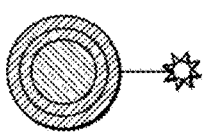

UCm-NANOPARTICLE COVERED WITH DIELECTRIC LAYER AND METAL NANOSHELL

*Fig. 10B-6*

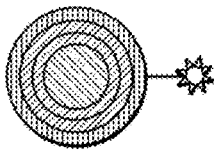

UCm NANOPARTICLE COVERED WITH DIELECTRIC LAYER AND METAL NANOSHELL WITH PROTECTIVE COATING LAYER

*Fig. 10B-7*

PLASMONICS-ACTIVE METEL STRUCTURES

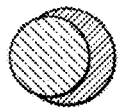

METAL NANOPARTICLE

Fig.10C-1

DIELECTRIC NANOPARTICLE CORE COVERED WITH METAL NANOCAP

Fig.10C-2

- ▨ METAL 1 (e.g. Au,Ag)
- ▧ METAL 2 (e.g. Au,Ag)
- ▦ UPCONVERSION MATERIAL
- ▦ PROTECTIVE COATING

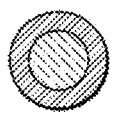

SPHERICAL METAL NANOSHELL COVERING UCm SPHEROID CORE

Fig.10C-3

OBLATE METAL NANO-SHELL COVERING UCm SPHEROID CORE

Fig.10C-4

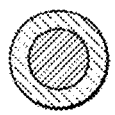

METAL NANOPARTICLE CORE COVERED WITH UCm NANOSHELL

Fig.10C-5

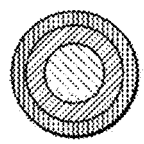

METAL NANOSHELL WITH UCm CORE AND PROTECTIVE COATING LAYER

Fig.10C-6

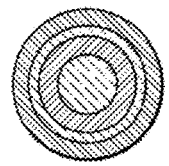

MULTI-LAYER METAL NANOSHELL COVERING UCm CORE AND NANOSHELL

Fig.10C-7

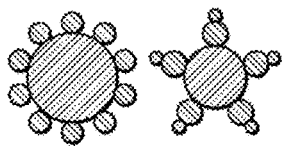

MULIT-NANOPARTICLE STRUCTURES

Fig.10C-8

METAL NANOCUBE AND NANO-TRIANGLE/NANO-PRISM

Fig.10C-9

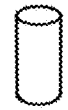

METAL CYLINDER

Fig 10C-10

PLASMONICS PHOTO-ACTIVE PROBES
WITH ENERGY UPCONVERTING MATERIALS

  PHOTO-ACTIVE (PA) MOLECULE (PHOTOSENSITIZER)

 METAL (e.g. Au, Ag)

 UPCONVERTING MATERIAL (UCm)

 PROTECTIVE COATING

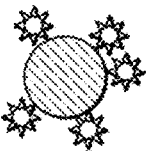

PA MOLECULES BOUND TO
UC NANOPARTICLE

*Fig. 10D-1*

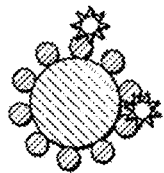

UCm-CONTAINING NANO-
PARTICLE COVERED WITH
METAL NANOPARTICLES

*Fig. 10D-2*

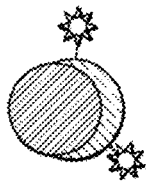

METAL NANOPARTICLE
COVERED WITH UCm NANOCAP

*Fig. 10D-3*

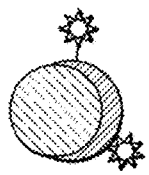

UCm-CONTAINING NANOPARTICLE
COVERED WITH METAL NANOCAP

*Fig. 10D-4*

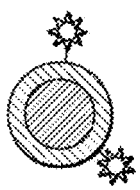

METAL NANOPARTICLE
COVERED WITH UCm NANOSHELL

*Fig. 10D-5*

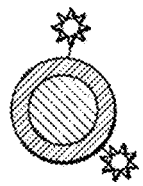

UCm-CONTAINING NANOPARTICLE
COVERED WITH METAL NANOSHELL

*Fig. 10D-6*

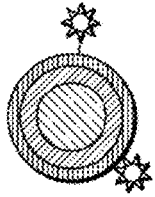

UCm-CONTAINING NANOPARTICLE
COVERED WITH METAL NANOSHELL
WITH PROTECTIVE COATING LAYER

PLASMONICS PHOTO-ACTIVE PROBES
WITH BIORECEPTORS

☆ PHOTO-ACTIVE (PA) MOLECULE (PHOTOSENSITIZER)

⊸ BIORECEPTOR (Ab, DNA, etc.)

▨ METAL (e.g. Au, Ag)

▨ UPCONVERTING MATERIAL (UCm)

▨ PROTECTIVE COATING

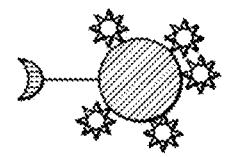

PA MOLECULES BOUND TO METAL NANOPARTICLE

*Fig. 12A-1*

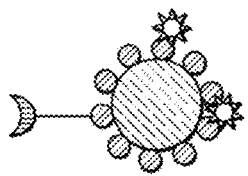

A-LINKED UCm NANO-PARTICLE COVERED WITH METAL NANOPARTICLES

*Fig. 12A-2*

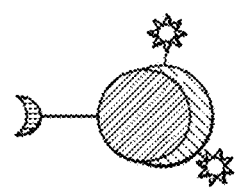

METAL NANOPARTICLE COVERED WITH UCm NANOCAP WITH LINKED PA

*Fig. 12A-3*

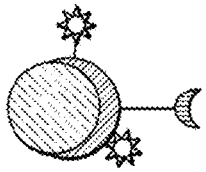

UCm NANOPARTICLE COVERED WITH METAL NANOCAP AND LINKED PA

*Fig. 12A-4*

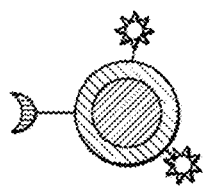

METAL NANOPARTICLE COVERED WITH UCm NANOSHELL WITH PA

*Fig 12A-5*

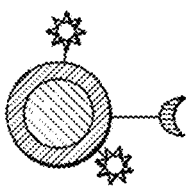

UCm NANOPARTICLE COVERED WITH METAL NANOSHELL

*Fig. 12A-6*

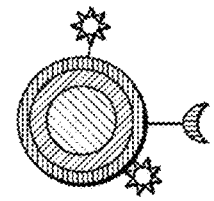

UCm NANOPARTICLE COVERED WITH METAL NANOCAP WITH PROTECTIVE COATING LAYER

*Fig. 12A-7*

PLASMONICS PHOTO-ACTIVE PROBES
UCm-PA SYSTEMS WITH BIORECEPTORS

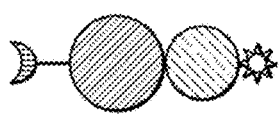

PA MOLECULES BOUND TO
UCm AND TO PLASMONIC
METAL NANOPARTICLE

*Fig.12B-1*

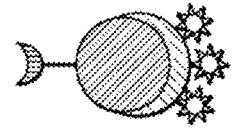

PLASMONIC METAL NANO-
PARTICLE WITH UCm NANOCAP
COVERED WITH PA MOLECULES

*Fig.12B-2*

☆ PHOTO-ACTIVE (PA) MOLECULE (PHOTOSENSITIZER)

◁ OPTIONAL BIORECEPTOR (Ab,DNA,etc.)

▨ PLASMONICS-ACTIVE METAL (e.g. Au,Ag)

▧ ENERGY UPCONVERTING MATERIAL (UCm)

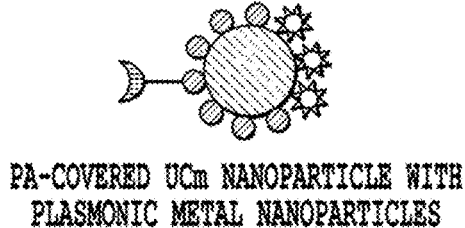

PA-COVERED UCm NANOPARTICLE WITH
PLASMONIC METAL NANOPARTICLES

*Fig.12B-3*

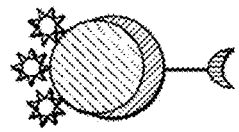

UCm-CONTAINING NANOPARTICLE
COVERED WITH PA MOLECULES AND
PLASMONIC METAL NANOCAP

*Fig.12B-4*

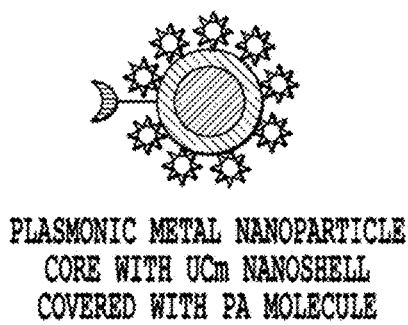

PLASMONIC METAL NANOPARTICLE
CORE WITH UCm NANOSHELL
COVERED WITH PA MOLECULE

*Fig.12B-5*

Inside the cell, photon radiation
releases PA which can go to target
area (e.g., nucleus)

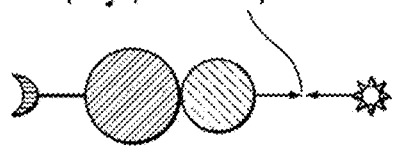

PA MOLECULE BOUND TO UCm (ATTACHED
TO PLASMONICS METAL NANOPARTICLE)
NANOPARTICLE BY DETACHABLE
BIOCHEMICAL BOND

*Fig.12B-6*

EEC NANOPARTICLE IMPROVE
DELIVERY OF PA MOLECULE
(e.g. PSORALEN) INTO TARGET
DISEASED CELLS

EEC NANOPARTICLE
PA MOLECULE
PHOTO-LABILE BOND

*Fig. 13A*

INDIE THE CELL, PHOTON
RADIATION RELEASES PA WHICH
CAN GO INTO THE NUCLEUS

PHOTON RADIATION
TO DETACH BOND
⇒ NUCLEUS

*Fig. 13B*

RADIATION OF SUITABLE
WAVELENGTH (NIR TO X-RAY)
INDUCES PLASMONIC FIEKD TO
ACTIVATE PA INTERACALATED
INTO DNA

DNA
X-RAY RADIATION

*Fig. 13C*

NIR EXCITATION      X-RAY EXCITATION

NANOPARTICLE CHAIN PA
PROBES FOR DUAL
PLASMONIC EXCITATION $d_1$   $d_2$

PLASMONIC-ACTIVE
NANOPARTICLE SIZE
FOR NIR EXCITATION

PLASMONIC-ACTIVE
NANOPARTICLE SIZE
FOR NX-RAY EXCITATION

*Fig. 14*

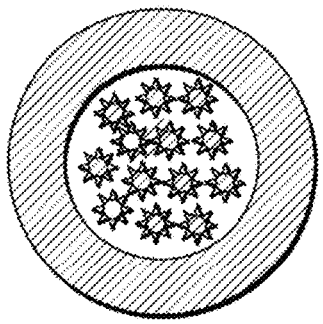
Fig. 15A
ENCAPSULATED PHOTOACTIVE
DRUG MOLECULES
PLASMONIC EXCITATION
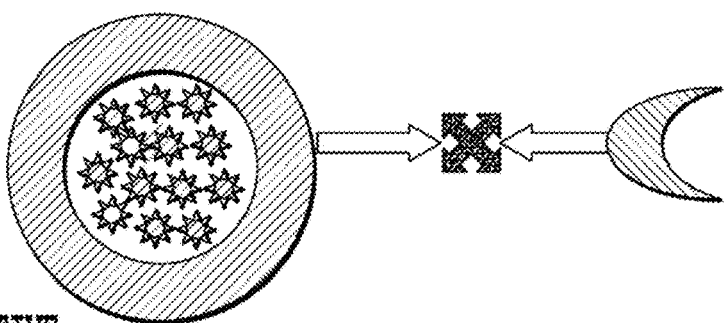
Fig. 15B
ENCAPSULATED PHOTOACTIVE
DRUG MOLECULES
WITH BIORECEPTOR
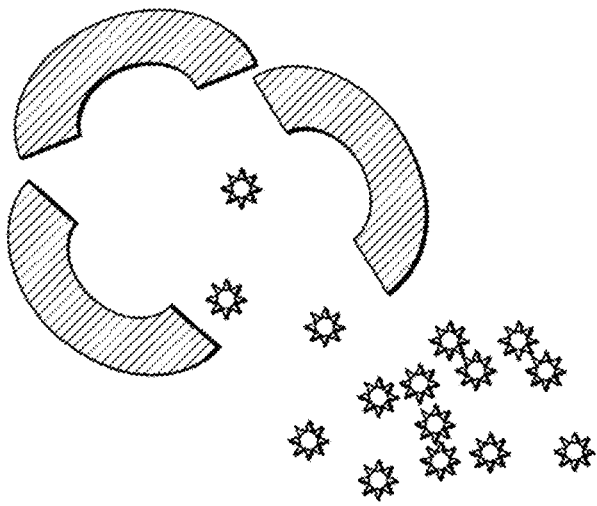
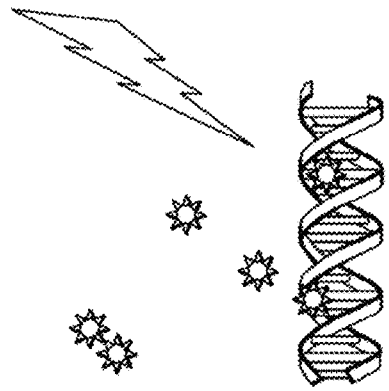
Fig. 15C
RELEASE OF
PHOTOACTIVE DRUG
MOLECULES
Fig. 15D
PHOTONIC ACTIVATION
OF PHPTOACTIVE DRUG
MOLECULES

NON-INVASIVE ENERGY UPCONVERSION METHODS AND SYSTEMS FOR IN-SITU PHOTOBIOMODULATION

CROSS REFERENCE TO RELATED APPLICATIONS

This application is a continuation of U.S. patent application Ser. No. 12/764,184, filed Apr. 21, 2010, which is related to U.S. patent application Ser. No. 11/935,655, filed Nov. 6, 2007 and Ser. No. 12/059,484, filed Mar. 31, 2008; U.S. patent application Ser. No. 12/389,946, filed Feb. 20, 2009; U.S. patent application Ser. No. 12/417,779, filed Apr. 3, 2009, U.S. patent application Ser. No. 12/725,108, filed Mar. 16, 2010, and provisional patent application 61/161,328, filed Mar. 18, 2009, and 61/259,940, filed Nov. 10, 2009; the entire contents of each of which are hereby incorporated by reference. This application is also related to and claims priority from provisional patent application 61/171,152, filed Apr. 21, 2009; the entire contents of each of which are hereby incorporated by reference.

BACKGROUND OF THE INVENTION

Field of Invention

The present invention relates to methods and systems for treating a disorder or condition in a subject, that provide better distinction between normal, healthy cells and those cells suffering the disorder or condition (hereafter "target cells") and preferably that can be performed using energy up-conversion in non-invasive or minimally invasive techniques.

Discussion of the Background

Presently, light (i.e., electromagnetic radiation from the radio frequency through the visible to the X-ray wavelength range) is used in a number of industrial, communication, electronic, and pharmaceutical processes. Light in the infrared and visible range is typically generated from an electrical energy source which for example either heats a material to extremely high temperatures where black body emission occurs (as in an incandescent lamp). Light in the visible and ultraviolet range is typically generated by heating a gas to an electrical discharge where transitions from one electronic state of the gas atom or molecule occurs with the emission of light. There are also semiconductor based light sources (as in light emitting diodes and semiconducting lasers) where electrons/holes in a material recombine to produce light emission.

With the development of ultraviolet sources, ultraviolet radiation is being increasingly utilized for industrial, chemical, and pharmaceutical purposes. Typically, ultraviolet sources use gas discharge lamps to generate emitted light in the ultraviolet range. The emitted light is then optically filtered to remove many of not all of the non-ultraviolet frequencies. Ultraviolet light can also be produced in semiconductor phosphors from the excitation of these phosphors from high energy sources such as, for example, X-ray irradiation.

With the development of infrared radiation sources, infrared radiation is being increasingly utilized for communications and signaling purposes. Typically, infrared sources use broad spectrum light sources referred to as glowbars to generate a broad spectrum of light centered in the infrared range or use lasers to emit very specific infrared wavelengths. For the broad band sources, the emitted light is optically filtered to remove many of not all of the non-infrared frequencies.

It is generally desirable to have devices, materials, and capabilities to convert light from one frequency range to another. Down conversion has been one way to convert higher energy light to lower energy, as used in the phosphors noted above. Up conversion has also been shown where lower energy light is converted to higher energy light. Typically, this process is a multi-photon absorption process where two or more photons are used to promote an excited electronic state in a host medium which in turn radiates at a wavelength of light that has a higher energy than the energy of the incident light which promoted the multi-photon absorption process. Both down conversion and up conversion have been studied and documented in the past.

Indeed, workers have studied the phenomenon of photoluminescence, which is the ability of certain solids, known as phosphors, to emit light when driven or charged by an external energy source. Many well-known phosphors are triggered by high-energy electrons or photons and emit photons of lower energy. However, there is another type of phosphor which can store energy for long periods of time in certain energy states. Relaxation from these energy states at a later time can be stimulated by less energetic photons. Relaxation from these energy states results in photon emission. The effect of this phenomenon is that energy is stored in the form of trapped electron-hole pairs for later use. Materials which exhibit this phenomenon will be referred to as electron trapping, or electron trapping phosphors, and materials in which emission of light is activated by infrared lumination are called infrared phosphors.

It has been recognized recently that certain infrared phosphors can actually operate at high speeds and are capable of converting pulsed infrared light to the visible range (violet through red). This "upconversion" occurs at the expense of the original charging illuminating light and can actually exhibit optical gain. It has been observed that phosphoresence can continue for as long as several days before a new short recharge is required.

Photobiomodulation

Photobiomodulation also known as low level laser therapy (LLLT), cold laser therapy, and laser biostimulation, is an emerging medical and veterinary technique in which exposure to low-level laser light can stimulate or inhibit cellular function leading to beneficial clinical effects. The "best" combination of wavelength, intensity, duration and treatment interval is complex and sometimes controversial with different diseases, injuries and dysfunctions needing different treatment parameters and techniques.

Certain wavelengths of light at certain intensities (delivered by laser, LED or another monochromatic source) will, for example, aid tissue regeneration, resolve inflammation, relieve pain and boost the immune system. The exact mechanism is still being explored and debated but it is agreed that the mechanism is photochemical rather than heat-related. Observed biological and physiological effects include changes in cell membrane permeability, and up-regulation and down-regulation of adenosine triphosphate and nitric oxide.

All light-induced biological effects depend on the parameters of the irradiation (wavelength, dose, intensity, irradiation time, depth of a target cell, and continuous wave or pulsed mode, pulse parameters). (See, e.g., Karu I T, Low-Power Laser Therapy", in Biomedical Photonics Handbook, Vo-Dinh T. Ed., CRC Press, Boca Raton, Fla., pp. 48-1 to 48-25, (2003)). Laser average power is typically in the range of 1-500 mW; some high peak power, short pulse width devices are in the range of 1-100 W with typically 200 ns pulse widths. The average beam irradiance then is typically 10 mW/cm$^2$-5 W/cm$^2$. The wavelength is typically in the range 600-1000 nm. The red-to-near infrared (NIR) region is preferred for photobiomodulation. Other wavelengths may be also used, e.g., UV light for neurons and green light for prostate tissue. Maximum biological responses are occurring when irradiated at 620, 680, 760, and 820-830 nm (Karu T I, et al., (1998). The Science of Low Power Laser Therapy. Gordon and Breach Sci. Publ., London). Large volumes and relatively deeper layers of tissues can be successfully irradiated by laser only (e.g., inner and middle ear diseases, injured siatic or optical nerves, inflammations). The LEDs are used for irradiation of surface injuries.

A photoacceptor must first absorb the light used for the irradiation. After promotion of electronically excited states, primary molecule processes from these states can lead to a measurable biological effect (via secondary biochemical reaction, or photosignal transduction cascade, or cellular signaling) at the cellular level. A photoacceptor for eukaryotic cells in red-to-NIR region is believed to be the terminal enzyme of the respiratory chain cytochrome c oxidase located in cell mitochondrion. In the violet-to blue spectra region, flavoprotein (e.g., NADHdehydrogenase in the beginning of the respiratory chain) is also among the photoacceptors.

Clinical applications of photobiomodulation include, for example, treating soft tissue and bone injuries, chronic pain, wound healing and nerve and sensory regeneration/restoration, and possibly even resolving viral and bacterial infections, treating neurological and phychiatric diseases (e.g., epilepsy and Parkinson's disease) (e.g., Zhang F., et al., Nature, 446:617-9 (Apr. 5, 2007; Han X., et al., PloS ONE, 2(3):e299 (Mar. 21, 2007); Arany P R, et al., Wound Repair Regen., 15(6):866-74 (2007); Lopes C B, et al., Photomed. Laser Surg., 25(2):96-101 (2007)). One clinical application showing great promise is the treatment of inflammation, where the anti-inflammatory effect of location-and-dose-specific laser irradiation produces similar outcomes as NSAIDs, but without the potentially harmful side-effects (Bjordal J M, Couppé C, Chow R T, Tunér J, Ljunggren E A (2003). "A systematic review of low level laser therapy with location-specific doses for pain from chronic joint disorders". The Australian journal of physiotherapy 49(2): 107-16).

An NIR light treatment can prevent cell death (apoptosis) in cultured neurons (brain) cells (Wong-Reiley M T, et al., JBC, 280(6):4761-71 (2005)). Specific wavelengths of light can promote cellular proliferation to the activation of mitochondria, the energy-producing organelles within the cell via cytochrome c oxidase. An NIR treatment can augment mitochondrial function and stimulate antioxidant protective pathways. The evidence that the NIR treatment can augment mitochondrial function and stimulate antioxidant protective pathways comes from photobiomodulation experiments carried out using a laboratory model of Parkinson's disease (PD) (cultures of human dopaminergic neuronal cells) (Whelan H., et. al., SPIE, Newsroom, pages 1-3 (2008)).

It has also been shown that light has both inductive and inhibitory effect on cell growth and division in a red tide flagellate, *Chattonella antique* (Nemote Y., Plant and Cell Physiol., 26(4):669-674 (1985)).

When the excitable cells (e.g., neurons, cardiomyocites) are irradiated with monochromatic visible light, the photoacceptors are also believed to be components of respiratory chain. It is clear from experimental data (Karu, T. I., (2002). Low-power laser therapy. In: CRC Biomedical Photonics Handbook, T. Vo-Dinh, Editor-in-Chief, CRC Press, Boca Raton (USA)) that irradiation can cause physiological and morphological changes in nonpigmental excitable cells via absorption in mitochondria. Later, similar irradiation experiments were performed with neurons in connection with low-power laser therapy. It was shown in 80's that He—Ne laser radiation alters the firing pattern of nerves; it was also found that transcutaneous irradiation with HeNe laser mimicked the effect of peripheral stimulation of a behavioral reflex. These findings were found to be connected with pain therapy (Karu T I, et al., (2002)).

When photoacceptors absorb photons, electronic excitation followed by photochemical reactions occurring from lower excitation states (first singlet and triplet) takes place. It is also known that electronic excitation of absorbing centers alters their redox properties. Until yet, five primary reactions have been discussed in literature (Karu T I, et al., (2002)). Two of them are connected with alteration of redox properties and two mechanisms involve generation of reactive oxygen species (ROE). Also, induction of local transient (very short time) heating of absorbing chromophores is possible. Details of these mechanisms can be found in (Karu T I, et. al., (2002); Karu T I, et al., (1998). The Science of Low Power Laser Therapy. Gordon and Breach Sci. Publ., London).

Photobiological action via activation of respiratory chain is believed to be a general mechanism occurring in cells. Crucial events of this type of cell metabolism activation are occurring due to a shift of cellular redox potential into more oxidized direction as well as due to ATP extrasynthesis. Susceptibility to irradiation and capability for activation depend on physiological status of irradiated cells: the cells, which overall redox potential is shifted to more reduced state (example: some pathological conditions) are more sensitive to the irradiation. The specificity of final photobiological response is determined not at the level of primary reactions in the respiratory chain but at the transcription level during cellular signaling cascades. In some cells, only partial activation of cell metabolism happens by this mechanism (example: redox priming of lymphocytes).

Far red and NIR radiation have been shown to promote wound healing, e.g., infected, ischemic, and hypoxic wounds (Wong-Reley, W T T, JBC, 280(6):4761-4771 (2005)). Red-to-NIR radiation also protects the retina against the toxic actions of methanol-derived formic acid in a rodent model of methanol toxicity and may enhance recovery from retinal injury and other ocular diseases in which mitochondrial dysfunction is postulated to play a role (Eells J T., PNAS, 100(6):3439-44 (2003)). Another clinical application of photobiomodulation is repair of soft and bone tissues by IR laser irradiation (Martinez M E, et al., Laser in Med. Sci., 2007). Invasive laser assisted liposuction is a recently developed method, wherein a laser fiber is introduced through a tube into the skin and directly to the fat cells causing the cells to rapture and drain away as liquid (Kim K H, Dermatol. Surg., 32(2):241-48 (2006)). Tissue around the area is coagulated. Yet, another application of photobiomodulation is a non-surgical varicose vein treatment (an endovenous laser therapy), wherein a laser is threaded through an incision and the full length of the varicose vein (Kim H S, J. Vasc. Interv. Radiol., 18(6):811 (2007)). When the laser is slowly withdrawn, heat is applied to the vein walls, causing the vein to permanently close and disappear.

Technological advances such as laser have redefined the surgical treatment of enlarged prostate. The green light laser is a laser that vaporizes and removes the enlarged prostate tissue (Heinrich E., Eur. Urol., 52(6):1632-7 (2007)). The significance of the color of the laser light (green) is that this results in absorption by hemoglobin which is contained within red blood cells and not absorbed by water. The procedure may also be known as laser prostatectomy or laser Transurethral resection of the prostate (TURP). The technique involves painting the enlarged prostate with the laser until the capsule of the prostate is reached. By relieving this portion of the prostate, patients are able to void much easier through a wide-open channel in the prostate. The procedure needs to be performed under general or spinal anesthesia. An advantage of the procedure is that even patients taking blood thinners (e.g., aspirin to prevent stroke) can be treated because there is less bleeding compared to a traditional surgery.

Yet, another area of application of photobiomodulation is a direct control of brain cell activity with light. The technique is based upon NIR spectroscopy and is simpler to use and less expensive than other methods such as functional magnetic resonance imaging and positron emission tomography.

Whenever a region of the brain is activated, that part of the brain uses more oxygen. This technique works by measuring the blood flow and oxygen consumption in the brain. The light emitted by NIR laser diodes is carried through optical fibers to a person's head. The light penetrates the skull where it assesses the brain's oxygen level and blood volume. The scattered light is then collected by optical fibers, sent to detectors and analyzed by a computer. By examining how much of the light is scattered and how much is absorbed, portions of the brain and extract information about brain activity can be mapped. By measuring the scattering, it is determined where the neurons are firing. This means that scientists can simultaneously detect both blood profusion and neural activity. The technique could be used in many diagnostic, prognostic and clinical applications. For example, it could be used to find hematomas in children, to study blood flow in the brain during sleep apnea, and to monitor recovering stroke patients on a daily, or even hourly, basis (that would be impractical to do with MRI). To validate the technique, hemoglobin oxygen concentrations in the brain obtained simultaneously by NIR spectroscopy and by functional MRI, the current "gold standard" in brain studies, was compared. Both methods were used to generate functional maps of the brain's motor cortex during a periodic sequence of stimulation by finger motion and rest. Spatial congruence between the hemoglobin signal and the MRI signal in the motor cortex related to finger movement was demonstrated. The researchers also demonstrated collocation between hemoglobin oxygen levels and changes in scattering due to brain activities. The changes in scattering associated with fast neuron signals came from exactly the same locations.

A low-intensity laser light-oxygen cancer therapy is another application of photobiomodulation. The light-oxygen effect (LOE), which involves activation of or damage to biosystems by optical radiation at low optical doses by direct photoexcitation of molecular oxygen dissolved in a biosystem so that it is converted to the singlet state, i.e., by photogeneration of molecular singlet oxygen from $O_2$ dissolved in cells, similar to photodynamic effect (Zakharov S D, et al., Quantum Electronics, 29(12):1031-53 (1999)). It was shown that the He—Ne laser radiation destroys tumor cells in the presence or absence of the photosensitiser. The LOE can be activated by small optical doses, which are 4-5 orders of magnitude lower that those found if a comparison is made with the familiar analogue in the form of the photodynamic effect (PDE).

Photobiostimulation Using "Caged" Molecules and Light-Sensitive Proteins

This type of photobiomodulation methods fall into two general categories: one set of methods uses light to uncage a compound that then becomes biochemically active, binding to a downstream effector. For example, this method involves applying "caged" chemicals to a sample and then using light to open the cage to invoke a reaction. Modified glutamate is useful for finding excitatory connections between neurons, since the uncaged glutamate mimics the natural synaptic activity of one neuron impinging upon another. This method is used for elucidation of neuron functions and imaging in brain slices using, for example, two-photon glutamine uncageing (Harvey C D, et al., Nature, 450:1195-1202 (2007); Eder M, et al., Rev. Neurosci., 15:167-183 (2004)). Other signaling molecules can be released by UV light stimulation, e.g., GABA, secondary messengers (e.g., $Ca^{2+}$ and $Mg^{2+}$), carbachol, capsaicin, and ATP (Zhang F., et al., 2006).

The other major photostimulation method is the use of light to activate a light-sensitive protein such as rhodopsin (ChR2), which can then excite the cell expressing the opsin.

It has been shown that channelrhodopsin-2, a monolithic protein containing a light sensor and a cation channel, provides electrical stimulation of appropriate speed and magnitude to activate neuronal spike firing. Recently, photoinhibition, the inhibition of neural activity with light, has become feasible with the application of molecules such as the light-activated chloride pump halorhodopsin to neural control. Together, blue-light activated channelrhodopsin-2 and the yellow light-activated chloride pump halorhodopsin enable multiple-color, optical activation and silencing of neural activity.

ChR2 photostimulaiton involves genetic targeting ChR2 to neurons and light pulsing the neurons expressing ChR2 protein. The experiments have been conducted in vitro and in vivo in mice by in vivo deep-brain photostimulaiton using optical fibers to deliver light into the lateral hypothalamus (Adamantidis A R, et al., Nature 450:420-425 (2007)). Genetic targeting of ChR2 allows exclusive stimulation of defined cellular subsets and avoids the need for addition of the caged glutamate, facilitating photostimulation in vivo (Wang H., et al., PNAS, 104(19):8143-48 (2007)). ChR2 photostimulation has been used for restoring visual activity in mice with impaired vision, to evoke behavioral responses in worms and flies (Wang H., et al., 2007). The robust associative learning induced by ChR2-assisted photostimulaiton in mice opens the door to study the circuit basis of perception and cognition in vivo (Huber D., et al., 2007). This kind of neuronal targeting and stimulation might have clinical application, e.g., deep brain stimulation to treat Parkinson's disease and other disorders, controlling behavioral, perceptional and cognitive characteristics, and for imaging and studying how the brain works (Zhang F., et al., Nature Methods, 3(10):785-792 (2006); Wong-Riley M T., et al., JBC, 280(6):4761-4771 (2005)).

Another gene, chloride pump (NpHR), which is borrowed from a microbe called an archaebacterium, can make neurons less active in the presence of yellow light. Combined, the two genes ChR2 and NpHR can now make neurons obey pulses of light like drivers obey a traffic signal: Blue means "go" (emit a signal), and yellow means "stop" (don't emit).

Light-sensitive proteins can be introduced into cells or live subjects via a number of techniques including electroporation, DNA microinjection, viral delivery, liposomal transfection and calcium-phosphate precipitation.

A third photostimulation technique is chemical modification of ion channels and receptors to render them light-responsive. Some of the most fundamental signaling mechanisms in a cell involve the release and uptake of $Ca^{2+}$ ions. $Ca^{2+}$ is involved in controlling fertilization, differentiation, proliferation, apoptosis, synaptic plasticity, memory, and developing axons. It has been shown that $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Directly controlling a brain cell activity with light is a novel means for experimenting with neural circuits and could lead to therapies for some disorders. This accomplishment is a step toward the goal of mapping neural circuit dynamics on a millisecond timescale to see if impairments in these dynamics underlie severe psychiatric symptoms. Knowing the effects that different neurons have could ultimately help researchers figure out the workings of healthy and unhealthy brain circuits. If use of the technique can show that altered activity in a particular kind of neuron underlies symptoms, for example, this insight will allow development of targeted genetic or pharmaceutical treatments to fix those neurons. Conceivably, direct control of neuronal activity with light could someday become a therapy in itself.

In living organisms, scientists were able to cause worms, *C. elegans*, to stop swimming while their genetically altered motor neurons were exposed to pulses of yellow light intensified through a microscope. In some experiments, exposure to blue light caused the worms to wiggle in ways they weren't moving while unperturbed. When the lights were turned off, the worms resumed their normal behavior. Meanwhile, in experiments in living brain tissues extracted from mice, the researchers were able to use the technique to cause neurons to signal or stop on the millisecond timescale, just as they do naturally. Other experiments showed that cells appear to suffer no ill effects from exposure to the light. They resume their normal function once the exposure ends.

The most direct application of an optical neuron control is experimenting with neural circuits to determine why unhealthy ones fail and how healthy ones work.

In patients with Parkinson's disease, for example, researchers have shown that electrical "deep brain stimulation" of cells can help patients, but they don't know precisely why. By allowing researchers to selectively stimulate or dampen different neurons in the brain, the light stimulation techniques could help in determining which particular neurons are benefiting from deep brain stimulation. That could lead to making the electrical treatment, which has some unwanted side effects, more targeted.

Another potential application is experimenting with simulating neural communications. Because neurons communicate by generating patterns of signals-sometimes on and sometimes off like the Os and is of binary computer code-flashing blue and yellow lights in these patterns could compel neurons to emit messages that correspond to real neural instructions. In the future, this could allow researchers to test and tune sophisticated neuron behaviors. Much farther down the road, the ability to artificially stimulate neural signals, such as movement instructions, could allow doctors to bridge blockages in damaged spinal columns, perhaps restoring some function to the limbs of paralyzed patients.

Finally, the technique could be useful in teasing out the largely unknown functioning of healthy brains.

Problems with LLLT, Cold Laser Therapy, and Laser Biostimulation

The laser systems currently used for biostimulation do not allow performing photobiomodulation in a region deep within thick tissue without a surgical invasion. Laser therapy is mostly conducted in surface or near surface target cells and tissue because penetration of UV and red-to-N IR radiation used for photobiomodulation and photobiostimulaiton is no more than a few centimeters beneath the surface of the skin. In addition, imaging and stimulation of brain cells is mainly possible in thin brain slices, or a thin monolayer or suspension of cells. For deeper tissue laser therapy in situ, a subject undergoes various invasive surgical procedures, e.g., invasive insertion of a fiber via incisions into a fat layer or veins, implanting a radiation source in deep tissue, or implanting a glass window above the barrel cortex (Huber D., et al., Nature, 451:61-66 (2007)). It is further well recognized that another problem associated with the existing methods of photobiomodulation is in differentiation of normal cells from target cells.

Traditional Methods in Phototherapy

Photopheresis, also known as extracorporeal photochemotherapy (ECP), involves the removal and reinfusion of autologous blood after the white blood cell portion was collected, treated extracorporeally with a photosensitizing drug and irradiated with ultraviolet A light. When reinfused into the patient's body, lymphocytes bound to the photoactivated drug act like a vaccine to alert the immune system to destroy any similar T-cells circulating in the blood. Photopheresis has been successfully used for treatment of cell proliferation disorders. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Of these, cancer is perhaps the most well known.

Excellent results have been observed since its initial approval by the FDA in 1988. Photopheresis is currently approved for the treatment of refractory cutaneous T-cell lymphoma.

Extracorporeal photopheresis is a leukapheresis-based immunomodulatory therapy that has been approved by the US Food and Drug Administration for the treatment of cutaneous T-cell lymphoma (CTCL). ECP, also known as extracorporeal photochemotherapy, is performed at more than 150 centers worldwide for multiple indications. Long-term follow-up data are available from many investigators that indicate ECP produces disease remission and improved survival for CTCL patients. In addition to CTCL, ECP has been shown to have efficacy in the treatment of other T-cell mediated disorders, including chronic graft versus host disease (GVHD) and solid organ transplant rejection. ECP use for the treatment of autoimmune disease, such as systemic sclerosis and rheumatoid arthritis, is also being explored.

ECP is generally performed using the UVAR XTS Photopheresis System developed by Therakos, Inc (Exton, Pa.). The process is performed through one intravenous access port and has 3 basic stages: (1) leukapheresis, (2) photoactivation, and (3) reinfusion, and takes 3-4 hours to complete. A typical treatment session would resemble the following sequence of events:

(1) One 16-gauge peripheral intravenous line or central venous access is established in the patient;

(2) Blood (225 mL) is passed through 3 cycles of leukapheresis, or 125 mL of blood is passed through 6 cycles, depending on the patient's hematocrit value and body size. At the end of each leukapheresis cycle, the red blood cells and plasma are returned to the patient;

(3) The collected WBCs (including approximately 5% of the peripheral blood mononuclear cells) are mixed with heparin, saline, and 8-methoxypsoralen (8-MOP), which intercalates into the DNA of the lymphocytes upon exposure to UVA light and makes them more susceptible to apoptosis when exposed to UVA radiation;

(4) The mixture is passed as a 1-mm film through a sterile cassette surrounded by UVA bulbs, resulting in an average UVA exposure of 2 J/cm$^2$; and (5) The treated WBC mixture is returned to the patient.

Over the past 20 years, on-going research has explored the mechanism of action of ECP. The combination of 8-MOP and UVA radiation causes apoptosis of the treated T cells and may cause preferential apoptosis of activated or abnormal T cells, thus targeting the pathogenic cells of CTCL or GVHD. However, given that only a small percentage of the body's lymphocytes are treated, this seems unlikely to be the only mechanism of action.

Other evidence suggests that ECP also induces monocytes to differentiate into dendritic cells capable of phagocytosing and processing the apoptotic T-cell antigens. When these activated dendritic cells are reinfused into the systemic circulation, they may cause a systemic cytotoxic CD8$^+$ T-lymphocyte-mediated immune response to the processed apoptotic T-cell antigens.

Finally, animal studies indicate that photopheresis may induce antigen-specific regulatory T cells, which may lead to suppression of allograft rejection or GVHD.

However, there are still many limitations to ECP. For example, ECP requires patient to be connected to a machine for hours per treatment. It requires establishing peripheral intravenous line or central venous access, which may be difficult to do in certain disease states such as systemic sclerosis or arthritis. There is also a risk of infection at the venous or central line site, or in the central line catheter. Further, it requires removing typically several hundred milliliters of whole blood from the patient, hence, the treatment is limited to patients who has sufficiently large initial volume of blood to be withdrawn. The American Association of Blood Blanks recommend a limit of extracorporeal volume to 15% of the patient's whole body blood volume. Therefore, the size of the volume that can be treated generally has to be at least 40 kg or more. Risk of contracting blood-born pathogen (Hepatitis, HIV, etc.) due to exposure to contaminated operating system is also a concern.

Alternatively, a patient can be treated in vivo with a photosensitive agent followed by the withdrawal of a sample from the patient, treatment with UV radiation in vitro (ex vivo), and reinjecting the patient with the treated sample. This method is known for producing an autovaccine. A method of treating a patient with a photosensitive agent, exposing the patient to an energy source and generating an autovaccine effect wherein all steps are conducted in vivo has not been described. See WO 03/049801, U.S. Pat. Nos. 6,569,467; 6,204,058; 5,980,954; 6,669,965; 4,838,852; 7,045,124, and 6,849,058. Moreover, the side effects of extracorporeal photopheresis are well known and include nausea, vomiting, cutaneous erythema, hypersensitivity to sunlight, and secondary hematologic malignancy. Researchers are attempting to use photopheresis in experimental treatments for patients with cardiac, pulmonary and renal allograft rejection; autoimmune diseases, and ulcerative colitis.

Phototherapy is a relatively new light-based treatment, which has recently been approved by the United States Food & Drug Administration (FDA) for the treatment of both early and late-stage lung cancer. For tumors occurring deep in tissue, second generation sensitizers, which have absorbance in the NIR region, such as porphyrin-based systems [R. K. Pandey, "*Synthetic Strategies in designing Porphyrin-Based Photosensitizers*", in *Biomedical Photonics Handbook*, Vo-Dinh T., Ed., CRC Press, Boca Raton Fla. (2003)], chlorines, phthalocyanine, and naphthalocyanine have been investigated.

There are two main types of reactions in phototherapy:

(1) Type I reactions involve electrons and hydrogen atoms, which are transferred between photo-active molecules (also called photosensitizers) and substrates or solvent molecules. Oxygen may participate in subsequent reactions: e.g., psoralens in photopheresis and PUVA.

(2) Type II reactions involve singlet oxygen formation by energy transfer from PA molecules in the lowest triplet state to oxygen in the ground state: e.g., photodynamic therapy (PDT)

Photodynamic therapy (PDT) is a treatment modality that uses a photosensitizing
agent and laser light to kill cells. PDT is a relatively new light-based treatment, which has recently been approved by the United States Food & Drug Administration (FDA) for the treatment of both early and late-stage lung cancer. Other countries have approved PDT for treatment of various cancers as well. Unlike chemotherapy, radiation, and surgery, PDT is useful in treating all cell types, whether small cell or non-small cell carcinoma. PDT involves treatment of diseases such as cancer using light action on a special photoactive class of drugs, by photodynamic action in vivo to destroy or modify tissue [Dougherty T. J. and Levy J. G., "Photodynamic Therapy and Clinical Applications", in *Biomedical Photonics Handbook*, Vo-Dinh T., Ed., CRC Press, Boca Raton Fla. (2003)]. PDT, which was originally developed for treatment of various cancers, has now been used to include treatment of pre-cancerous conditions, e.g. actinic keratoses, high-grade dysplasia in Barrett's esophagus, and non-cancerous conditions, e.g. various eye diseases, e.g. age related macular degeneration (AMD). Photodynamic therapy (PDT) is approved for commercialization worldwide both for various cancers (lung, esophagus) and for AMD.

The PDT process requires three elements: (1) a PA drug (i.e., photosensitizer), (2) light that can excite the photosensitizer and (3) endogenous oxygen. The putative cytotoxic agent is singlet oxygen, an electronically excited state of ground state triplet oxygen formed according to the Type II photochemical process, as follows.

PA+hv→$^1$PA*(S) Excitation
$^1$PA*(S)→$^3$PA*(T) Intersystem crossing for singlet to triplet state
$^3$PA*(T)+O$_2$→$^1$O*$_2$+PA Energy transfer from the drug to singlet oxygen
where PA=photo-active drug at the ground state; $^1$PA*(S)= excited singlet state; $^3$PA*(T)=excited triplet state; $^1$O*$_2$=singlet excited state of oxygen Because the triplet state has a relatively long lifetime (μsec to seconds) only photosensitizers that undergo efficient intersystem crossing to the excited triplet state will have sufficient time for collision with oxygen in order to produce singlet oxygen. The energy difference between ground state and singlet oxygen is 94.2 kJ/mol and corresponds to a transition in the near-infrared at ~1270 nm. Most PA photosensitizers in clinical use have triplet quantum yields in the range of 40-60% with the singlet oxygen yield being slightly lower. Competing processes include loss of energy by deactivation to ground state by fluorescence or internal conversion (loss of energy to the environment or surrounding medium).

However, while a high yield of singlet oxygen is desirable it is by no means sufficient for a photosensitizer to be clinically useful. Pharmacokinetics, pharmacodynamics, stability in vivo and acceptable toxicity play critical roles as well [Henderson B W, Gollnick S O, "*Mechanistic Principles of Photodynamic Therapy*", in *Biomedical Photonics Handbook*, Vo Dinh T., Ed., CRC Press, Boca Raton Fla. (2003)]. For example, it is desirable to have relatively selective uptake in the tumor or other tissue being treated relative to the normal tissue that necessarily will be exposed to the exciting light as well. Pharmacodynamic issues such as the subcellular localization of the photosensitizer may be important as certain organelles appear to be more sensitive to PDT damage than others (e.g. the mitochondria). Toxicity can become an issue if high doses of photosensitizer are necessary in order to obtain a complete response to treatment. An important mechanism associated with PDT drug activity involves apoptosis in cells. Upon absorption of light, the photosensitiser (PS) initiates chemical reactions that lead to the direct or indirect production of cytotoxic species such as radicals and singlet oxygen. The reaction of the cytotoxic species with subcellular organelles and macromolecules (proteins, DNA, etc) lead to apoptosis and/or necrosis of the cells hosting the PDT drug. The preferential accumulation of PDT drug molecules in cancer cells combined with the localized delivery of light to the tumor, results in the selective destruction of the cancerous lesion. Compared to other traditional anticancer therapies, PDT does not involve generalized destruction of healthy cells. In addition to direct cell killing, PDT can also act on the vasculature, reducing blood flow to the tumor causing its necrosis. In particular cases it can be used as a less invasive alternative to surgery.

There are several chemical species used for PDT including porphyrin-based sensitizers. A purified hematoporphyrin derivative, Photofrin®, has received approval of the US Food and Drug Administration. Porphyrins are generally used for tumors on or just under the skin or on the lining of internal organs or cavities because theses drug molecules absorbs light shorter than 640 nm in wavelength. For tumors occurring deep in tissue, second generation sensitizers, which have absorbance in the NIR region, such as porphyrin-based systems [R. K. Pandey, "*Synthetic Strategies in designing Porphyrin-Based Photosensitizers*', in *Biomedical Photonics Handbook*, Vo-Dinh T., Ed., CRC Press, Boca Raton Fla. (2003)], chlorines, phthalocyanine, and naphthalocyanine have been investigated.

PDT retains several photosensitizers in tumors for a longer time than in normal tissues, thus offering potential improvement in treatment selectivity. See Corner C., "Determination of [3H]— and [14C] hematoporphyrin derivative distribution in malignant and normal tissue," Cancer Res 1979, 3 9: 146-151; Young S W, et al., "Lutetium texaphyrin (PCI-0123) a near-infrared, water-soluble photosensitizer," Photochem Photobiol 1996, 63:892-897; and Berenbaum M C, et al., "Meso-Tetra(hydroxyphenyl)porphyrins, a new class of potent tumor photosensitisers with favorable selectivity," Br J Cancer 1986, 54:717-725. Photodynamic therapy uses light of a specific wavelength to activate the photosensitizing agent. Various light sources have been developed for PDT, which include dye lasers and diode lasers. Light generated by lasers can be coupled to optical fibers that allow the light to be transmitted to the desired site. See Pass 1-11, "Photodynamic therapy in oncology: mechanisms and clinical use," J Natl Cancer Inst 1993, 85:443-456. According to researchers, the cytotoxic effect of PDT is the result of photooxidation reactions, as disclosed in Foote C S, "Mechanisms of photooxygenation," Proa Clin Biol Res 1984, 170:3-18. Light causes excitation of the photosensitizer, in the presence of oxygen, to produce various toxic species, such as singlet oxygen and hydroxyl radicals. It is not clear that direct damage to DNA is a major effect; therefore, this may indicate that photoactivation of DNA crosslinking is not stimulated efficiently.

Furthermore, when laser light is administered via external illumination of tissue surfaces, the treatment effect of PDT is confined to a few millimeters (i.e. superficial). The reason for this superficial limitation is mainly the limited penetration of the visible light used to activate the photosensitizer. Thus, PDT is used to treat the surfaces of critical organs, such as lungs or intra-abdominal organs, without damage to the underlying structures. However, even these treatments require significantly invasive techniques to treat the surface of the affected organs. Clinical situations use the procedure in conjunction with surgical debulking to destroy remnants of microscopic or minimal gross disease. It is possible that the laser light and small amount of remaining microscopic and minimal gross disease results in too little or highly damaged structures. Pre-clinical data show that some immune response is generated, but clinical trials have reported no auto vaccine effect similar to that produced by extracorporeal photopheresis in clinical conditions. Instead, the immune response appears to be vigorous only under limited conditions and only for a limited duration.

PDT retains several photosensitizers in tumors for a longer time than in normal tissues, thus offering potential improvement in treatment selectivity. See corner C., "Determination of [3H]— and [14C] hematoporphyrin derivative distribution in malignant and normal tissue," Cancer Res 1979, 3 9: 146-151; Young S W, et al., "Lutetium texaphyrin (PCI-0123) a near-infrared, water-soluble photosensitizer," Photochem Photobiol 1996, 63:892-897; and Berenbaum M C, et al., "Meso-Tetra(hydroxyphenyl)porphyrins, a new class of potent tumor photosensitisers with favorable selectivity," Br J Cancer 1986, 54:717-725. Photodynamic therapy uses light of a specific wavelength to activate the photosensitizing agent. Various light sources have been developed for PDT that include dye lasers and diode lasers. Light generated by lasers can be coupled to optical fibers that allow the light to be transmitted to the desired site. See Pass 1-11, "Photodynamic therapy in oncology: mechanisms and clinical use," J Natl Cancer Inst 1993, 85:443-456. According to researchers, the cytotoxic effect of PDT is the result of photooxidation reactions, as disclosed in Foote C S, "Mechanisms of photooxygenation," Proa Clin Biol Res 1984, 170:3-18. Light causes excitation of the photosensitizer, in the presence of oxygen, to produce various toxic species, such as singlet oxygen and hydroxyl radicals. It is not clear that direct damage to DNA is a major effect; therefore, this may indicate that photoactivation of DNA crosslinking is not stimulated efficiently. Other successful application of PDT is, for example, cardiac ablasion therapy, e.g., treating cardiac arrhythmias and atrial fibrillation which are believed to be a significant cause of cerebral stroke.

U.S. Pat. No. 6,811,562 describes administering a photo-activatable agent and subjecting cardiac tissue containing the administered agent to laser irradiation having a wavelength from 350 to 700 nm using invasive techniques, e.g., a fiber optic element.

Yet, another application of PDT is photoangioplasty for arterial diseases including de novo atherosclerosis and restinosis (Rockson A G, et al., Circulation, 102:591-596 (2000); Hsiang Y N., et al., J. Endovasc. Surg., 2:365-371 (1995)). In human clinical applications, endovascular light (730 nm) is delivered through a cylindrical fiber after intravenous administration of motexafin lutetium. PDT is also used for preventing and treatment of intimal hyperlpasia in blood vessels in vivo (see, e.g., U.S. Pat. No. 6,609,014).

Age-related macular degeneration (AMD) is a cause of new blindness. Choroidal neovascularization leads to hemorrhage and fibrosis in a number of ocular diseases. Conventional treatments utilize the argon laser to occlude the leaking vessel by thermal coagulation. However, the percentage of patients eligible for this treatment is limited. PDT is used for treating AMD and involves injecting verteporfin followed by the application of non-thermal light at 692 nm.

Improvement of clinical appearance of psoriatic plaques and palmopustular psoriasis using PUVA with hematopotphyrin was first reported in 1937. Acne, apopecia areata, portwine stains and hair removal also show promise with PDT treatment.

The choice of therapy usually depends on the location and severity of the disorder, the stage of the disease, as well as the patient's response to the treatment.

While some treatments may only seek to manage and alleviate symptoms of the disorder, the ultimate goal of any effective therapy is the complete removal or cure of all disordered cells without damage to the rest of the body.

The Photo-spectral Therapy (PST) modality is different (if not complementary) to the phototherapy technique often referred to Photo-thermal Therapy (PTT). The use of plasmonics-enhanced photothermal properties of metal nanoparticles for photothermal therapy has been reviewed (Xiaohua Huang & Prashant K. Jain & Ivan H. El-Sayed & Mostafa A. El-Sayed, "*Plasmonic photothermal therapy (PPTT) using gold nanoparticles*", Lasers in Medical Science, August 2007). The PST technique is based on the radiative processes (fluorescence, phosphotscence, luminescence, Raman, etc) and the PPT method is based on the radiationless processes (IC, VR and heat conversion) in molecules.

A survey of known treatment methods reveals that these methods tend to face a primary difficulty of differentiating between normal cells and target cells when delivering treatment, often due to the production of singlet oxygen which is known to be non-selective in its attack of cells, as well as the need to perform the processes ex vivo, or through highly invasive procedures, such as surgical procedures in order to reach tissues more than a few centimeters deep within the subject. Another challenge for non-invasive therapeutic modalities is to have sufficient light energy to excite and photo-activate drug molecules deep inside tissue.

U.S. Pat. No. 5,829,448 describes sequential and simultaneous two photon excitation of photo-agents using irradiation with low energy photons such as infrared or near infrared light (NRI). A single photon and simultaneous two photon excitation is compared for psoralen derivatives, wherein cells are treated with the photo agent and are irradiated with NRI or UV radiation. The patent suggests that treating with a low energy irradiation is advantageous because it is absorbed and scattered to a lesser extent than UV radiation. However, the use of NRI or UV radiation is known to penetrate tissue to only a depth of a few centimeters. Thus any treatment deep within the subject would necessarily require the use of ex vivo methods or highly invasive techniques to allow the irradiation source to reach the tissue of interest. Also, this patent does not describe initiation energy sources emitting energy other than UV, visible, and near infrared energy; energy upgrading other than within the range corresponding to UV and IR light, and downgrading from high to low energy.

Chen et al., J. Nanosci. and Nanotech., 6:1159-1166 (2006); Kim et al., JACS, 129:2669-2675 (2007); U.S. 2002/0127224; and U.S. Pat. No. 4,979,935 each describe methods for treatment using various types of energy activation of agents within a subject. However, each suffers from the drawback that the treatment is dependent on the production of singlet oxygen to produce the desired effect on the tissue being treated, and is thus largely indiscriminate in affecting both healthy cells and the diseased tissue desired to be treated.

U.S. Pat. No. 6,908,591 discloses methods for sterilizing tissue with irradiation to reduce the level of one or more active biological contaminants or pathogens, such as viruses, bacteria, yeasts, molds, fungi, spores, prions or similar agents responsible, alone or in combination, for transmissible spongiform encephalopathies and/or single or multicellular parasites, such that the tissue may subsequently be used in transplantation to replace diseased and/or otherwise defective tissue in an animal. The method may include the use of a sensitizer such as psoralen, a psoralen-derivative or other photosensitizer in order to improve the effectiveness of the irradiation or to reduce the exposure necessary to sterilize the tissue. However, the method is not suitable for treating a patient and does not teach any mechanisms for stimulating the photosensitizers, indirectly.

U.S. Pat. No. 5,957,960 discloses a two-photon excitation device for administering a photodynamic therapy to a treatment site within a patient's body using light having an infrared or near infrared waveband. However, the reference fails to disclose any mechanism of photoactivation using energy modulation agent that converts the initiation energy to an energy that activates the activatable pharmaceutical agent and also use of other energy wavebands, e.g., X-rays, gamma-rays, electron beam, microwaves or radio waves.

U.S. Pat. No. 6,235,508 discloses antiviral applications for psoralens and other photoactivatable molecules. It teaches a method for inactivating viral and bacterial contaminants from a biological solution. The method includes mixing blood with a photosensitizer and a blocking agent and irradiating the mixture to stimulate the photosensitizer, inactivating substantially all of the contaminants in the blood, without destroying the red blood cells. The blocking agent prevents or reduces deleterious side reactions of the photosensitizer, which would occur if not in the presence of the blocking agent. The mode of action of the blocking agent is not predominantly in the quenching of any reactive oxygen species, according to the reference.

Also, U.S. Pat. No. 6,235,508 suggests that halogenated photosensitizers and blocking agents might be suitable for replacing 8-methoxypsoralen (8-MOP) in photopheresis and in treatment of certain proliferative cancers, especially solid localized tumors accessible via a fiber optic light device or superficial skin cancers. However, the reference fails to address any specific molecules for use in treating lymphomas or any other cancer. Instead, the reference suggests a process of photopheresis for antiviral treatments of raw blood and plasma.

U.S. Pat. No. 6,235,508 teaches away from 8-MOP and 4'-aminomethyl-4,5',8-trimethylpsoralen (AMT) and many other photoactivatable molecules, which are taught to have certain disadvantages. Fluorescing photosensitizers are said to be preferred, but the reference does not teach how to select a system of fluorescent stimulation or photoactivation using fluorescent photosensitizers. Instead, the fluorescing photosensitizer is limited to the intercalator that is binding to the DNA. The reference suggests that fluorescence indicates that such an intercalator is less likely to stimulate oxygen radicals.

U.S. published application 2002/0127224 discloses a method for a photodynamic therapy comprising administering light-emitting nanoparticles and a photoactivatable agent, which may be activated by the light re-emitted from the nanoparticles via a two-photon activation event. An initiation energy source is usually a light emitting diode, laser, incandescent lamp, or halogen light, which emits light having a wavelength ranging from 350 to 1100 nm. The initiation energy is absorbed by the nanoparticles. The nanoparticles, in turn, re-emit light having a wavelength from 500 to 1100 nm, preferably, UV-A light, wherein the re-emitted energy activates the photoactivatable agent. Kim et al., (JACS, 129:2669-75, Feb. 9, 2007) discloses indirect excitation of a photosensitizing unit (energy acceptor) through fluorescence resonance energy transfer (FRET) from the two-photon absorbing dye unit (energy donor) within an energy range corresponding to 300-850 nm. These references do not describe initiation energy sources emitting energy other than UV, visible, and near infrared energy; energy upgrading other than within the range corresponding to wavelength of 350-1100 nm, and downgrading from high to low energy.

These references fail to disclose any mechanism of photoactivation of an photoactivatable molecules other than by direct photoactivation by UV, visible, and near infrared energy.

Psoralens and Related Compounds

U.S. Pat. No. 6,235,508 further teaches that psoralens are naturally occurring compounds which have been used therapeutically for millennia in Asia and Africa. The action of psoralens and light has been used to treat vitiligo and psoriasis (PUVA therapy; Psoralen Ultra Violet A). Psoralen is capable of binding to nucleic acid double helices by intercalation between base pairs; adenine, guanine, cytosine and thymine (DNA) or uracil (RNA). Upon sequential absorption of two UV-A photons, psoralen in its excited state reacts with a thymine or uracil double bond and covalently attaches to both strands of a nucleic acid helix. The cross-linking reaction appears to be specific for a thymine (DNA) or a uracil (RNA) base. Binding proceeds only if psoralen is intercalated in a site containing thymine or uracil, but an initial photoadduct must absorb a second UVA photon to react with a second thymine or uracil on the opposing strand of the double helix in order to crosslink each of the two strands of the double helix, as shown below. This is a sequential absorption of two single photons as shown, as opposed to simultaneous absorption of two or more photons.

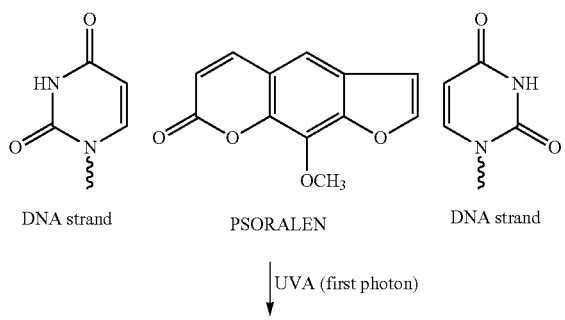

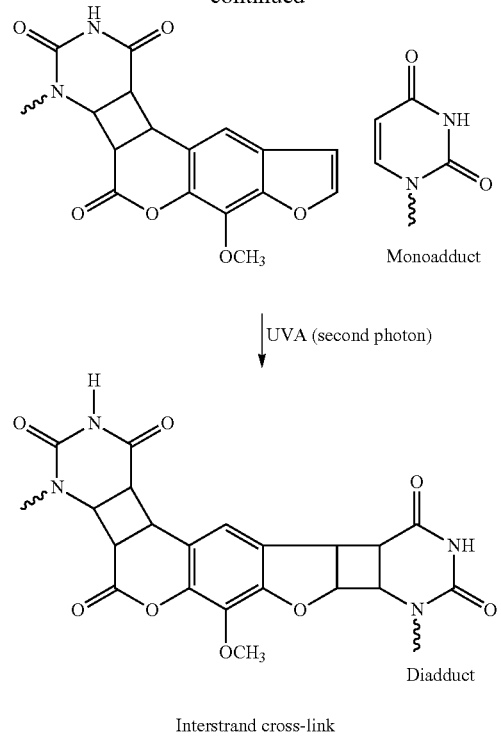

In addition, the reference teaches that 8-MOP is unsuitable for use as an antiviral, because it damages both cells and viruses. Lethal damage to a cell or virus occurs when the psoralen is intercalated into a nucleic acid duplex in sites containing two thymines (or uracils) on opposing strands but only when it sequentially absorbs 2 UVA photons and thymines (or uracils) are present. U.S. Pat. No. 4,748,120 of Wiesehan is an example of the use of certain substituted psoralens by a photochemical decontamination process for the treatment of blood or blood products.

Additives, such as antioxidants are sometimes used with psoralens, such as 8-MOP, AMT and I-IMT, to scavenge singlet oxygen and other highly reactive oxygen species formed during photoactivation of the psoralens. It is well known that UV activation creates such reactive oxygen species, which are capable of seriously damaging otherwise healthy cells. Much of the viral deactivation may be the result of these reactive oxygen species rather than any effect of photoactivation of psoralens. Regardless, it is believed that no auto vaccine effect has been observed.

The best known photoactivatable compounds are derivatives of psoralen or coumarin, which are nucleic acid intercalators. The use of psoralen and coumarin photosensitizers can give rise to alternative chemical pathways for dissipation of the excited state that are either not beneficial to the goal of viral inactivation, or that are actually detrimental to the process. For psoralens and coumarins, this chemical pathway is likely to lead to the formation of a variety of ring-opened species, such as shown below for coumarin:

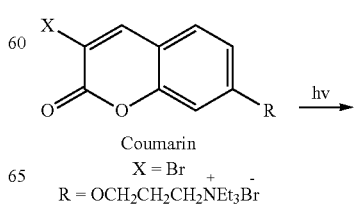

-continued

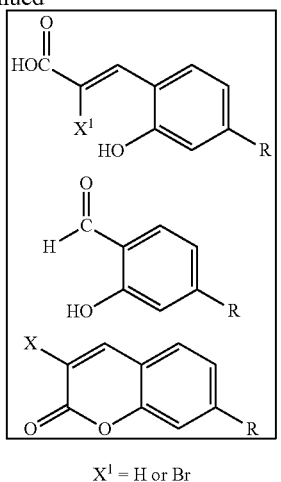

X¹ = H or Br

Research in this field over-simplifies mechanisms involved in the photoactivating mechanism and formation of highly reactive oxygen species, such as singlet oxygen. Both may lead to inactivating damage of tumor cells, viruses and healthy cells. However, neither, alone or combined, lead to an auto vaccine effect. This requires an activation of the body's own immune system to identify a malignant cell or virus as threat and to create an immune response capable of lasting cytotoxic effects directed to that threat. It is believed, without being limiting in any way, that photoactivation and the resulting apoptosis of malignant cells that occurs in extracorporeal photophoresis causes the activation of an immune response with cytotoxic effects on untreated malignant cells. While the complexity of the immune response and cytotoxic effects is fully appreciated by researchers, a therapy that harnesses the system to successfully stimulate an auto vaccine effect against a targeted, malignant cell has been elusive, except for extracorporeal photopheresis for treating lymphoma.

Midden (W. R. Midden, Psoralen DNA photobiology, Vol I1 (ed. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes. U.S. Pat. No. 6,235,508 teaches that 8-MOP and AMT are unacceptable photosensitizers, because each indiscriminately damages both cells and viruses. Studies of the effects of cationic side chains on furocoumarins as photosensitizers are reviewed in Psoralen DNA Photobiology, Vol. I, ed. F. Gaspano, CRC Press, Inc., Boca Raton, Fla., Chapter 2. U.S. Pat. No. 6,235,508 gleans the following from this review: most of the amino compounds had a much lower ability to both bind and form crosslinks to DNA compared to 8-MOP, suggesting that the primary amino functionality is the preferred ionic species for both photobinding and crosslinking.

U.S. Pat. No. 5,216,176 of Heindel discloses a large number of psoralens and coumarins that have some effectiveness as photoactivated inhibitors of epidermal growth factor. Halogens and amines are included among the vast functionalities that could be included in the psoralen/coumarin backbone. This reference is incorporated herein by reference.

U.S. Pat. No. 5,984,887 discloses using extracorporeal photopheresis with 8-MOP to treat blood infected with CMV. The treated cells as well as killed and/or attenuated virus, peptides, native subunits of the virus itself (which are released upon cell break-up and/or shed into the blood) and/or pathogenic noninfectious viruses are then used to generate an immune response against the virus, which was not present prior to the treatment.

Problems with PDT

It is well recognized that a major problem associated with the existing methods of diagnosis and treatment of cell proliferation disorders is in differentiation of normal cells from target cells. Radiation therapy works by irradiating cells with high levels of high energy radiation such as high energy photon, electron, or proton. These high energy beams ionize the atoms which make up a DNA chain, which in turn leads to cell death. Unlike surgery, radiation therapy does not require placing patients under anesthesia and has the ability to treat disorders deep inside the body with minimal invasion of the body. However, the high doses of radiation needed for such therapies damages healthy cells just as effectively as it does diseased cells. Thus, similar to surgery, differentiation between healthy and diseased cells in radiation therapy is only by way of location. There is no intrinsic means for a radiation beam to differentiate between a healthy cell from a diseased cell either. Another problem encountered in PDT therapy is the inability to treat target areas that are more than a few centimeters beneath the surface of the skin without significant invasive techniques. Another challenge for non-invasive therapeutic modalities is to have sufficient light energy to excite and photo-activate drug molecules deep inside tissue.

Therefore, there still exists a need for better and more effective treatments that can more precisely target the diseased cells without causing substantial side-effects or collateral damages to healthy tissues, and which are capable of treating disorders by non-invasive or minimum invasive techniques.

SUMMARY OF THE INVENTION

Accordingly, one object of the present invention is to provide a method for modifying a target structure which mediates or is associated with a biological activity in a subject that permits treatment of a subject in any area of the body while being non-invasive and having high selectivity for targeted cells relative to healthy cells using energy upconversion.

A further object of the present invention is to provide a method for modifying a target structure which mediates or is associated with a biological activity which can use any suitable energy source as an initiation energy source to induce a predetermined change in a target structure in a subject in situ to treat a condition, disorder or disease.

A further object of the present invention is to provide a method for modifying a target structure which mediates or is associated with a biological activity using a modulation agent which converts an initiation energy into an energy that causes nanoparticles placed in the vicinity of a target structure to emit light that induces a predetermined change in the target structure.

A further object of the present invention is to provide a method for modifying a target structure which mediates or is associated with a biological activity using a modulation agent which converts the energy emitted by the nanoparticles placed in the vicinity of a target structure so that the energy reemitted by the energy modulation agent induces a predetermined change in the target structure.

These and other objects of the present invention, which will become more apparent in conjunction with the following detailed description of the preferred embodiments, either alone or in combinations thereof, have been satisfied by the discovery of a method for modifying a target structure which mediates or is associated with a biological activity, comprising:

placing a nanoparticle in a vicinity of a target structure in a subject in need of treatment, wherein the nanoparticle is configured, upon exposure to a first wavelength $\lambda_1$, to generate a second wavelength $\lambda_2$ of radiation having a higher energy than the first wavelength $\lambda_1$, wherein the nanoparticle comprises a metallic shell on at least a fraction of a surface of the nanoparticle, a radial dimension of the metallic shell is set to a value so that a surface plasmon resonance in the metallic shell resonates at a frequency which provides spectral overlap with at least one of the first wavelength $\lambda 1$ and the second wavelength $\lambda 2$, and the nanoparticle is configured to emit light in the vicinity of or into the target structure upon interaction with an initiation energy having an energy in the range of $\lambda 1$; and applying the initiation energy including said first wavelength $\lambda 1$ from an initiation energy source to the subject, wherein the emitted light including said second wavelength $\lambda 2$ directly or indirectly contacts the target structure and induces a predetermined change in said target structure in situ, wherein said predetermined change modifies the target structure and modulates the biological activity of the target structure.

Yet a further object of the invention is further administer at least one energy modulation agent to said subject which converts said initiation energy into an energy that effects a predetermined change in said target structure.

A further object of the present invention is to provide a method for treatment of a condition, disorder or disease which can use any suitable energy source as the initiation energy source to activate the activatable pharmaceutical agent and thereby cause a predetermined change in a target structure to treat a condition, disorder or disease.

A further object of the present invention is to provide a method for treatment of a condition, disorder or disease using an energy cascade to activate an activatable pharmaceutical agent that then treats cells suffering from a condition, disorder or disease.

A further object of the present invention is to provide a method for generating an autovaccine effect in a subject, which can be in vivo thus avoiding the need for ex vivo treatment of subject tissues or cells, or can be ex vivo.

A further object of the present invention is to provide a method for generating an autovaccine effect in a subject, which can be in vivo thus avoiding the need for ex vivo treatment of subject tissues or cells, or can be ex vivo.

A further object of the present invention is to provide a method for or modifying a target structure which mediates or is associated with a biological activity, comprising:

a. modifying one or more cells to incorporate a photon emitting modification or substance;

b. inserting the modified cells at a targeted site of the subject;

c. placing in a vicinity of a target structure in a subject in need of treatment a nanoparticle, the nanoparticle is configured, upon exposure to the photons emitted from the modified cells having a first wavelength $\lambda_1$, to generate a second wavelength $\lambda_2$ of radiation having a higher energy than the first wavelength $\lambda_1$, wherein the nanoparticle includes a metallic shell on at least a fraction of a surface of the nanoparticle, a radial dimension of the metallic shell is set to a value so that a surface plasmon resonance in the metallic shell resonates at a frequency which provides spectral overlap with at least one of the first wavelength $\lambda_1$ and the second wavelength $\lambda_2$, and the nanoparticle is configured to emit energy upon interaction with an initiation energy having an energy in the range of $\lambda_1$;

d. administering (i) at least one activatable pharmaceutical agent capable of being activated directly or indirectly by the energy emitted by the nanoparticle to cause a predetermined change to the target structure in situ, and (ii) optionally, at least one energy modulation agent;

thus causing the predetermined change to the target structure to occur, wherein said predetermined change modifies the target structure and modulates the biological activity of the target structure.

A still further object of the present invention is to provide a kit, a system, and a pharmaceutical composition for use in the present invention methods.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 1 provides an exemplary electromagnetic spectrum in meters.

FIG. 2 is a graphical representation of an embodiment of the energy modulation agent-photo activator (PA) system of the present invention.

FIGS. 8A-1 to 8A-7 are schematic illustrations of various upconverter structures of the invention.

FIGS. 9B-1 and 9B-2 are micrographs showing ~15 nm cubic $Y_2O_3$ dielectric particles generated through the combustion method.

FIGS. 10A-1 to 10A-7 are schematic illustrations of other various upconverter structures of the invention.

FIGS. 10B-1 to 10B-7 are schematic illustrations of other various upconverter structures of the invention.

FIGS. 10C-1 to 10C-10 are schematic illustrations of plasmonics-active upconverter structures of the invention.

FIGS. 10D-1 to 10D-7 are schematic illustrations of photo-active molecules linked to plasmonics-active upconverter structures of the invention.

FIGS. 12A-1 to 12A-7 are schematic illustrations of other various upconverter structures of the invention where the dielectric core has appended thereon or attached by linkages a bioreceptor molecule.

FIGS. 12B-1 to 12B-6 are schematic illustrations of still other various upconverter structures of the invention where the dielectric core has appended thereon or attached by linkages a bioreceptor molecule.

FIG. 12B-7 is a depiction of the enhancement of emission as a function of wavelength for a configuration similar to that in FIG. 12B-6.

FIG. 12B-8 is a depiction of the enhancement of emission as a function of wavelength for a configuration where the molecule is located inside a metallic shell.

FIG. 12B-9 is a depiction of the excitation enhancement as a function of wavelength for a configuration similar to that in FIG. 12A-6.

FIG. 12B-10 is a depiction of the dependence of emission enhancement on wavelength for the structure and excitation shown in FIG. 12B-9.

FIG. 12B-11 is a depiction of the data of FIG. 12B-10 simplified to show the total enhancement verses the inside diameter of the metal shell.

FIGS. 13A to 13C are graphical representations of an embodiment of a PEPST energy modulation agent-PA system with detachable bond.

FIG. 14 is a graphical representation of an embodiment of PEPST probes for dual plasmonic excitation.

FIGS. 15A to 15D are graphical representations of an embodiment of a use of encapsulated photoactive agents.

DETAILED DESCRIPTION OF THE INVENTION

Figure 3:
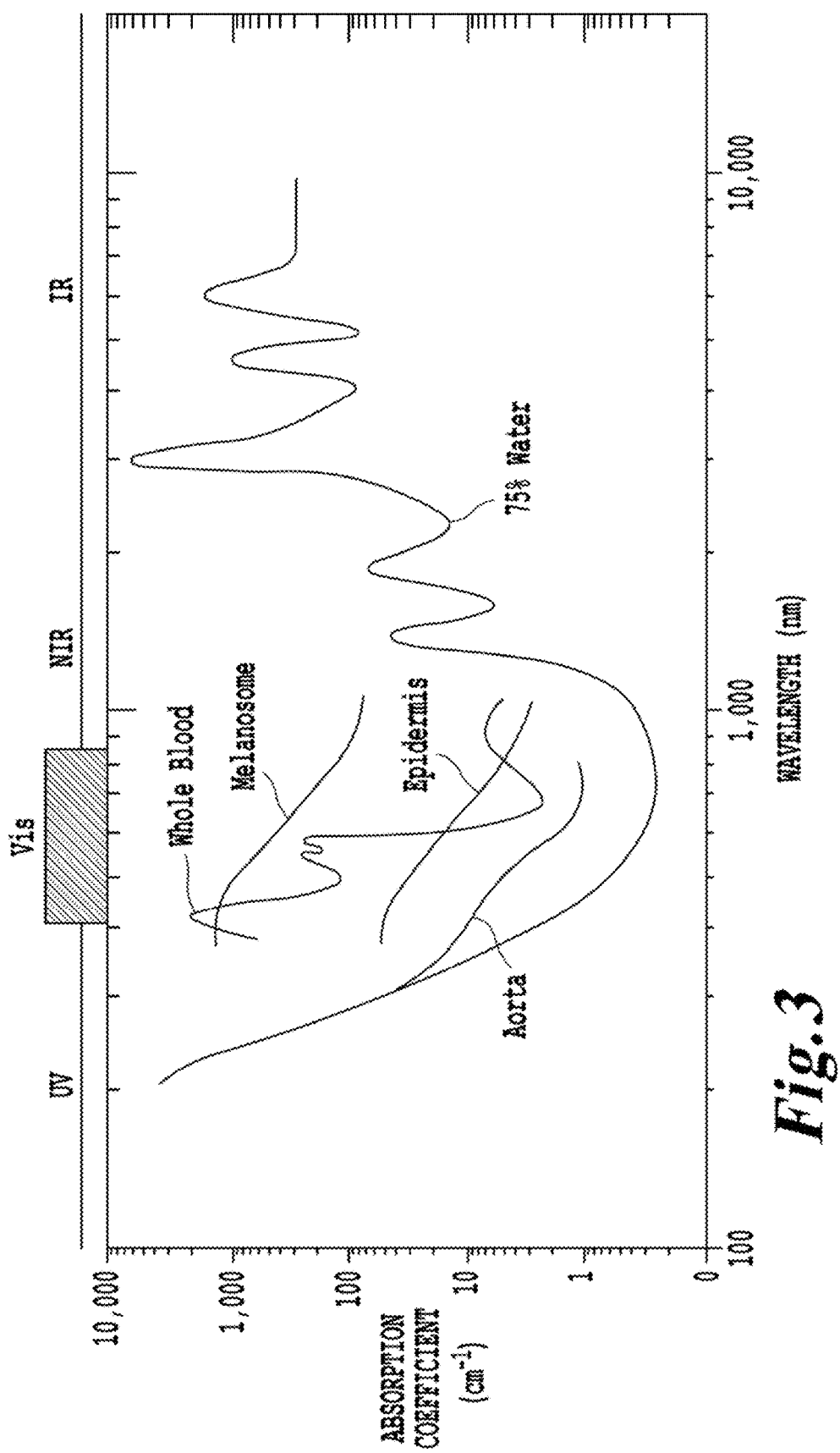
FIG. 3 is a graphical representation of the "therapeutic window" in tissue and absorption spectra of biological components.

The present invention sets forth a novel method for modifying a target structure in a subject which mediates or is associated with a biological activity that is effective, specific, and has few side-effects. Those cells suffering from a condition, disorder or disease are referred to herein as the target cells.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

Generally, the present invention provides a method for modifying a target structure which mediates or is associated with a biological activity, comprising:

placing a nanoparticle in a vicinity of a target structure in a subject in need of treatment, wherein the nanoparticle is configured, upon exposure to a first wavelength $\lambda_1$, to generate a second wavelength $\lambda_2$ of radiation having a higher energy than the first wavelength $\lambda_1$, wherein the nanoparticle comprises a metallic structure is deposited in relation to the nanoparticle, a radial dimension of the metallic shell is set to a value so that a surface plasmon resonance in the metallic shell resonates at a frequency which provides spectral overlap with at least one of the first wavelength λ1 and the second wavelength λ2, and the nanoparticle is configured to emit light in the vicinity of or into the target structure upon interaction with an initiation energy having an energy in the range of λ1; and applying the initiation energy including said first wavelength λ1 from an initiation energy source to the subject, wherein the emitted light including said second wavelength λ2 directly or indirectly contacts the target structure and induces a predetermined change in said target structure in situ, wherein said predetermined change modifies the target structure and modulates the biological activity of the target structure.

In one embodiment, the initiation energy produces plasmonics and/or exciton coupling enhanced light generation that is capable of inducing a predetermined change in the target structure with or without an energy modulation agent and/or a photoactive agent.

In various embodiments, the applied energy is considered to be up converted, as the photon energy carried by radiation 1 has an energy level equal to $hv_1$ (the product of Planck constant and frequency 1) is converted to a higher energy $hv_2$, where $hv_1$ is less than $hv_2$. In various embodiments, the applied energy is considered to be down converted, as energy at $hv_1$, is converted to a lower energy $hv_2$, where $hv_1$ is greater than $hv_2$.

In various embodiments of the invention, there are provided systems and methods for broad band up conversion from the microwave and RF regime to electromagnetic radiation of higher photonic energy in the UV, VIS, and IR regime. The invention can encompasses a variety of applications where the up and down conversions are conducted inside biological media (or) inside human and animal bodies.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of having a size less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

As noted above, an object of the present invention is to modify a target structure which mediates or is associated with a biological activity, and in one preferred embodiment to treat a condition, disorder or disease, in a subject using photobiomodulation.

In one preferred embodiment, the initiation energy source is applied indirectly via an energy modulation agent, preferably in proximity to the target cells. The present invention further provides methods for the treatment of a condition, disorder or disease, in which at least one energy modulation agent converts the initiation energy into an energy in the range of the first wavelength $\lambda_1$ that cause the nanoparticle to emit light in the range of the second wavelength $\lambda_2$ that is capable of inducing the predetermined change in said target structure. In other embodiment, the at least one energy modulation agent converts the initiation energy into an energy in the range of the first wavelength $\lambda_1$ that cause the nanoparticle to emit energy in the range of said second wavelength $\lambda_2$ that is capable of inducing the predetermined change in the target structure. In one preferred embodiment, the energy modulation agent is specifically located around, on, or in said target structure. In yet another embodiment, the energy modulation agent transforms the initiation electromagnetic energy into a photonic or another electromagnetic energy the range of the first wavelength $\lambda_1$ that cause the nanoparticle to emit light the range of said second wavelength $\lambda_2$ that is capable of inducing the predetermined change in said target structure. In one embodiment, the energy modulation agent is capable of downconverting the initiation energy. In another embodiment, the energy modulation agent is capable of upconverting the initiation energy.

As noted above, an object of the present invention is to modify a target structure which mediates or is associated with a biological activity, and in a preferred embodiment to treat a condition, disorder or disease, in a subject using photobiomodulation. Exemplary conditions, disorders or diseases may include, but are not limited to, cancer (e.g., prostate, breast, lung, and colon), autoimmune diseases, soft and bone tissue injury, chronic pain, wound healing, nerve regeneration, viral and bacterial infections, fat deposits (liposuction), varicose veins, enlarged prostate, retinal injuries and other ocular diseases, Parkinson's disease, and behavioral, perceptional and cognitive disorders. Exemplary conditions also may include nerve (brain) imaging and stimulation, a direct control of brain cell activity with light, control of cell death (apoptosis), and alteration of cell growth and division.

Accordingly, in one embodiment, the present invention provides methods that are capable of overcoming the shortcomings of the existing methods. In general, a method in accordance with the present invention utilizes an initiation energy from at least one source applied to a target structure in a subject in need of treatment, wherein the initiation energy indirectly contacts the target structure and induces a predetermined change in said target structure in situ, thus modifying a target structure which mediates or is associated with a biological activity, preferably treating a condition, disorder or disease. The initiation energy can preferably penetrate completely through the subject and can be applied from a single source or more than one source. Exemplary initiation energy may be UV radiation, visible light, infrared radiation (IR), x-rays, gamma rays, an electron beam, microwaves or radio waves.

In one embodiment, a plasmonics-active agent (e.g., a nanoparticle) upconverts the applied initiation energy, such that the upconverted initiation energy is capable of inducing the predetermined change in said target structure. "Energy upconversion" means that upon exposure to a first wavelength $\lambda_1$, an agent (e.g., energy modulation agent or plasmonics active agent or both) generates a second wavelength $\lambda_2$ of radiation having a higher energy than the first wavelength $\lambda_1$. In a different embodiment, an energy modulation agent upconverts the applied initiation energy, such that the upconverted initiation energy is absorbed, intensified or modified by at least one plasmonics-active agent into an energy that effects the predetermined change in said target structure. In another embodiment, the initiation energy is absorbed, intensified or modified by at least one plasmonics active agent into energy capable to be upconverted by an energy modulation agent (e.g., a nanoparticle) into an energy that is capable of inducing the predetermined change in said target structure. In yet another preferred embodiment, a method in accordance with the present invention utilizes the principle of energy transfer to and among molecular agents to control delivery and activation of cellular changes by irradiation such that delivery of the desired effect is more intensified, precise, and effective than the conventional techniques.

Further, the energy modulation agent can transform a photonic initiation energy into a photonic energy that effects a predetermined change in said target structure. In one preferred embodiment, the energy modulation agent down-converts the wavelength of the photonic initiation energy. In another preferred embodiment, the energy modulation agent can upconvert the wavelength of the photonic initiation energy. In a different embodiment the modulation agent is one or more members selected from a biocompatible fluorescing metal nanoparticle, fluorescing metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

Another object of the present invention is to treat a condition, disorder or disease in a subject using an activatable pharmaceutical agent. Exemplary conditions, disorders or diseases may include, but are not limited to, cancer, autoimmune diseases, cardiac ablasion (e.g., cardiac arrhythmia and atrial fibrillation), photoangioplastic conditions (e.g., de novo atherosclerosis, restinosis), intimal hyperplasia, arteriovenous fistula, macular degeneration, psoriasis, acne, hopecia areata, portwine spots, hair removal, rheumatoid and inflammatory arthritis, joint conditions, lymph node conditions, and cognitive and behavioral conditions.

Accordingly, in one embodiment, the present invention provides methods utilizing the principle of energy transfer to and among molecular agents to control delivery and activation of pharmaceutically active agents such that delivery of the desired pharmacological effect is more focused, precise, and effective than the conventional techniques.

In yet another preferred embodiment, the initiation energy source is applied directly or indirectly to the activatable pharmaceutical agent and/or a plasmonics-active agent (e.g., nanoparticles), preferably in proximity to the target cells.

Within the context of the present invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the modulation agent and/or activatable pharmaceutical agent within a subject. In one embodiment, the initiation energy source cannot be within line-of-sight of the energy modulation agent and/or the activatable pharmaceutical agent. By "cannot be within line-of-sight" is meant that if a hypothetical observer were located at the location of the energy modulation agent or the activatable pharmaceutical agent, that observer would be unable to see the source of the initiation energy.

Although not intending to be bound by any particular theory or be otherwise limited in any way, the following theoretical discussion of scientific principles and definitions are provided to help the reader gain an understanding and appreciation of the present invention.

As used herein, the term "subject" is not intended to be limited to humans, but may also include animals, plants, or any suitable biological organism.

As used herein, the phrase "a disease or condition" refers to a condition, disorder or disease that may include, but are not limited to, cancer, soft and bone tissue injury, chronic pain, wound healing, nerve regeneration, viral and bacterial infections, fat deposits (liposuction), varicose veins, enlarged prostate, retinal injuries and other ocular diseases, Parkinson's disease, and behavioral, perceptional and cognitive disorders. Exemplary conditions also may include nerve (brain) imaging and stimulation, a direct control of brain cell activity with light, control of cell death (apoptosis), and alteration of cell growth and division. Yet other exemplary a condition, disorder or disease may include, but are not limited to, cardiac ablasion (e.g., cardiac arrhythmia and atrial fibrillation), photoangioplastic conditions (e.g., de novo atherosclerosis, restinosis), intimal hyperplasia, arteriovenous fistula, macular degeneration, psoriasis, acne, hopecia areata, portwine spots, hair removal, rheumatoid and inflammatory arthritis, joint conditions, and lymph node conditions.

As used herein, the term "target structure" refers to an eukaryotic cell, prokaryotic cell, a subcellular structure, such as a cell membrane, a nuclear membrane, cell nucleus, nucleic acid, mitochondria, ribosome, or other cellular organelle or component, an extracellular structure, virus or prion, and combinations thereof.

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, regulation of cytochrome c oxidase and flavoproteins, activation of mitochondria, stimulation antioxidant protective pathway, modulation of cell growth and division, alteration of firing pattern of nerves, alteration of redox properties, generation of reactive oxygen species, modulation of the activity, quantity, or number of intracellular components in a cell, modulation of the activity, quantity, or number of extracellular components produced by, excreted by, or associated with a cell, or a combination thereof. Predetermined cellular changes may or may not result in destruction or inactivation of the target structure.

As used herein, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy. In preferred embodiments, the energy modulation agent receives higher energy (e.g. x-ray) and re-emits in lower energy (e.g. UV-A). Some modulation agents may have a very short energy retention time (on the order of fs, e.g. fluorescent molecules) whereas others may have a very long half-life (on the order of minutes to hours, e.g. luminescent or phosphorescent molecules). Suitable energy modulation agents include, but are not limited to, a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence. Various exemplary uses of these are described below in preferred embodiments.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

The energy modulation agent may be preferably directed to the desired site (e.g. a tumor) by systemic administration to a subject. For example, a UV-A emitting energy modulation agent may be concentrated in the tumor site by physical insertion or by conjugating the UV-A emitting energy modulation agent with a tumor specific carrier, such as a lipid, chitin or chitin-derivative, a chelate or other functionalized carrier that is capable of concentrating the UV-A emitting source in a specific target tumor.

Additionally, the energy modulation agent can be used alone or as a series of two or more energy modulation agents wherein the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable pharmaceutical agent and/or to cause a photonics-active agent (e.g., a nanoparticle) to upconvert the remitted energy.

Exemplary energy modulation agents may include, but are not limited to, at least one energy modulation agent selected from the group consisting of a biocompatible fluorescing metal nanoparticle, fluorescing metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

As used herein, an "activatable pharmaceutical agent" is an agent that normally exists in an inactive state in the absence of an activation signal. When the agent is activated by a matching activation signal under activating conditions, it is capable of effecting the desired pharmacological effect on a target cell (i.e. preferably a predetermined cellular change).

Signals that may be used to activate a corresponding agent may include, but are not limited to, photons of specific wavelengths (e.g. x-rays, UV, IR, NIR or visible light), electromagnetic energy (e.g. radio or microwave), thermal energy, acoustic energy, or any combination thereof.

Activation of the agent may be as simple as delivering the signal to the agent or may further premise on a set of activation conditions. For example, in the former case, an activatable pharmaceutical agent, such as a photosensitizer, may be activated by UV-A radiation. Once activated, the agent in its active-state may then directly proceed to effect a cellular change.

Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors.

Selection of an activatable pharmaceutical agent greatly depends on a number of factors such as the desired cellular change, the desired form of activation, as well as the physical and biochemical constraints that may apply. Exemplary activatable pharmaceutical agents may include, but are not limited to, agents that may be activated by photonic energy, electromagnetic energy, acoustic energy, chemical or enzymatic reactions, thermal energy, or any other suitable activation mechanisms.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

The treatment of the present invention can be by the unique methods described in U.S. application Ser. No. 11/935,655, filed Nov. 6, 2007 (incorporated by reference above), or by a modified version of a conventional treatment such as PDT, but using a plasmonics-active agent to enhance the treatment by modifying or enhancing the applied energy or, in the case of using an energy modulation agent, modifying either the applied energy, the emitted energy from the energy modulation agent, or both.

In one preferred embodiment, the activatable pharmaceutical agent is capable of chemically binding to the DNA or mitochondria at a therapeutically effective amount. In this embodiment, the activatable pharmaceutical agent, preferably a photoactivatable agent, is exposed in situ to an activating energy emitted from an energy modulation agent, which, in turn receives energy from an initiation energy source.

Suitable activatable agents include, but are not limited to, photoactive agents, sono-active agents, thermo-active agents, and radio/microwave-active agents. An activatable agent may be a small molecule; a biological molecule such as a protein, a nucleic acid or lipid; a supramolecular assembly; a nanoparticle; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the present invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

Table 1 lists some photoactivatable molecules capable of being photoactivated to induce an auto vaccine effect.

TABLE 1

| | | | | | SSET and TTET rate constants for bichromophoric peptides | | | | | |
|---|---|---|---|---|---|---|---|---|---|---|
| Compound | $\lambda_{ex}$ (nm) | $E_{SSET}$ | $K_S$ of donor ($S^{-1}$) | $K_{SSET}$ ($S^{-1}$) | $K_{SSET}$ ($S^{-1}$) (Average) | $R_0$ (Å) | R (Å) | $R_{model}$ (Å) (Average) | $E_{TTET}$ | $k_{TTET}$ ($S^{-1}$) |
| 1B | 224 | 96.3 | $9.5 \times 10^0$ | $2.44 \times 10^8$ | $1.87 \times 10^8$ | 14.7 | 9 | 9.5 | | |
| | 266 | 95 | | $1.8 \times 10^8$ | | | | | 2.5 | $5 \times 10^2$ |
| | 280 | 94 | | $1.36 \times 10^8$ | | | | | | |
| 1A | 224 | 80 | $9.5 \times 10^0$ | $3.8 \times 10^7$ | $3.67 \times 10^7$ | 14.7 | 11.8 | 14.1 | | |
| | 266 | 79 | | $3.6 \times 10^7$ | | | | | 2 | $3.6 \times 10^2$ |
| | 280 | 79 | | $3.6 \times 10^7$ | | | | | | |
| 2B | 224 | 77 | $9.5 \times 10^0$ | $3.1 \times 10^7$ | $3.9 \times 10^7$ | 14.7 | 11.9 | 5.5 | | |
| | 266 | 81 | | $3.9 \times 10^7$ | | | | | 32 | $9.4 \times 10^3$ |
| | 280 | 83 | | $4.7 \times 10^7$ | | | | | | |
| 2A | 224 | 69 | $9.5 \times 10^0$ | $2.1 \times 10^7$ | $3 \times 10^7$ | 14.7 | 12.2 | 8.1 | 74.3 | $5.7 \times 10^4$ |
| | 266 | 80 | | $3.7 \times 10^7$ | | | | | | |
| | 280 | 77 | | $3.2 \times 10^7$ | | | | | | |

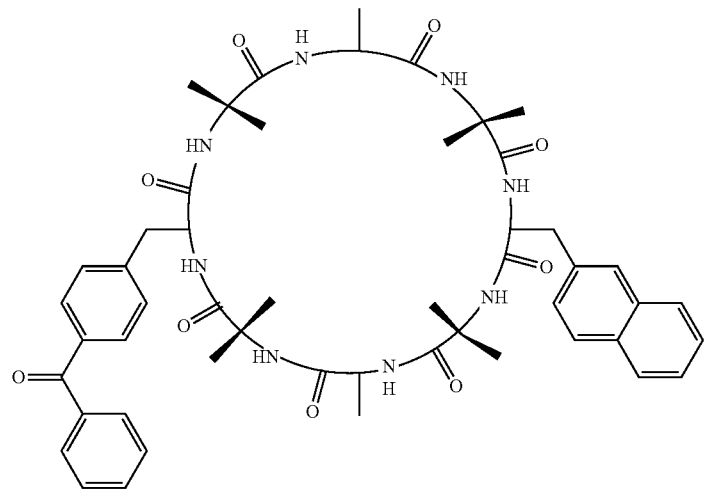

1A

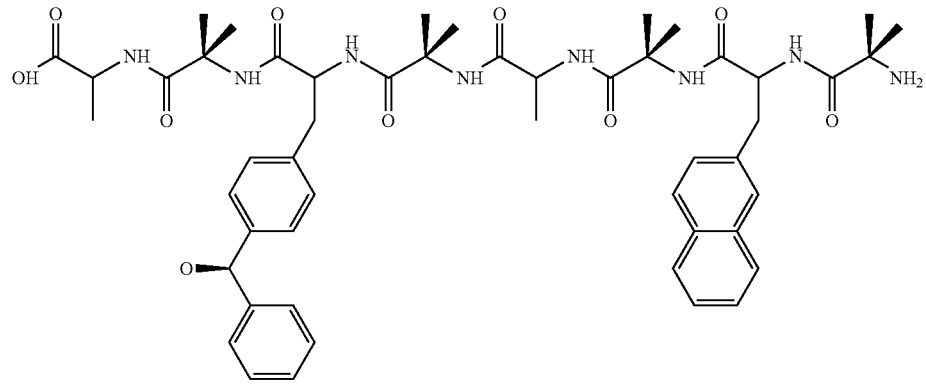

1B

-continued

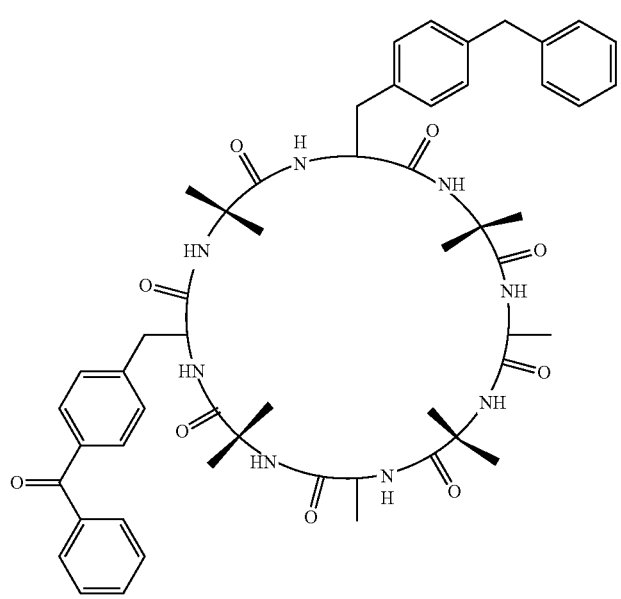

2A

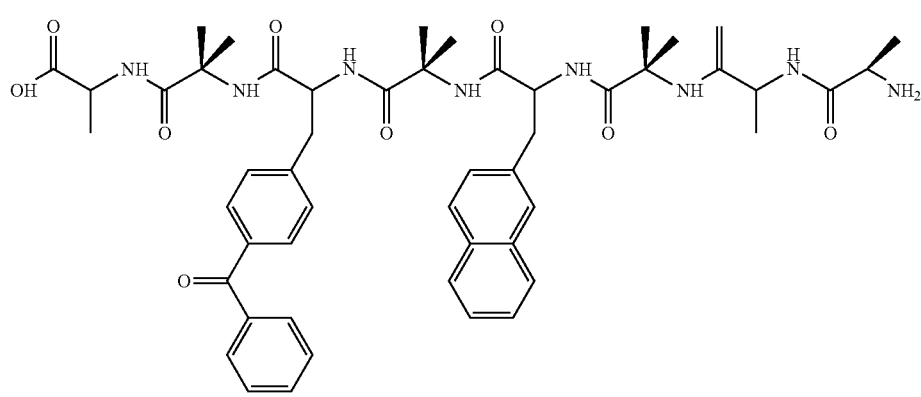

2B

Table 2 lists some additional endogenous photoactivatable molecules.

TABLE 2

Biocompatible, endogenous fluorophore emitters.

| Endogenous Fluorophores | Excitation Max. (nm) | Emission Max. (nm) |
|---|---|---|
| Amino acids | | |
| Tryptophan | 280 | 350 |
| Tyrosine | 275 | 300 |
| Phenylalanine | 260 | 260 |
| Structural Proteins: | | |
| Collagen | 325, 360 | 400, 405 |
| Elastin | 290, 325 | 340, 400 |
| Enzymes and Coenzymes: | | |
| flavin adenine dinucleotide | 450 | 535 |
| reduced nicotinamide dinucleotide | 290, 351 | 440, 460 |
| reduced nicotinamide dinucelotide phosphate | 336 | 464 |
| Vitamins: | | |
| Vitamins A | 327 | 510 |
| Vitamins K | 335 | 480 |
| Vitamins D | 390 | 480 |

TABLE 2-continued

Biocompatible, endogenous fluorophore emitters.

| Endogenous Fluorophores | Excitation Max. (nm) | Emission Max. (nm) |
|---|---|---|
| Vitamins $B_6$ compounds: | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |
| Lipids: | | |
| Phospholipids | 436 | 540, 560 |
| Lipofuscin | 340-395 | 540, 430-460 |
| Cercid | 340-395 | 430-460, 540 |
| Porphyrins | 400-450 | 630, 690 |

Figure 9A:
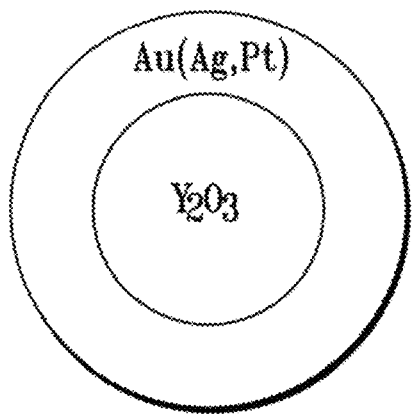
FIG. 9A is a schematic illustration of a particular nanometer sized upconverter structure of the invention.
Figures 2, 9B:
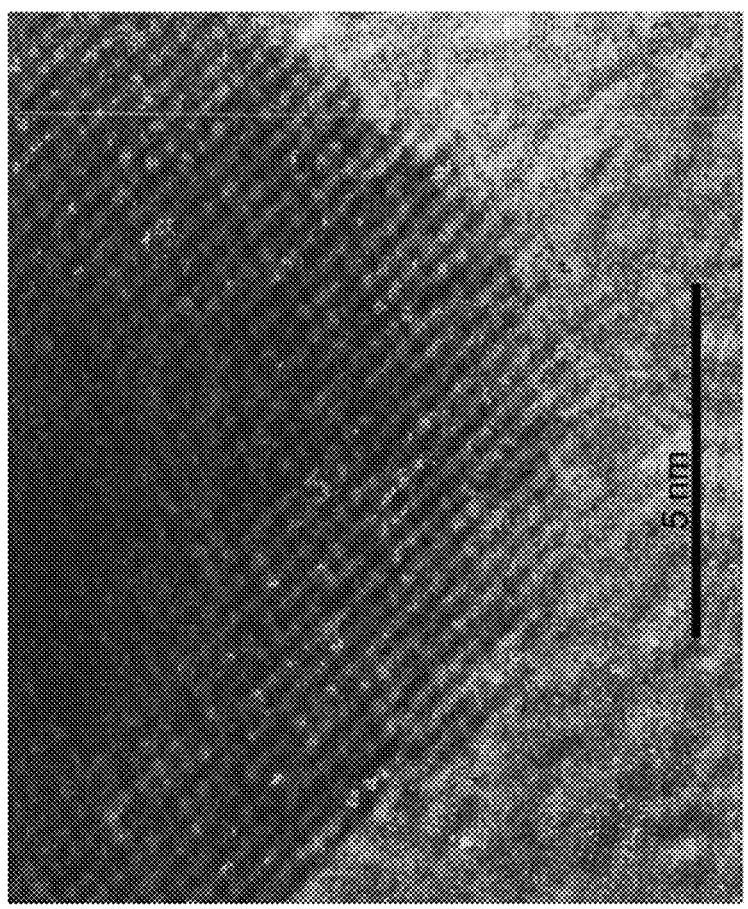
Figures 1, 9B:
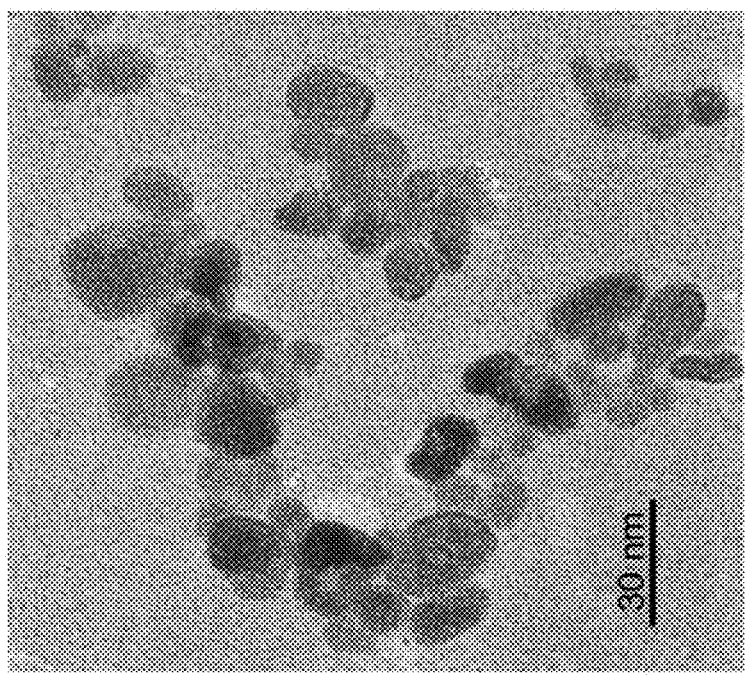

FIG. 1 provides an exemplary electromagnetic spectrum in meters (1 nm equals $10^{-9}$ meters).

Although the activatable pharmaceutical agent and the energy modulation agent can be distinct and separate, it will be understood that the two agents need not be independent and separate entities. In fact, the two agents may be associated with each other via a number of different configurations. Where the two agents are independent and separately movable from each other, they generally interact with each other via diffusion and chance encounters within a common surrounding medium. Where the activatable pharmaceutical agent and the energy modulation agent are not separate, they may be combined into one single entity.

The initiation energy source can be any energy source capable of providing energy at a level sufficient to cause cellular changes directly or via a modulation agent which transfer the initiation energy to energy capable of causing the predetermined cellular changes. Also, the initiation energy source can be any energy source capable of providing energy at a level sufficient activate the activatable agent directly, or to provide the energy to a modulation agent with the input needed to emit the activation energy for the activatable agent (indirect activation). Preferable initiation energy sources include, but are not limited to, UV-A lamps or fiber optic lines, a light needle, an endoscope, and a linear accelerator that generates x-ray, gamma-ray, or electron beams. In a preferred embodiment, the initiation energy is capable of penetrating completely through the subject. Within the context of the present invention, the phrase "capable of penetrating completely through the subject" is used to refer to energy that can penetrate to any depth within the subject to activate the activatable pharmaceutical agent. It is not required that the any of the energy applied actually pass completely through the subject, merely that it be capable of doing so in order to permit penetration to any desired depth to activate the activatable pharmaceutical agent. Exemplary initiation energy sources that are capable of penetrating completely through the subject include, but are not limited to, UV light, visible light, IR radiation, x-rays, gamma rays, electron beams, microwaves and radio waves. In one embodiment, a single or multiple energy sources can be used. The initiation energy can be applied from (i) an initiation energy source that is external to the subject; or (ii) an initiation energy source that is internal to the subject, which is placed or delivered internally into the subject and/or the target structure.

An additional embodiment of the present invention is to provide a method for treatment of a condition, disease or disorder by the in-situ generation of energy in a subject in need thereof, where the energy generated can be used directly to effect a change thereby treating the condition, disease or disorder, or the energy can be used to activate an activatable pharmaceutical agent, which upon activation effects a change thereby treating the condition, disease or disorder. The energy can be generated in-situ by any desired method, including, but not limited to, chemical reaction such as chemiluminescence, or by conversion of an energy applied to the subject externally, which is converted in-situ to a different energy (of lower or higher energy than that applied), through the use of one or more energy modulation agents.

The phenomenon of ultra weak emission from cellular systems has been a topic of various inquiries since the 1900s. This topic can be traced back to the early investigations of the Russian biologist Gurwitsch Alexander G. Gurwitsch more than seventy years ago, who speculated that ultraweak photon emission transmit information in cells [A. G. Gurwitsch, S. S. Grabje, and S. Salkind, "Die Natur des spezifischen Erregers der Zellteilung," *Arch. Entwicklungsmech. Org.* 100, 11-40, 1923].

In the 1970s, this area of research was investigated by a number of investigators. The presence of biological radiation from a variety of cells was later investigated by several research groups in Europe and Japan using low-noise, sensitive photon-counting detection systems [B. Ruth and F.-A. Popp, "Experimentelle Untersuchungen zur ultraschwachen Photonenemission biologischer Systeme," *Z. Naturforsch., A: Phys. Sci.* 31c, 741-745, 1976; T. I. Quickenden and S. S. Que-Hee, "The spectral distribution of the luminescence emitted during growth of the yeast *Saccharomyces cerevisiae* and its relationship to mitogenetic radiation," *Photochem. Photobiol.* 23, 201-204, 1976; H. Inaba, Y. Shimizu, Y. Tsuji, and A. Yamagishi, "Photon counting spectral analysing system of extra-weak chemi- and bioluminescence for biochemical applications," *Photochem. Photobiol.* 30, 169-175, 1979]. Popp and coworkers suggested the evidence of some 'informational character' associated with the ultraweak photon emission from biological systems, often referred by Popp as "bio-photons". Other studies reported ultra-weak photon emission from various species including plant, and animals cells [H. J. Niggli, C. Scaletta, Y. Yan, F.-A. Popp, and L. A. Applegate, "Ultraweak photon emission in assessing bone growth factor efficiency using fibroblastic differentiation," *J. Photochem. Photobiol., B,* 64, 62-68, 2001;]. Results of experiments of UV-irradiated skin fibroblasts indicated that repair deficient xeroderma pigmentosum cells show an efficient increase of ultraweak photon emission in contrast to normal cells. [H. J. Niggli, "Artificial sunlight irradiation induces ultraweak photon emission in human skin fibroblasts," *J. Photochem. Photobiol., B* 18, 281-285 (1993)].

A delayed luminescence emission was also observed in biological systems [F.-A. Popp and Y. Yan, "Delayed luminescence of biological systems in terms of coherent states," *Phys. Lett. A* 293, 93-97 (2002); A. Scordino, A. Triglia, F. Musumeci, F. Grasso, and Z. Rajfur, "Influence of the presence of Atrazine in water on in-vivo delayed luminescence of acetabularium acetabulum," *J. Photochem. Photobiol., B,* 32, 11-17 (1996); This delayed luminescence was used in quality control of vegetable products [A. Triglia, G. La Malfa, F. Musumeci, C. Leonardi, and A. Scordino, "Delayed luminescence as an indicator of tomato fruit quality," *J. Food Sci.* 63, 512-515 (1998)] or for assessing the quality or quality changes of biological tissues [Yu Yan, Fritz-Albert Popp *, Sibylle Sigrist, Daniel Schlesinger, Andreas Dolf, Zhongchen Yan, Sophie Cohen, Amodsen Chotia, "Further analysis of delayed luminescence of plants", *Journal of Photochemistry and Photobiology B: Biology* 78, 235-244 (2005)].

It was reported that UV excitation can further enhance the ultra-weak emission and a method for detecting UV-A-laser-induced ultra-weak photon emission was used to evaluate differences between cancer and normal cells. [H. J. Niggli et al, Laser-ultraviolet-A-induced ultraweak photon emission in mammalian cells, *Journal of Biomedical Optics* 10(2), 024006 (2005)].

Accordingly, in one embodiment of the present invention, upon applying an initiation energy from at least one source to a target structure in a subject in need of treatment, the initiation energy contacts the target structure and induces a predetermined change in said target structure in situ, wherein the predetermined change is the enhancement of energy emission from the target, which then mediates, initiates or enhances a biological activity of other target structures in the subject, or of a second type of target structure (e.g., a different cell type).

In another embodiment, the initiation energy can itself be energy emitted by at least one cell excited by metabolic processes or some other internal or external trigger, and said applying is conducted via cell-to-cell energy transfer. There are those that maintain that the health of the body depends on certain bioelectric vibrations that are susceptible to chemical or physical toxic factors. Fröhlich notes that there are coherent electric vibrations in the frequency range 100 GHz to 1 THz, excited in cells by metabolic processes (see Fröhlich H. Coherent electric vibrations in biological systems and the cancer problem, IEEE Transactions on Microwave Theory and Techniques, Vol. MTT-26, No. 8, August, 1978, pp 613-617). This idea is based on observation of the inhibition or stimulation of the growth of yeast and bacteria as functions of the applied frequency, showing very stable and repetitive resonances. If such vibrational states are indeed metabolically excited, then they should be manifested in Raman spectroscopy. Actually, their existence has been demonstrated during periods of metabolic activity of lysozyme and *E. coli* (700 GHz to 5 THz). Emissions have also been observed at lower frequencies (150 GHz or less). These vibrations occur in the tissue of higher organisms and they have been hypothesized exercise some control on cellular growth (see also S. J. Webb et al, Nature, Vol. 218, Apr. 27, 1968, pp. 374-375; and S. J. Webb et al et al, Nature Vol. 222, Jun. 21, 1969, pp. 1199-1200). Cancerization could result from a modification of these vibrations by the invasion of foreign molecules, e.g., the presence of free electrons in the condition bands of proteins. There is some evidence for the presence of double spectral lines at 1.5 and 6 THz in breast carcinoma, which may be an indication of an interaction between normal cellular vibrations and free electrons. In such coherent frequency communication between cells, it is believed that the medium through which the communication is transmitted is the water within and around the cells (see Smith, Coherent Frequencies, Consciousness and the Laws of Life, 9$^{th}$ International Conference CASYS '09 on *Computing Anticipatory Systems*, Liege, Belgium, Aug. 3-8, 2009).

Accordingly, in a further embodiment of the present invention, the initiation energy is an energy capable of triggering an altered metabolic activity in one or more cells, preferably in the 100 GHz to 10 THz region, and is applied directly to one or more cells, to trigger the cell(s) to undergo altered metabolic activity, and optionally, to further trigger emissions from the cell(s) to thereby cascade the effects of the emissions to other similar or different cell types adjacent thereto, in essentially a triggered entry into the natural emissions process described above, preferably where the medium through which the emissions are communicated is water-based, most preferably where the medium is the water contained within and surrounding the cells.

A further embodiment of the present invention combines the treatment of a condition, disease or disorder with the generation of heat in the affected target structure in order to enhance the effect of the treatment. For example, in the treatment of a cell proliferation disorder using a photoactivatable pharmaceutical agent (such as a psoralen or derivative thereof), one can activate the photoactivatable pharmaceutical agent by applying an initiation energy which, directly or indirectly, activates the pharmaceutical agent. As noted elsewhere in the present application, this initiation energy can be of any type, so long as it can be converted to energy suitable for activating the pharmaceutical compound. In addition to applying this initiation energy, in this embodiment of the present invention, energy is applied that causes heating of the target structure. In the case of a cell proliferation disorder such as cancer, the heating would increase the proliferation rate of the cancer cells. While this may seem counterintuitive at first, when the cell proliferation disorder is being treated using a DNA intercalation agent, such as psoralen or a derivative thereof, this increase in cell proliferation can actually assist the psoralen in causing apoptosis. In particular, when psoralen becomes intercalated into DNA, apoptosis occurs when the cell goes through its next division cycle. By increasing the rate at which the cells divide, one can use the present invention methods to enhance the onset of apoptosis.

For this embodiment, the heat can be generated in any desired manner. Preferably, the heat can be generated using the application of microwaves or NIR energy to the target structure or by the use of use of nanoparticles of metal or having metal shells. In the nanoparticles embodiment, as is done in tumor thermotherapy, magnetic metal nanoparticles can be targeted to cancer cells using conventional techniques, then used to generate heat by application of a magnetic field to the subject under controlled conditions. (DeNardo S J, DeNardo G L, Nataraj an A et al.: Thermal dosimetry predictive of efficacy of 111In-ChL6 NPAMF-induced thermoablative therapy for human breast cancer in mice. J. Nucl. Med. 48(3), 437-444 (2007).)

Alternatively, one can generate heat through the application of NIR to nanoparticles having metal shells which is converted into thermal energy. (Hirsch L R, Stafford R J, Bankson J et al.: Nanoshell-mediated near-infrared thermal therapy of tumors under magnetic resonance guidance. Proc. Natl Acad. Sci. USA100(23), 13549-13554 (2003)).

In one embodiment, the source of the initiation energy can be a radiowave emitting nanotube, such as those described by K. Jensen, J. Weldon, H. Garcia, and A. Zettl in the Department of Physics at the University of California at Berkeley (see http://socrates.berkeley.edu/~argon/nanoradio/radio.html, the entire contents of which are hereby incorporated by reference). These nanotubes can be administered to the subject, and preferably would be coupled to the activatable pharmaceutical agent or the energy modulation agent, or both, or be located in proximity of a target cell such that upon application of the initiation energy, the nanotubes would accept the initiation energy (preferably radiowaves), then emit radiowaves in close proximity to the activatable pharmaceutical agent, or in close proximity to the energy modulation agent, or to the target cell to then cause the predetermined cellular changes or activation of the activatable pharmaceutical agent. In such an embodiment, the nanotubes would act essentially as a radiowave focusing or amplification device in close proximity to the activatable pharmaceutical agent or energy modulation agent or the target cell.

In one embodiment, a method for modifying a target structure which mediates or is associated with a biological activity, comprises:

placing in a vicinity of a target structure in a subject in need of treatment an agent receptive to microwave radiation or radiofrequency radiation; and applying as an initiation energy said microwave radiation or radiofrequency radiation by which the agent directly or indirectly generates emitted light in the infrared, visible, or ultraviolet range, wherein the emitted light contacts the target structure and induces a predetermined change in said target structure in situ, wherein said predetermined change modifies the target structure and modulates the biological activity of the target structure.

The initiation energy can be applied from (i) an external to the subject initiation energy source; or (ii) an internal to the subject initiation energy source which is placed internally into the subject and/or the target structure.

Alternatively, the energy emitting source may be an energy modulation agent that emits energy in a form suitable for absorption by the transfer agent or a target cell. For example, the initiation energy source may be acoustic energy and one energy modulation agent may be capable of receiving acoustic energy and emitting photonic energy (e.g. sonoluminescent molecules) to be received by another energy modulation agent that is capable of receiving photonic energy. Other examples include transfer agents that receive energy at x-ray wavelength and emit energy at UV wavelength, preferably at UV-A wavelength. As noted above, a plurality of such energy modulation agents may be used to form a cascade to transfer energy from initiation energy source via a series of energy modulation agents to activate the activatable agent or the predetermined cellular change.

In one preferred embodiment, the initiation energy source can be a chemical energy source. The chemical energy source can be a member selected from the group consisting of phosphorescent compounds, chemiluminescent compounds, bioluminescent compounds, and light emitting enzymes.

Signal transduction schemes as a drug delivery vehicle may be advantageously developed by careful modeling of the cascade events coupled with metabolic pathway knowledge to sequentially or simultaneously cause the predetermined cellular change or activate multiple activatable pharmaceutical agents to achieve multiple-point alterations in cellular function.

Photoactivatable agents may be stimulated by an energy source, such as irradiation, resonance energy transfer, exciton migration, electron injection, or chemical reaction, to an activated energy state that is capable of effecting the predetermined cellular change desired. In a preferred embodiment, the photoactivatable agent, upon activation, binds to DNA or RNA or other structures in a cell. The activated energy state of the agent is capable of causing damage to cells, inducing apoptosis.

One preferred method for modifying a target structure which mediates or is associated with a biological activity, comprises:

placing a nanoparticle in a vicinity of a target structure in a subject in need of treatment, wherein the nanoparticle is configured, upon exposure to a first wavelength $\lambda_1$, to generate a second wavelength $\lambda_2$ of radiation having a higher energy than the first wavelength $\lambda_1$, wherein
the nanoparticle comprises a metallic structure deposited in relation to the nanoparticle,
a radial dimension of the metallic structure is set to a value so that a surface plasmon resonance in the metallic structure resonates at a frequency which provides spectral overlap with at least one of the first wavelength $\lambda_1$ and the second wavelength $\lambda_2$, and
the nanoparticle is configured to emit energy upon interaction with an initiation energy having an energy in the range of $\lambda_1$;
administering to the subject (a) at least one activatable pharmaceutical agent that is capable of effecting a predetermined change in the target structure when activated, optionally, in the presence of (b) at least one energy modulation agent, wherein if the at least one energy modulation agent present:
(i) the at least one energy modulation agent converts the initiation energy into a reemitted energy in the range of the first wavelength $\lambda_1$ that causes the nanoparticle to emit energy in the range of the second wavelength $\lambda_2$ that is capable of activating the at least one activatable pharmaceutical agent in situ, and/or
(ii) said nanoparticle upconverts the initiation energy to generate an energy in the range of the second wavelength $\lambda_2$ that is converted by the at least one energy modulation agent, and an energy reemitted by the energy modulation agent is capable of activating the at least one activatable pharmaceutical agent,
applying the initiation energy including said first wavelength $\lambda_1$ from an initiation energy source to the subject,
wherein the energy emitted by the nanoparticle including said second wavelength $\lambda_2$ directly or indirectly activates the activatable pharmaceutical agent in situ,
thus causing the predetermined change to the target structure to occur, wherein said predetermined change modifies the target structure and modulates the biological activity of the target structure.

In one preferred embodiment, at least one energy modulation agent is a plurality of the energy modulation agents, and (i) the initiation energy is converted, through a cascade energy transfer between the plurality of the energy modulation agents, to an energy that causes the nanoparticle to emit the energy capable of activating the at least one activatable pharmaceutical agent, and/or (ii) the energy emitted by the nanoparticle is converted, through a cascade energy transfer between the plurality of the energy modulation agents, to an energy capable of activating the at least one activatable pharmaceutical agent.

In one preferred embodiment, at least one activatable pharmaceutical agent comprises an active agent contained within a photocage, wherein upon exposure to the initiation energy source, an energy emitted by the nanoparticle and/or an energy reemitted by the at least one energy modulation agent, the photocage disassociates from the active agent, rendering the active agent available.

Another preferred method for modifying a target structure which mediates or is associated with a biological activity, comprises:
a. modifying one or more cells to incorporate a photon emitting modification or substance;
b. inserting the modified cells at a targeted site of the subject;
c. placing in a vicinity of a target structure in a subject in need of treatment a nanoparticle, the nanoparticle is configured, upon exposure to the photons emitted from the modified cells having a first wavelength $\lambda_1$, to generate a second wavelength $\lambda_2$ of radiation having a higher energy than the first wavelength $\lambda_1$, wherein
the nanoparticle includes a metallic structure deposited in relation to the nanoparticle,
a radial dimension of the metallic structure is set to a value so that a surface plasmon resonance in the metallic structure resonates at a frequency which provides spectral overlap with at least one of the first wavelength $\lambda_1$ and the second wavelength $\lambda_2$, and
the nanoparticle is configured to emit energy upon interaction with an initiation energy having an energy in the range of $\lambda_1$;
d. administering (i) at least one activatable pharmaceutical agent capable of being activated directly or indirectly by the energy emitted by the nanoparticle to cause a predetermined change to the target structure in situ, and (ii) optionally, at least one energy modulation agent,
thus causing the predetermined change to the target structure to occur, wherein said predetermined change modifies the target structure and modulates the biological activity of the target structure.

In one embodiment, one or more cells are subject's own cells that have been removed prior to said modifying. In another embodiment, the photon emitting modification or substance is a member selected from the group consisting of light emitting genes; phosphorescent compounds, chemiluminescent compounds, bioluminescent compounds and light emitting enzymes.

The concept of multi-photon excitation is based on the idea that two or more photons of low energy can excite a fluorophore in a quantum event, resulting in the emission of a fluorescence photon, typically at a higher energy than the two or more excitatory photons. This concept was first described by Maria Göppert-Mayer in her 1931 doctoral dissertation. However, the probability of the near-simultaneous absorption of two or more photons is extremely low. Therefore a high flux of excitation photons is typically required, usually a femtosecond laser. This had limited the range of practical applications for the concept.

Perhaps the most well-known application of the multi-photon excitation concept is the two-photon microscopy pioneered by Winfried Denk in the lab of Watt W. Webb at Cornell University. He combined the idea of two-photon absorption with the use of a laser scanner.

There is an important difference between "sequential" and "simultaneous" two photon excitation. In sequential two-photon excitation to a higher allowed energy level, the individual energies of both the first photon and the second photon must be appropriate to promote the molecule directly to the second allowed electronic energy level and the third allowed electronic energy level. In contrast, simultaneous two-photon excitation requires only that the combined energy of the first of two photons and the second of two photons be sufficient to promote the molecule to a second allowed electronic energy level.

In two-photon excitation microscopy, an infrared laser beam is focused through an objective lens. The Ti-sapphire laser normally used has a pulse width of approximately 100 femtoseconds and a repetition rate of about 80 MHz, allowing the high photon density and flux required for two photons absorption and is tunable across a wide range of wavelengths. Two-photon technology is patented by Winfried Denk, James Strickler and Watt Webb at Cornell University.

Two known applications are two-photon excited fluorescence (TPEF) and non-linear transmission (NLT). The most commonly used fluorophores have excitation spectra in the 400-500 nm range, whereas the laser used to excite the fluorophores lies in the ~700-1000 nm (infrared) range. If the fluorophore absorbs two infrared photons simultaneously, it will absorb enough energy to be raised into the excited state. The fluorophore will then emit a single photon with a wavelength that depends on the type of fluorophore used (typically in the visible spectrum). Because two photons need to be absorbed to excite a fluorophore, the probability of emission is related to the intensity squared of the excitation beam. Therefore, much more two-photon fluorescence is generated where the laser beam is tightly focused than where it is more diffuse. Effectively, fluorescence is observed in any appreciable amount in the focal volume, resulting in a high degree of rejection of out-of-focus objects. The fluorescence from the sample is then collected by a high-sensitivity detector, such as a photomultiplier tube. This observed light intensity becomes one pixel in the eventual image; the focal point is scanned throughout a desired region of the sample to form all the pixels of the image. Two-photon absorption can be measured by several techniques.

Accordingly, in one aspect, the radiative signal may be of the exact energy required to active the photoactive agent. In this aspect, the radiative energy may be directly targeted at the desired coordinate or region where the photoactive agent is present. The initiation energy source in this embodiment may be, for example, x-rays, gamma rays, an electron beam, microwaves or radio waves.

In another aspect, the radiative signal may be of a lower energy than the excitation energy of the photoactive agent. In this aspect, the radiative signal does not have sufficient energy to activate the photoactive agent in a conventional way. Activation of the photoactive agent may be achieved via an "energy upgrade" mechanism such as the multi-photon mechanism described above. Activation of the photoactive agent may further be mediated by an intermediary energy transformation agent. For example, the radiative energy may first excite a fluorophore that emits a photon at the right energy that excites the photoactive agent. The signal is delivered to the target photoactive agent by way of this intermediary agent. In this way, in addition to energy upgrading (and downgrading, as described below), a signal relay mechanism is also introduced. The initiation energy source may be x-rays, gamma rays, an electron beam, microwaves or radio waves. In one embodiment, the energy upgrades are obtained via 2, 3, 4, or 5 photon absorptions.

Work in the area of photodynamic therapy has shown that the amount of singlet oxygen required to cause cell lysis, and thus cell death, is $0.32 \times 10^{-3}$ mol/liter or more, or $10^9$ singlet oxygen molecules/cell or more. In one preferred embodiment, it is preferable to avoid production of an amount of singlet oxygen that would cause cell lysis, due to its indiscriminate nature of attack, lysing both target cells and healthy cells. Accordingly, it is preferred in one preferred embodiment that the level of singlet oxygen production caused by the initiation energy used or activatable pharmaceutical agent upon activation be less than level needed to cause cell lysis.

One advantage is that multiple wavelengths of emitted radiation may be used to
selectively stimulate one or more photoactivatable agents or energy modulation agents capable of stimulating the one or more photoactivatable agents. The energy modulation agent is preferably stimulated at a wavelength and energy that causes little or no damage to healthy cells, with the energy from one or more energy modulation agents being transferred, such as by Foerster Resonance Energy Transfer, to the photoactivatable agents that damage the cell and cause the onset of the desired cellular change, e.g., apoptosis of the cells.

Another advantage is that side effects can be greatly reduced by limiting the production of free radicals, singlet oxygen, hydroxides and other highly reactive groups that are known to damage healthy cells. Furthermore, additional additives, such as antioxidants, may be used to further reduce undesired effects of irradiation.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a photoactivatable molecule.

Alternatively, one can administer the initiation energy source to the subject. Within the context of the present invention, the administering of the initiation energy source means the administration of an agent, that itself produces the initiation energy, in a manner that permits the agent to arrive at the target cell within the subject without being surgically inserted into the subject. The administration can take any form, including, but not limited to, oral, intravenous, intraperitoneal, inhalation, etc. Further, the initiation energy source in this embodiment can be in any form, including, but not limited to, tablet, powder, liquid solution, liquid suspension, liquid dispersion, gas or vapor, etc. In this embodiment, the initiation energy source includes, but is not limited to, chemical energy sources, nanoemitters, nanochips, and other nanomachines that produce and emit energy of a desired frequency. Recent advances in nanotechnology have provided examples of various devices that are nanoscale and produce or emit energy, such as the Molecular Switch (or Mol-Switch) work by Dr. Keith Firman of the EC Research and Development Project, or the work of Cornell et al. (1997) who describe the construction of nanomachines based around ion-channel switches only 1.5 nm in size, which use ion channels formed in an artificial membrane by two gramicidin molecules: one in the lower layer of the membrane attached to a gold electrode and one in the upper layer tethered to biological receptors such as antibodies or nucleotides. When the receptor captures a target molecule or cell, the ion channel is broken, its conductivity drops, and the biochemical signal is converted into an electrical signal. These nanodevices could also be coupled with the present invention to provide targeting of the target cell, to deliver the initiation energy source directly at the desired site.

In another embodiment, the present invention includes the administration of a source of chemical energy such as chemiluminescence, phosphorescence or bioluminescence. The source of chemical energy can be a chemical reaction between two or more compounds, or can be induced by activating a chemiluminescent, phosphorescent or bioluminescent compound with an appropriate activation energy, either outside the subject or inside the subject, with the chemiluminescence, phosphorescence or bioluminescence being allowed to activate the activatable pharmaceutical agent in vivo after administration. In one embodiment, the activatable pharmaceutical agent and the source of chemical energy can be administered. The administration can be performed sequentially in any order or simultaneously. In the case of certain sources of such chemical energy, the administration of the chemical energy source can be performed after activation outside the subject, with the lifetime of the emission of the energy being up to several hours for certain types of phosphorescent materials for example. There are no known previous efforts to use resonance energy transfer of any kind to activate an intercalator to bind DNA.

Yet another example is that nanoparticles or nanoclusters of certain atoms may be introduced such that are capable of resonance energy transfer over comparatively large distances, such as greater than one nanometer, more preferably greater than five nanometers, even more preferably at least 10 nanometers. Functionally, resonance energy transfer may have a large enough "Foerster" distance ($R_0$), such that nanoparticles in one part of a cell are capable of stimulating activation of photoactivatable agents disposed in a distant portion of the cell, so long as the distance does not greatly exceed $R_0$. For example, gold nanospheres having a size of 5 atoms of gold have been shown to have an emission band in the ultraviolet range, recently.

In one embodiment, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells. Thus, an auto-immune response may not be induced.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

Any of the photoactivatable agents may be exposed to an excitation energy source implanted in a subject preferably near a target site. The photoactive agent may be directed to a receptor site by a carrier having a strong affinity for the receptor site. Within the context of the present invention, a "strong affinity" is preferably an affinity having an equilibrium dissociation constant, at least in the nanomolar, nM, range or higher. Preferably, the carrier may be a polypeptide and may form a covalent bond with a photoactive agent, for example. The polypeptide may be an insulin, interleukin, thymopoietin or transferrin, for example. Alternatively, a photoactive agent may have a strong affinity for the target cell without binding to a carrier.

A receptor site may be any of the following: nucleic acids of nucleated blood cells, molecule receptor sites of nucleated blood cells, the antigenic sites on nucleated blood cells, epitopes, or other sites where photoactive agents are capable of destroying a targeted cell.

In one embodiment, thin fiber optic lines are inserted in the subject and laser light is used to photoactivate the agents. In another embodiment, a plurality of sources for supplying electromagnetic radiation energy or energy transfer is provided by one or more molecules administered to a patient. The molecules may emit stimulating radiation in the correct band of wavelength to stimulate the target structure directly or to simulate the photoactivatable agents, or the molecules may transfer energy by a resonance energy transfer or other mechanism directly to the target structure or the photoactivatable agent or indirectly by a cascade effect via other molecular interactions.

In another embodiment, the patient's own cells are removed and genetically modified to provide photonic emissions. For example, tumor or healthy cells may be removed, genetically modified to induce bioluminescence and may be reinserted at the site of the disease or condition to be treated. The modified, bioluminescent cells may be further modified to prevent further division of the cells or division of the cells only so long as a regulating agent is present.

In a further embodiment, a biocompatible emitting source, such as a fluorescing metal nanoparticle or fluorescing dye molecule, is selected that emits in the UV-A band. The UV-A emitting source is directed to the site of a disease or condition. The UV-A emitting source may be directed to the site of the disease or condition by systemically administering the UV-A emitting source. Preferably, the UV-A emitting source is concentrated in the target site, such as by physical insertion or by conjugating the UV-A emitting molecule with a specific carrier that is capable of concentrating the UV-A emitting source in a specific target structure, as is known in the art.

In one preferred embodiment, the UV-A emitting source is a gold nanoparticle comprising a cluster of 5 gold atoms, such as a water soluble quantum dot encapsulated by polyamidoamine dendrimers. The gold atom clusters may be produced through a slow reduction of gold salts (e.g. $HAuCl_4$ or $AuBr_3$) or other encapsulating amines, for example. One advantage of such a gold nanoparticle is the increased Foerster distance (i.e. $R_0$), which may be greater than 100 angstroms. The equation for determining the Foerster distance is substantially different from that for molecular fluorescence, which is limited to use at distances less than 100 angstroms. It is believed that the gold nanoparticles are governed by nanoparticle surface to dipole equations with a $1/R^4$ distance dependence rather than a $1/R^6$ distance dependence. For example, this permits cytoplasmic to nuclear energy transfer between metal nanoparticles and a photoactivatable molecule, such as a psoralen and more preferably an 8-methoxypsoralen (8-MOP) administered orally to a patient, which is known to be safe and effective at inducing an apoptosis of leukocytes.

In another embodiment, a UV- or light-emitting luciferase is selected as the emitting source for exciting a photoactivatable agent. A luciferase may be combined with ATP or another molecule, which may then be oxygenated with additional molecules to stimulate light emission at a desired wavelength. Alternatively, a phosphorescent emitting source may be used. One advantage of a phosphorescent emitting source is that the phosphorescent emitting molecules or other source may be electroactivated or photoactivated prior to insertion into a target site either by systemic administration or direct insertion into the region of the target site. Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

In another embodiment, a combined electromagnetic energy harvester molecule is designed, such as the combined light harvester disclosed in J. Am. Chem. Soc. 2005, 127, 9760-9768, the entire contents of which are hereby incorporated by reference. By combining a group of fluorescent molecules in a molecular structure, a resonance energy transfer cascade may be used to harvest a wide band of electromagnetic radiation resulting in emission of a narrow band of fluorescent energy. By pairing a combined energy harvester with a photoactivatable molecule, a further energy resonance transfer excites the photoactivatable molecule, when the photoactivatable molecule is nearby stimulated combined energy harvester molecules. Another example of a harvester molecule is disclosed in Figure 4 of "Singlet-Singlet and Triplet-Triplet Energy Transfer in Bichromophoric Cyclic Peptides," M.S. Thesis by M. O. Guler, Worcester Polytechnic Institute, May 18, 2002, which is incorporated herein by reference.

In another embodiment, a Stokes shift of an emitting source or a series of emitting sources arranged in a cascade is selected to convert a shorter wavelength energy, such as X-rays, to a longer wavelength fluorescence emission such a optical or UV-A, which is used to stimulate a photoactivatable molecule at the location of the target structure. Preferably, the photoactivatable molecule is selected to cause the predetermined change in target structure without causing substantial harm to normal, healthy cells.

In an additional embodiment, the photoactivatable agent can be a photocaged complex having an active agent contained within a photocage. The active agent is bulked up with other molecules that prevent it from binding to specific targets, thus masking its activity. When the photocage complex is photoactivated, the bulk falls off, exposing the active agent. In such a photocage complex, the photocage molecules can be photoactive (i.e. when photoactivated, they are caused to dissociate from the photocage complex, thus exposing the active agent within), or the active agent can be the photoactivatable agent (which when photoactivated causes the photocage to fall off), or both the photocage and the active agent are photoactivated, with the same or different wavelengths. For example, a toxic chemotherapeutic agent can be photocaged, which will reduce the systemic toxicity when delivered. Once the agent is concentrated in the tumor, the agent is irradiated with an activation energy. This causes the "cage" to fall off, leaving a cytotoxic agent in the tumor cell. Suitable photocages include those disclosed by Young and Deiters in "Photochemical Control of Biological Processes", *Org. Biomol. Chem.*, 5, pp. 999-1005 (2007) and "Photochemical Hammerhead Ribozyme Activation", *Bioorganic & Medicinal Chemistry Letters*, 16(10), pp. 2658-2661 (2006), the contents of which are hereby incorporated by reference.

In one preferred embodiment, the use of light for uncaging a compound or agent is used for elucidation of neuron functions and imaging, for example, two-photon glutamine uncaging (Harvey C D, et al., Nature, 450:1195-1202 (2007); Eder M, et al., Rev. Neurosci., 15:167-183 (2004)). Other signaling molecules can be released by UV light stimulation, e.g., GABA, secondary messengers (e.g., $Ca^{2+}$ and $Mg^{2+}$), carbachol, capsaicin, and ATP (Zhang F., et al., 2006). Chemical modifications of ion channels and receptors may be carried out to render them light-responsive. $Ca^{2+}$ is involved in controlling fertilization, differentiation, proliferation, apoptosis, synaptic plasticity, memory, and developing axons. In yet another preferred embodiment, $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Genetic targeting allows morphologically and electrophysipologically characterization of genetically defined cell populations. Accordingly, in an additional embodiment, a light-sensitive protein is introduced into cells or live subjects via a number of techniques including electroporation, DNA microinjection, viral delivery, liposomal transfection, creation of transgenic lines and calcium-phosphate precipitation. For example, lentiviral technology provides a convenient combination a conventional combination of stable long-term expression, ease of high-titer vector production and low immunogenicity. The light-sensitive protein may be, for example, channelrhodopsin-2 (ChR2) and chloride pump halorhodopsin (NpHR). The light protein encoding gene(s) along with a cell-specific promoter can be incorporated into the lentiviral vector or other vector providing delivery of the light-sensitive protein encoding gene into a target cell. ChR2 containing a light sensor and a cation channel, provides electrical stimulation of appropriate speed and magnitude to activate neuronal spike firing, when the cells harboring Ch2R are pulsed with light.

In one embodiment, a lanthanide chelate capable of intense luminescence is used. For example, a lanthanide chelator may be covalently joined to a coumarin or coumarin derivative or a quinolone or quinolone-derivative sensitizer. Sensitizers may be a 2- or 4-quinolone, a 2- or 4-coumarin, or derivatives or combinations of these examples. A carbostyril 124 (7-amino-4-methyl-2-quinolone), a coumarin 120 (7-amino-4-methyl-2-coumarin), a coumarin 124 (7-amino-4-(trifluoromethyl)-2-coumarin), aminoinethyltrimethylpsoralen or other similar sensitizer may be used. Chelates may be selected to form high affinity complexes with lanthanides, such as terbium or europium, through chelator groups, such as DTPA. Such chelates may be coupled to any of a wide variety of well known probes or carriers, and may be used for resonance energy transfer to a psoralen or psoralen-derivative, such as 8-MOP, or other photoactive molecules capable of binding DNA. In one alternative example, the lanthanide chelate is localized at the site of the disease using an appropriate carrier molecule, particle or polymer, and a source of electromagnetic energy is introduced by minimally invasive procedures to irradiate the target structure, after exposure to the lanthanide chelate and a photoactive molecule.

In another embodiment, a biocompatible, endogenous fluorophore emitter is selected to stimulate resonance energy transfer to a photoactivatable molecule. A biocompatible emitter with an emission maxima within the absorption range of the biocompatible, endogenous fluorophore emitter may be selected to stimulate an excited state in fluorophore emitter. One or more halogen atoms may be added to any cyclic ring structure capable of intercalation between the stacked nucleotide bases in a nucleic acid (either DNA or RNA) to confer new photoactive properties to the intercalator. Any intercalating molecule (psoralens, coumarins, or other polycyclic ring structures) may be selectively modified by halogenation or addition of non-hydrogen bonding ionic substituents to impart advantages in its reaction photochemistry and its competitive binding affinity for nucleic acids over cell membranes or charged proteins, as is known in the art.

Skin photosensitivity is a major toxicity of photosensitizers. Severe sunburn occurs if skin is exposed to direct sunlight for even a few minutes. Early murine research hinted at a vigorous and long term stimulation of immune response; however, actual clinical testing has failed to achieve the early promises of photodynamic therapies. The early photosensitizers for photodynamic therapies targeted type II responses, which created singlet oxygen when photoactivated in the presence of oxygen. The singlet oxygen caused cellular necrosis and was associated with inflammation and an immune response. Some additional photosensitizers have been developed to induce type I responses, directly damaging cellular structures.

Porfimer sodium (Photofrin; QLT Therapeutics, Vancouver, BC, Canada), is a partially purified preparation of hematoporphyrin derivative (HpD). Photofrin has been approved by the US Food and Drug Administration for the treatment of obstructing esophageal cancer, microinvasive endobronchial non-small cell lung cancer, and obstructing endobronchial non-small cell lung cancer. Photofrin is activated with 630 nm, which has a tissue penetration of approximately 2 to 5 mm. Photofrin has a relatively long duration of skin photosensitivity (approximately 4 to 6 weeks).

Tetra (m-hydroxyphenyl) chlorin (Foscan; Scotia Pharmaceuticals, Stirling, UK), is a synthetic chlorine compound that is activated by 652 nm light. Clinical studies have demonstrated a tissue effect of up to 10 mm with Foscan and 652 nm light. Foscan is more selectively a photosensitizer in tumors than normal tissues, and requires a comparatively short light activation time. A recommended dose of 0.1 mg/kg is comparatively low and comparatively low doses of light may be used. Nevertheless, duration of skin photosensitivity is reasonable (approximately 2 weeks). However, Foscan induces a comparatively high yield of singlet oxygen, which may be the primary mechanism of DNA damage for this molecule.

Motexafin lutetium (Lutetium texaphryin) is activated by light in the near infrared region (732 nm). Absorption at this wavelength has the advantage of potentially deeper penetration into tissues, compared with the amount of light used to activate other photosensitizers (FIGS. 2A and 2B). Lutetium texaphryin also has one of the greatest reported selectivities for tumors compared to selectivities of normal tissues. Young S W, et al.: Lutetium texaphryin (PCI-0123) a near-infrared, water-soluble photosensitizer. Photochem Photobiol 1996, 63:892-897. In addition, its clinical use is associated with a shorter duration of skin photosensitivity (24 to 48 hours). Lutetium texaphryin has been evaluated for metastatic skin cancers. It is currently under investigation for treatment of recurrent breast cancer and for locally recurrent prostate cancer. The high selectivity for tumors promises improved results in clinical trials.

In general, the approach may be used with any source for the excitation of higher electronic energy states, such as electrical, chemical and/or radiation, individually or combined into a system for activating an activatable molecule. The process may be a photopheresis process or may be similar to photopheresis. While photopheresis is generally thought to be limited to photonic excitation, such as by UV-light, other forms of radiation may be used as a part of a system to activate an activatable molecule. Radiation includes ionizing radiation which is high energy radiation, such as an X-ray or a gamma ray, which interacts to produce ion pairs in matter. Radiation also includes high linear energy transfer irradiation, low linear energy transfer irradiation, alpha rays, beta rays, neutron beams, accelerated electron beams, and ultraviolet rays. Radiation also includes proton, photon and fission-spectrum neutrons. Higher energy ionizing radiation may be combined with chemical processes to produce energy states favorable for resonance energy transfer, for example. Other combinations and variations of these sources of excitation energy may be combined as is known in the art, in order to stimulate the activation of an activatable molecule, such as 8-MOP. In one example, ionizing radiation is directed at a solid tumor and stimulates, directly or indirectly, activation of 8-MOP, as well as directly damaging the DNA of malignant tumor cells. In this example, either the effect of ionizing radiation or the photopheresis-like activation of 8-MOP may be thought of as an adjuvant therapy to the other.

Work in the area of photodynamic therapy has shown that the amount of singlet oxygen required to cause cell lysis, and thus cell death, is $0.32 \times 10^{-3}$ mol/liter or more, or $10^9$ singlet oxygen molecules/cell or more. However, in the present invention, it is most preferable to avoid production of an amount of singlet oxygen that would cause cell lysis, due to its indiscriminate nature of attack, lysing both target cells and healthy cells. Accordingly, it is most preferred in the present invention that the level of singlet oxygen production caused by the initiation energy used or activatable pharmaceutical agent upon activation be less than level needed to cause cell lysis.

In yet another embodiment, the activatable pharmaceutical agent, preferably a photoactive agent, is directed to a receptor site by a carrier having a strong affinity for the receptor site. The carrier may be a polypeptide and may form a covalent bond with a photo active agent, for example. The polypeptide may be an insulin, interleukin, thymopoietin or transferrin, for example. Alternatively, a photoactive pharmaceutical agent may have a strong affinity for the target cell without a binding to a carrier.

For example, a treatment may be applied that acts to slow or pause mitosis. Such a treatment is capable of slowing the division of rapidly dividing healthy cells or stem cells without pausing mitosis of cancerous cells. Thus, the difference in growth rate between the non-target cells and target cells are further differentiated to enhance the effectiveness of the methods of the present invention.

In a further embodiment, methods in accordance with the present invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

In another aspect, the present invention also provides methods for producing an autovaccine, comprising:

(1) providing a population of target cells;

(2) pacing in a vicinity of a target structure in the target cells a nanoparticle, the nanoparticle is configured, upon exposure to a first wavelength $\lambda_1$, to generate a second wavelength $\lambda_2$ of radiation having a higher energy than the first wavelength $\lambda_1$, wherein
  the nanoparticle comprises a metallic structure deposited in relation to the nanoparticle,
  a radial dimension of the metallic structure is set to a value so that a surface plasmon resonance in the metallic structure resonates at a frequency which provides spectral overlap with at least one the first wavelength $\lambda_1$ and the second wavelength $\lambda_2$, and
  the nanoparticle is configured to emit energy in the vicinity of or into the target structure upon interaction with an initiation energy having an energy in the range of $\lambda_1$;

(3) treating the target cells ex vivo in an environment separate and isolated from the subject with a psoralen or a derivative thereof;

(4) applying the initiation energy from an initiation energy source including said first wavelength $\lambda_1$ to the target cells ex vivo, wherein the emitted energy including said second wavelength $\lambda_2$ directly or indirectly contacts the target structure and induces a predetermined cellular change in the target cells, and, optionally, applying at least one energy modulation agent; and (5) returning the thus changed cells back to the subject to induce in the subject an autovaccine effect against the target cell, wherein the changed cells act as an autovaccine.

In a different embodiment, the predetermined change enhances the expression of, promotes the growth of, or increases the quantity of said target structure; enhances, inhibits or stabilizes the usual biological activity of said target structure compared to a similar untreated target structure, and/or alters the immunological or chemical properties of said target structure. In a different embodiment, said target structure is a compound that is modified by said predetermined change to be more or less antigenic or immunogenic.

The activatable pharmaceutical agent and derivatives thereof as well as the energy modulation agent, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

One preferred pharmaceutical composition for modifying a target structure which mediates or is associated with a biological activity, comprises:

a nanoparticle, wherein the nanoparticle is configured, upon exposure to a first wavelength $\lambda 1$, to generate a second wavelength $\lambda 2$ of radiation having a higher energy than the first wavelength $\lambda 1$,
  the nanoparticle comprises a metallic structure deposited in relation to the nanoparticle,
  a radial dimension of the metallic structure is set to a value so that a surface plasmon resonance in the metallic structure resonates at a frequency which provides spectral overlap with at least one of the first wavelength $\lambda 1$ and the second wavelength $\lambda 2$, and
  the nanoparticle is configured to emit light in the vicinity of or into the target structure upon interaction with an initiation energy having an energy in the range of $\lambda 1$;
wherein the energy modulation agent, if present,
  (i) is capable of converting the initiation energy to an energy that causes the nanoparticle to generate an energy in the range of the second wavelength $\lambda 2$ which is capable, directly or indirectly, of inducing a predetermined change in the target structure with or without the activatable pharmaceutical agent; and/or
  (ii) said nanoparticle upconverts the initiation energy into an energy in the range of said second wavelength $\lambda 2$ that is converted by the energy modulation agent, and an energy reemitted by the energy modulation agent is capable of inducing, directly or indirectly, the predetermined change in the target structure; and
a pharmaceutically acceptable carrier.

In one embodiment, the pharmaceutical composition can also comprise an energy source, for example, a chemical energy source which can be a member selected from the group consisting of phosphorescent compounds, chemiluminescent compounds, bioluminescent compounds and light emitting enzymes. In another embodiment, the pharmaceutical composition comprises at least one energy modulation agent and/or at least one activatable pharmaceutical agent.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Methods of administering agents according to the present invention are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection.

Such transfected cells may be inserted or otherwise targeted at the site where diseased cells are located. In this embodiment, the initiation energy source may be a biochemical source as such ATP, in which case the initiation energy source is considered to be directly implanted in the transfected cell. Alternatively, a conventional micro-emitter device capable of acting as an initiation energy source may be transplanted at the site of the diseased cells.

It will also be understood that the order of administering the different agents is not particularly limited. Thus in some embodiments the activatable pharmaceutical agent may be administered before the energy modulation agent, while in other embodiments the energy modulation agent may be administered prior to the activatable pharmaceutical agent. It will be appreciated that different combinations of ordering may be advantageously employed depending on factors such as the absorption rate of the agents, the localization and molecular trafficking properties of the agents, and other pharmacokinetics or pharmacodynamics considerations.

A further embodiment is the use of the present invention for the treatment of skin cancer. In this example, a photo-activatable agent, preferably psoralen, is given to the patient, and is delivered to the skin lesion via the blood supply. An activation source having limited penetration ability (such as UV or IR) is shined directly on the skin—in the case of psoralen, it would be a UV light, or an IR source. With the use of an IR source, the irradiation would penetrate deeper and generate UV via two single photon events with psoralen.

In a further embodiment, methods according to this aspect of the present invention further include a step of separating the components of the treated cells into fractions and testing each fraction for autovaccine effect in a host. The components thus isolated and identified may then serve as an effective autovaccine to stimulate the host's immune system to suppress growth of the targeted cells.

In different aspect of the invention, a kit for modifying a target structure which mediates or is associated with a biological activity, comprising:

a nanoparticle, wherein the nanoparticle is configured, upon exposure to a first wavelength $\lambda_1$, to generate a second wavelength $\lambda_2$ of radiation having a higher energy than the first wavelength $\lambda_1$,
the nanoparticle comprises a metallic structure deposited in relation to the nanoparticle,
a radial dimension of the metallic structure is set to a value so that a surface plasmon resonance in the metallic structure resonates at a frequency which provides spectral overlap with at least one of the first wavelength $\lambda_1$ and the second wavelength $\lambda_2$, and
the nanoparticle is configured to emit light in the vicinity of or into the target upon interaction with an initiation energy having an energy in the range of $\lambda_1$;
optionally, an energy modulation agent, wherein the energy modulation agent, if present, (i) converts the initiation energy to an energy in the range of the first wavelength $\lambda_1$, to generate the second wavelength $\lambda_2$ of radiation by the nanoparticle capable of causing, either directly or indirectly, a predetermined change in the target structure with or without the activatable pharmaceutical agent; and/or
(ii) said nanoparticle upconverts the initiation energy to an energy in the range of said second wavelength $\lambda 2$ that is converted by the energy modulation agent, and an energy reemitted by the energy modulation agent causes, directly or indirectly, the predetermined change in the target structure with or without an activatable pharmaceutical agent; and
one or more containers suitable for storing the agents in stable forms.

In another embodiment, the kit can further comprise instructions for administering the nanoparticle. In another embodiment, the kit comprises at least one energy modulation agent and/or the activatable pharmaceutical agent to a subject.

In one embodiment, a system for modifying a target structure which mediates or is associated with a biological activity, comprises:

a nanoparticle, wherein the nanoparticle is configured, upon exposure to a first wavelength $\lambda 1$, to generate a second wavelength $\lambda 2$ of radiation having a higher energy than the first wavelength $\lambda 1$,
a metallic structure deposited in relation to the nanoparticle,
wherein
a radial dimension of the metallic structure is set to a value so that a surface plasmon resonance in the metallic structure resonates at a frequency which provides spectral overlap with at least one of the first wavelength $\lambda 1$ and the second wavelength $\lambda 2$, and
the nanoparticle is configured to emit energy in the vicinity of or into the target structure upon interaction with an initiation energy having an energy in the range of $\lambda 1$;
a mechanism for placing the nanoparticle in the subject; and
an initiation energy source to provide the initiation energy capable to be upconverted by the nanoparticle, wherein the emitted energy is capable of inducing a predetermined change in the target structure in situ,
wherein said predetermined change is capable of modifying the target structure and modulating the biological activity of the target structure.

In another preferred embodiment, the system further comprises at least one agent selected from the group consisting of at least one energy modulation agent, at least one activatable pharmaceutical agent and at least one plasmonics-active agent.

In yet another embodiment, when at least one energy modulation agent is present in the system, (i) the energy modulation agent is capable of converting the initiation energy to an energy that causes the nanoparticle to generate an energy in the range of the second wavelength $\lambda 2$ which is capable, directly or indirectly, of inducing a predetermined change in the target structure with or without the activatable pharmaceutical agent; and/or
(ii) said nanoparticle is capable of upconverting the initiation energy into an energy in the range of said second wavelength $\lambda 2$ that is converted by the energy modulation agent, and an energy reemitted by the energy modulation agent is capable of inducing, directly or indirectly, the predetermined change in the target structure.

The reagents and chemicals useful for the present invention may be packaged in kits to facilitate application of the present invention. In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change, at least one energy modulation agent capable of activating the at least one activatable agent when energized, at least one plasmonics agent and containers suitable for storing the agents in stable form, and preferably further comprising instructions for administering the at least one activatable pharmaceutical agent, at least one plasmonics agent and at least one energy modulation agent to a subject, and for applying an initiation energy from an initiation energy source to activate the activatable pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

The activatable pharmaceutical agent and derivatives thereof as well as the energy modulation agent and plasmonics compounds and structures, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

An advantage of the methods of the present invention is that by specifically targeting cells affected by a cell proliferation disorder, such as rapidly dividing cells, and triggering a cellular change, such as apoptosis, in these cells in situ, the immune system of the host may be stimulated to have an immune response against the diseased cells. Once the host's own immune system is stimulated to have such a response, other diseased cells that are not treated by the activatable pharmaceutical agent may be recognized and be destroyed by the host's own immune system. Such autovaccine effects may be obtained, for example, in treatments using psoralen and UV-A.

The present invention methods can be used alone or in combination with other therapies for treatment of cell proliferation disorders. Additionally, the present invention methods can be used, if desired, in conjunction with recent advances in chronomedicine, such as that detailed in Giacchetti et al, *Journal of Clinical Oncology*, Vol 24, No 22 (August 1), 2006: pp. 3562-3569. In chronomedicine it has been found that cells suffering from certain types of disorders, such as cancer, respond better at certain times of the day than at others. Thus, chronomedicine could be used in conjunction with the present methods in order to augment the effect of the treatments of the present invention.

In preferred embodiments, the initiation energy source may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.)

In other embodiments, endoscopic or laproscopic devices equipped with appropriate initiation energy emitter may be used as the initiation energy source. In such systems, the initiation energy may be navigated and positioned at the pre-selected coordinate to deliver the desired amount of initiation energy to the site.

Plasmonics Enhanced Photospectral Therapy (PEPST)

In the PEPST embodiment of the present invention, the present invention is significantly different from the phototherapy technique often referred to Photo-thermal Therapy (PTT). To illustrate the difference between the present invention PEPST, a form of photospectral therapy (PST) and the PTT technique, the photochemical processes involved in PST and PPT is discussed below.

When drug molecules absorb excitation light, electrons undergo transitions from the ground state to an excited electronic state. The electronic excitation energy subsequently relaxes via radiative emission (luminescence) and radiationless decay channels. When a molecule absorbs excitation energy, it is elevated from $S_0$ to some vibrational level of one of the excited singlet states, $S_n$, in the manifold $S_1, \ldots, S_n$. In condensed media (tissue), the molecules in the $S_n$ state deactivate rapidly, within $10^{-13}$ to $10^{-11}$s via vibrational relaxation (VR) processes, ensuring that they are in the lowest vibrational levels of $S_n$ possible. Since the VR process is faster than electronic transitions, any excess vibrational energy is rapidly lost as the molecules are deactivated to lower vibronic levels of the corresponding excited electronic state. This excess VR energy is released as thermal energy to the surrounding medium. From the state, the molecule deactivates rapidly to the isoenergetic vibrational level of a lower electronic state such as $S_{n-1}$ via an internal conversion (IC) process. IC processes are transitions between states of the same multiplicity. The molecule subsequently deactivates to the lowest vibronic levels of $S_{n-1}$ via a VR process. By a succession of IC processes immediately followed by VR processes, the molecule deactivates rapidly to the ground state $S_1$. This process results in excess VR and IC energy released as thermal energy to the surrounding medium leading to the overheating of the local environment surrounding the light absorbing drug molecules. The heat produced results in local cell or tissue destruction. The light absorbing species include natural chromophores in tissue or exogenous dye compounds such as indocyanine green, naphthalocyanines, and porphyrins coordinated with transition metals and metallic nanoparticles and nanoshells of metals. Natural chromophores, however, suffer from very low absorption. The choice of the exogenous photothermal agents is made on the basis of their strong absorption cross sections and highly efficient light-to-heat conversion. This feature greatly minimizes the amount of laser energy needed to induce local damage of the diseased cells, making the therapy method less invasive. A problem associated with the use of dye molecules is their photobleaching under laser irradiation. Therefore, nanoparticles such as gold nanoparticles and nanoshells have recently been used. The promising role of nanoshells in photothermal therapy of tumors has been demonstrated [Hirsch, L. R., Stafford, R. J., Bankson, J. A., Sershen, S. R., Rivera, B., Price, R. E., Hazle, J. D., Halas, N. J., and West, J. L., *Nanoshell-mediated near-infrared thermal therapy of tumors under magnetic resonance guidance*. PNAS, 2003. 100(23): p. 13549-13554]. The use of plasmonics-enhanced photothermal properties of metal nanoparticles for photothermal therapy has also been reviewed (Xiaohua Huang & Prashant K. Jain & Ivan H.

El-Sayed & Mostafa A. El-Sayed, "*Plasmonic photothermal therapy (PPTT) using gold nanoparticles,*" *Lasers in Medical Science*, August 2007)

The PST method of the present invention, however, is based on the radiative processes (fluorescence, phosphorescence, luminescence, Raman, etc) whereas the PTT method is based on the radiationless processes (IC, VR and heat conversion) in molecules.

Non-Invasive Photonic Therapy

Current techniques such as photopheresis require removal and reinfusion of blood from patients, the proposed photonics based modalities can excite non-invasively and directly from outside the body. FIG. 2 illustrates the concept of non-invasive photonic therapy. The EEC can serve as an Energy Down-Converting (EDC) or Energy Up-Converting (EUC) material.

Photonics treatment modalities include both optical and non-optical technologies that deal with electromagnetic radiation, which is the energy propagated through space by electric and magnetic fields. The electromagnetic spectrum is the extent of that energy, ranging from gamma rays and X rays throughout ultraviolet, visible, infrared, microwave and radio frequency energy.

Spectral Range of Light Used for PEPST

Theoretically the plasmonics enhanced effect can occur throughout the electromagnetic region provided the suitable nanostructures, nanoscale dimensions, metal types are used. Therefore, the PEPST concept is valid for the entire electromagnetic spectrum, i.e, energy, ranging from gamma rays and X rays throughout ultraviolet, visible, infrared, microwave and radio frequency energy. However, for practical reasons, visible and NIR light are used for silver and gold nanoparticles, since the plasmon resonances for silver and gold occurs in the visible and NIR region, respectively. Especially for gold nanoparticles, the NIR region is very appropriate for non-invasive therapy.

Photon Excitation in the Therapeutic Window of Tissue.

There are several methods using light to excite photoactivate compounds non-invasively. We can use light having wavelengths within the so-called "therapeutic window" (700-1300 nm). The ability of light to penetrate tissues depends on absorption. Within the spectral range known as the therapeutic window (or diagnostic window), most tissues are sufficiently weak absorbers to permit significant penetration of light. This window extends from 600 to 1300 nm, from the orange/red region of the visible spectrum into the NIR. At the short-wavelength end, the window is bound by the absorption of hemoglobin, in both its oxygenated and deoxygenated forms. The absorption of oxygenated hemoglobin increases approximately two orders of magnitude as the wavelength shortens in the region around 600 nm. At shorter wavelengths many more absorbing biomolecules become important, including DNA and the amino acids tryptophan and tyrosine. At the infrared (IR) end of the window, penetration is limited by the absorption properties of water. Within the therapeutic window, scattering is dominant over absorption, and so the propagating light becomes diffuse, although not necessarily entering into the diffusion limit. FIG. 3 shows a diagram of the therapeutic window of tissue. The following section discusses the use of one-photon and multi-photon techniques for therapy.

Two methods that can be used for excitation: one-photon or multi-photon excitation (MPE).

Multi-Photon Excitation for Energy Upconversion (UC)

One energy upconversion (UC) technique involves multi-photon excitation (MPE) discussed in a previous report. If the two-photon technique is used, one can excite the PA molecules with light at 700-1000 nm, which can penetrate deep inside tissue, in order to excite molecules that absorb in the 350-500 nm spectral region. This approach can excite the psoralen compounds, which absorb in the 290-350 nm spectral region and emit in the visible. With one-photon method, the photo-activator (PA) drug molecules can directly absorb excitation light at 600-1300 nm. In this case we can design a psoralen-related system (e.g., psoralesn having additional aromatic rings) or use other PA systems: photodynamic therapy drugs, ALA, etc. In this MPE method the EEC material or the PA drug is designed to absorb the multi-photon excitation energy and emit a photon with energy higher than the original one-photon excitation.

Energy Upconversion Using Rare-Earth Doped Compound and Similar Materials

The process of energy upconversion using rare-earth doped materials have been extensively studied for photonics applications, its mostly known area of research being for UPC solid state lasers. See some refs on UC processes: (J. F. Suyver *, A. Aebischer, D. Biner, P. Gerner, J. Grimm, S. Heer, K. W. Kra¨mer, C. Reinhard, H. U. Gu¨del *Novel materials doped with trivalent lanthanides and transition metal ions showing near-infrared to visible photon upconversion*, Optical Materials 27 (2005) 1111-1130); R. Paschotta, N. Moore, W. A. Clarkson, A. C. Trooper, D. C. Hanna, G. Maze, IEEE J. Sel. Top. Quantum Electron. 3, 1997.1100; C. C. Ye, M. Hempstead, D. W. Hewak, D. N. Payne, IEEE Photon. Technol. Lett. 9_1997.1104; D. M. Baney, G. Ramkin, K. W. Chang, Opt. Lett. 21_1996.1372; D. S. Funk, J. G. Eden, Proc. SPIE 2841 1996.42; B. R. Reddy and P. Venkateswarlu, *Infrared to visible energy upconversion in $Er^{3+}$-doped oxide glass*, Appl. Phys. Lett. 64, 1327 (1994); G. S. Maciel*, A. Biswas and P. N. Prasad, *Infrared-to-visible $Eu^{3+}$ energy upconversion due to cooperative energy transfer from an $Yb^{3+}$ ion pair in a sol-gel processed multi-component silica glass*, Optics Communications, Volume 178, Issues 1-3, 1 May 2000, Pages 65-69; and Kapoor, *Highly efficient infrared-to-visible energy upconversion in Er 3+:Y 2 O 3*, Optics letters [0146-9592] yr: 2000 vol: 25 pg: 338).

This method requires the use of a material that is designed to absorb the multi-photon excitation energy and emit a photon with energy higher than the original excitation photon. In general the energy up-converting process involve an absorber ion and an emitter ion in a crystal. A multi-photon (e.g., 2-photon) excitation energy (e.g., NIR) excites the absorber ion, which transfers this energy radiationlessly to the emitter ion that emits a photon that has an energy higher than the excitation photon energy. Note there is a slight difference with the MPE upconverting method which does not necessarily require a materials (designed to absorb the multi-photon excitation energy). Three-photon upconversion processes involving energy transfer from Yb3+ to Tb3+ have been reported to produce efficient UV emission in the glass ceramic containing Tb3+/Yb3+:CaF2 nanocrystals [L. Huang, T. Yamashita, R. Jose, Y. Arai, T. Suzuki, and Y. Ohishi, Appl. Phys. Lett. 90, 131116_2007_]. Chen et al reported a Tm3+/Yb3+:β-YF3 nanocrystals embedded glass ceramic which yields intense UV upconversion luminescence through the four- or five-photon processes [—Daqin Chen, Yuansheng Wang, a_Yunlong Yu, and Ping Huang, *Intense ultraviolet upconversion luminescence from Tm3+/Yb3+:β-YF3nanocrystals embedded glass ceramic*, Appl. Phys. Lett, 91, 051920, 2007]. Chen et al reported ultraviolet upconversion fluorescence in rare-earth-ion-doped $Y_2O_3$ induced by infrared diode laser excitation [G. Y. Chen, G.

Somesfalean, Z. G. Zhang, Q. Sun, and F. P. Wang, *Optics Letters*, Vol. 32, Issue 1, pp. 87-89]

Concept for Plasmonics-Enhanced Upconversion (PE-UC)

Basic Principle of Plasmonics and Enhanced Electromagnetic Fields

Where as the photothermal properties of plasmonics metal nanoparticles have been used, to our knowledge the spectroscopic absorption and emission of plasmonics-active nanoparticles in phototherapy have not been reported.

To differentiate our proposed treatment modality from photothermal therapy techniques (some of which also use gold nanoparticles for localized heating of tumors), we refer our technique to as "plasmonics-enhanced energy upconversion (PE-UC). In PEPST, the plasmonics-enhanced spectroscopic properties (spectral absorption, emission, scattering) are the major factors involved in the treatment.

The PEP ST principle is based on the enhancement mechanisms of the electromagnetic field effect. There are two main sources of electromagnetic enhancement: (1) first, the laser electromagnetic field is enhanced due to the addition of a field caused by the polarization of the metal particle; (2) in addition to the enhancement of the excitation laser field, there is also another enhancement due to the molecule radiating an amplified emission (luminescence, Raman, etc.) field, which further polarizes the metal particle, thereby acting as an antenna to further amplify the Raman/Luminescence signal.

Electromagnetic enhancements are divided into two main classes: a) enhancements that occur only in the presence of a radiation field, and b) enhancements that occur even without a radiation field. The first class of enhancements is further divided into several processes. Plasma resonances on the substrate surfaces, also called surface plasmons, provide a major contribution to electromagnetic enhancement. An effective type of plasmonics-active substrate consists of nanostructured metal particles, protrusions, or rough surfaces of metallic materials. Incident light irradiating these surfaces excites conduction electrons in the metal, and induces excitation of surface plasmons leading to Raman/Luminescence enhancement. At the plasmon frequency, the metal nanoparticles (or nanostructured roughness) become polarized, resulting in large field-induced polarizations and thus large local fields on the surface. These local fields increase the Luminescence/Raman emission intensity, which is proportional to the square of the applied field at the molecule. As a result, the effective electromagnetic field experienced by the analyte molecule on theses surfaces is much larger than the actual applied field. This field decreases as $1/r^3$ away from the surface. Therefore, in the electromagnetic models, the luminescence/Raman-active analyte molecule is not required to be in contact with the metallic surface but can be located anywhere within the range of the enhanced local field, which can polarize this molecule. The dipole oscillating at the wavelength $\lambda$, of Raman or luminescence can, in turn, polarize the metallic nanostructures and, if $\lambda$ is in resonance with the localized surface plasmons, the nanostructures can enhance the observed emission light (Raman or luminescence). There are two main sources of electromagnetic enhancement: (1) first, the laser electromagnetic field is enhanced due to the addition of a field caused by the polarization of the metal particle; (2) in addition to the enhancement of the excitation laser field, there is also another enhancement due to the molecule radiating an amplified Raman/Luminescence field, which further polarizes the metal particle, thereby acting as an antenna to further amplify the Raman/Luminescence signal. Plasmonics-active metal nanoparticles also exhibit strongly enhanced visible and near-infrared light absorption, several orders of magnitude more intense compared to conventional laser phototherapy agents. The use of plasmonic nanoparticles as highly enhanced photoabsorbing agents has thus introduced a much more selective and efficient phototherapy strategy. The tunability of the spectral properties of the metal nanoparticles and the biotargeting abilities of the plasmonic nanostructures make the PEPST method promising.

Figure 4A:
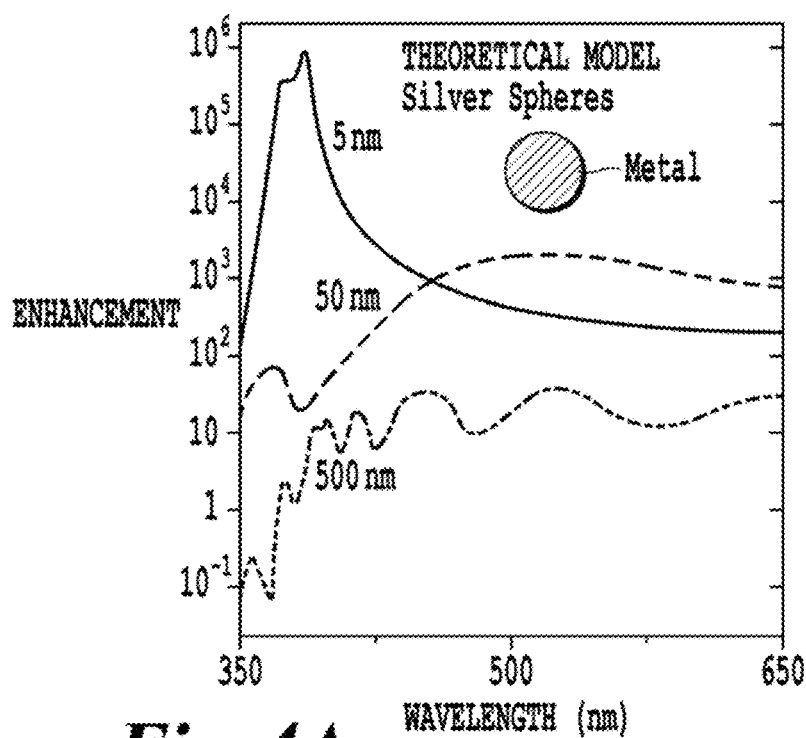
FIGS. 4A and 4B are graphical representations of plasmonic nanostructures and their theoretical electromagnetic enhancement at different excitation wavelengths.
Figure 4B:
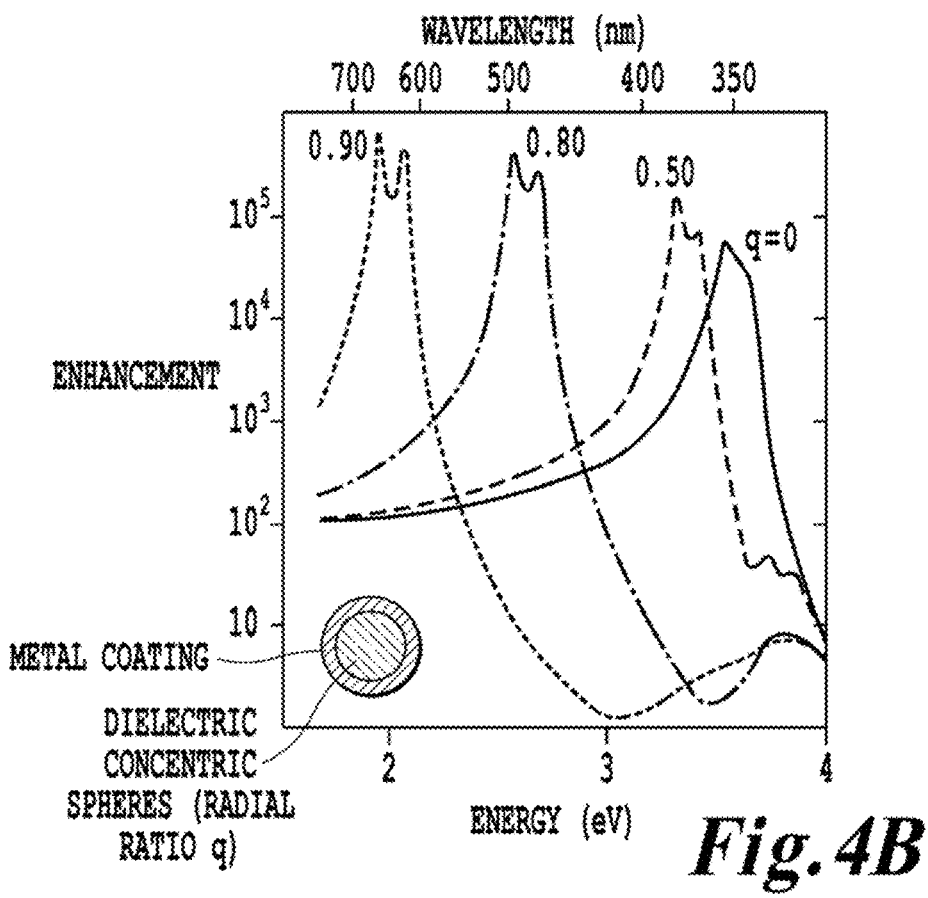

The novel PEPST concept is based on several important mechanisms:

Increased absorption of the excitation light by the plasmonic metal nanoparticles, resulting in enhanced photoactivation of drug molecules Increased absorption of the excitation light by the plasmonic metal nanoparticles that can serve as more efficient EEC systems, yielding more light for increase excitation PA molecules Increased absorption of the excitation light by the photoactive drug system adsorbed on or near the plasmonic metal nanoparticles Increased light absorption of the EEC molecules adsorbed on or near the metal nanoparticles Amplified emission from the EEC molecules adsorbed on or near the metal nanoparticles Increased absorption of emission light emitted by the EEC by the PA molecule One of several phenomena that can enhance the efficiency of light emitted (Raman or luminescence). from molecules adsorbed or near a metal nanostructures Raman scatter is the SERS effect. In 1984, the PI's laboratory first reported the general applicability of SERS as an analytical technique, and the possibility of SERS measurement for a variety of chemicals including several homocyclic and heterocyclic polyaromatic compounds [T. Vo-Dinh, M. Y. K. Hiromolo, G. M. Begun and R. L. Moody, "*Surface-enhanced Raman spectroscopy for trace organic analysis,*" Anal. Chem., vol. 56, 1667, 1984]. Extensive research has been devoted to understanding and modeling the Raman enhancement in SERS since the mid 1980's. FIG. 4, for example, shows the early work by Kerker modeling electromagnetic field enhancements for spherical silver nanoparticles and metallic nanoshells around dielectric cores as far back as 1984 [M. M. Kerker, *Acc. Chem. Res.*, 17, 370 (1984)]. This figure shows the result of theoretical calculations of electromagnetic enhancements for isolated spherical nanospheres and nanoshells at different excitation wavelengths. The intensity of the normally weak Raman scattering process is increased by factors as large as $10^{13}$ or $10^{15}$ for compounds adsorbed onto a SERS substrate, allowing for single-molecule detection. As a result of the electromagnetic field enhancements produced near nanostructured metal surfaces, nanoparticles have found increased use as fluorescence and Raman nanoprobes.

The theoretical models indicate that it is possible to tune the size of the nanoparticles and the nanoshells to the excitation wavelength. Experimental evidence suggests that the origin of the $10^6$- to $10^{15}$-fold Raman enhancement primarily arises from two mechanisms: a) an electromagnetic "lightning rod" effect occurring near metal surface structures associated with large local fields caused by electromagnetic resonances, often referred to as "surface plasmons"; and b) a chemical effect associated with direct energy transfer between the molecule and the metal surface.

According to classical electromagnetic theory, electromagnetic fields can be locally amplified when light is incident on metal nanostructures. These field enhancements can be quite large (typically $10^6$- to $10^7$-fold, but up to $10^{15}$-fold enhancement at "hot spots"). When a nanostructured metallic surface is irradiated by an electromagnetic field (e.g., a laser beam), electrons within the conduction band begin to oscillate at a frequency equal to that of the incident light. These oscillating electrons, called "surface plasmons," produce a secondary electric field which adds to the incident field. If these oscillating electrons are spatially confined, as is the case for isolated metallic nanospheres or roughened metallic surfaces (nanostructures), there is a characteristic frequency (the plasmon frequency) at which there is a resonant response of the collective oscillations to the incident field. This condition yields intense localized field enhancements that can interact with molecules on or near the metal surface. In an effect analogous to a "lightning rod," secondary fields are typically most concentrated at points of high curvature on the roughened metal surface.

Among various materials, luminescent nanoparticles have attracted increasing technological and industrial interest. In the context of the present invention, nanoparticle refers to a particle having a size less than one micron. While the description of the invention describes specific examples using nanoparticles, the present invention in many embodiments is not limited to particles having a size less than one micron. However, in many of the embodiments, the size range of having a size less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

U.S. Pat. No. 4,705,952 (the contents of which are hereby incorporated herein by reference) describes an infrared-triggered phosphor that stored energy in the form of visible light of a first wavelength and released energy in the form of visible light of a second wavelength when triggered by infrared light. In some cases, U.S. Pat. No. 4,705,952 describes that "the upconversion continues for as long as several days before a new short recharge is required." The phosphors in U.S. Pat. No. 4,705,952 were compositions of alkaline earth metal sulfides, rare earth dopants, and fusible salts. The phosphors in U.S. Pat. No. 4,705,952 were more specifically phosphors made from strontium sulfide, barium sulfide and mixtures thereof; including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention.

Figure 5:
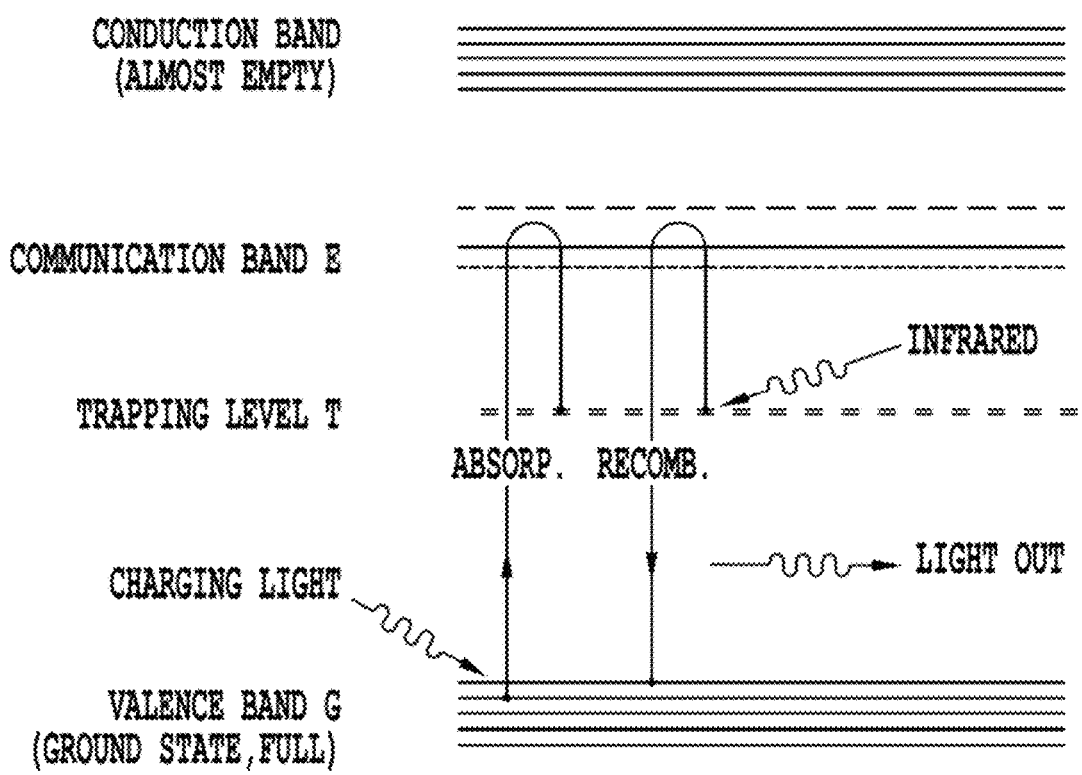
FIG. 5 is an energy diagram of an infrared phosphor system.

The energy relations present in the upconverter in U.S. Pat. No. 4,705,952 are shown in the energy diagram of FIG. 1, where energy states E and T are introduced by two selected impurities. Excitation of these states by absorption of light having a minimum energy of E minus G will cause electrons to be raised to the band at energy state E. When charging illumination ceases, many of the excited electrons will fall to energy state T and remain trapped there. The trapping phenomenon is illustrated at the left of FIG. 1. Later exposure to triggering illumination of infrared light can supply E minus T energies, permitting the infrared-triggered phosphor in excited state T to transition to level E, as shown at the right of FIG. 5. A photon is emitted during this transition process. The resulting light emission is characterized by a wavelength associated with E minus G.

If the depth of the trap is several times higher than the thermal energy, more than 99% of the electrons are in the electron-hole trap. If the depth of the traps is about 1 eV, then in the dark, most of the traps are filled, band E is almost empty and electron hole recombination is negligible. In some cases, U.S. Pat. No. 4,705,952 describes that "the storage times become extremely long, on the order of years." The material is thus adapted to receive infrared photons and to emit higher energy photons in a close to 1:1 relation. With storage times this long, these infrared-triggered phosphors can be used in various embodiments of the present invention as a viable mechanism for both medical and non-medical applications where commercial IR lasers are used to activate phosphorescence in a medium, thereby internally in a medium or in a patient generating visible or ultraviolet light.

Considerable effort has gone into the synthesis of luminescent nanoparticles, and numerous investigations of the optical properties have been performed. The synthesis of oxide nanoparticles such as those that are based on the lanthanides have been achieved by a number of processes including solid-gel (sol-gel) techniques, gas phase condensation or colloidal chemical methods. While efforts to make concentrated colloidal solutions of highly uniform size luminescent nanoparticles have met with some technical difficulties, synthesis of useful amounts of some 5 nanometer sized lanthanide doped oxides have been achieved as shown in a paper by Bazzi et al entitled *Synthesis and luminescent properties of sub 5-nm lanthanide oxide particles*, in the Journal of Luminescence 102 (2003) pages 445-450, the entire contents of which are incorporated herein by reference. Materials such as these and the other materials discussed below are useful materials for upconversion although the prior art to date has not concentrated on particular application of these materials for materials, chemical, medical, pharmaceutical, or industrial processing. Indeed, the work by Bazzi et al concentrated on understanding the properties on lanthanide oxide nanonparticles with an emphasis on the microstructural properties and optical emission properties (i.e. concentrated on the fluorescence and down conversion properties of these materials). Nevertheless, the materials described by Bazzi et al are useful in various embodiments of the invention.

The present inventors have realized that such upconversion materials can be used in various materials, chemical, medical, pharmaceutical, or industrial processing. In one example of others to be described below, a nanoparticle of a lanthanide doped oxide can be excited with near infrared laser light such as 980 nm and 808 nm to produce both ultraviolet, visible, and near infrared light depending on the dopant trivalent rare earth ion(s) chosen, their concentration, and the host lattice. The ultraviolet, visible, and/or near infrared light can then be used to drive photoactivatable reactions in the host medium containing the lanthanide doped oxide.

Other work reported by Suyver et al in *Upconversion spectroscopy and properties of $NaYF_4$ doped with $Er^{3+}$, $Tm^{3+}$ and or $Yb^{3+}$*, in Journal of Luminescence 117 (2006) pages 1-12, the entire contents of which are incorporated herein by reference, recognizes in the $NaYF_4$ material system upconversion properties. Yet, there is no discussion as to the quality or quantity of upconverted light to even suggest that the amount produced could be useful for various materials, chemical, medical, pharmaceutical, or industrial processing. The materials described by Suyver et al are useful in various embodiments of the invention.

Reference will now be made in detail to the present preferred embodiment of the invention, an example of which is illustrated in the accompanying drawings, in which like reference characters refer to corresponding elements.

Figure 6:
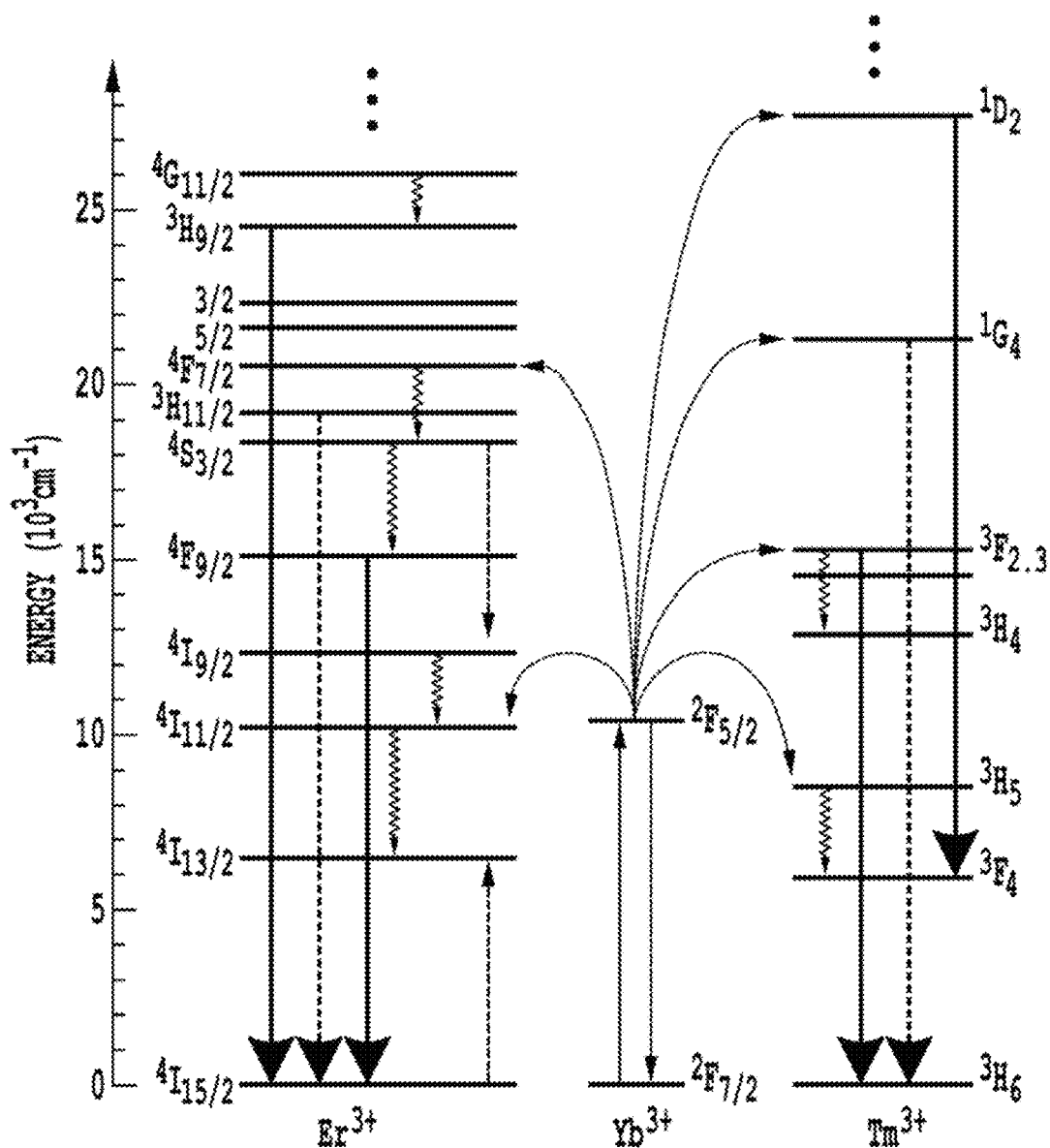
FIG. 6 is a schematic energy level diagram showing upconversion excitation and visible emissions schemes for $Er^{3+}$, $Tm^{3+}$ and or $Yb^{3+}$ ions.

FIG. 6 is a schematic reproduced from Suyver et al showing a schematic energy level diagram of upconversion excitation and visible emissions schemes for $Er^{3+}$, $Tm^{3+}$ and or $Yb^{3+}$ ions. Full, dotted, dashed, and curly arrows indicate respectively radiative, non-radiative energy transfer, cross relaxation and other relaxation processes.

The lanthanide doped oxides differ from more traditional multi-photon up conversion processes where the absorption of, for example, two photons is needed in a simultaneous event to promote an electron from a valence state directly into an upper level conduction band state where relaxation across the band gap of the material produces fluorescence. Here, the co-doping produces states in the band gap of the $NaYF_4$ such that the $Yb^{3+}$ ion has an energy state at $^2F_{5/2}$ pumpable by a single photon event and from which other single photon absorption events can populate even higher states. Once in this exited state, transitions to higher energy radiative states are possible, from which light emission will be at a higher energy than that of the incident light pumping the $^2F_{5/2}$ energy state. In other words, the energy state at $^2F_{5/2}$ of the $Yb^{3+}$ ion is the state that absorbs 980 nm light permitting a population build up serving as the basis for the transitions to the higher energy states such as the $^4F_{7/2}$ energy state. Here, transitions from the $^4F_{7/2}$ energy state produce visible emissions.

Figure 7:
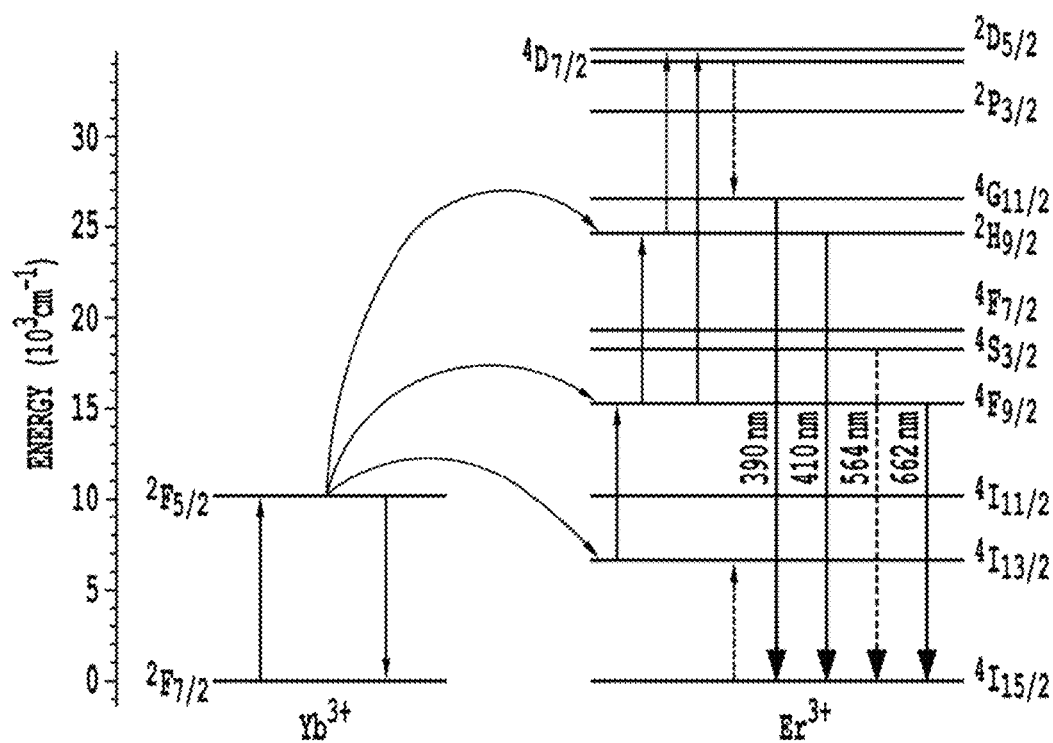
FIG. 7 is an energy diagram showing energy states for a four-photon upconversion process in $Y_2O_3$ nanocrystals.

Chen et al have described a four photon upconversion in *Four-photon upconversion induced by infrared diode laser excitation in rare-earth-ion-doped $Y_2O_3$ nanocrystals*, Chemical Physics Letters, 448 (2007) pp. 127-131 In that paper, emissions at 390 nm and at 409 nm were associated with a four-photon upconversion process in the $Y_2O_3$ nanocrystals. FIG. 7 reproduced below from Chen et al shows a ladder of states by which an infrared light source can progressively pump until the $^4D_{7/2}$ state is reached. From this upper state, transitions downward in energy occur until the $^4G_{1/2}$ state is reached, where a transition downward in energy emits a 390 nm photon. The materials described by Chen et al are useful in various embodiments of the invention.

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as $Er^{3+}$ doped $BaTiO_3$ nanoparticles and $Yb^+$ doped $CsMnCl_3$) are suitable in various embodiments of the invention.

Further materials specified for up conversion in the invention include CdTe, CdSe, ZnO, CdS, $Y_2O_3$, MgS, CaS, SrS and BaS. Such up conversion materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}MnS_y$, $Ca_{1-x}Mn_xS_y$, $Ba_{1-x}Mn_xS_y$, and $Sr_{1-x}$, etc. (wherein, $0<x\le1$, and $0<y\le1$). Complex compounds of the above-described semiconductors are also contemplated for use in the invention— e.g. $(M_{1-z}N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\le1$, $0<y\le1$, $0<z\le1$). Two examples of such complex compounds are $Zn_{0.4}Cd_{0.4}Mn_{0.2}S$ and $Zn_{0.9}Mn_{0.1}S_{0.8}Se_{0.2}$. Additional conversion materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn, Yb; MgS; Mn, Yb; CaS; Mn, Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, ... $0<z\le1$, $o<q\le1$).

Some nanoparticles such as $ZnS:Tb^{3+}$, $Er^{3+}$; $ZnS:Tb^{3+}$; $Y_2O_3:Tb^{3+}$; $Y_2O_3:Tb^{3+}$, $Er^{3+}$; $ZnS:Mn^{2+}$; $ZnS:Mn,Er^{3+}$ are known in the art to function for both downconversion luminescence and upconversion luminescence.

Because upconversion stimulates or produces emission at shorter wavelengths, there are applications directed to medicine where the longer wavelength light is more capable than a shorter wavelength light of penetrating deep into biological tissue. Accordingly, with upconverter materials pre-positioned inside for example a biological tissue or an aqueous solution, the longer wavelength light (such as from a commercial IR laser) can be used in one embodiment to image deep skin tissue (with the upconverter materials emitting visible or NIR light for detection), and/or the longer wavelength light in one embodiment can be used to excite the upconverters in the biological tissue and thereafter produce shorter wavelength light (e.g., ultraviolet light) to drive photochemical or pharmaceutical reactions in the body. Details of these particular applications will be discussed in more detail later.

FIGS. 8A-1 to 8A-7 are schematic representations of a depiction of an upconverter material (i.e., a photoactive material) according to one embodiment of the invention. FIGS. 8A-1 to 8A-7 show a number of structural configurations for placement of a dielectric core upconverter material (which is of a nanometer sized scale) in proximity to a metal shell. Incident light at a wavelength $\lambda_1$ interacts with the upconverting dielectric core. The interaction of light $\lambda_1$ with the dielectric core produces a secondary emission at a frequency $\lambda_2$ which has a shorter wavelength than $\lambda_1$ and accordingly has a higher energy than $\lambda_1$. While the exact physical mechanisms for the upconversion may depend on the particular upconversion material and process being used in a particular application, for the purposes for discussion and illustration, the following explanation is offered.

In the context of FIGS. 8A-1 to 8A-7, when a wavelength $\lambda_1$ interacts with a dielectric material core, three separate processes are well understood for the upconversion process involving trivalent rare earth ions. These three processes are:
1) excited state absorption whereby two photons are absorbed sequentially by the same ion to excite and populate one or more states;
2) energy transfer upconversion which is a transfer of excitation from one ion to another already in an excited state; and
3) a cooperative process of multiphotons where two nearby ions in excited states are emitting collectively from a virtual state.

Regardless of which one of these processes is occurring between the chosen ion(s) and the host lattice, the end result is a photon of energy greater than the excitation energy being emitted from the host lattice for the upconversion process.

Therefore, the particular ion being activated (whether it be a dopant ion or a host ion of a lattice such as in the neodymium oxide) will be chosen based on the host material being processed, in order that the dopant ion or the host ion in the dielectric core provide ion states which are pumpable by the NIR source to generate the resultant emission $\lambda_2$. While many of these materials have been studied in the past in the bulk state, prior to the invention, the targeted use of these materials in the noncrystalline and nanosize range for various materials, chemical, medical, pharmaceutical, or industrial processing have not been exploited, especially at the size of dielectric cores and with the application of metallic shells.

Hence, the invention in one embodiment provides a nanoscale upconversion system for producing a photostimulated reaction in a medium. The system includes a nanoparticle configured, upon exposure to a first wavelength $\lambda_1$ of radiation, to generate a second wavelength $\lambda_2$ of radiation having a higher energy than the first wavelength $\lambda_1$. The system includes a metallic shell encapsulating at least a fraction of the nanoparticle and includes a receptor disposed in the medium in proximity to the nanoparticle. The receptor upon activation by the second wavelength $\lambda_2$ generates directly or indirectly the photostimulated reaction. In one embodiment of the invention, a physical characteristic of the metallic structure is set to a value where a surface plasmon resonance in the metallic structure resonates at a frequency which provides spectral overlap with at least one of the first wavelength $\lambda_1$ and the second wavelength $\lambda_2$.

Within the context of the invention, the term "physical characteristic" of the metallic shell or core can relate to any characteristic of the metal itself or the shell or core dimensions or shape which affects the surface plasmon resonance frequency. Such physical characteristics can include, but are not limited to, a conductivity, a radial dimension, a chemical composition or a crystalline state of the metal shell or core.

In various embodiments, the metallic structures can be a metallic shell encapsulating at least a fraction of the nanoparticle in the metallic shell wherein a conductivity, a radial dimension, or a crystalline state of the metallic shell sets the surface plasmon resonance in the metallic structure to resonate at a frequency which provides spectral overlap with either the first wavelength $\lambda_1$ or the second wavelength $\lambda_2$. In various embodiments, the metallic structures can be a multi-layer metallic shell encapsulating at least a fraction of the nanoparticle in the metallic shell wherein a conductivity, a radial dimension, or a crystalline state of the metallic shell sets the surface plasmon resonance in the metallic structure to resonate at the first wavelength $\lambda_1$ and the second wavelength $\lambda_2$. This capability permits radiation at $\lambda_2$ to be amplified.

In various embodiments, the metallic structures can be a metallic particle existing in one or more multiple structures. These multiple structures can have a variety of shapes including for example sphere, spheroid, rod, cube, triangle, pyramid, pillar, crescent, tetrahedral shape, star or combination thereof disposed adjacent the nanoparticle wherein a conductivity, a dimension (e.g. a lateral dimension or a thickness), or a crystalline state of the metallic structure sets the surface plasmon resonance in the metallic particle or rod to resonate at a frequency which provides spectral overlap with either the first wavelength $\lambda_1$ or the second wavelength $\lambda_2$. Such shapes are described in the present figures and in the figures in U.S. Ser. No. 12/401,478 which is incorporated by reference in its entirety. The shape choice can affect the frequency of the surface plasmon resonance. It is known that the plasmon band is changed by the shape of nanoparticles (e.g., prolate and obloid spheroids). The paper "Spectral bounds on plasmon resonances for Ag and Au prolate and oblate nanospheroids," in the Journal of Nanophotonics, Vol. 2, 029501 (26 Sep. 2008), the entire contents of which are incorporated by reference, shows plasmon resonance shifts for shaping of Ag and plasmon resonance shifts for shaping of Au of prolate and obloid spheroids. In one embodiment of the invention, with an increasing aspect ratio for a metallic structure of the invention, the prolate spheroid resonance is red shifted relative to a sphere with no lower limit (under the assumptions of a Drude dispersion model). On the other hand, the oblate resonances are "blue shifted" as the spheroid becomes increasingly flat, but up to a limit.

In various embodiments, the metallic structures can be a metallic structure disposed interior to the nanoparticle wherein a conductivity or a dimension (e.g. a lateral dimension or a thickness) of the metallic structure sets the surface plasmon resonance in the metallic structure to resonate at a frequency which provides spectral overlap with either the first wavelength $\lambda_1$ or the second wavelength $\lambda2$. In various embodiments, the metallic structures can be a metallic multi-layer structure disposed interior to the nanoparticle wherein a conductivity or a dimension (e.g. a lateral dimension or a thickness) of the metallic structure sets the surface plasmon resonance in the metallic structure to resonate at the first wavelength $\lambda_1$ and the second wavelength $\lambda_2$. This capability once again permits radiation at $\lambda_1$ and $\lambda_2$ to be amplified.

In another embodiment, the invention provides a nanoparticle structure including a sub 1000 nm dielectric core and a metallic structure disposed in relation to the nanoparticle. The dielectric core includes at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$. Such nanoparticle structures can exhibit in certain embodiments surface plasmon resonance in the metallic structures to enhance upconversion of light from a first wavelength $\lambda_1$ to a second wavelength $\lambda_2$.

In another embodiment, the invention provides a nanoparticle structure including a sub 10 nm dielectric core and a metallic shell encapsulating at least a fraction of the nanoparticle. The dielectric core includes any of the dielectric cores noted above. Such nanoparticle structures can exhibit in certain embodiments surface plasmon resonance in the metallic shell to enhance upconversion of light from a first wavelength $\lambda_1$ to a second wavelength $\lambda_2$.

As described above, a metallic structure is in particular designed with a layer thickness to enhance the photon upconversion process through plasmonic enhancement. The thickness of the structure is "tuned" in its thickness to the absorption process by having a dimension in which plasmons (i.e., electrons oscillations) in the structure have a resonance in frequency which provides spectral overlap with the absorption band targeted. Thus, if the upconversion is to be stimulated by 980 nm NIR light, then the thickness of the structure is "tuned" in a thickness to where a plasmon resonance resonates at a frequency also of 980 nm (or in the neighborhood thereof as plasmon resonances are typically broad at these wavelengths).

Such a plasmon resonating structure can be made of numerous transition metals, including though not limited to gold, silver, platinum, palladium, nickel, ruthenium, rhenium, copper, and cobalt. When formed of a gold nanoshell, the recommended thickness to resonate with 980 nm light is approximately 3.5 nm surrounding an 80 nm upconverting core, as projected by extended Mie theory calculations. (See Jain et al., *Nanolett.* 2007, 7(9), 2854 the entire contents of which are incorporated herein by reference.) FIG. 8C is reproduced from Jain et at and illustrates the capability in the present invention to "tune" the metal shell to have a spectral overlap with the excitation and/or emission radiation wavelengths. This capability of matching or tuning of the frequencies provides an enhancement of the absorption which would not be present with a dielectric core alone.

In one embodiment of the invention, the metallic structures can be an alloy such as for example a Au:Ag alloy. The alloy content can be set to adjust the frequency of the surface plasmon resonance. For instance, the alloy content may be one factor providing a surface plasmon resonance at 365 nm. In one embodiment, specifically a silver concentration of 65 to 75%, and more specifically a silver concentration of 67% is used for a 365 nm surface plasmon resonance. In one embodiment of the invention, the metallic structures can be an alloy such as for example a Pt:Ag alloy. The alloy content can be set to adjust the frequency of the surface plasmon resonance. In one embodiment of the invention, the metallic structures can be an alloy such as for example a Pt:Au alloy. The alloy content can be set to adjust the frequency of the surface plasmon resonance.

In one embodiment of the invention, the nanoparticle can be an alloy of two or more materials. In this embodiment, the alloy can have a composition between the two or more materials which is set to a compositional value where excitation of the alloy at first wavelength $\lambda_1$ produces emission at the second wavelength $\lambda_2$. In one embodiment of the invention, the nanoparticle can be a zinc sulfide and zinc selenide alloy. In one embodiment of the invention, the nanoparticle can be a zinc sulfide and cadmium sulfide alloy.

In one embodiment of the invention, the zinc sulfide and zinc selenide nanoparticle alloy can have an alloy content set to provide a surface plasmon resonance at 365 nm and specifically having a zinc sulfide concentration of 65 to 75%, and more specifically a zinc sulfide concentration of 67%. In one embodiment of the invention, the zinc sulfide and cadmium sulfide nanoparticle alloy can have an alloy content is set to provide a surface plasmon resonance at 365 nm and specifically having a zinc sulfide concentration of 65 to 75%, and more specifically a zinc sulfide concentration of 67%.

Some techniques for producing nanoparticles and nanoparticle alloys which are suitable for the invention are described in the following documents, all of which are incorporated herein in their entirety: U.S. Pat. Nos. 7,645,318; 7,615,169; 7,468,146; 7,501,092; U.S. Pat. Appl. Publ. No. 2009/0315446; 2008/0277270; 2008/0277267; 2008/0277268; and WO 2009/133138.

In one embodiment of the invention, the nanoparticle can be a dielectric or semiconductor configured to generate the wavelength $\lambda_2$. In one embodiment of the invention, the nanoparticle can include multiple dielectrics or semiconductors respectively configured to emit at different wavelengths for $\lambda_2$. In one embodiment of the invention, multiple nanoparticles having different dielectrics or semiconductors can be included in a mixture of the nanoparticles dispersed in the medium.

In one embodiment of the invention, a quantum dot mixture can be used for the multiple nanoparticles. Quantum dots are in general nanometer size particles whose energy states in the material of the quantum dot are dependent on the size of the quantum dot. For example, quantum dots are known to be semiconductors whose conducting characteristics are closely related to the size and shape of the individual crystal. Generally, the smaller the size of the crystal, the larger the band gap, the greater the difference in energy between the highest valence band and the lowest conduction band becomes. Therefore, more energy is needed to excite the dot, and concurrently, more energy is released when the crystal returns to its resting state. In fluorescent dye applications, this equates to higher frequencies of light emitted after excitation of the dot as the crystal size grows smaller, resulting in a color shift from red to blue in the light emitted.

Specifically, in one embodiment of the invention, a quantum dot mixture (QDM) coating can be deposited using CVD and or sol-gel techniques using standard precipitation techniques. The QDM coating can be made of a silicate structure that does not diminish UV output. Within the silicate family, silica ($SiO_2$) is suitable since it maximizes UV transmission through the coating. The coating can further include a second layer of a biocompatible glass. Such bio-compatible glass and glass ceramic compositions can contain calcium, a lanthanide or yttrium, silicon, phosphorus and oxygen. Other biocompatible materials and techniques are described in the following patents which are incorporated herein in their entirety: U.S. Pat. Nos. 5,034,353; 4,786,617; 3,981,736; 3,922,155; 4,120,730; and U.S. Pat. Appl. Nos. 2008/0057096; 2006/0275368; and 2010/0023101.

Since the present invention is directed towards use of these various structures within a living patient, when the exposed portion of the particle comprises a potentially cytotoxic compound, it may be necessary to add a further coating or shell of a biocompatible and biostable substance, such as SiO2, in order to avoid toxicity within the patient.

In one embodiment of the invention, the thickness of the metal shell is set depending on the absorption frequency (or in some cases the emission frequency) of the particular dopant ions in the dielectric core to enhance the total efficiency of the emission process of the upconverted light. Accordingly, the thickness of the metal shell can be considered as a tool that in one instance enhances the absorption of $\lambda_1$, and in another instance can be considered as a tool that enhances the emission of $\lambda_2$, or in other situations can be considered an enhancement feature that in combination enhances the overall net process.

Additionally, plasmon-phonon coupling may be used to reduce a resonance frequency through the tuning of the bands to a degree off resonance. This may be useful in optimizing resonance energy transfer processes for the purpose of coupling the core-shell nanoparticles to sensitive chromophores or drug targets. Accordingly, when a recipient 4 is outside of the shell, the recipient 4 will receive enhanced light $\lambda_2$ by the above-described plasmonic effect than would occur if the shell were absent from the structure.

Figure 8B:
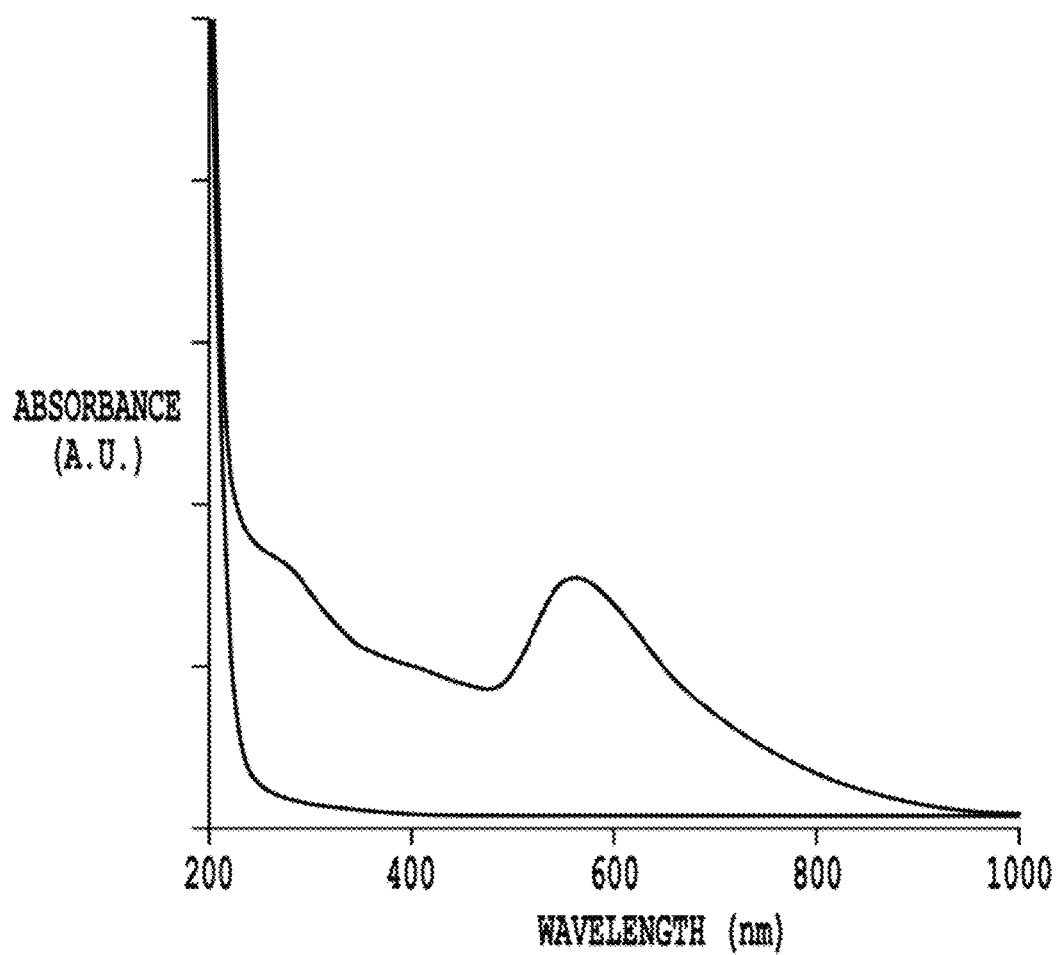
FIG. 8B is an UV-visible absorption spectra of cubic $Y_2O_3$ and gold-coated $Y_2O_3$ dispersed using 10 mM triarginine.
Figure 8C:
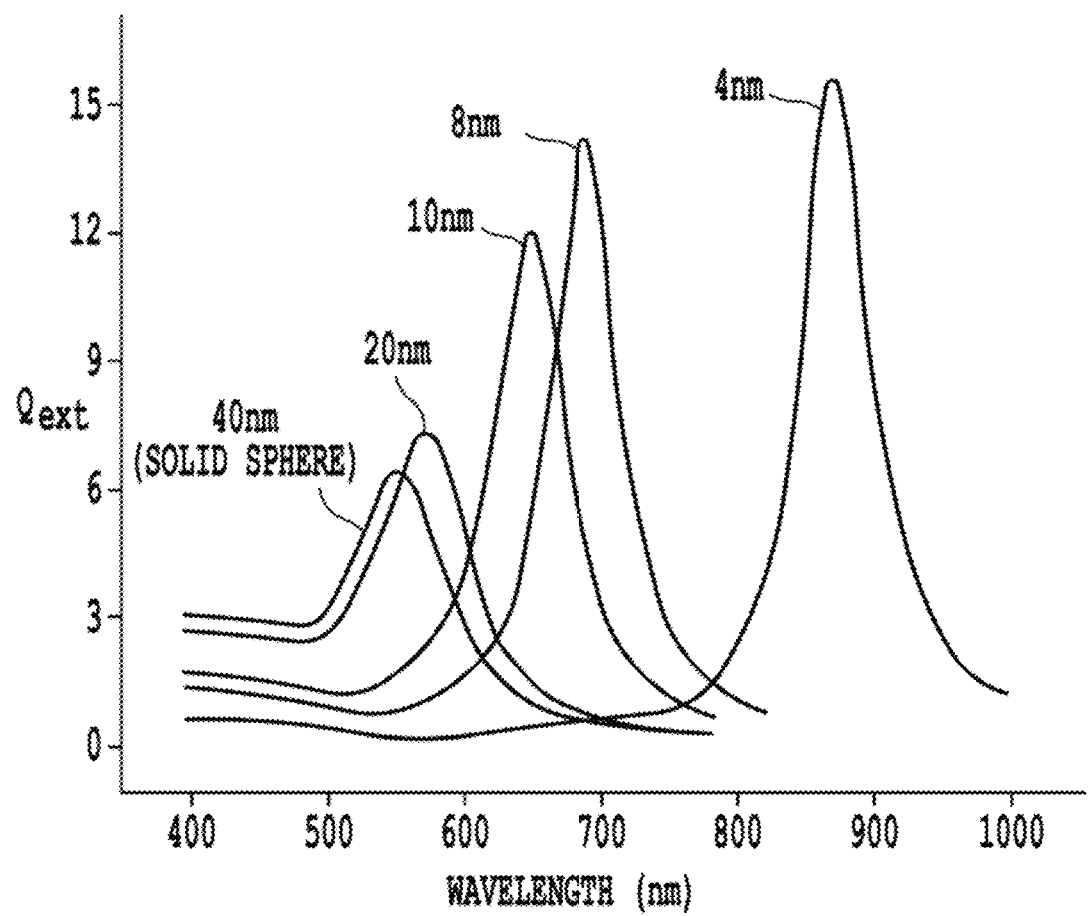
FIG. 8C is a schematic illustration of plasmon resonance as a function of shell thickness.

In one example, FIG. 8B shows UV-visible absorption spectra of cubic Y2O3 (lower trace) and gold-coated Y2O3 (upper trace) dispersed using 10 mM tri-arginine. Details of the preparation of the nanoparticle system are provided below. The absorption spectrum of Y2O3 alone (lower trace) is fairly featureless, showing absorption due to the tri-arginine near 200 nm and a gentle slope associated with scattering and absorption by the Y2O3 nanoparticles extending into the visible portion of the spectrum. The gold-coated Y2O3 (upper trace), on the other hand, exhibit a strong absorption band at 546 nm, which is characteristic of the plasmonics resonance band due to the gold shell around the Y2O3 cores. This feature is a plasmon band. If this feature were due to solid gold nanoparticles in solution, this feature would be centered at or below 530 nm. Moreover, red-shifting of the plasmon absorption to 546 nm is consistent with the presence of a gold shell around a dielectric core.

In one embodiment of the invention, the materials for the upconverter dielectric core can include a wide variety of dielectric materials, as described above. In various embodiments of the invention, the upconverter dielectric core includes more specifically lanthanide doped oxide materials.

Lanthanides include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Other suitable dielectric core materials include non-lanthanide elements such as yttrium (Y) and scandium (Sc). Hence suitable dielectric core materials include $Y_2O_3$, $Y_2O_2S$, $NaYF_4$, $NaYbF_4$, Na-doped $YbF_3$, YAG, YAP, $Nd_2O_3$, $LaF_3$, $LaCl_3$, $La_2O_3$, $TiO_2$, $LuPO_4$, $YVO_4$, $YbF_3$, $YF_3$, or $SiO_2$. These dielectric cores can be doped with Er, Eu, Yb, Tm, Nd, Tb, Ce, Y, U, Pr, La, Gd and other rare-earth species or a combination thereof.

Lanthanides usually exist as trivalent cations, in which case their electronic configuration is (Xe) $4f^n$, with n varying from 1 ($Ce^{3+}$) to 14 ($Lu^{3+}$). The transitions within the f-manifold are responsible for many of the photo-physical properties of the lanthanide ions, such as long-lived luminescence and sharp absorption and emission lines. The f-electrons are shielded from external perturbations by filled Ss and Sp orbitals, thus giving rise to line-like spectra. The f-f electronic transitions are LaPorte forbidden, leading to long excited state lifetimes, in the micro- to millisecond range.

Accordingly, examples of doped materials in the invention include oxides such as yttrium oxide and neodymium oxide and aluminum oxide as well as sodium yttrium fluoride and nanocrystalline perovskites and garnets such as yttrium aluminum garnet (YAG) and yttrium aluminum perovskite (YAP). Of these materials, doping is required for some, but not all of these materials, for promoting upconversion efficiencies. In various embodiments of the invention, the host nanocrystals are doped with trivalent rare earth lanthanide ions from those lanthanide series elements given above.

More specifically, in various embodiments of the invention, pairs of these dopants are introduced in order to make accessible more energy states in the host crystal. The activation and pumping of these energy states follows closely the principles discussed above with regard to FIG. 7. Doping concentrations in the invention can range from 0.2% to 20% roughly per ion into the host lattice or in a weight or mol % variation. The efficiency of the upconversion processes of specific bands in these materials can be modulated by the percentages doped to induce and enhance targeted emissions. Lanthanide doped upconverters while not limited to, can use the following mol percent dopant compositions: 5% Er, 10% Yb, 0.2% Tm+3% Yb, and 1% Er+10% Yb.

The size of the nanocrystal will also have an effect on the efficiency of the upconversion process, as a larger nanocrystal will have more sites for dopant ions to be accommodated into the host lattice, therefore enabling more emissions from the same doped host than if the nanocrystal were smaller. While the dopant percentages listed above are not rigidly fixed, these numbers provide rudimentary teachings of the typical percentages one would use in obtaining a particular dielectric core material of the invention.

Moreover, some of these host crystals (e.g., neodymium oxide) in one embodiment of the invention may require no specific doping to facilitate upconversion, which has been seen in one instance in $Nd_2O_3$ with an excitation wavelength of 587 nm producing emissions at 372 nm, 402 nm, and 468 nm. See Que, W et al. Journal of Applied Physics 2001, vol 90, pg 4865, the entire contents of which is incorporated herein by reference. Doping neodymium oxide with $Yb^{3+}$, in one embodiment of the invention, would enhance upconversion through sensitizing the $Nd^{3+}$ ions with a lower energy $Yb^{3+}$ activator.

In one embodiment of the invention, the dielectric core is coated, such as for example with a metallic shell 4, to enhance electron-phonon coupling and thereby increase upconversion efficiency, as discussed above. In another embodiment of the invention, the shell can include a $SiO_2$- and/or $TiO_2$-coating, and this coating is in one embodiment coated on doped $Y_2O_3$ upconverting nanoparticles to thereby, in some instances, increase the upconversion efficiency relative to an uncoated nanocrystal. Further, in one embodiment of the invention, the coating can be a polymer. In one embodiment, this coating is provided on $NaYF_4$:Ln/ $NaYF_4$ dielectric core. Such coatings can increase the upconversion efficiency relative to an uncoated upconverter.

In another embodiment of the invention, phonon modes of an undoped host-lattice (e.g., $Y_2O_3$) nanocrystals are modulated, for example, by Au, Ag, Pt, and Pd shells 4 of varying thicknesses. In various embodiments of the invention, the upconverter dielectric core and the shell 4 system includes as upconverting nanocrystals $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells. In this system, the core diameter and shell outer/inner diameter of the metallic coatings can be set to dimensions that are expected to be tunable to a plasmon mode overlap.

In other embodiments as discussed below, the metal coating or the metallic structure can exist inside the dielectric and the relative position of the metal structure to the dielectric structure can enhance plasmon resonance. These structures with the metallic structure inside can be referred to as a metallic core up converter or a metallic core down converter. The metallic core technique for energy conversion is useful since it takes advantage of metal nano-particles that have improved surface morphology compared to shell coatings on core dielectrics. The metal or metallic alloy in the inner core metallic energy converter can be selected to tune its plasmonic activity. These structures with the metallic structure outside can be referred to as a core up converter or a core down converter. These core up converter or a core down converter structures offer advantages for biocompatibility as the core materials can be surrounded in a gold biocompatible shell.

Figure 8D:
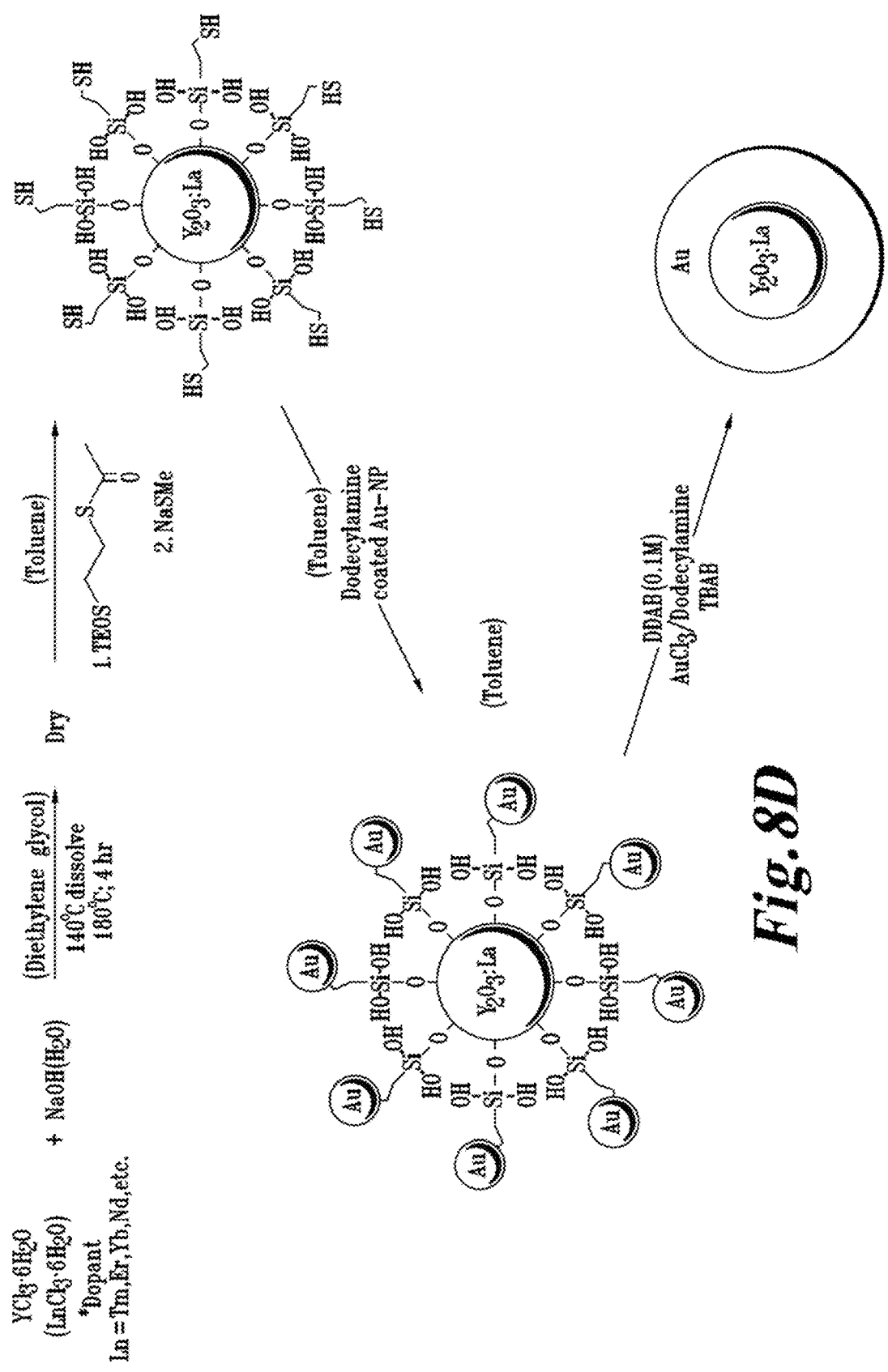
FIG. 8D is a schematic illustration of a process for forming and a resultant Ln-doped $Y_2O_3$ core with a Au shell.

FIG. 8D is a schematic illustration of a process for forming and a resultant Ln-doped $Y_2O_3$ core with a Au shell. One illustrative method for producing sub-10 nm Ln-doped $Y_2O_3$ nanoparticles with a metal shell can be achieved through the polyol method. See Bazzi, R. et al. *Journal of Luminescence*, 2003, 102-103, 445-450, the entire contents of which are incorporated by reference. In this approach, yttrium chloride hexahydrate and lanthanum-series chloride hexahydrates are combined in an appropriate ratio with respect to their cation concentration into suspension with diethylene glycol (0.2 mol chloride per liter of DEG). To this suspension is added a solution of NaOH and water (0.2 mol/L and 2 mol/L, respectively). The suspension is heated to 140° C. in a solvent recondensing/reflux apparatus for a period of 1 hour. Upon completion of the 1 hour of heating the solution has become transparent and nucleation of the desired nanoparticles has occurred. The temperature is then increased to 180° C. and the solution is boiled/refluxed for 4 hours yielding $Y_2O_3$:Ln nanoparticles. This solution is then dialyzed against water to precipitate the nanoparticles or solvent is distilled off and excess water added to precipitate the same. The nanoparticles are collected through centrifugation and dried in vacuo.

The dried nanoparticles are then calcined at 900° C. for 2 hours to afford single phase, cubic $Y_2O_3$ nanocrystals with lanthanide dopants equally distributed through the $Y_2O_3$ nanocrystal. This methodology may be modified to allow for synthesis in a pressurized environment, thereby allowing for complete expression in the cubic phase, allowing for a shorter calcining times and lower temperatures leading to less nanoparticle agglomeration and size growth.

Nanocrystals are then resuspended in toluene with sonication and treated with 2-triethoxysilyl-1-ethyl thioacetate (300 mM) in toluene. Volatile components of the reaction mixture are removed in vacuo and the remaining residue is resuspended in toluene and treated with NaSMe. Volatile components of the reaction mixture are again removed in vacuo and the remaining residue is purified through reprecipitation, centrifugation, and drying. The thiol-terminated, surface-modified nanocrystals are then resuspended in 0.1 M DDAB (didodecylammonium bromide) in toluene and a solution of colloidal gold nanoparticles (~1 nm in diameter) coated in dodecylamine (prepared as per Jana, et al. *J. Am. Chem. Soc.* 2003, 125, 14280-14281, the entire contents of which are incorporated herein by reference) is added. The gold shell is then completed and grown to the appropriate shell thickness through additions of $AuCl_3$ and dodecylamine in the presence of reducing equivalents of tetrabutylammonium borohydride. Thiol terminated organic acids may then be added to allow for increased water solubility and the completed gold metal shell, Ln-doped, $Y_2O_3$ nanoparticles may be separated in the presence of water through extraction or dialysis.

Figure 8E:
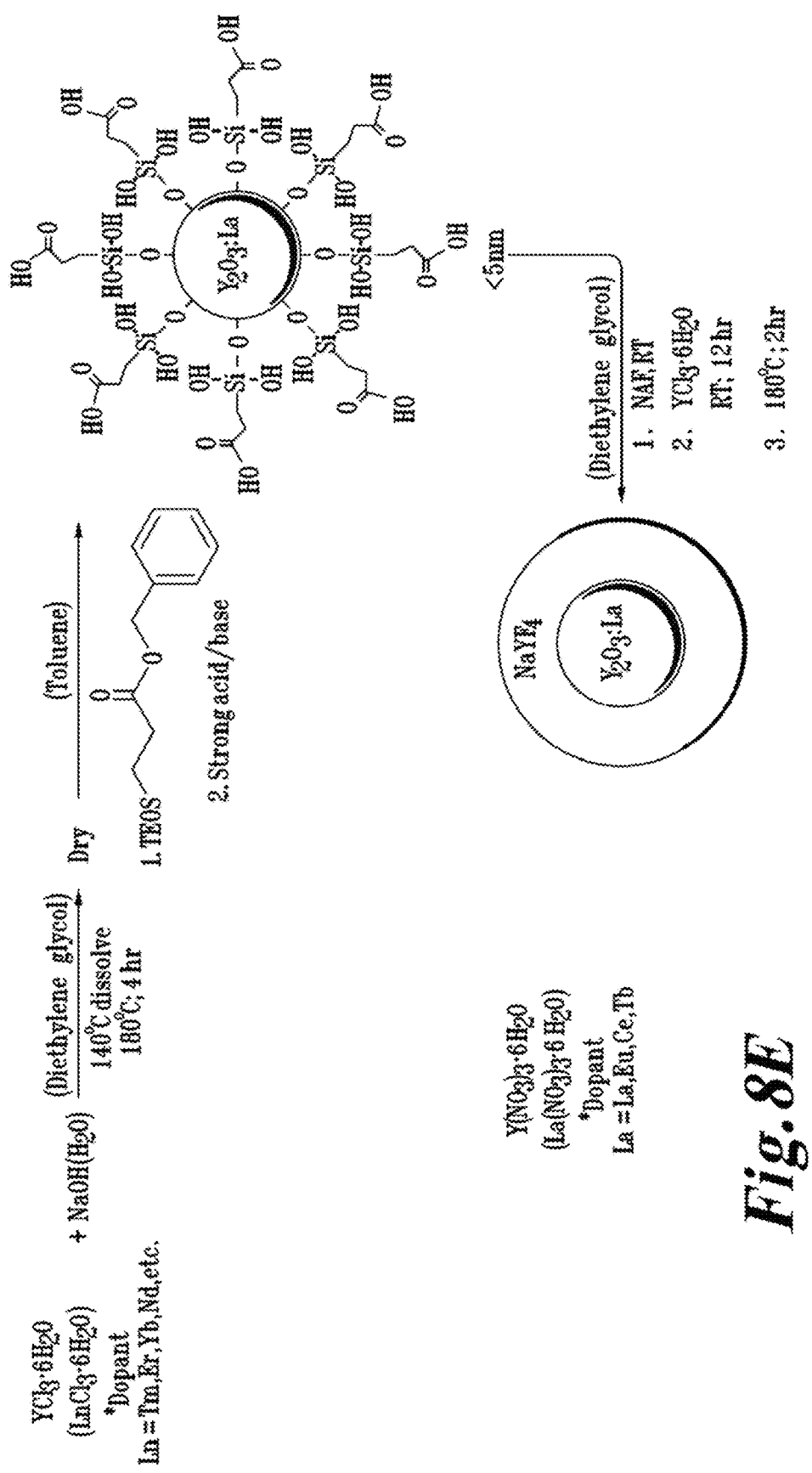
FIG. 8E is a schematic illustration of a process for forming and a resultant Ln-doped $Y_2O_3$ core with a $NaYF_4$ shell.

FIG. 8E is a schematic illustration of a process for forming and a resultant Ln-doped $Y_2O_3$ core with a $NaYF_4$ shell. In this embodiment of the present invention, Ln-doped $Y_2O_3$ cores for example may be shelled with $NaYF_4$, $Nd_2O_3$, Ga2O3, $LaF_3$, undoped $Y_2O_3$, or other low phonon mode dielectric material using a secondary polyol approach following silyl protection of the core nanocrystal. It has been shown that low phonon mode host lattices (such as $Y_2O_3$, $NaYF_4$, etc.) are useful for aiding in the upconversion process. This has been attributed to the nature of electron-phonon coupling to low phonon modes and the removal of non-radiative decay processes within the host-lattice/ion crystal. Accordingly, in one embodiment of the present invention, the dielectric core materials are made of low mode phonon host lattices (such as $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$, or alloys or combinations thereof, etc.).

Different sized $Y_2O_3$ NPs can also be synthesized via a combustion method developed by Song et al. In this method, $Y(NO_3)_3$ and glycine solution were heated to evaporate excess water until spontaneous ignition occurred. Cubic $Y_2O_3$ NPs can be obtained upon 2 hr of annealing at 500° C. One advantage of this method is that the $Y_2O_3$ particle size can be changed by varying the ratio between $Y(NO_3)_3$ and glycine. Another advantage is that different ratios of dopants (e.g. Yb and Er) can be added in the $Y_2O_3$ precursor solution and different doped $Y_2O_3$ NPs which have different emission properties can thus be synthesized. Due to insolubility, $Y_2O_3$ NPs are known to form precipitate in water. Upon functionalization with glutamic acid, $Y_2O_3$ NPs can result in a good suspension in water and the well-dispersed NPs shown in FIGS. 9B-1 and 9B-2. XRD measurement showed that the as-synthesized $Y_2O_3$ NPs have a cubic structure and this crystal structure is further proved by the lattice spacing as shown in FIGS. 9B-1 and 9B-2. Ligand substitution with excess 3-mercaptopropionic acid or 3-mercaptopropylphosphonic acid in the presence of refluxing diethylene glycol can then be used to functionalize these particles with Au nanoparticles in similar fashion to treatment with mercaptoalkylsilanes, as is described below.

Nanocrystals are then resuspended in toluene with sonication and treated with 2-triethoxysilyl-1-ethyl thioacetate (300 mM) in toluene. Volatile components of the reaction mixture are removed in vacuo and the remaining residue is resuspended in toluene and treated with NaSMe. Volatile components of the reaction mixture are again removed in vacuo and the remaining residue is purified through reprecipitation, centrifugation, and drying. The thiol-terminated, surface-modified nanocrystals are then resuspended in 0.1 M DDAB (didodecylammonium bromide) in toluene and a solution of colloidal gold nanoparticles (~1 nm in diameter) coated in dodecylamine (prepared as per Jana, et al. *J. Am. Chem. Soc.* 2003, 125, 14280-14281, the entire contents of which are incorporated herein by reference) is added. The gold shell is then completed and grown to the appropriate shell thickness through additions of $AuCl_3$ and dodecylamine in the presence of reducing equivalents of tetrabutylammonium borohydride. Thiol terminated organic acids may then be added to allow for increased water solubility and the completed gold metal shell, Ln-doped, $Y_2O_3$ nanoparticles may be separated in the presence of water through extraction or dialysis.

Dried $Y_2O_3$ nanoparticles are resuspended in toluene with sonication and treated with 2-triethoxysilyl-1-propionic acid, benzyl ester (300 mM) in toluene. Volatile components of the reaction mixture are removed in vacuo and the remaining residue is resuspended in toluene and treated with a strong base. Volatile components of the reaction mixture are again removed in vacuo and the remaining residue is purified through reprecipitation, centrifugation, and drying. The carboxyl-terminated, surface-modified nanocrystals are then resuspended in a solution of sodium fluoride in DEG and treated with yttrium nitrate hexahydrate at room temperature, stirring for 12 hours (for $NaYF_4$ exemplar). The reaction mixture is then brought to 180° C. for 2 hours to grow the $NaYF_4$ shell through Ostwald ripening. Nanoparticles are purified through reprecipitation, as described previously. Organic acid terminated polymers, polyethylene glycol, polyethynyleneimine, or other FDA approved, bioavailable polymer may then be added to allow for increased water solubility and the completed $NaYF_4$ shell, Ln-doped, $Y_2O_3$ nanoparticles may be resuspended in water for medical use.

In various embodiments of the invention, the upconverter dielectric core can be coated with thiol-terminated silanes to provide a coating of $SiO_2$ about the core of similar reactivity to $Y_2O_3$. These thiolated nanoparticles are then exposed to colloidal Au (1-2 nm) which associates to the nanoparticle surface and, with addition of $HAuCl_4$ and a reducing agent, Ostwald ripening coalesces the Au surface into a uniform shell of a designated thickness. Solubility enhancement of $NaYF_4$ and other $CaF_2$ lattices can be increased by the use of coupled trioctylphosphine-oleic amine, polyethylene glycol, and polyethyleneimine surfactants. These surfactants associate to the surface of the nanoparticles with functional head groups and are soluble in either organic or aqueous solvents to permit colloidal suspension of the nanoparticles In one embodiment of the invention, the above-described methodology is used to synthesize novel upconverting core-shell nanoparticles of $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells where core and shell diameters varying from 2 to 20 nm. In these novel material systems, the tuned ratio of core-to-shell diameter may permit a plasmon-phonon resonance which should amplify absorption of NIR light and/or upconverted emission. In these novel material systems, control of the core and shell diameters is one factor determining the size dependent effect and subsequent tuning of plasmon-phonon resonance.

In one embodiment of the invention, this methodology is used to synthesize novel mixed core-shell materials can include semiconducting $Y_2O_3$ and $NaYF_4$ cores doped with various Ln series metals, which have been shown to possess large upconverting efficiencies. These doped $Y_2O_3$ and $NaYF_4$ cores will have shells of Au(Ag,Pt, Pd) or undoped $Y_2O_3$ and $NaYF_4$ matrices which have the potential to enhance or tune the phonon modes needed for energy transfer in the upconversion process. Solubility can be enhanced, for example, by addition of thiolated organics (Au shell), organic chain triethanolsilane ($Y_2O_3$ shell), and tri-octylphospine-oleic amine ($NaYF_4$ shell). All core-shell nanoparticles may further be solublized into a colloidal suspension with the addition of triarginine peptide, polyethylene glycol, and polyethyleneimine surfactants.

Since $Y_2O_3$ nanocrystals have a scintillation emission (down conversion) optimal for exciting drug derivatives of potential clinical importance, smaller nanocrystals offer advantages for biological targeting applications. Given the permeability of biological tissues to X-ray irradiation, down conversion from X-rays to visible light through $Y_2O_3$ nanocrystals offers a means of detecting the presence of nanoparticles coupled to biological malignancies (e.g. cancer, autoimmune degenerated tissue, foreign contaminants) through antibodies, Fab fragments, or cell-surface receptor specific peptides linked to the nanoparticle surface. Subsequently, down converting nanoparticles offer a means of generating UV/VIS/NIR light for photoactive drug activation directly at the treatment site, deep within biological tissue where UV and VIS light (if applied externally) would likely not penetrate. Furthermore, upconverting $Y_2O_3$:Ln nanocrystals can be utilized in one embodiment of the invention for their absorption and emissive properties within the NIR window applicable for medical imaging.

In one embodiment of the invention, small nanocrystals of these materials are prepared using rare-earth (RE) precursors (e.g. chloride, nitrate, alkoxides) which are mixed with a defined amount of water in a high boiling polyalcohol (e.g., diethylene glycol) solvent. The dehydrating properties of the alcohol and the high temperature of the solution promote a non-aqueous environment for the formation of oxide particles, as opposed to hydroxide, particles. Other solvents which can be used include: ethylene glycol, triethylene glycol, propylene glycol, dipropylene glycol, tripropylene glycol, etc. (thereby providing solvents with different boiling points). With these procedures, one expects sub-5 nm nanocrystals to be coated with Au, Ag, Pt, Pd (or combinations thereof) layers. FIG. 9A illustrates one such coated sub-5 nm nanocrystal.

Accordingly the synthesis of these nanocrystals and other dielectric core elements can follow the methods described below.

In particular, one method of forming yttrium oxide nanocrystals according to the present invention is to obtain precursors of the yttrium and rare earth ions in their salt forms, preferably in a chloride salt of the hexahydrate form, which is more soluble than non-hexahydrate forms. These salts are then combined in the correct molar ratios as listed below to create a yttrium oxide containing solution in a high boiling polyalcohol solvent with an added base of the correct proportion. An initial cation concentration of 0.2 moles per liter is mixed with a sodium hydroxide solution in water (0.2 moles per liter of sodium hydroxide per liter of reaction solution; 2 moles of $H_2O$ per liter per solution). The precursors were added together in the polyalcohol solvent, stirred for one hour at 140° C. After the salts are completely dissolved, the solution is brought to reflux at 180° C. and heated for four hours. The reaction is then cooled to room temperature yielding a transparent colloidal suspension of rare earth doped, yttrium oxide nanocrystals. The purification of this colloid produces the basic nanometer size of dielectric core shown in FIG. 9A. The metallic shell can then be prepared using the processes described below.

Similar methods can be employed for the preparation of the other upconversion materials described above, such as for example for the preparation of 1) nanoparticles of 2% neodymium and 8% ytterbium doped yttrium oxide,
2) europium and ytterbium doped yttrium oxide, and
3) any combination of rare earth trivalent ions doped into a neodymium oxide nanocrystal.

Figure 9C:
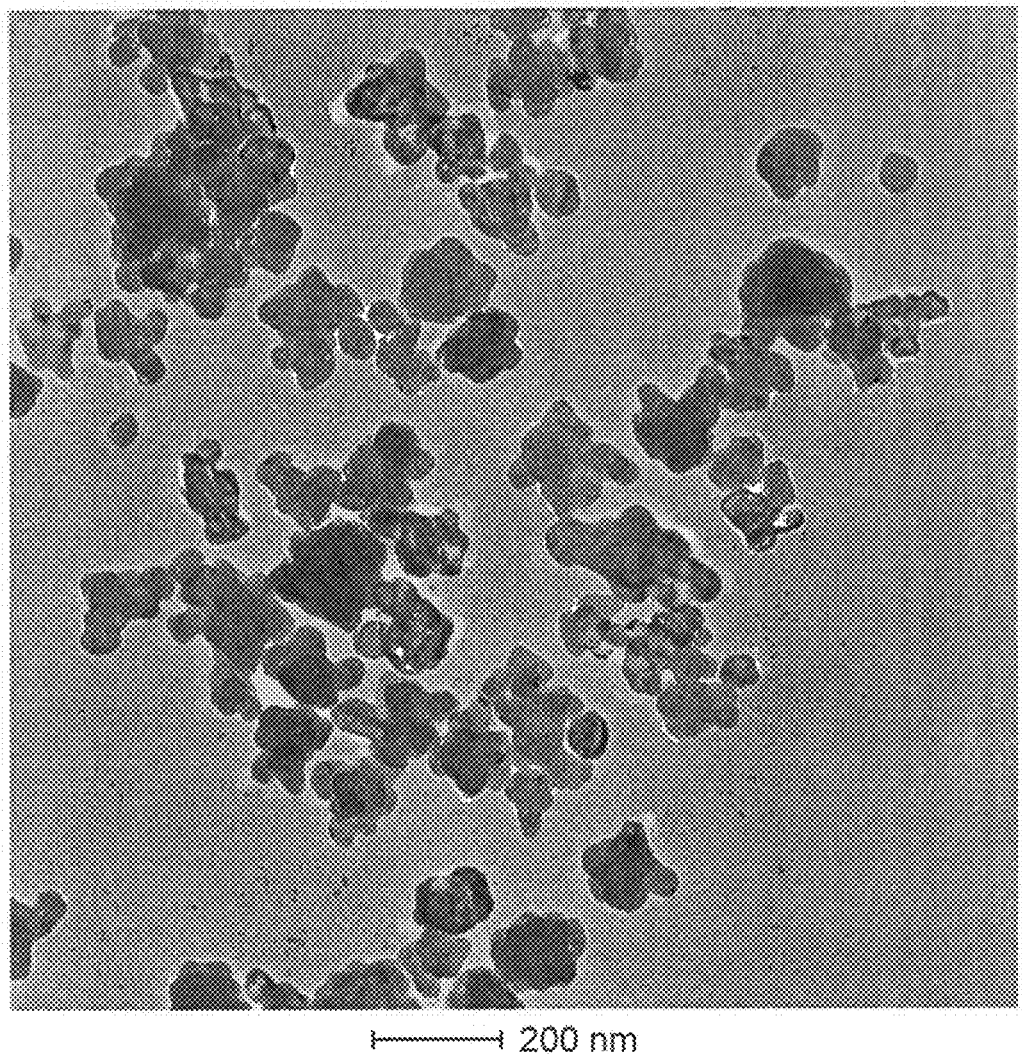
FIG. 9C is a micrograph showing NaYF$_4$ dielectric particles in the size range of ~70-200 nm range.

In another embodiment of the invention, $NaYF_4$ dielectric particles have been fabricated with individual particles in the ~70-200 nm size range as shown in FIG. 9C. To produce these particles NaCl, $TmCl_3$, $YCl_3$ and $YbCl_3$ stock solutions (0.2M) were prepared by dissolving the corresponding chlorides in water. A PEI stock solution (5%) was prepared by dissolving PEI ($M_n$~10,000) in water. 10 mL NaCl solution, 8 mL $YCl_3$ solution, 1.8 mL $YbCl_3$ solution and 0.2 mL $TmCl_3$ solution were added to a round-bottom flask containing 60 mL of ethanol and 20 mL of PEI solution. After stirring at room temperature for approximately 10 minutes, 2 mmol of $NH_4F$ was added and the solution was stirred for an additional 10 minutes. The solution was then transferred to a Teflon-lined autoclave which was placed in an oven at 200° C. for 24 hours. After cooling to room temperature, the particles were isolated by centrifugation and then washed three times using 50/50 $H_2O$-ethanol. A white powder was obtained after rotary evaporation.

Figure 9D:
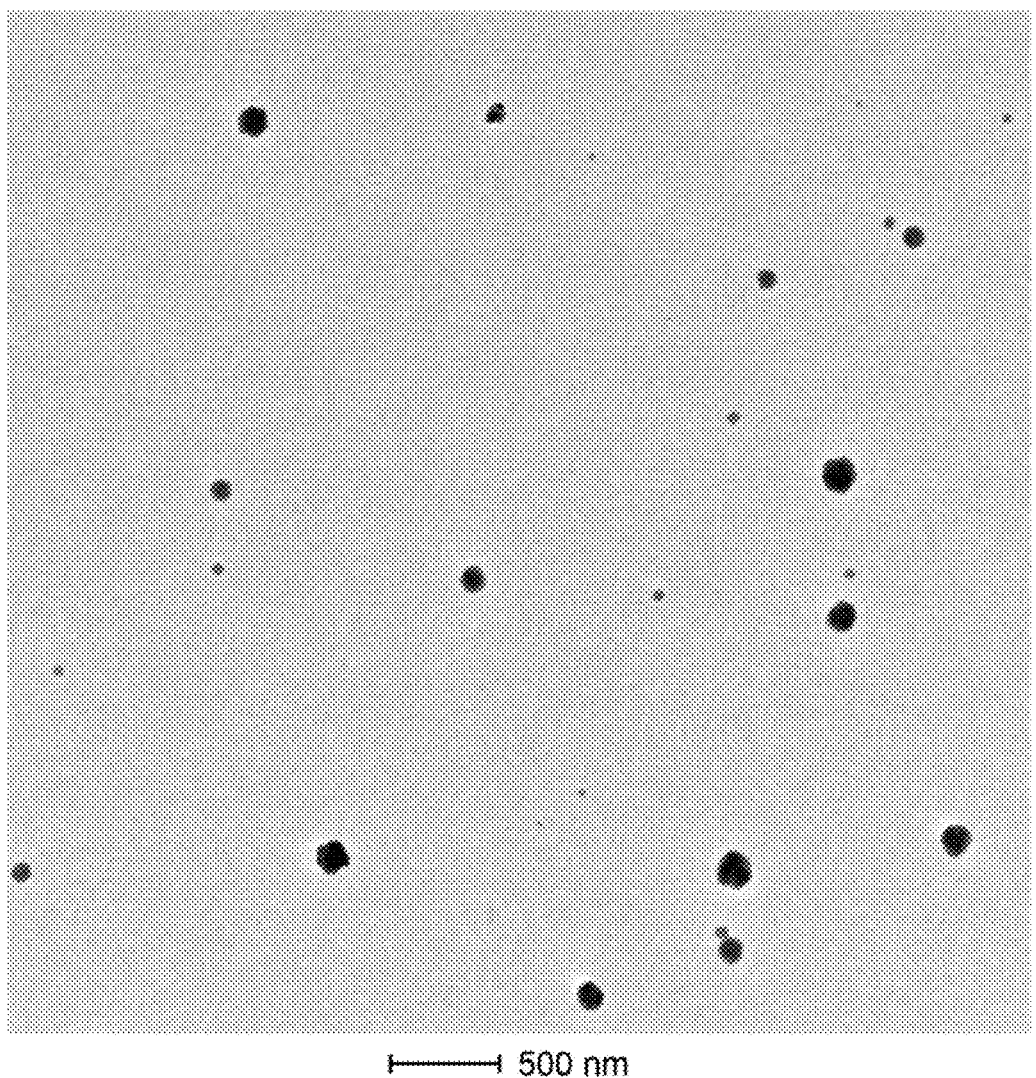
FIG. 9D is a micrograph showing NaYF$_4$ dielectric particles with two size distributions of ~50 nm and ~150 nm.
Figure 9E:
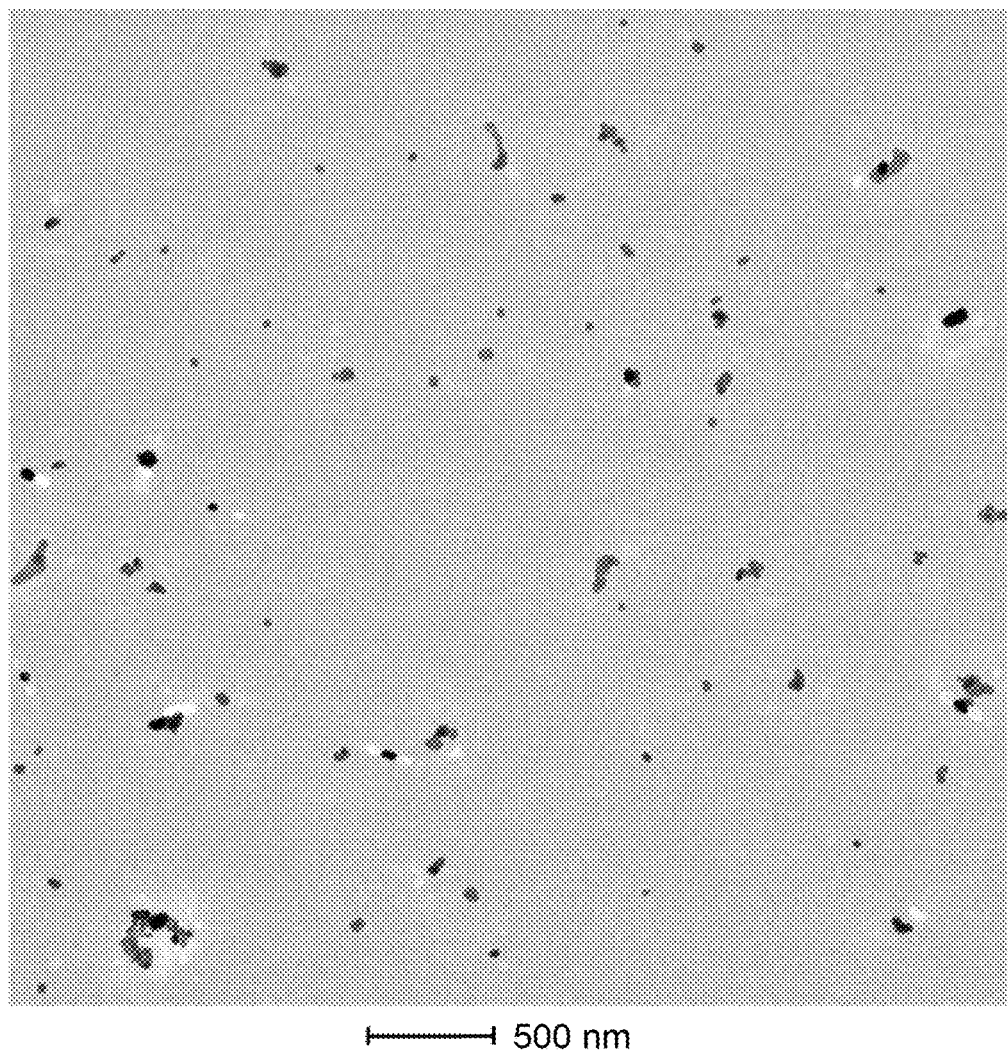
FIG. 9E is a micrograph showing YbF$_3$ dielectric particles of a size of 35 nm+/−5 nm.
Figure 9F:
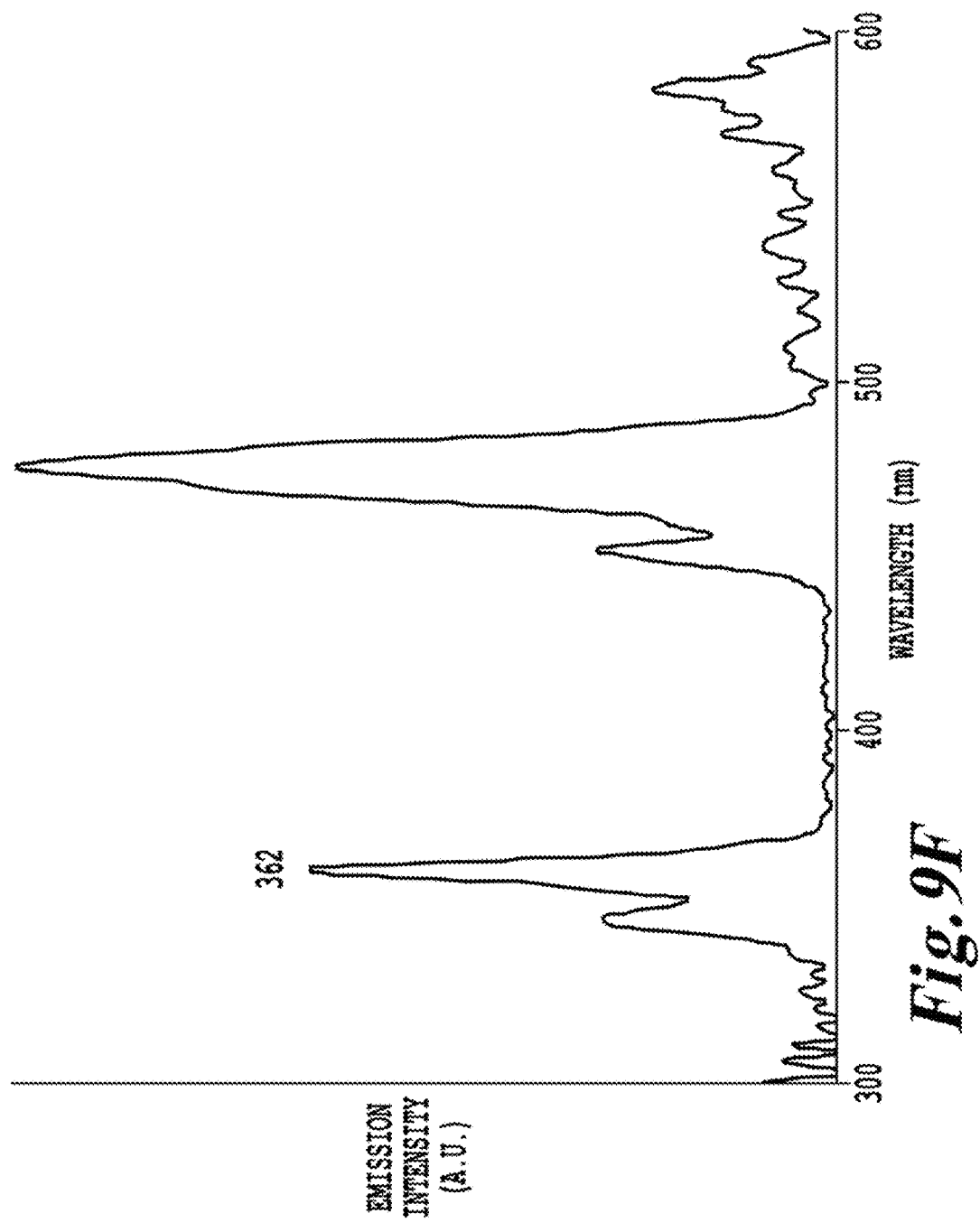
FIG. 9F is an optical emission spectrum from YbF$_3$; Tm (2%) dielectric particles, excited at 980 nm.
Figure 9G:
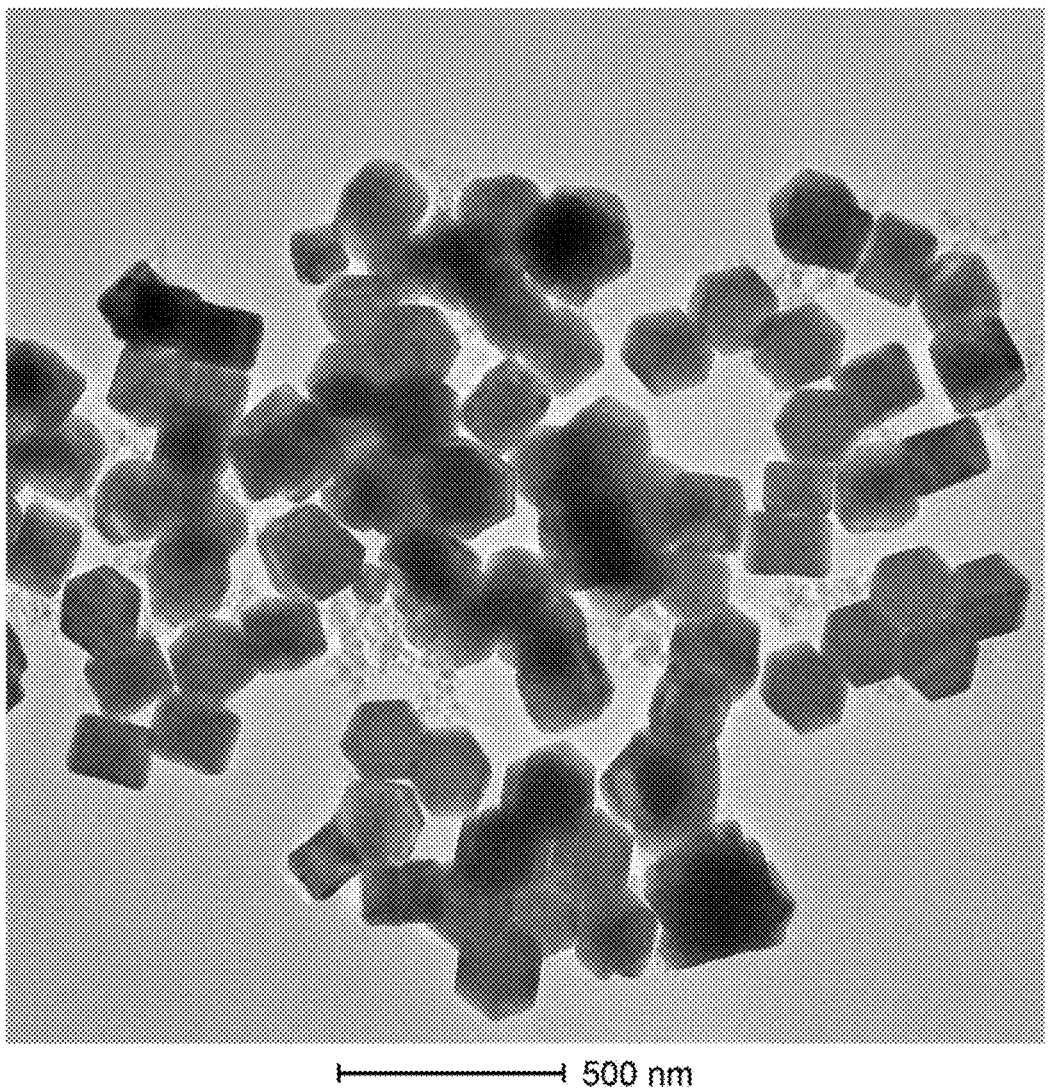
FIGS. 9G to 9J are micrographs showing NaYbF$_4$ dielectric particles in the ~20-150 nm size range.
Figure 9H:
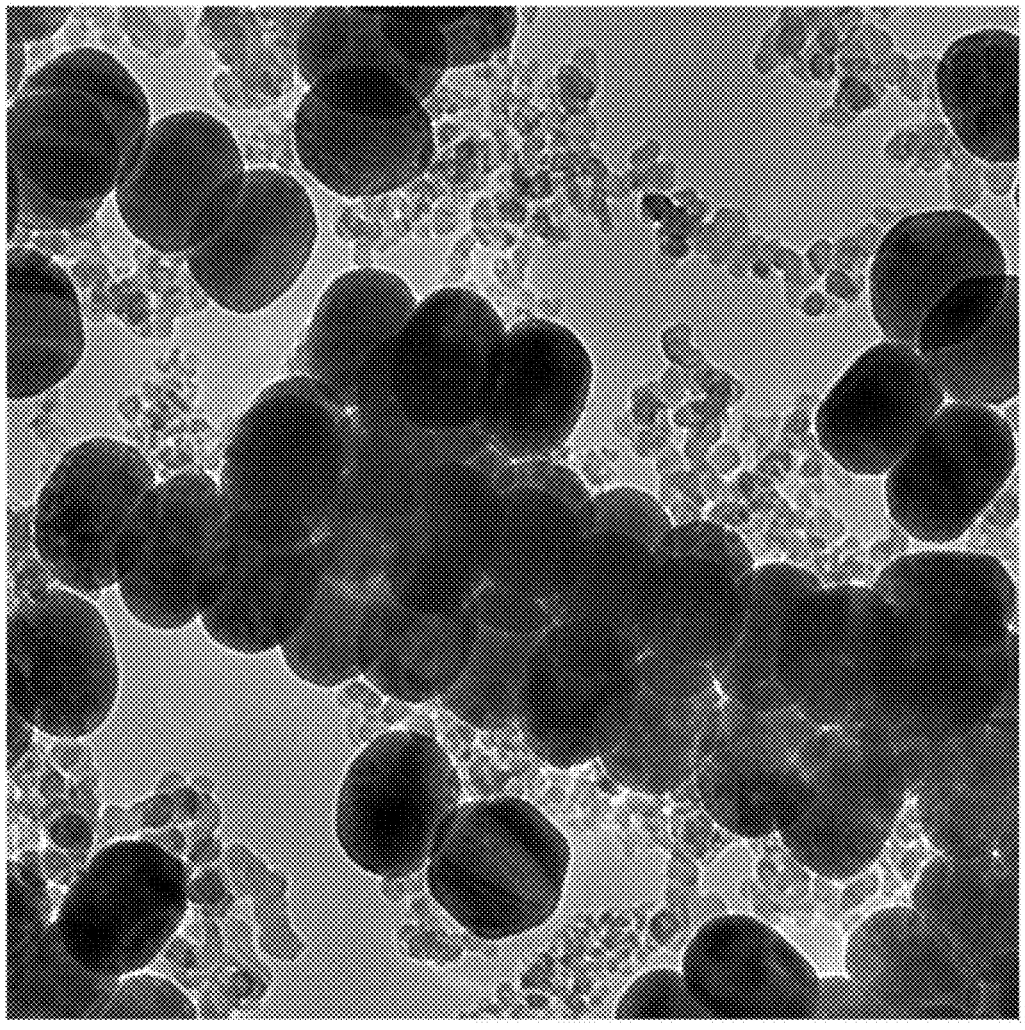
Figure 9I:
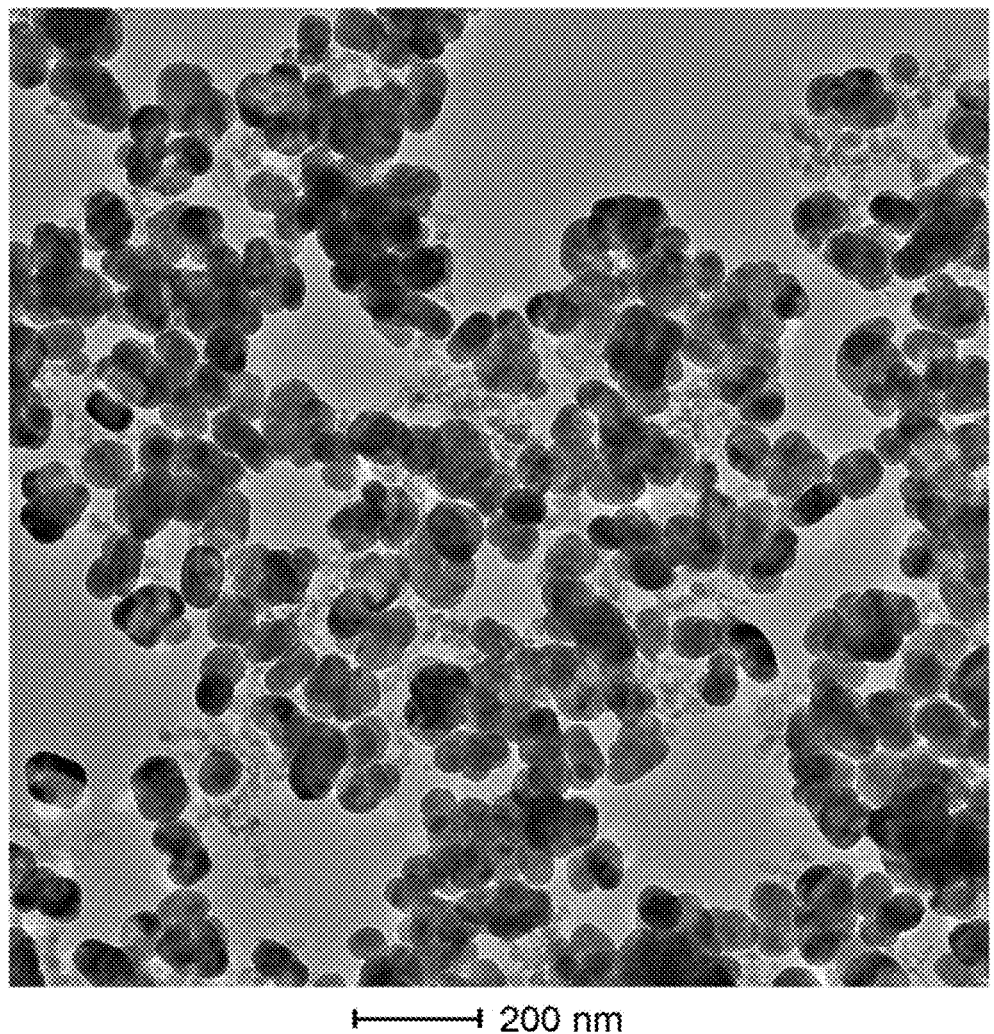
Figure 9J:
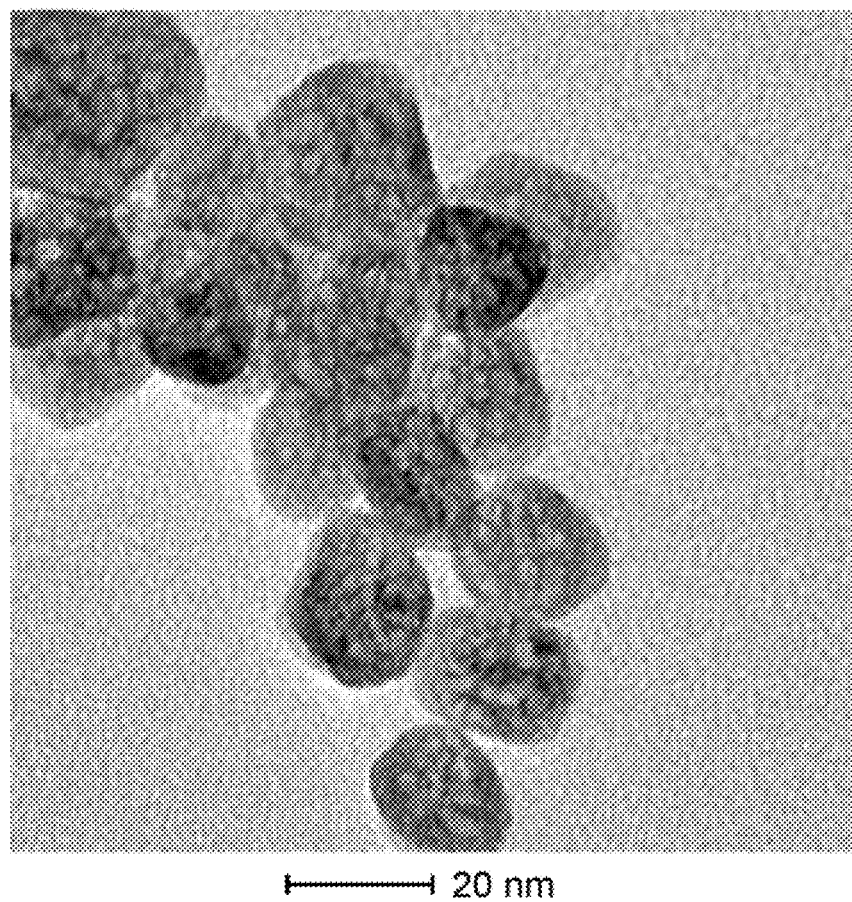

Further, $NaYF_4$ dielectric particles have been produced and isolated into dispersed particles with two size distributions of ~50 nm and ~150 nm, as shown in FIG. 9D. The procedure to generate these particles is the same as that listed above, except that the $YbCl_3$ stock solution was prepared by dissolving $Yb_2O_3$ in HCl. Further, $YbF_3$ dielectric particles have been produced and isolated into homogeneous particles of a size of 35 nm+/−5 nm, as shown in FIG. 9E. Generation of these particles was similar to that listed above, except that the concentrations of all the salts were halved (the PEI concentration remaining constant), and $YbCl_3$ was used instead of $YCl_3$. As such, two $YbCl_3$ stock solutions (0.1 M) were prepared; the first by dissolving $YbCl_3 \cdot 6H_2O$ in water and the second by dissolving $Yb_2O_3$ in concentrated hydrochloric acid. The remainder of the synthetic methodology remained the same. An optical emission spectrum from these $NaYF_4$ dielectric core particles, excited at 980 nm, is shown in FIG. 9F.

In another embodiment of the invention, $NaYbF_4$ dielectric particles have been fabricated with individual particles in the ~20-200 nm size range as shown in FIGS. 9G to 9J. These particles were generated through a thermal decomposition method based on the work of Boyer, J-C. et al. *Nano Lett.*, 2007, 7(3), 847-852 and Shan, J. et al. *Nanotechnology*, 2009, 20, 275603-275616, the entire contents of which are incorporated by reference. The particles were prepared by composing a slurry of NaTFA (2.5-4 mmol), 34 mL 1-octadecene, and 6 mL oleic acid, $Y(TFA)_3$, $Yb(TFA)_3$, and $Ln(TFA)_3$ (Ln=Tm) in given proportion totaling 2 mmol of trifluoroacetate salt. The slurry was heated under vigorous stirring to 125° C. in a 100 mL, 2-neck round bottom flask with magnetic stir bar and reflux condenser until full dissolution occurred and any residual water was removed through a vent needle. 6 mL trioctylphosphine or oleic acid was then added. The reaction apparatus was then transferred to a molten salt bath ($KNO_3$:$NaNO_3$; 50:50 by mol %) held at temperatures varying from 350-414° C. and held at temperature for 15-60 minutes. The reaction was then cooled to RT, poured into an equivalent volume of absolute ethanol, sonicated, vortexed, and centrifuged at 21 k rcf (approx. 14 k RPM) for 30 minutes. The resulting pellet was resuspended and centrifuged in similar fashion with hexanes, followed by two washes of 50:50; water:ethanol, and a final wash of absolute ethanol. The purified nanocrystals were then dried in air overnight.

FIGS. 10A-1 to 10A-7 show some of the various embodiments of the upconverter structures of the invention that can be designed: (1) a structure including upconverter (UC) molecules bound to a metal (gold) nanoparticle; (2) a structure including an UC-containing nanoparticle covered with metal nanoparticles, (3) a metal nanoparticle covered with an UC-containing nanocap; (4) an UC-containing nanoparticle covered with metal nanocap, (5) a metal nanoparticle covered with UC nanoshell, (6) an UC-containing nanoparticle covered with metal nanoshell, (7) an UC-containing nanoparticle covered with metal nanoshell with protective coating layer. The configurations (while shown in the FIGS. 10A-1 to 10A-7 series with UC-containing materials) would be applicable for enhancement for down converting materials. Moreover, in one embodiment of the invention, dielectric spacers (for examples silicates as discussed below) can be used with the structure of FIG. 10A-2 to space apart the particle type metallic structures. In another embodiment of the invention, dielectric spacers can be used with the structure of FIGS. 10A-4 and 10A-6 to space apart the metal layers, whether or not these layers are partial metal layers as in FIG. 10A-4 or continuous metal layers as in FIG. 10A-6. See FIGS. 10A-2, 10A-4 and 10A-6.

The plasmonic properties of various metallic structures, which have been investigated in the art and are suitable for the invention, include metallic nanoshells of spheroidal shapes [S. J. Norton and T. Vo-Dinh, "*Plasmonic Resonances of Nanoshells of Spheroidal Shape*", IEEE Trans. Nanotechnology, 6, 627-638 (2007)], oblate metal nanospheres [S. J. Norton, T. Vo-Dinh, "*Spectral bounds on plasmon resonances for Ag and Au prolate and oblate nanospheroids*", J. Nanophotonics, 2, 029501 (2008)], linear chains of metal nanospheres [S. J. Norton and T. Vo-Dinh, "*Optical response of linear chains of metal nanospheres and nanospheroids*", J. Opt. Soc. Amer., 25, 2767 (2008)], gold nanostars [C. G. Khoury and T. Vo-Dinh, "*Gold Nanostars for Surface-Enhanced Raman Scattering: Synthesis, Characterization and Applications*", J. Phys. Chem C, 112, 18849-18859 (2008)], nanoshell dimmers [C. G. Khoury, S. J. Norton, T. Vo-Dinh, "*Plasmonics of 3-D Nanoshell Dimers Using Multipole Expansion and Finite Element Method, ACS Nano*, 3, 2776-2788 (2009)], and multi-layer metallic nanoshells [S. J. Norton, T. Vo-Dinh, "*Plasmonics enhancement of a luminescent or Raman-active layer in a multilayered metallic nanoshell*", Applied Optics, 48, 5040-5049 (2009)]. The entire contents of each of the above noted references in this paragraph are incorporated herein by reference. In various embodiments of the invention, multi-layer metallic nanoshells discussed in this application have the potential capability to enhance electromagnetically two spectral regions. Accordingly, the metallic structures of the invention can be used in the upconverting mode to enhance both the excitation at wavelength $\lambda_1$ and the emission at wavelength $\lambda_2$ This feature also can be used in the down converting to enhance primarily the emission at wavelength $\lambda_2$ and potentially the excitation at wavelength $\lambda_1$.

Such metallic structures in various embodiments of the invention include conducting materials made for example of metals, or doped glasses or doped semiconductors. These conducting materials can be in the form of pure or nearly pure elemental metals, alloys of such elemental metals, or layers of the conducting materials regardless of the constituency. The conducting materials can (as noted above) include non-metallic materials as minor components which do not at the levels of incorporation make the composite material insulating.

Similarly, in various embodiments of the invention, the up or down converting materials can include at least one of a dielectric, a glass, or a semiconductor. The up or down converting materials can include an alloy of two or more dielectric materials, an alloy of two or more glasses, or an alloy of two or more semiconductors.

Accordingly, FIGS. 10A-1 to 10A-7 represent embodiments of the invention where the dielectric core is supplemented with a shell. The shell can include a metal layer of a prescribed thickness. The metal layer can include materials such as nickel, gold, iron, silver, palladium, platinum and copper and combinations thereof. The shell functions as a plasmonic shell where surface plasmons can form in the metal between the dielectric core and the outer environment acting as an exterior dielectric. The shell (as shown) may not be a complete shell. Partial metallic shells or metallic shells of varying thicknesses are also acceptable in the invention.

FIGS. 10B-1 to 10B-7 show yet other embodiments of upconversion structures that have a dielectric layer between the metal and the UC materials.

Figures 7, 12B:
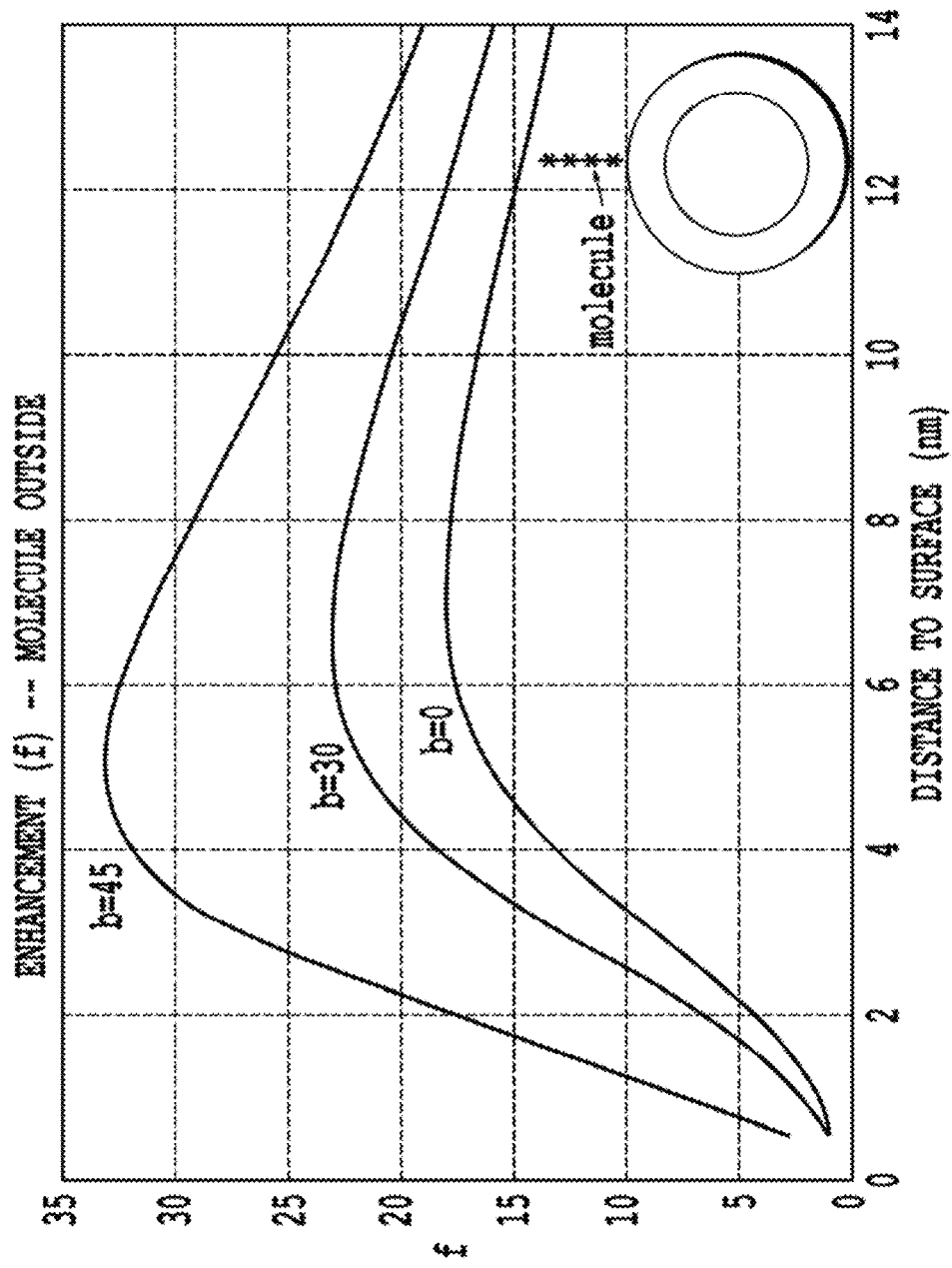
Figures 8, 12B:
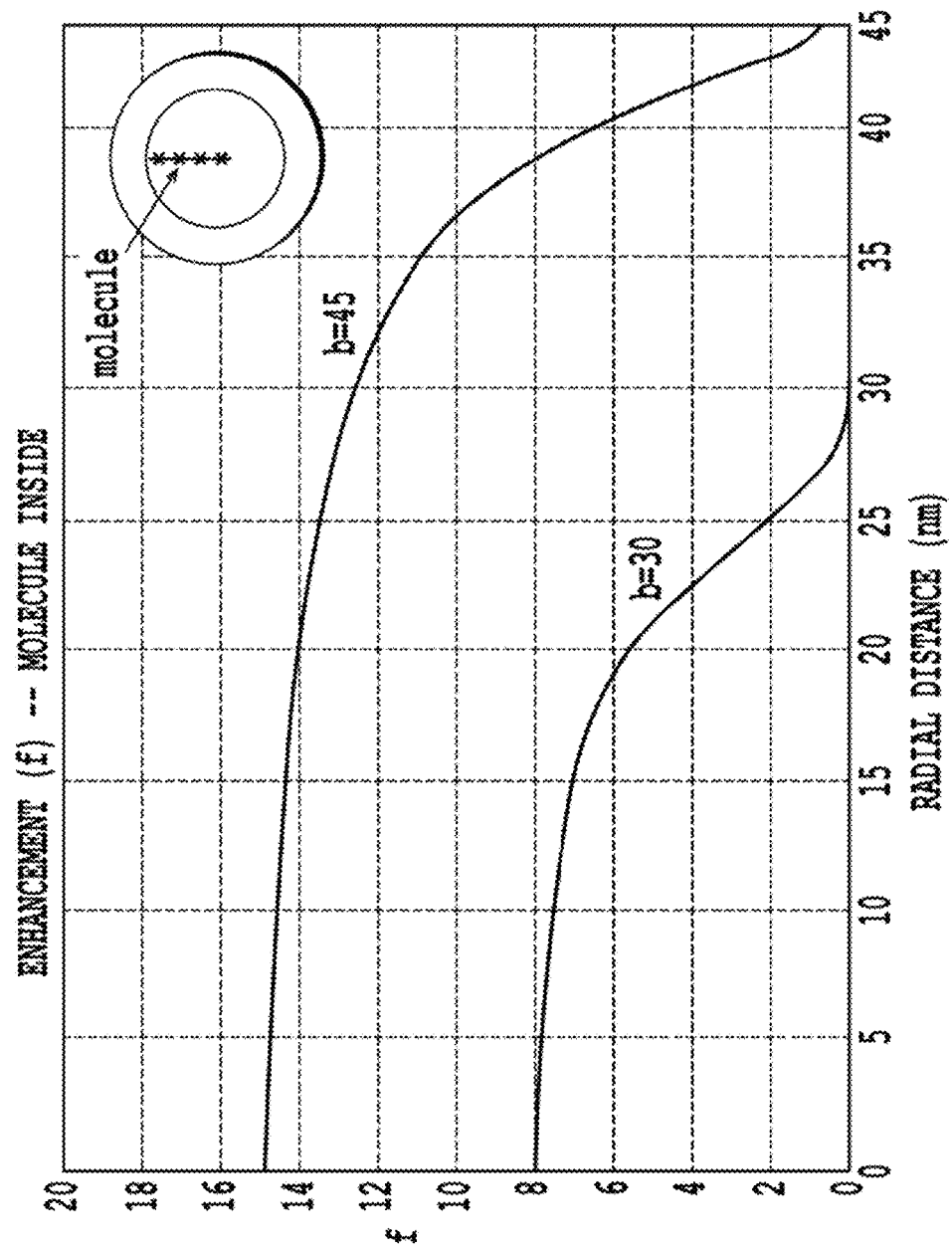
Figures 9, 12B:
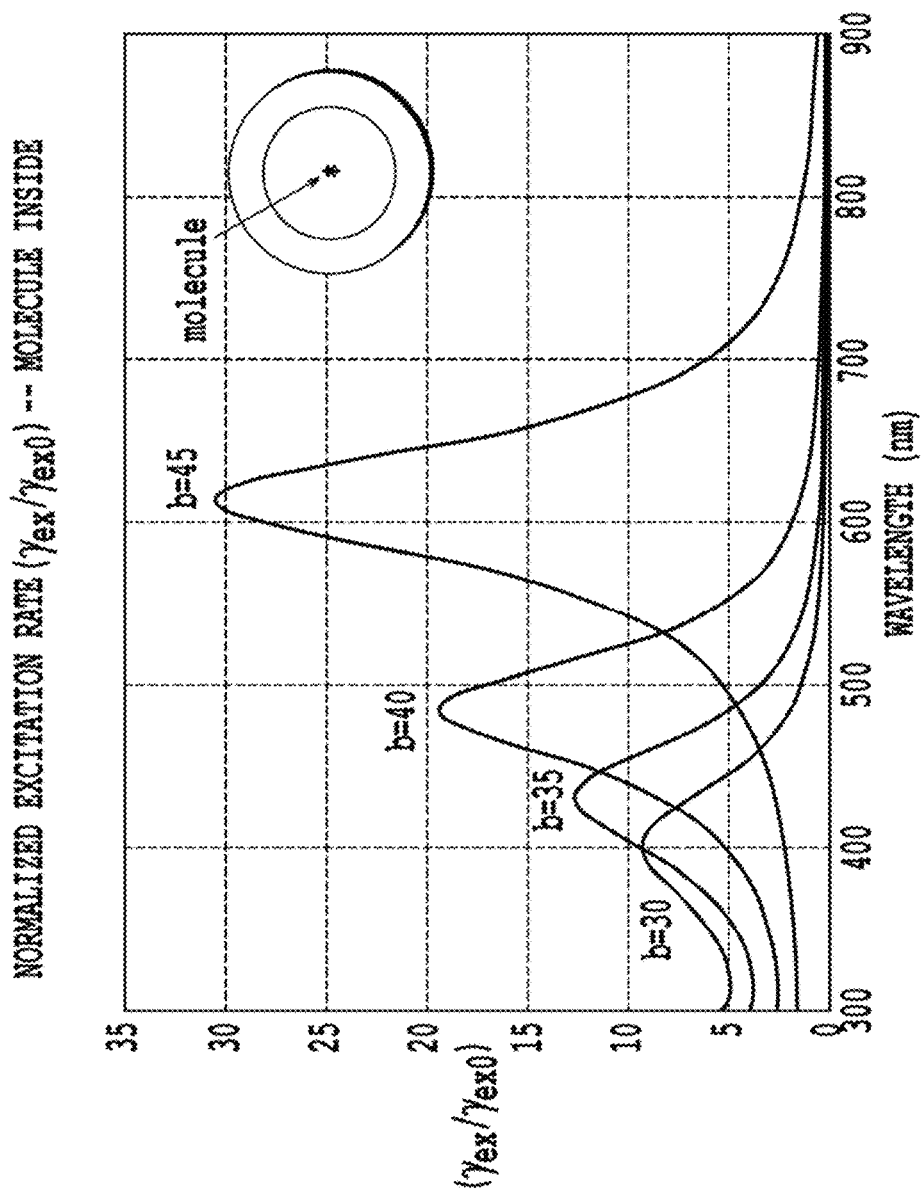
Figures 10, 12B:
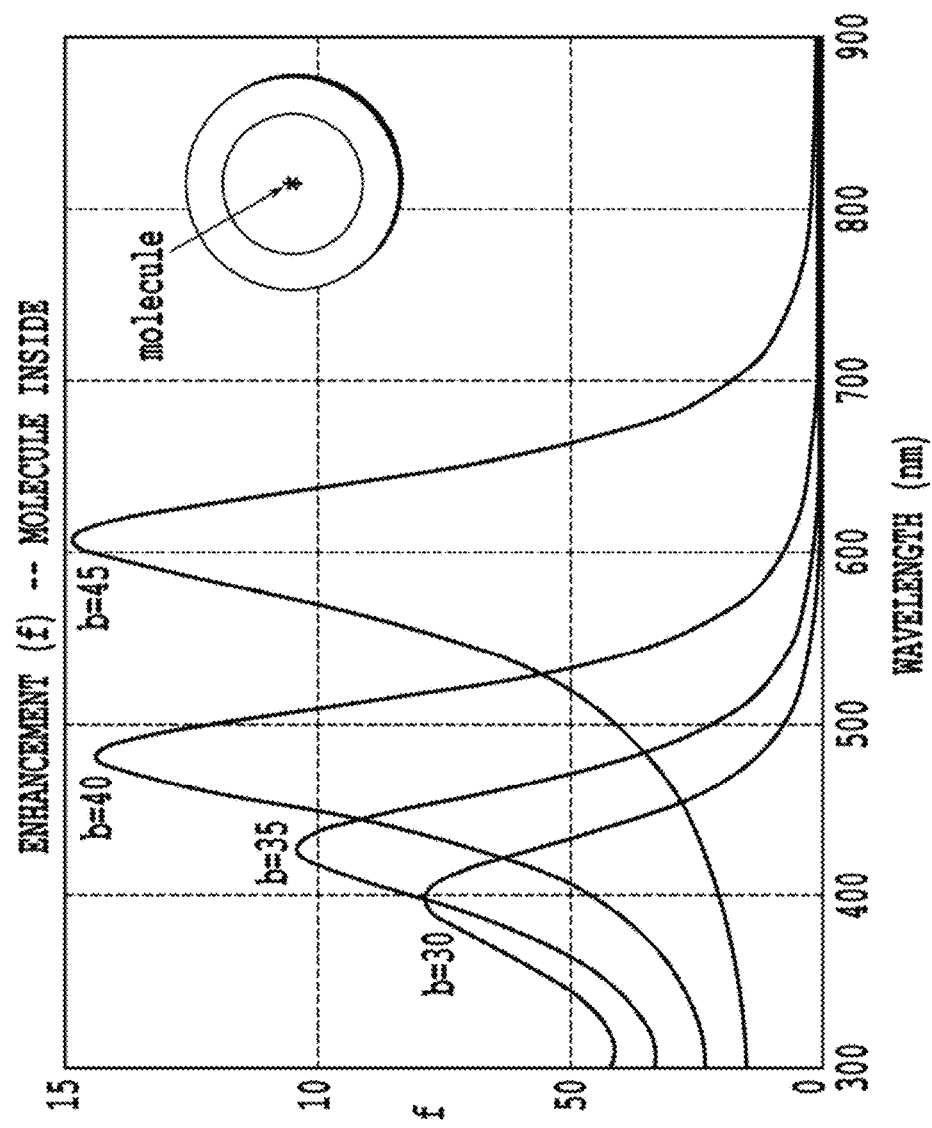

FIGS. 10C-1 to 10C-10 show still further embodiments of plasmonics-active nanostructures having upconverting (UC) materials that can be designed: (1) a metal nanoparticle, (2) an UC nanoparticle core covered with metal nanocap, (3) a spherical metal nanoshell covering an UC spheroid core, (4) an oblate metal nanoshell covering UC spheroid core, (5) a metal nanoparticle core covered with UC nanoshell, (6) a metal nanoshell with protective coating layer, (7) multi layer metal nanoshells covering an UC spheroid core, (8) multi-nanoparticle structures, (9) a metal nanocube and nanotriangle/nanoprism, and (10) a metal cylinder.

FIGS. 10D-1 to 10D-7 show yet other embodiments of plasmonics-active nanostructures having upconverting materials with linked photo-active (PA) molecules that can be designed. For example, for the case of psoralen (as the PA molecule), the length of the linker between the PA molecule and the UC material or the metal surface is tailored such that it is sufficiently long to allow the PA molecules to be active (attach to DNA) and short enough to allow efficient excitation of light from the UC to efficiently excite the PA molecules. FIGS. 10D-1 to 10D-7 show (1) PA molecules bound to an UC nanoparticle, (2) an UC material-containing a nanoparticle covered with metal nanoparticles, (3) a metal nanoparticle covered with UC material nanocap, (d) an UC material-containing nanoparticle covered with metal nanocap, (5) a metal nanoparticle covered with an UC material nanoshell, (6) an UC material-containing nanoparticle covered with metal nanoshell, (7) an UC material-containing nanoparticle covered with metal nanoshell with protective coating layer.

IR frequencies have significant penetration into the human body and permit the primary excitation $\lambda_1$ to penetrate subcutaneously into the body tissue. Upon their penetration into the body tissue, the dielectric core of the invention interacts with the incident radiation $\lambda_1$ to generate the secondary light $\lambda_2$ as described above. Therefore, permitting the generation in situ to the body of a wavelength $\lambda_2$ which may be in the UV or visible range is appropriate for activations of psoralen or other types of drugs known to be activated by a UV or visible light source.

Since the dielectric cores of this invention have the ability to be selectively stimulated by discrete wavelengths of $\lambda_1$ and produce discrete emission wavelengths at $\lambda_2$, the medial applications can be manipulated so that a number of dual purpose diagnostic/treatment tools can be produced.

For example, in one embodiment of the invention, a material such as the above-described co-doped yttrium oxide is introduced into the body. Yttrium oxide as a host is known to be a down converter from X-ray radiation. In this particular example, X-ray incident radiation on the yttrium oxide will produce UV light which would in turn be used to activate drugs such as psoralen for the treatment of cancer. Meanwhile, the co-doped yttrium oxide as a upconverter could be used where the NIR excitation could produce an emission at a wavelength that was different than that produced from the X-ray down conversion radiation. In this manner, the progression of the yttrium oxide (with drug attached as the recipient 4) into a target organ to be treated could be monitored using the NIR light as the excitation source and collecting the visible light in some type of CCD camera. Once the yttrium oxide particles were absorbed into the respective tumor cells for treatment, at that point in time, X-ray radiation could be initiated and thereby activating the psoralen tagged yttrium oxide and providing an effective means for treating the tumor cell.

Figure 23:
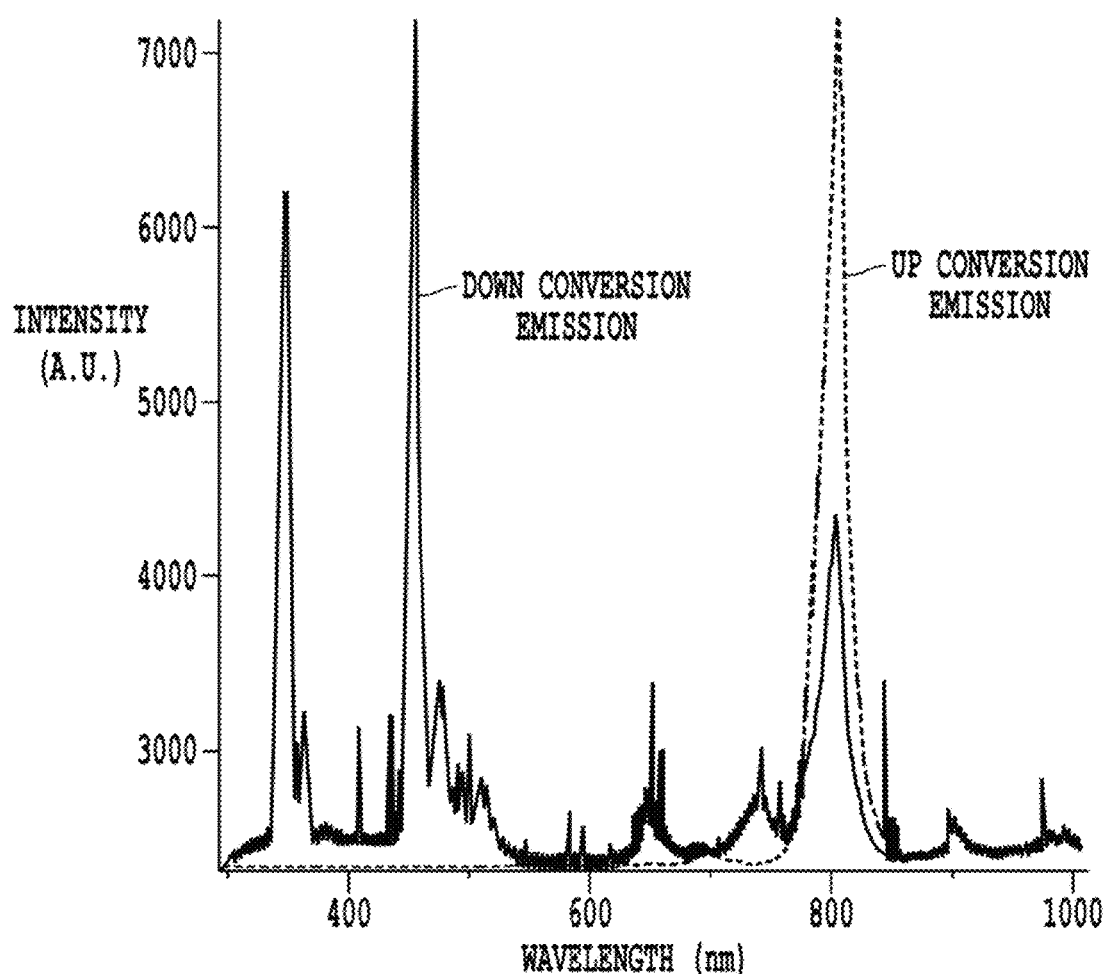
FIG. 23 is a depiction of both down conversion and up conversion emission from a thulium doped nanoparticle (NaYbF$_4$; 3% Tm).
Figure 24:
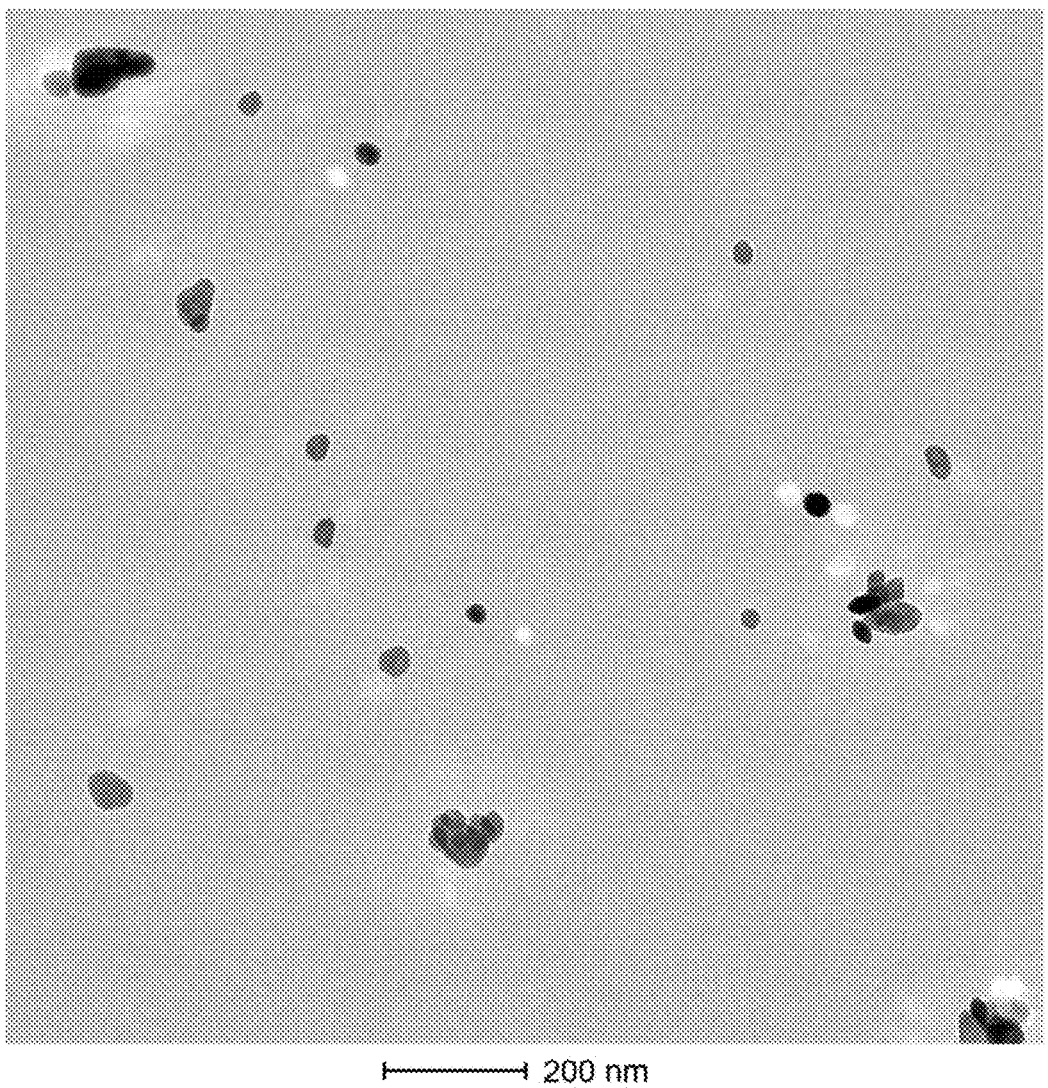
FIG. 24 is a micrograph of a representative 35 nm PEI Coated YbF$_3$; Tm (2%) particle.

FIG. 23 is a depiction of down conversion and up conversion emission from a NaYbF$_3$; Tm nanoparticle. The up conversion lines were excited at 980 nm. The down conversion lines were excited with 320 kV x-rays. FIG. 24 is a micrograph of a representative 35 nm PEI Coated YbF$_3$; Tm (2%) particle.

Alternatively, in another dual purpose diagnostic/treatment example, one can choose a system where the NIR wavelength is specifically tuned for diagnostics as explained above while excitation with a separate wavelength of NIR can be used to produce UV light (through another upconversion channel) that would itself activate a recipient molecule (e.g. psoralen for cancer treatment) without the necessity of X-ray and down conversion activation. This feature then permits one to use a drug which either would be acceptable for deep body penetration through X-ray radiation or would be acceptable for more shallow body penetration through NIR radiation to treat cancer cells that were located in different parts of the body relative to the surface of the body. Moreover, fiber optics could be used to direct the NIR light (through a surgical incision for example) directly to a target. By locally activating the psoralen and by the known autovaccine effect, this initially local NIR activated treatment may be effective at treating cancer outside the NIR irradiated area.

Examples of such dual use drugs which all exhibit NIR activation and upconversion for the purpose of imaging and/or to excite psoralen would include the dual dopants of yttrium oxide, the dual dopants of neodymium oxide, triply doped ytterbium thulium neodymium oxides, the dual dopants of sodium yttrium fluoride, and the dual dopants of lanthanum fluoride. For example, by providing a ytterbium-thulium doped yttrium oxide containing 95% verses 5% dopant concentration with another lanthanide, one will produce diagnostic/treatment functions through pure NIR excitation, having the drug treatment excitable at 980 nanometers verses the diagnostic imaging process excitable at 808 nanometers with different emissions coming from each excitation process.

In one embodiment, the upconverter structures of the invention are complexed with the X-ray down converting particles or other energy modulation agents permitting for example X-ray irradiation to also assist in this process. In one embodiment, the X-ray down converting particles or other energy modulation agents or metallic structures described herein permit X-ray irradiation to be used alone or in combination with the up converting particles.

Gold Nanoshell Preparations with Dielectric Cores:

The present invention can utilize a wide variety of synthesized metallic-coated core-shell nanoparticles prepared from a number of wet chemical procedures. The techniques described below are provided for the purposes of illustration and not for the purpose of limiting the invention to these particular techniques. In the present invention, gold nanoshells can be prepared using the method or similar methods described in Hirsch L R, Stafford R J, Bankson J A, Sershen S R, Rivera B, Price R E, Hazle J D, Halas N J, West J L (2003) *Nanoshell-mediated near infrared thermal therapy of tumors under MR Guidance*. Proc Natl Acad Sci 100:13549-13554, the entire contents of which are incorporated herein by reference. This method uses a mechanism involving nucleation and then successive growth of gold nanoparticles around a dielectric core. Dielectric nanoparticles of sizes less than for example 100, 200, or 300 nm, as well as larger sizes, used for the core of the nanoshells, can then be monodispersed in a solution of 1% APTES in EtOH. The gold "seed" colloid can then be synthesized using the Frens method (see details below) and deposited onto the surface of the dielectric nanoparticles via molecular linkage of silyl terminated amine groups. The gold "seed" covers the aminated nanoparticle surface, first as a discontinuous gold metal layer and gradually growing forming a continuous gold shell.

Additionally, various photochemical methods have been reported for the fabrication of gold nanoparticles and gold films [Refs: A. Pal, T. Pal, D. L. Stokes, and T. Vo-Dinh, "*Photochemically prepared gold nanoparticles: A substrate for surface-enhanced Raman scattering*", Current Science, 84, 1342-1346 (2003; A. Pal, D. L. Stokes and T. Vo-Dinh, "*Photochemically Prepared Gold Metal film in a Carbohydrate-based Polymer: a Practical Solid substrate for Surface-enhanced Raman Scattering*, Current Science, 87, 486-491 (2004)]. These articles in their entirety are incorporated herein by reference. The present invention in various embodiments utilizes a class of core-shell nanoparticles based on rare earth oxide (REO) cores having noble metal shells. A number of nanoparticle/metal shell systems can be fabricated using the photochemical procedures described below or other suitably modified procedures.

The REO core material is a well-suited core material for the present invention due to doping for either upconversion- or downconversion-based fluorescence, and due to the fact that the plasmonically-active metal shells can be easily functionalized with targeting peptides, fluorophores, or SERS-active molecules using well-established techniques. For the purpose of illustration, the design and fabrication of one such hybrid nanoparticle system is described below where the nanoparticle system includes an yttrium oxide (Y$_2$O$_3$) core, a gold (Au) shell, and a short arginine and lysine-rich peptide, e.g., transactivator of transcription (TAT) residues 49-57, functionalized with various fluorescent dyes using N-hydroxysuccinimide (NHS) coupling chemistry. This peptide and similar molecules can show greatly enhanced cellular uptake and nuclear localization of DNA, nanoparticles, liposomes, peptides and proteins. Further, this particular portion of the TAT sequence has been shown to be non-toxic, making the resulting fluorescently-labeled nanoparticles potentially suitable for in vivo imaging applications.

Materials:

Yttrium oxide nanoparticles (e.g., 99.9% purity, 32-36 nm average diameter, cubic crystal structure) were obtained from Nanostructured and Amorphous Materials, Inc. (Houston, Tex.). Tri-arginine (H-Arg-Arg-Arg-OH) acetate was obtained from Bachem (Torrance, Calif.), and gold tribromide ($AuBr_3$) was obtained from Alfa Aesar (Ward Hill, Mass.). Dimethyl sulfoxide (DMSO) was purchased from CalBioChem (La Jolla, Calif.) and was used as received. A cysteine-modified version of the TAT peptide (residues 49-57, sequence Arg-Lys-Lys-Arg-Arg-Arg-Gln-Arg-Arg-Cys-$CONH_2$, molecular weight 1442 g/mol, hereafter referred to as "TAT") was obtained from SynBioSci (Livermore, Calif.). Succinimidyl-[4-(psoralen-8-yloxy)] butyrate (SPB) was obtained from Pierce (Rockford, Ill.), and Marina Blue, Alexa 350 and Alexa 546 NHS esters were obtained from Invitrogen (Carlsbad, Calif.). Ultrapure 18.2 MΩ deionized (DI) water purified with a Millipore Synergy filtration system (Millipore, Billerica, Mass.) was used to make all solutions.

Yttrium Oxide Dispersion:

Tip sonication was used to disperse autoclaved $Y_2O_3$ nanoparticles at 10 mg/mL in 10 mM tri-arginine solution which had been pre-filtered at 0.22 microns. Following moderate mixing in a sealed, sterile container on a stir plate for 24 hours to allow tri-arginine attachment and improved $Y_2O_3$ dispersion, the solution was centrifuged at 8200 relative centrifugal force (RCF) to remove fused particles and large aggregates.

Gold Shell Formation:

Supernatant from the initial $Y_2O_3$ dispersion was diluted 1:1 (v/v) with 5.7 mM $AuBr_3$ dissolved in sterile DI water and pre-filtered at 0.22 microns, then exposed to high-intensity fluorescent light (Commercial Electric, Model 926) for 16 hours in a sealed, sterile glass container with moderate mixing. During the time course of this photochemical process, the reddish-brown $AuBr_3$ solution turned yellow immediately after addition of the $Y_2O_3$ in tri-arginine; became clear and visually colorless; then developed an intense purple color as Au shells formed on the $Y_2O_3$ cores. In the absence of the $Y_2O_3$ cores, neither the intense purple color associated with plasmonic absorption by gold nanoshells nor the deep red color associated with solid gold nanoparticles appears. Use of heat rather than light in the presence of $Y_2O_3$ particles tends to produce a large number of solid gold nanoparticles rather than or in addition to core-shell structures, as evidenced by strong absorption at ~530 nm.

Particle Functionalization with TAT:

Gold-coated $Y_2O_3$ nanoparticles were centrifuged at 16 k RCF for 15 minutes, and the pellet was re-dispersed in a 50% volume of sterile DI water by a short tip sonication. The particles were further purified by two additional centrifugations at 16 k RCF for 15 minutes each, with redispersion in a 100% volume of sterile DI water following the second centrifugation and final redispersion in a 100% volume of 1 mg/mL (0.7 mM) TAT peptide dissolved in sterile DI water and pre-filtered at 0.22 microns.

This solution was vigorously mixed at room temperature for one hour to allow thiol anchoring to the gold shell via the c-terminal cysteine residue. Variations in the TAT concentration, temperature and reaction time can all change the extent of surface coverage and the potential for further functionalization.

Peptide Functionalization with Dye Molecules:

The TAT-functionalized, gold-coated $Y_2O_3$ particles were purified by triplicate centrifugation at 16 k RCF, with the first two re-dispersions in sterile DI water and the final re-dispersion in sterile 100 mM bicarbonate buffer at pH 9.0. Each NHS ester (SPB, Alexa 350, Marina Blue and Alexa 546) was dissolved at 10 mg/mL in dimethyl sulfoxide (DMSO), and 100 microliters of a given NHS-functionalized dye were added to a 1 mL aliquot of TAT-functionalized, gold-coated $Y_2O_3$. The solutions were reacted for one hour at room temperature in the dark with vigorous mixing to allow attachment of dye molecules to primary amines along the TAT peptide (such as the attachment of N terminus and the lysine side chains).

The psoralen-functionalized nanoparticles were centrifugally cleaned using a 1:1 volume of DMSO in water to remove any residual SPB crystals, then all dye-functionalized core-shell nanoparticles were purified by triplicate centrifugation at 16 k RCF for 15 minutes. Each centrifugation step was followed by re-dispersion in a 100% volume of sterile DI water. Presuming removal of 95+% of non-attached dye molecules during each centrifugation step, no more than 0.01% of the unbound dye is estimated to remain in the final solution.

Figure 10E:
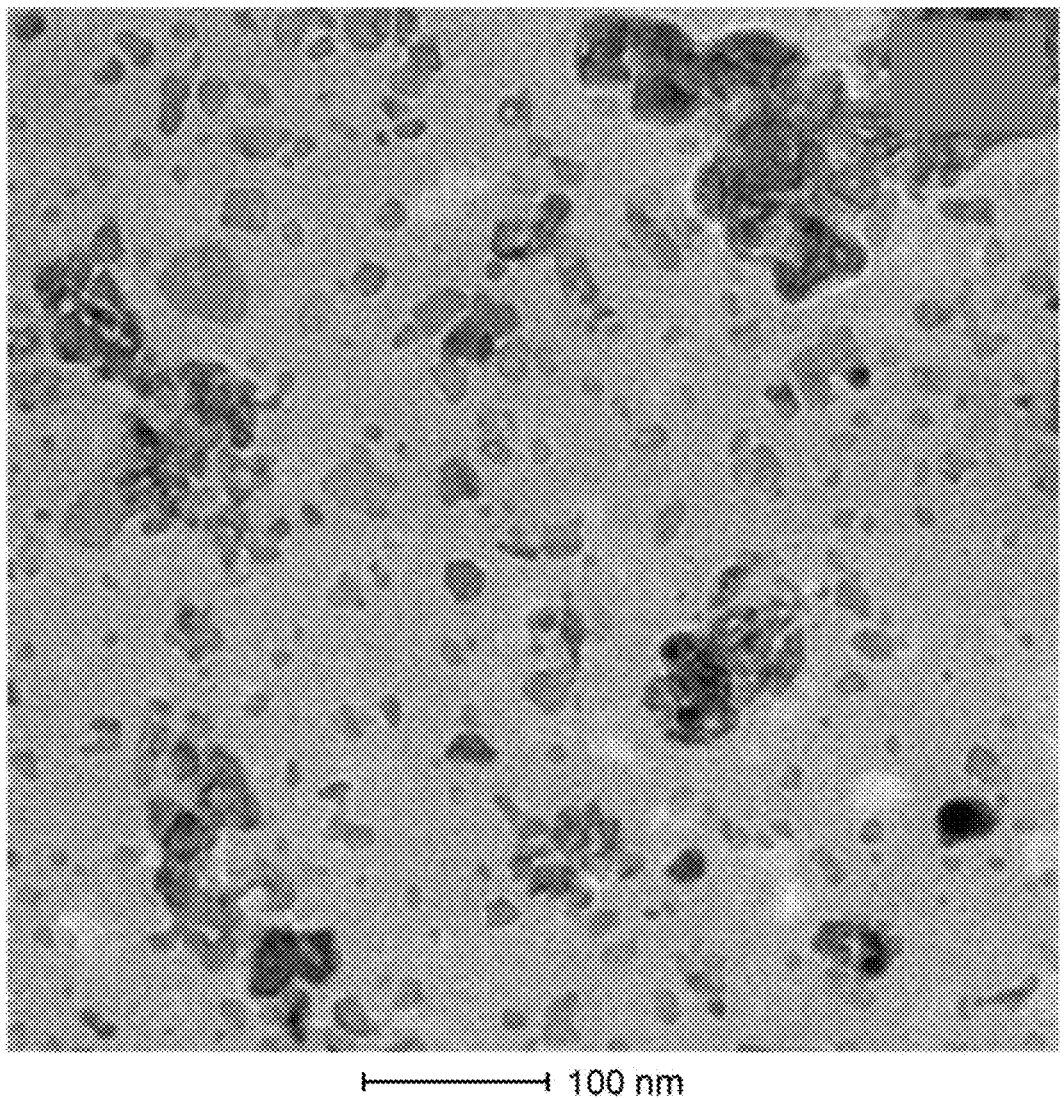
FIG. 10E is a TEM micrograph of uncoated Y$_2$O$_3$ nanoparticles.
Figure 10F:
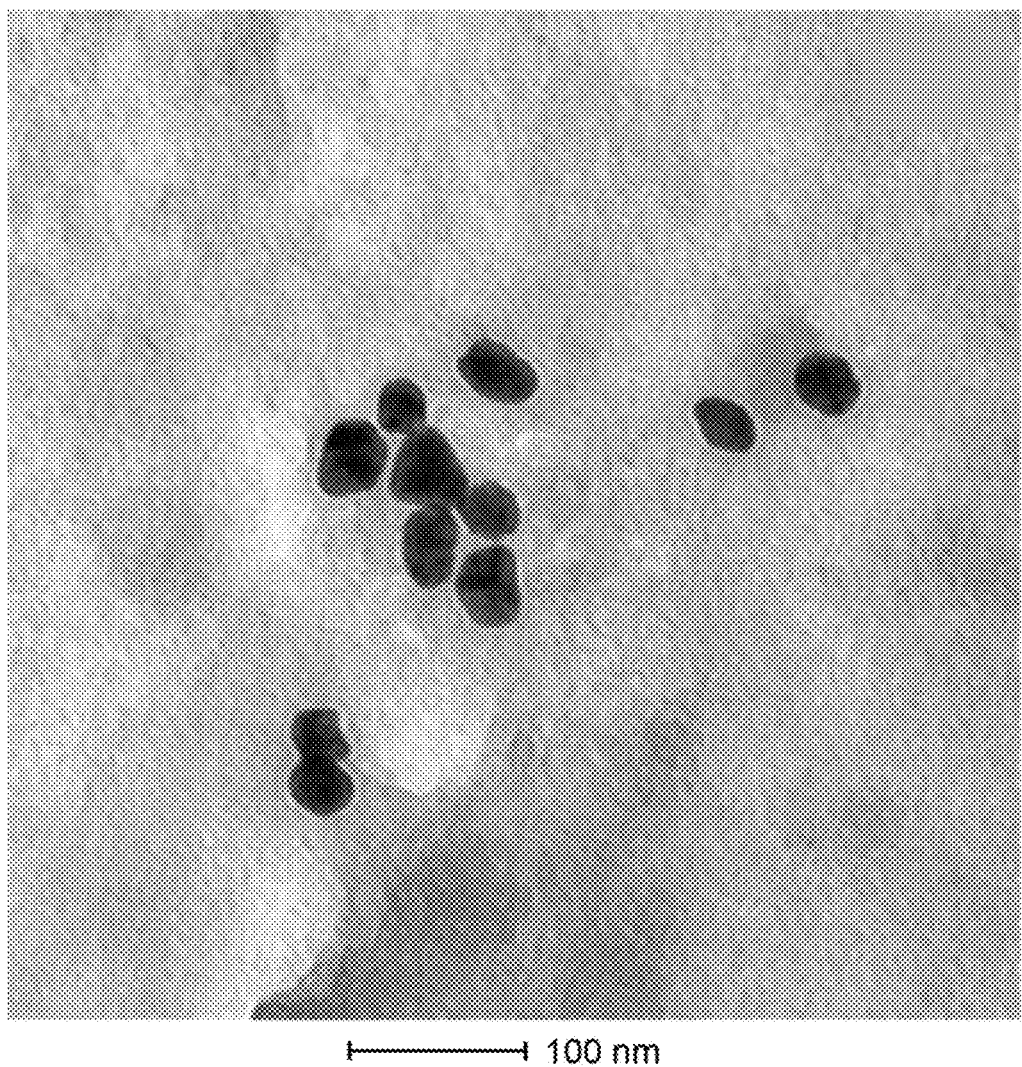
FIG. 10F is a TEM micrograph of gold coated Y$_2$O$_3$ nanoparticles of the invention.

Nanoparticle Characterization:

Transmission electron microscopy (TEM) provides additional evidence for the presence of gold-coated $Y_2O_3$ particles. FIG. 10E, for example, shows a representative TEM image of as purchased $Y_2O_3$ nanoparticles. The particles are quite polydisperse, but exhibit an average diameter of approximately 35 nm. FIG. 10F shows similar images for $Y_2O_3$ particles coated with a gold shell using the synthetic procedure described above. Like the underlying $Y_2O_3$ cores, the gold-coated yttrium oxide particles are somewhat polydisperse with an average diameter of approximately 50 nm.

Figure 10G:
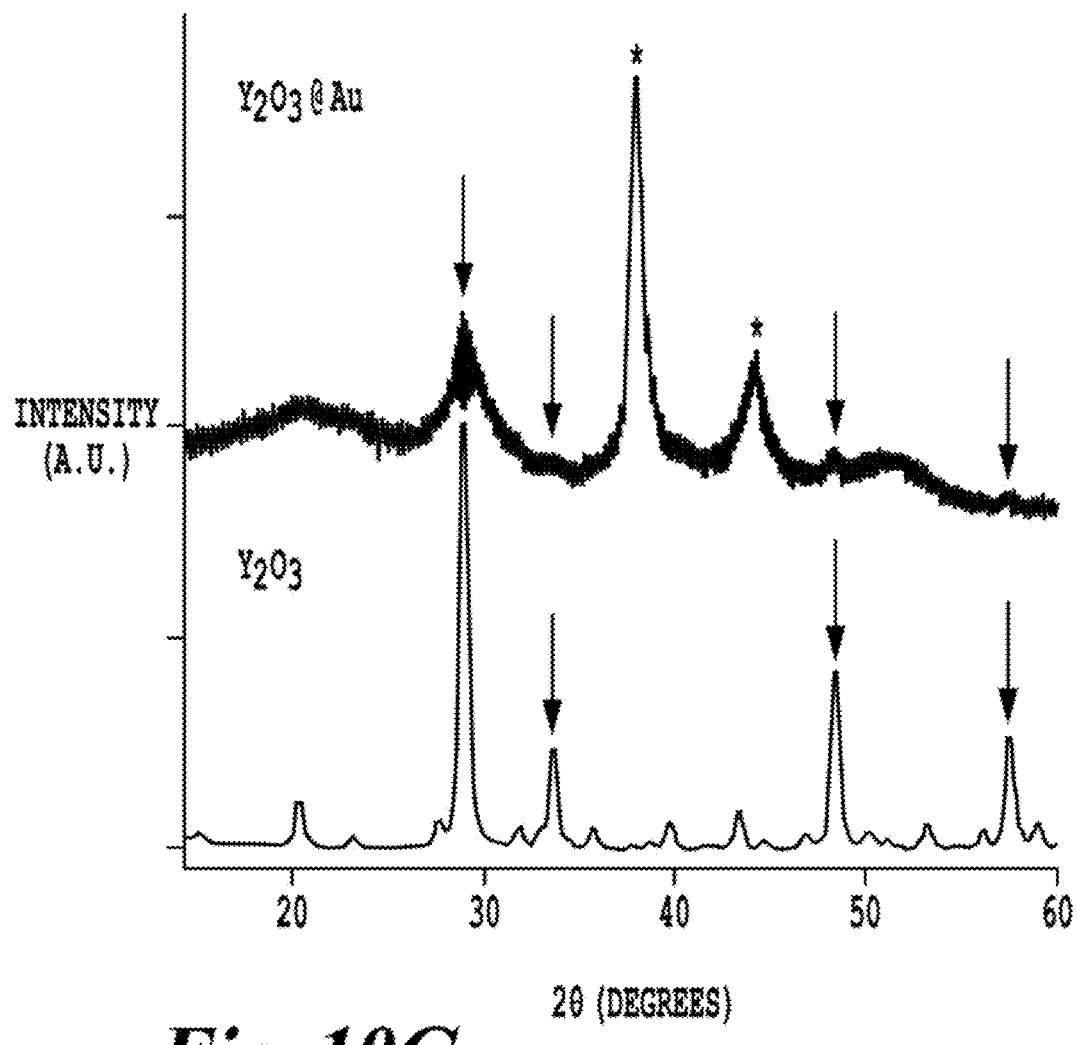
FIG. 10G is X-ray diffraction data from gold coated Y$_2$O$_3$ nanoparticles of the invention.

Perhaps the most conclusive demonstration that these nanoparticles are in fact gold-coated $Y_2O_3$ comes from comparison of X-ray diffraction data (XRD). FIG. 10G shows diffractograms for both the initial cubic $Y_2O_3$ nanoparticles (lower trace) and the final gold-coated core-shell particles (upper trace). Strong peaks at 2θ=29, 33.7, 48.5 and 57.5 degrees in the lower trace are indicative of cubic $Y_2O_3$. The most pronounced features in the upper trace are two gold-associated peaks at 2θ=38.2 and 44.4 degrees. In addition, the four strongest cubic $Y_2O_3$ peaks at 2θ=29, 33.7, 48.5 and 57.5 degrees are also visibly superimposed on the baseline diffractogram from the gold nanoshells. The reason for the broadening of the $Y_2O_3$ peak at 2θ=29 degrees is not definite, but may be a result of gold-$Y_2O_3$ interactions or, alternatively, the preferential size-selection of small $Y_2O_3$ particles during the 8200 RCF centrifugation used to remove large $Y_2O_3$ particles and aggregates.

Gold Colloidal Nanoparticles:

In various embodiments of the present invention, gold nanoparticles without a dielectric core are used in the medium being irradiated to enhance either the intensity of the initiation energy (i.e., the primary source: for example an IR laser for upconversion or an xray beam for down conversion) or to enhance the light generated from the upconverting or down converting nanoparticles). The techniques described below for the fabrication of metal nanoparticles with and without cores and with and without additional layers and linkageas are provided for the purposes of illustration and not for the purpose of limiting the invention to these particular techniques. Indeed, the present invention can utilize a wide variety of synthesized metallic, multilayer core-shell nanoparticles prepared from a number of wet chemical procedures. Exemplary parameters and procedures for producing these nanoparticles systems are described below. Starting materials included ultrapure water (deionized), $HAuCl_4*3H_2O$, $AgNO_3$, $Y_2O_3$, NaOH, $NH_4OH$, sodium citrate, hydroxylamine hydrochloride, hydrazine monohydrate, sodium borohydride, aminopropyltrimethoxy silane (APTMS), sodium silicate, tetraethyl orthosilicate (TEOS), methanol, ethanol, isopropanol, oleic_acid, and oleylamine.

a. Synthesis of Gold Nanoparticles

The Frens method (see G. Frens, Nat. Phys. Sci. 241 (1973) 20, the entire contents of which are incorporated herein by reference) can be used to synthesize gold nanoparticles. In this process, $5.0 \times 10^{-6}$ mol of $HAuCl_4$ was dissolved in 19 mL of deionized water. The resulting solution was faintly yellow. The solution was heated and vigorously stirred in a rotary evaporator for 45 minutes. One mL of 0.5% sodium citrate was added, and the solution was stirred for an additional 30 minutes. Addition of sodium citrate has multiple purposes. First, citrate acts as a reducing agent. Second, citrate ions that adsorb onto the gold nanoparticles introduce surface charge that stabilizes the particles through charge repulsion, thus preventing nanocluster formation.

b. Synthesis of Gold Nanoparticles Having 15-nm Diameter

Figure 10H:
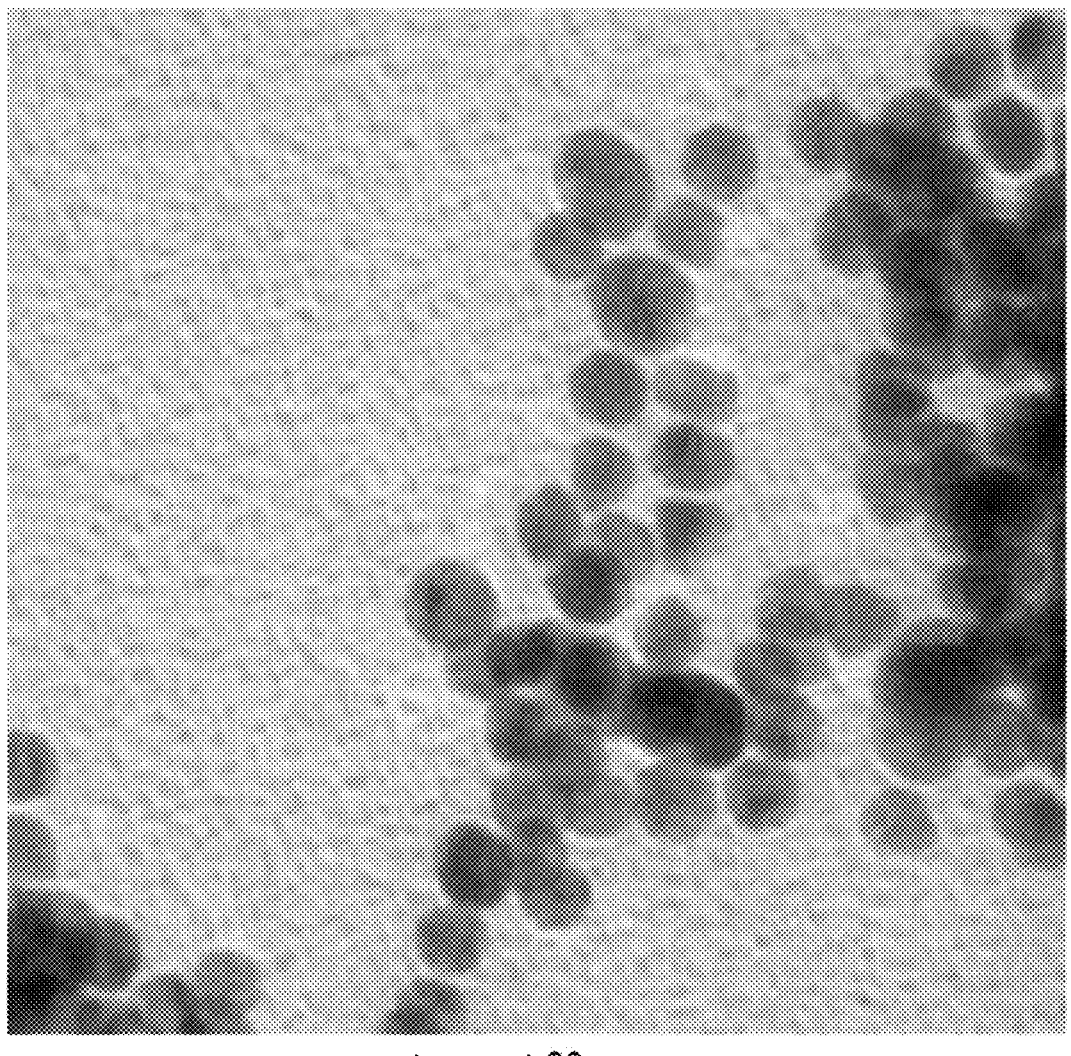
FIG. 10H is a TEM micrograph of 15-nm gold nanoparticles prepared according to one embodiment of the present invention using the citrate reduction technique.

Two mL of 1% gold chloride in 90 mL DI water was heated to 80° C. for 15 minutes, then 80 mg sodium citrate in 10 ml DI water was added. The solution was boiled and vigorously stirred for 30 minutes. FIG. 10H shows pictures of ~15-nm gold nanoparticles prepared using citrate reduction.

c. Synthesis of 30-nm Gold Nanoparticles

Figure 10I:
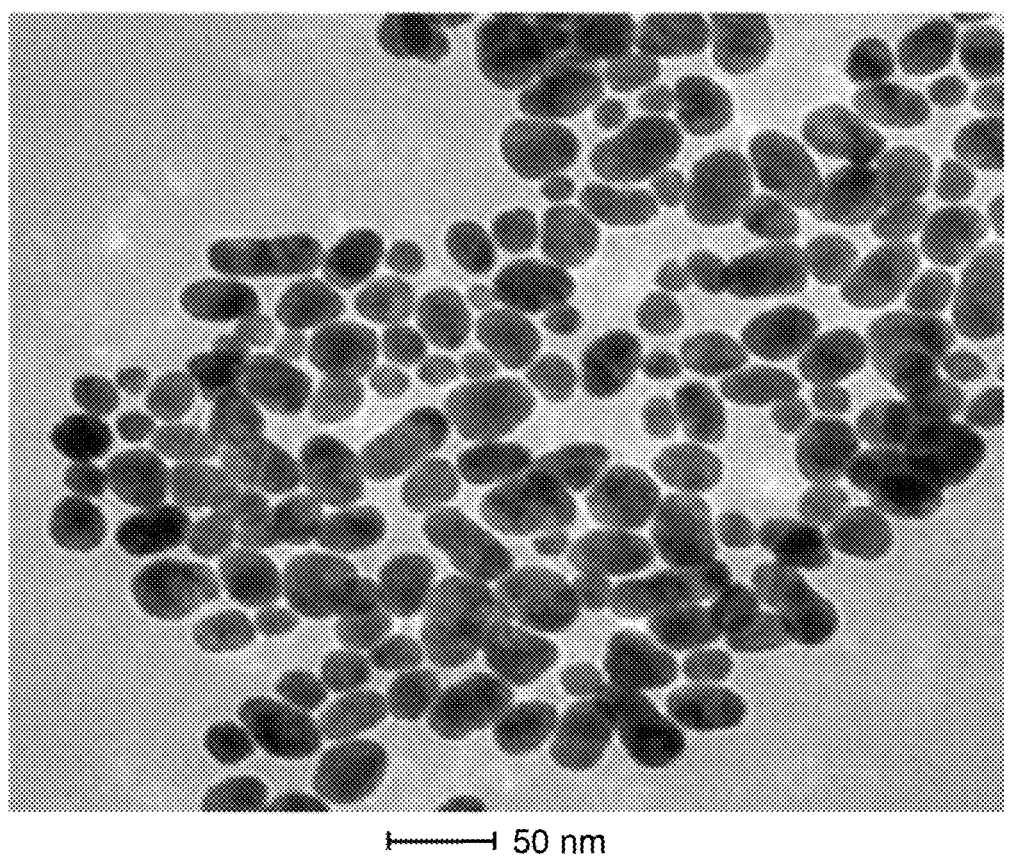
FIG. 10I is a TEM micrograph of 30-nm gold nanoparticles prepared according to one embodiment of the present invention using the citrate reduction technique.

Two mL of 1% $HAuCl_4$ solution in a 100-mL round-bottom flask were mixed with 20 mg of sodium citrate, then boiled and vigorously stirred for 30 minutes. FIG. 10I shows TEM images of 30-nm gold nanoparticles prepared using the citrate reduction technique.

d. Synthesis of 60-nm Gold Nanoparticles

Figure 10J:
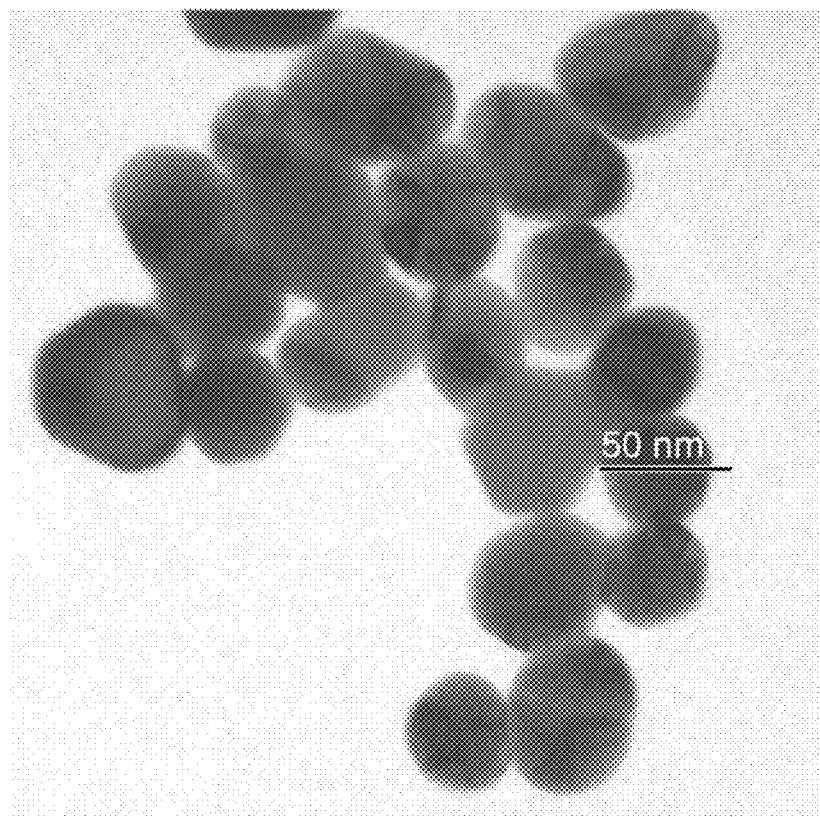
FIG. 10J is a TEM micrograph of 60-nm gold nanoparticles prepared according to one embodiment of the present invention using the citrate reduction technique.
Figure 10K:
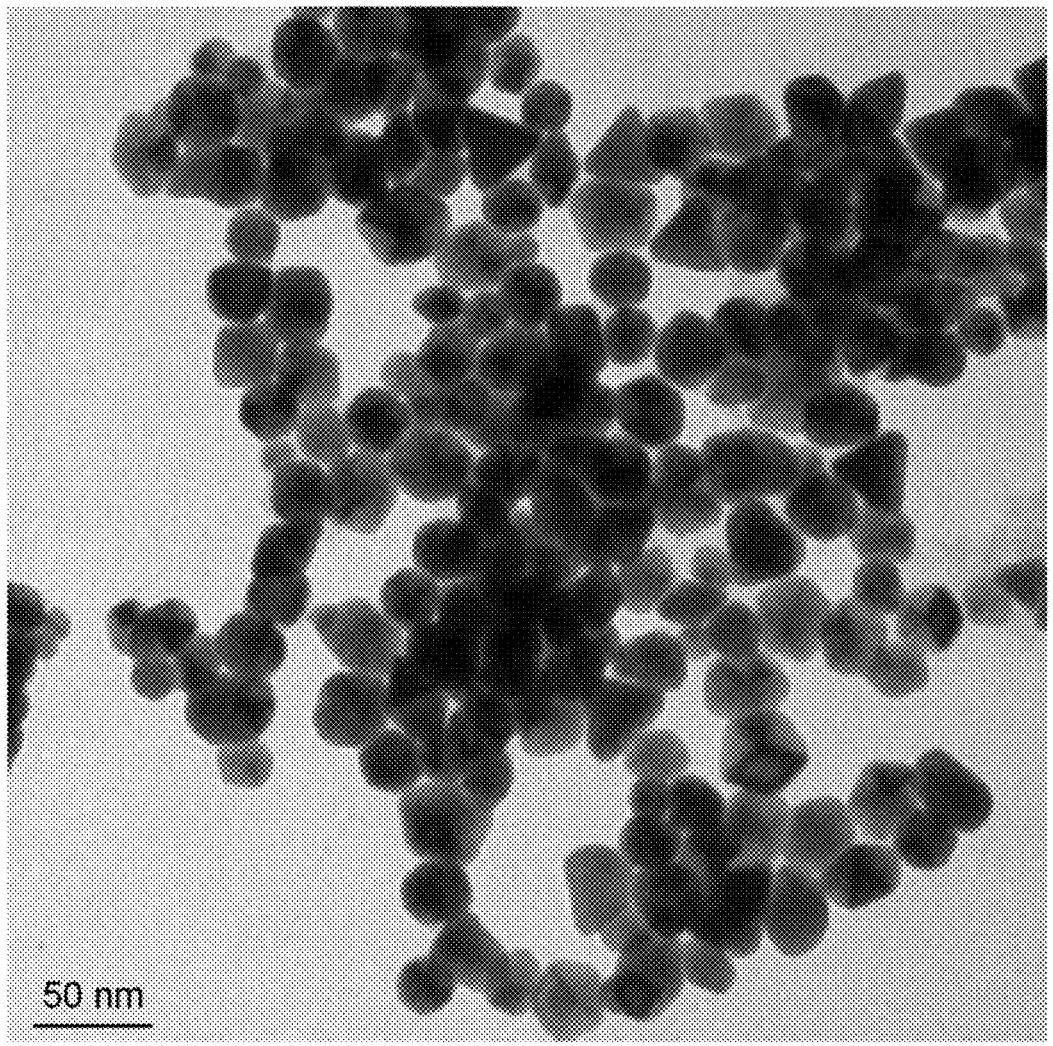
FIG. 10K is a TEM micrograph of 30-nm gold nanoparticles prepared according to one embodiment of the present invention using the hydrazine monohydrate reduction technique.

Two mL of 1% $HAuCl_4$ in 100 mL of water were mixed with 10 mg of sodium citrate. The solution was boiled and vigorously stirred for 30 minutes. FIG. 10J shows TEM pictures of 60-nm gold nanoparticles prepared using the citrate reduction technique.

e. Use of Hydrazine Monohydrate as a Reducing Agent:

100 microliters (0.1 mL) of 12 millimolar gold chloride solution was diluted with 80 ml $H_2O$ in a beaker. The initial pH of the gold solution was 3.67. The temperature of the solution was increased to 80° C. for 30 minutes, at which point 0.3 mL hydrazine monohydrate was added to the gold solution. The solution pH shifted to 7.64. Over time, gold solution changed to a very light pink color. FIG. 10K shows TEM pictures of ~30-nm gold nanoparticles prepared using the hydrazine monohydrate reduction technique.

Figure 10L:
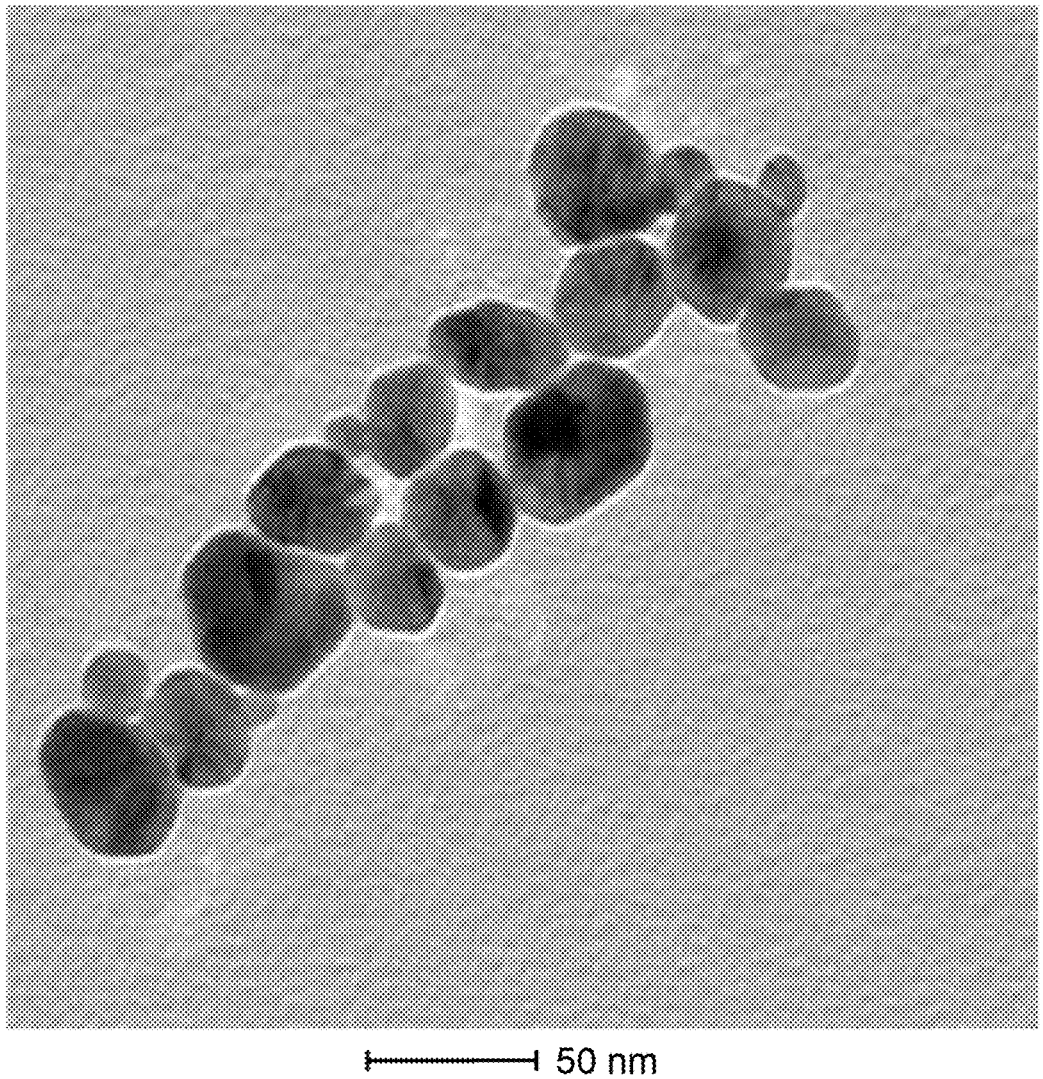
FIG. 10L is a TEM micrograph of silver nanoparticles formed by and used in the present invention.

Colloidal Silver Nanoparticles:

Silver nanoparticles, like the gold nanoparticles described above, can be used in the present invention to enhance either the intensity of the initiation energy (i.e., the primary source: for example an IR laser for upconversion or an X-ray beam for down conversion) or to enhance the light generated from the upconverting or downconverting nanoparticles). Silver nanoparticles have been prepared from $AgNO_3$ using a variety of reducing agents. FIG. 10L shows a TEM image of silver nanoparticles prepared using the procedures described below.

Use of Sodium Citrate as a Reducing Agent:

In this method, 50 mL of a $10^{-3}$ M $AgNO_3$ aqueous solution was heated to boiling. Then, 1 mL of a 1% trisodium citrate ($C_6H_5O_7Na_3$) was added to the solution, and the solution was maintained at boiling for 1 hour before being allowed to cool. The resultant colloidal mixture exhibited a dark grey color.

Use of Hydroxylamine Hydrochloride as a Reducing Agent:

A colloidal solution was formed by dissolving 0.017 g of silver nitrate ($AgNO_3$) in 90 mL water. 21 mg of hydroxylamine hydrochloride ($NH_2OH.HCl$) was dissolved in 5 mL water and 4.5 ml of 0.1 M sodium hydroxide was added. This mixture was added to the $AgNO_3$ solution. In just in a few seconds, a grey-brown solution appeared.

Use of Sodium Borohydride as a Reducing Agent:

Aqueous solutions containing 10 mL $10^{-3}$ M $AgNO_3$ and 30 mL $10^{-3}$ M $NaBH_4$ were mixed under ice-cooled conditions. The $AgNO_3$ solution was added dropwise to the $NaBH_4$ solution with vigorous stirring. The resultant mixture was allowed to age 1 hour before stirring the resultant mixture again for 10 minutes.

Metallic/Dielectric, Multi-Layer, Core-Shell Nanoparticles:

As seen in FIGS. 10A-1 to 10A-7, 10B-1 to 10B-7, 10C-1 to 10C-10 and 10D-1 to 10D-7, the present invention in various embodiments utilizes multilayer dielectric/metal structures.

Figure 10M:
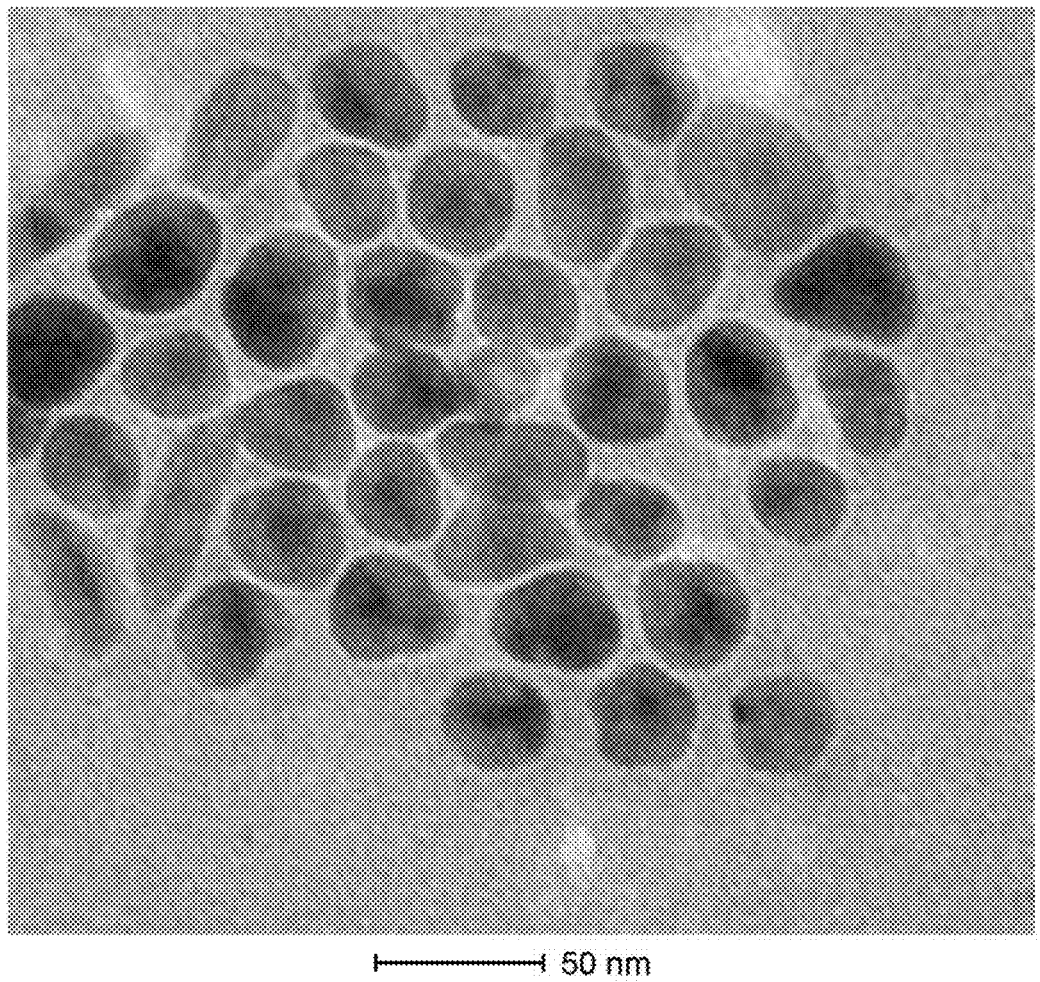
FIG. 10M is a TEM micrograph of Au coated with Ag nanoparticles formed by and used in the present invention.

Au Nanoparticles Coated with Ag or Ag Nanoparticles Coated with Au:

Core-shell nanoparticles such as gold-coated silver nanoparticles and silver-coated gold nanoparticles have been synthesized in an aqueous medium using CTAB as a surfactant and ascorbic acid as a reducing agent. Core nanoparticles (i.e. Au or Ag) were prepared using the above procedures, then coated with secondary, tertiary, etc. shells. For example, spherical gold nanoparticles (~15 nm) were prepared by boiling $HAuCl_4$ in the presence of sodium citrate. For coating gold with a layer of silver, 1 mL of 0.1 M ascorbic acid solution, 0.5 mL of 10 mM $AgNO_3$ solution, and 0.5 mL of the previously formed Au colloid were sequentially added to 20 mL of a 50 mM CTAB solution. Subsequently, 0.1 mL of 1.0 M NaOH was added dropwise, which led to a fast color change (from red to yellow). FIG. 10M shows TEM images of Au nanoparticles coated with Ag.

A similar procedure was used to prepare Ag nanoparticles coated with Au. The use of solutions of a mixture of $AgNO_3$ and $HAuCl_4$ would yield an alloy of Ag and Au.

Au@Ag@Au@Ag Multi Shell Nanoparticles:

Multishell nanoparticles such as Au@Ag@Au@Ag were prepared using CTAB as a surfactant, and ascorbic acid and NaOH as reducing agents. Spherical gold nanoparticles (~15 nm) were prepared by boiling $HAuCl_4$ in the presence of sodium citrate. To coat gold cores with a layer of silver, 20 mL of a 50 mM CTAB, 1 mL of 0.1 M ascorbic acid, 0.5 mL of 10 mM $AgNO_3$, and 0.5 mL of the Au colloid were sequentially mixed. Subsequently, 0.1 mL of 1.0 M NaOH was added in a dropwise manner, which led to a fast color change from red to yellow.

Figure 10N:
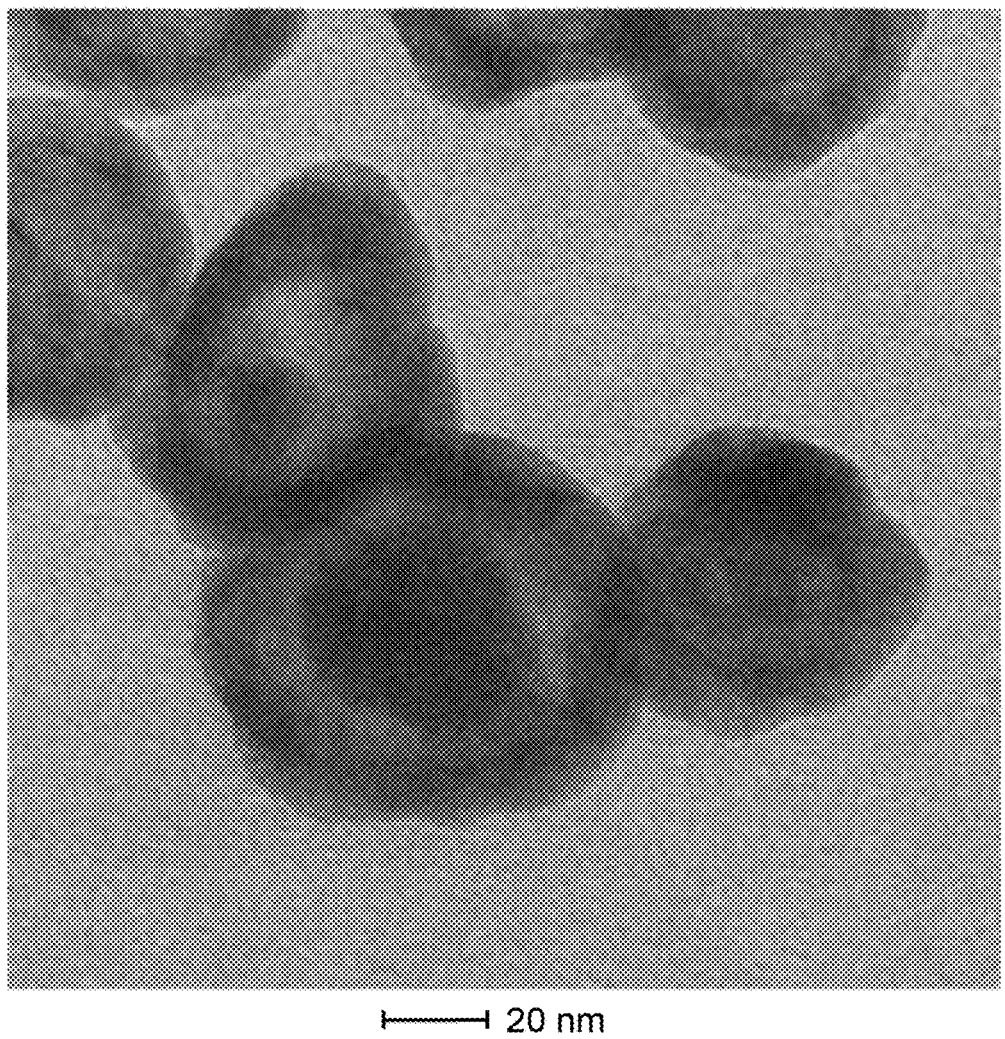
FIG. 10N is a TEM micrograph of Au/Ag/Au/Ag multi-shell nanoparticles formed by and used in the present invention.

Then, another gold layer was coated by mixing 20 mL of the Ag-coated Au colloid in water with 1 mL of the ascorbic acid solution. The resulting mixture was then added to 0.05 mL of 0.10 M HAuCl$_4$ in a dropwise manner. The solution color changed to deep blue at this stage. Subsequently, an outer silver shell was formed on the previously formed Au@Ag@Au nanoparticles by mixing 20 mL of colloid with 0.5 mL 10 mM AgNO$_3$ followed by drop wise addition of 0.2 mL of 1.0 M NaOH. The solution then showed a color change to orange. FIG. 10N shows TEM images of Au@Ag@Au@Ag multi-shell nanoparticles.

All of the above core-shell nanoparticle solutions were stable in solution.

Y$_2$O$_3$ Coated with SiO$_2$, Y$_2$O$_3$ Coated with Au, Y$_2$O$_3$ Coated with Ag or Au Coated SiO$_2$ Coreshell Nanoparticles:

Procedures similar to those used in the preparation of core-shell gold or silver nanoparticles can be employed to synthesize Y$_2$O$_3$ coated with Au or Y$_2$O$_3$ coated with Ag.

Metal (Au Coated with SiO$_2$) or REO Nanoparticles Coated with SiO$_2$:

SiO$_2$ can be coated on gold, silver and REO nanoparticles. There are various procedures available in the literature. See for example W. Stöber, A. Fink, E. Bohn, J. *Colloid Interface Sci.* 26 (1962) 62-69; Y. Kobayashi, H. Katakami, E. Mine, D. Nagao, M. Konno, L. M. Liz-Marzám, *Journal of Colloid and Interface Science* 283 (2005) 392-396; L. M. Liz-Marzan, M. Giersig and P. Mulvaney, *Langmuir* 1996, 12, 4329-4335; S. P. Mulvaney, M. D. Musick, C. D. Kearting, M. J. Natan, *Langmuir* 2003, 19, 4784-4790; Q. Lu, A. Li, F. YunGuo, L. Sun and L. C. Zhao, *Nanotechnology* 19 (2008) 205704; Jana, et. al., *Chem. Mater., Vol.* 19, p. 5074-5082 (2007), the entire contents of each of these references are incorporated herein by reference. In this silica-coating method, which involves condensation of alkoxysilanes on the nanoparticle surface, various types of functional silanes which have alcoxysilyl groups (e.g., methoxysilyl, ethoxysilyl, isopropoxysilyl, etc.) at one end and an amino or thiol group at the other end are typically used. It has been shown that alcoxysilyl groups undergo hydrolysis in a basic or acidic medium to form a silica shell.

The present invention employs two different strategies to induce silica polymerization on the nanoparticle surface. In the case of REO nanoparticles, the silanization process involves condensation of silanes with the hydroxyl groups on the REO particle surface. For Au and Ag, mercapto or amino silane can be used as a linker. In this case, the thiol group of this linker silane chemisorbs onto the metal nanoparticle surface, and the alcoxysilane groups initiate silica shell formation on the nanoparticle surface.

Optimization of the silanization conditions has been performed in order to fabricate water-soluble nanoparticles. There are in general two primary steps in the silane conjugation scheme. First, it is important that excess ligands be removed from the starting nanoparticles. Second, temperature, heating time, and pH all play critical roles in the rate of silane hydrolysis. Both alkyl amines and aminosilane, for example, can serve as a base for the catalytic hydrolysis of alkoxysilane at 65-70° C. In some procedures, nanoparticle-silane conjugates begin to precipitate within 3-5 min of reaction, and finish within 15-30 min. If a specific shell thickness is desired, the hydrolysis can be stopped at any time by quenching the reaction to room temperature or by separating the precipitate from the solution. This is useful because further heating of the precipitated nanoparticle-silane conjugates without separating them from free silanes can produce interparticle cross-linking via hydrolysis. If excess precursor is removed, intra-particle crosslinking can proceed without the potential of interparticle cross-linking.

Chemical Synthesis of Multi-Layer Core-Shell Structures Using Y$_2$O$_3$

To deposit multiple shells on Y$_2$O$_3$ nanoparticles, Y$_2$O$_3$ nanoparticles were initially coated with Ag via UV photo-reduction in a procedure similar to that discussed above for gold shells. In the present invention, a number of approaches can be utilized for the addition of a gold shell. These include 1) a sodium citrate process, 2) a sodium borohydride reduction, 3) a hydrazine monohydrate reduction, 4) a solution containing hydroxyl amine and NaOH, and 5) a mixture of CTAB, ascorbic acid, and NaOH.

Use of Sodium Citrate as a Reducing Agent:

A typical experiment used 0.1 to 1 mL of Y$_2$O$_3$ coated with Ag (~50 nm), 1 to 3 mL of 2.5 H10$^{-3}$ M HAuCl$_4$, and 50 mL distilled water in a 100 ml round bottom flask. This solution was boiled with constant stirring, and 3 mL of 1 wt % sodium citrate was added. The resultant colloidal solution color became black with a pH of approximately pH 6.5. The solution was stirred for another 15 min and then allowed to stand.

Use of Sodium Borohydride as Reducing Agent:

A typical experiment used 0.1 to 1 mL of Y$_2$O$_3$ coated with Ag (~50 nm), 1 to 3 mL of 2.5 H10$^{-3}$ M HAuCl$_4$, and 50 mL distilled water in a 100 mL round bottom flask. Under constant stirring this solution was boiled prior to addition of 0.1 to 1 mL of 0.1 M NaBH$_4$ solution. The resultant colloidal solution became black and aggregated within a few minutes.

These fabrication procedures provide the present invention with a number of nanoparticle systems for application to a variety of media or materials where the nanoparticles can directly or indirectly generate light from an initiation energy or enhance the generated light or the radiation initiation energy.

In a further embodiment of the invention, the upconverter structures of the invention can be incorporated into a material (e.g., biocompatible polymer) that can form a nanocap onto the metal (gold) nanoparticles. The material can be a gel or biocompatible polymer that can have long-term continuous release properties. Suitable gel or biocompatible polymers include, but are not limited to poly(esters) based on polylactide (PLA), polyglycolide (PGA), polycarpolactone (PCL), and their copolymers, as well as poly(hydroxy-alkanoate)s of the PHB-PHV class, additional poly(ester)s, natural polymers, particularly, modified poly(saccharide)s, e.g., starch, cellulose, and chitosan, polyethylene oxides, poly(ether)(ester) block copolymers, and ethylene vinyl acetate copolymers.

In a further embodiment, the metallic nanoparticles without a dielectric core can be provided in the medium along with the upconverting metal-covered dielectric core nanoparticles so that the "pure" metallic nanoparticles can enhance interaction of the upconverted light with another agent or recipient in the medium (such as for example a photosensitizer, a photoactivatable drug, or a photoinitiator).

Figure 11A:
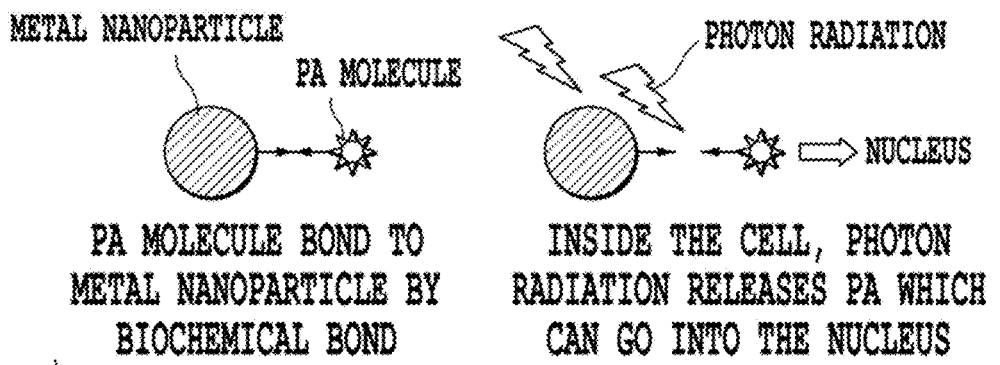
FIGS. 11A to 11C are schematic illustrations of other various upconverter structures of the invention where a recipient molecule is bound to the metal nanoparticles via a linker that can be dissociated by a photon radiation.
Figure 11B:
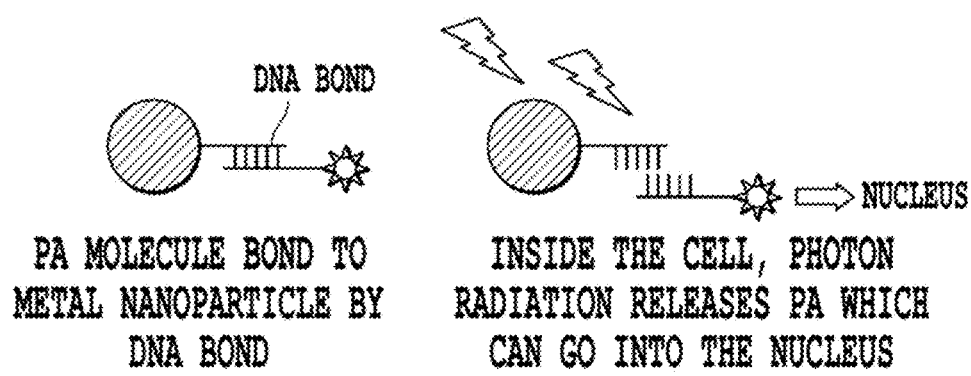
Figure 11C:
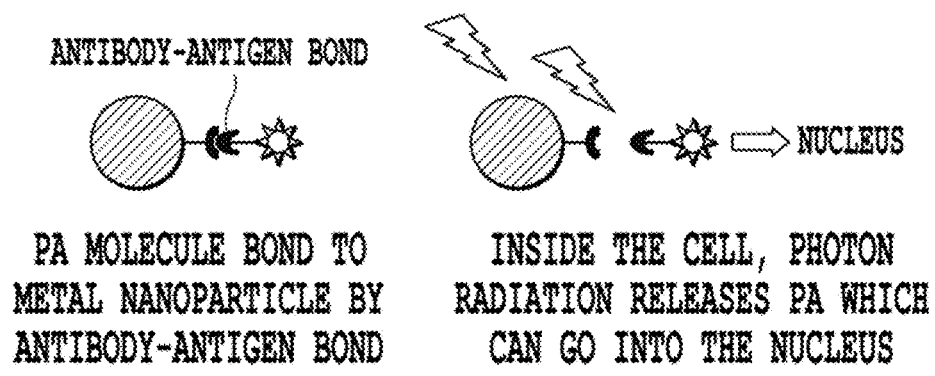

FIG. 11A to 11C show other possible embodiments where a recipient molecule is bound to the metal nanoparticles via a linker that can be cut by photon radiation. Such a linker includes, but is not limited to, a biochemical bond, a DNA bond, an antibody-antigen bond, or other bond which, when excited by light, reorganizes its bonding electrons to non- or anti-bonding state. In another embodiment, the linker is a chemically labile bond that will be broken by the chemical environment inside the cell. In various embodiments, it may be more difficult for metal nanoparticles to enter targeted sites in the medium than for smaller molecules.

Aggregation of metal (such as silver or gold) nanoparticles (nanospheres, nanorods, etc) is often a problem, especially with citrate-capped gold nanospheres, cetyl trimethylammonium bromide (CTAB)-capped gold nanospheres, nanorods, and nanoshells because they have poor stability when they are dispersed in buffer solution due to the aggregating effect of salt ions. The biocompatibility can be improved and nanoparticle aggregation prevented by capping the nanoparticles with polyethylene glycol (PEG) (by conjugation of thiol-functionalized PEG with metal nanoparticles).

The majority of immobilization schemes involving metal surfaces, such as gold or silver, utilize a prior derivatization of the surface with alkylthiols, forming stable linkages. Alkylthiols readily form self-assembled monolayers (SAM) onto silver surfaces in micromolar concentrations. The terminus of the alkylthiol chain can be used to bind biomolecules, or can be easily modified to do so. The length of the alkylthiol chain has been found to be an important parameter, keeping the biomolecules away from the surface, with lengths of the alkyl group from 4 to 20 carbons being preferred.

There are many methods related to the preparation of stable oligonucleotide conjugates with gold particles by using thiol-functionalized biomolecules that have previously been shown to form strong gold-thiol bonds. These methods described below can be used in various embodiments of the invention. Oligonucleotides with 5'-terminal alkanethiol functional groups as anchors can be bound to the surface of gold nanoparticles, and the resulting labels were robust and stable to both high and low temperature conditions [R. Elghanian, J. J. Storhoff, R. C. Mucic, R. L. Letsinger and C. A. Mirkin, *Selective colorimetric detection of polynucleotides based on the distance-dependent optical properties of gold nanoparticles*. Science 277 (1997), pp. 1078-1081], the entire contents of which are incorporated herein by reference. A cyclic dithiane-epiandrosterone disulfide linker has been developed for binding oligonucleotides to gold surfaces. Id. Li et al. have reported a trithiol-capped oligonucleotide that can stabilize gold metal nanoparticles having diameters=100 nm, while retaining hybridization properties that are comparable to acyclic or dithiol-oligonucleotide modified particles [Z. Li, R. C. Jin, C. A. Mirkin and R. L. Letsinger, *Multiple thiol-anchor capped DNA-gold nanoparticle conjugates*. Nucleic Acids Res. 30 (2002), pp. 1558-1562], the entire contents of which are incorporated herein by reference.

In general, silver nanoparticles can not be effectively passivated (i.e., made less reactive) by alkylthiol-modified oligonucleotides using the established experimental protocols that were developed for gold particles. One method of generating core-shell particles having a core of silver and a thin shell of gold has allowed silver nanoparticles to be readily functionalized with alkylthiol-oligonucleotides to prepare pure gold particle-oligonucleotide conjugates, suitable in various embodiments of the invention. [Y. W. Cao, R. Jin and C. A. Mirkin, *DNA-modified core-shell Ag/Au nanoparticles*. J. Am. Chem. Soc. 123 (2001), pp. 7961-7962], the entire contents of which are incorporated herein by reference.

Silver surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold. See Burges, J. D.; Hawkridge, F. M. in Langmuir 1997, 13, 3781-6, the entire contents of which are incorporated herein by reference. After self-assembled monolayer (SAM) formation on gold/silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds.

Such bonding schemes have applications not only by providing a mechanism by which the nanoparticles can be controllably dispersed and delivered within a medium, but may also play a role in the formation of encapsulated upconverter structures of the invention.

With the upconverter structures of the invention, a plasmonics effect is advantageous. A plasmonics effect can occur throughout the electromagnetic region provided the suitable nanostructures, nanoscale dimensions, metal types are used. Plasmonic effects are possible over a wide range of the electromagnetic spectrum, ranging from gamma rays and X rays throughout ultraviolet, visible, infrared, microwave and radio frequency energy. However, for practical reasons, visible and NIR light are used for metal structures such as for example silver and gold nanoparticles, since the plasmon resonances for silver and gold occur in the visible and NTR region, respectively. Especially for gold nanoparticles, the NTR region is very appropriate for the delivery of energy into a medium where otherwise optical scatter at shorter wavelengths would present a problem, such as for example in the treatment of waste water or the sterilization of food products having high concentrations of suspended solids or the delivery of photoactivatible drugs into a living cell.

The invention includes several methods for using light to excite photoactivate or photostimulate compounds in the medium. Light having wavelengths within the so-called "window" (designed to penetrate any container holding the medium to be processed and/or to transmit through the medium) can be used. Moreover, while certain aspects of the invention prefer that the excitation light be nominally non-absorbing (or nearly transparent) in the medium, due to the plasmonic advantages, the invention is still useful in mediums even when there is considerable scatter and absorption.

The ability of light to penetrate the medium depends on absorption and scatter. Within the hydrous medium, a window extends from 600 to 1300 nm, from the orange/red region of the visible spectrum into the NIR. See T. Vo-Dinh, Biomedical Photonics Handbook, CRC, 2003. At the short-wavelength end, absorbing biomolecules become important, including DNA and the amino acids tryptophan and tyrosine. At the infrared (IR) end of the window, penetration is limited by the absorption properties of water (water vibrational overtone absorptions start to become important at 950 nm). Within the window, scattering is dominant over absorption, and so the propagating light becomes diffuse, although not necessarily entering into the diffusion limit.

In various embodiments of the invention, the upconverter structures are covered with a layer (1-30 nm) of dielectric material (e.g. silica or polymer). The dielectric layer (or nanoshell) is designed to prevent quenching of the luminescence light emitted from a dielectric core (e.g., a La doped-dielectric core). Quenching can sometimes occur due to direct contact of a metal to the receptor or media. To address this issue, recipient molecules are bound to (or in proximity of) the metal shell via a spacer (linker). The spacer is designed to prevent quenching of the luminescence light emitted by the dielectric core.

FIGS. 12A-1 to 12A-7 show embodiments of the present invention where the dielectric core has appended thereon or attached by linkages a recipient molecule such as a photoactive molecule. An appended molecule is one that is typically directly bonded either by a covalent bond or a dative association. Linkers are typically added to covalently tether the molecule to the nanocrystal. In various embodiments of the present invention, either mechanism can be used to secure the recipient molecule. The photo-active molecule 6 is receptive to interaction with the generated light $\lambda_2$ such that upon interaction with the light $\lambda_2$ chemical reactions or pharmaceutical reactions are induced therein or there from. For example, UV light generated from the upconverter structures can either change the state of the photo-active molecule to a reactive state, or can sever the linkages releasing the recipient molecule 6 into the medium. As shown in FIGS. 12A-1 to 12A-7, in one embodiment of the invention, the upconverter material is itself separated from a metal component. The exact distances between the recipient molecule and the dielectric core can be varied by using certain chemical linking compounds and as explained below that may also provide certain steric or synergistic effects.

As shown in FIGS. 12A-1 to 12A-7, in one embodiment of the invention, the recipient molecule can be a bioreceptor. Bioreceptors are the key to specificity for targeting disease cells or mutate genes or specific biomarkers. They are responsible for binding the biotarget of interest to the drug system for therapy. Bioreceptors can take many forms and the different bioreceptors that have been used are as numerous as the different analytes that have been monitored using biosensors. However, bioreceptors can generally be classified into different major categories. These categories include: 1) antibody/antigen, 2) enzymes, 3) nucleic acids/DNA, 4) cellular structures/cells, 5) peptides, 6) saccharides, and 5) biomimetic. FIGS. 8A-1 to 8A-7 illustrate various upconversion structures with bioreceptors that can be designed. The probes are similar to those previously described but also have a bioreceptor for tumor targeting. Accordingly, in one embodiment of the present invention, the upconversion structures include (a) photoactive (PA) molecules bound to a metal nanoparticle having a bioreceptor, (b) PA-linked UC material nanoparticle covered with metal nanoparticles, having a bioreceptor, (c) a metal nanoparticle covered with an UC material nanocap with linked PA molecule, having a bioreceptor, (d) an UC material nanoparticle covered with metal nanocap and linked PA, having a bioreceptor, (e) a metal nanoparticle covered with an UC material nanoshell with PA, having a bioreceptor, (f) an UC material nanoparticle covered with metal nanoshells, having a bioreceptor, (g) an UC material nanoparticle covered with a metal nanoshell with a protective coating layer, having bioreceptor.

FIGS. 12B-1 to 12B-6 show yet other embodiments of plasmonics-active nanostructures having upconverting material (UC) with linked photo-active (PA) molecules and also having a bioreceptor. Accordingly, in one embodiment of the present invention, the upconversion structures include (1) PA molecules bound to UC material and to a plasmonic metal nanoparticle, (2) a plasmonic metal nanoparticle with an UC material nanocap covered with PA molecules, (3) a PA-covered UC material nanoparticle with plasmonic metal nanoparticles, (4) an UC material-containing nanoparticle covered with PA molecules and a plasmonic metal nanocap, (5) a plasmonic metal nanoparticle core with an UC material nanoshell covered with PA molecule, and (6) a PA molecule bound to UC material (attached to a plasmonics metal nanoparticle) by detachable biochemical bond.

In the embodiments in FIGS. 12A-1 to 12A-7 and FIGS. 12B-1 to 12B-6, the bioreceptors can be antibody probes, DNA probes, and/or enzyme probes.

For antibody probes, antibody based targeting is more active, specific and efficient. The antibodies are selected to target a specific tumor marker (e.g., anti-epidermal growth factor receptor (EGFR) antibodies targeted against over expressed EGFR on oral and cervical cancer cells; anti-Her2 antibodies against over expressed Her2 on breast cancer cells) Antibodies are biological molecules that exhibit very specific binding capabilities for specific structures. An antibody is a complex biomolecule, made up of hundreds of individual amino acids arranged in a highly ordered sequence. For an immune response to be produced against a particular molecule, a certain molecular size and complexity are necessary: proteins with molecular weights greater then 5000 Da are generally immunogenic. The way in which an antigen and its antigen-specific antibody interact may be understood as analogous to a lock and key fit, by which specific geometrical configurations of a unique key permits it to open a lock. In the same way, an antigen-specific antibody "fits" its unique antigen in a highly specific manner. This unique property of antibodies is the key to their usefulness in immunosensors where only the specific analyte of interest, the antigen, fits into the antibody binding site.

For DNA probes, the operation of gene probes is based on hybridization processes Hybridization involves the joining of a single strand of nucleic acid with a complementary probe sequence. Hybridization of a nucleic acid probe to DNA biotargets (e.g., gene sequences of a mutation, etc) offers an accurate measure for identifying DNA sequences complementary to that of the probe. Nucleic acids strands tend to be paired to their complements in the corresponding double-stranded structure. Therefore, a single-stranded DNA molecule will seek out its complement in a complex mixture of DNA containing large numbers of other nucleic acid molecules. Hence, nucleic acid probe (i.e., gene probe) detection methods are very specific to DNA sequences. Factors affecting the hybridization or reassociation of two complementary DNA strands include temperature, contact time, salt concentration, and the degree of mismatch between the base pairs, and the length and concentration of the target and probe sequences.

Biologically active DNA probes can be directly or indirectly immobilized onto a drug system, such as the EEC system (e.g., gold nanoparticle, a semiconductor, quantum dot, a glass/quartz nanoparticles, etc.), surface to ensure optimal contact and maximum binding. When immobilized onto gold nanoparticles, the gene probes are stabilized and, therefore, can be reused repetitively. Several methods can be used to bind DNA to different supports. The method commonly used for binding DNA to glass involves silanization of the glass surface followed by activation with carbodiimide or glutaraldehyde. In one embodiment, silanization methods are used for binding to glass surfaces using 3 glycidoxypropyltrimethoxysilane (GOP) or aminopropyltrimethoxysilane (APTS) and may be used to covalently link DNA via amino linkers incorporated either at the 3' or 5' end of the molecule during DNA synthesis.

For enzyme probes, enzymes are often chosen as bioreceptors based on their specific binding capabilities as well as their catalytic activity. In biocatalytic recognition mechanisms, the detection is amplified by a reaction catalyzed by macromolecules called biocatalysts. With the exception of a small group of catalytic ribonucleic acid molecules, all enzymes are proteins. Some enzymes require no chemical groups other than their amino acid residues for activity.

Others require an additional chemical component called a cofactor, which may be either one or more inorganic ions, such as $Fe^{2+}$, $Mg^{2+}$, $Mn^{2+}$, or $Zn^{2+}$, or a more complex organic or metalloorganic molecule called a coenzyme. The catalytic activity provided by enzymes allows for much lower limits of detection than would be obtained with common binding techniques. The catalytic activity of enzymes depends upon the integrity of their native protein conformation. If an enzyme is denatured, dissociated into its subunits, or broken down into its component amino acids, its catalytic activity is destroyed. Enzyme-coupled receptors can also be used to modify the recognition mechanisms.

The novel materials and upconverter structures of the invention include in various embodiments nanoparticles of neodymium and ytterbium doped yttrium oxide, europium and ytterbium doped yttrium oxide, and any combination of rare earth trivalent ions doped into a neodymium oxide nanocrystal. The dual doped yttrium oxide of composition neodymium and ytterbium and also the dual doped europium and ytterbium are new for the yttrium oxide host lattice, although such dual doped systems have been shown to work in other host lattices such as YAG.

These dual doped lanthanide glasses have been shown to upconvert efficiently on bulk materials, and thereby can provide new upconverter structures at the nanoscale. There are a number of advantages offered by these yttrium oxide nanostructures of the invention. The small scale synthetic methodology for creating nanoscale yttrium oxide is easier to control and produce in yttrium oxide than in YAG. The host structure of yttrium oxide scintillates (by down conversion) at a valuable emission wavelength to excite known pharmaceutical materials as the recipients. Finally, these combinations of dopants in yttrium oxide provide new emission colors for the yttrium oxide nanocrystal in an imaging format.

In one embodiment of the invention, a dual dopant permits excitation of either ion in the host glass. For instance, excitation by 980 nm light excites an ytterbium ion, where through transfer of energy from one excited state of the ytterbium ion to another dopant provides a mechanism for upconversion emission of light in the ultraviolet, visible, and NIR spectral regions.

Neodymium oxide is a dielectric nanostructural material that can also be synthesized by the same polyalcohol method described above with regard to yttrium oxide nanocrystal preparation. Doped neodymium oxide is expected to also show upconversion processes. Neodymium oxide as a host structure possesses lower optical phonon modes than all other oxide based materials. Lower frequency of phonon may be best suited for electronic transfer between ions. In general, phonon modes are vibrations in a crystal lattice whose frequencies are dependent on the crystal lattice structure and materials. Energy released by upconversion (effectively atomic emission) is transmitted through the photons. With photons, energy can be transferred via Forster, Dexter, or photon capture pathways. Meanwhile, for holes and electrons, charge tunneling is one mechanism for energy transfer. For photons, lower phonon modes typically exhibit less destructive interference, thereby being more suitable for upconverted emission. Accordingly, in one embodiment of the invention, the lower energy phonon modes for neodymium oxide are expected to provide for a stronger electron phonon coupling transfer to occur between the dopants inside of the neodymium oxide. Neodymium oxide has also shown the same low toxic effects as yttrium oxide and therefore is suitable for insertion in living biological tissue.

Accordingly, the novel upconversion emitters of this invention involve a number of configurable structures and materials which will permit their use in a variety of applications. Further, many of the dielectric cores described in the invention exhibit down conversion properties. The invention in several applications described below utilizes both the upconversion and down conversion properties of a particular nanoparticle material system. In some of the applications described below, particles designed for down conversion can be used in conjunction with separate particles designed for upconversion.

In some embodiments of the invention, down converting materials (such as those described herein) are used separately without the need to include up converting materials.

Accordingly, the invention in various embodiments can use a wide variety of down conversion materials. These down conversion materials can include quantum dots, semiconductor materials, alloys of semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties.

Further, the down conversion materials for the invention described here can be coated with insulator materials such as for example silica which will reduce the likelihood of any chemical interaction between the luminescent particles and the medium. For biomedical applications, nanoparticles with toxicity as low as possible are desirable. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$. Other suitable down conversion materials which would seem the most biocompatible are zinc sulfide, $ZnS:Mn^{2+}$, ferric oxide, titanium oxide, zinc oxide, zinc oxide containing small amounts of $Al_2O_3$ and AgI nanoclusters encapsulated in zeolite.

Alkali lead silicate Glass compositions were also useful for down-converting x-rays into UV and visible. These glass compositions contain $SiO_2$, $B_2O_3$, $Na_2O$, $K_2O$ and PbO. The range of compositions include in mole %: $SiO_2$ from 44% to 73%, $B_2O_3$ from 0% to 3%, $Na_2O$ from 0.5% to 4%, $K_2O$ from 0.5% to 11% and PbO from 5% to 55%. A whole range of compositions are possible. Furthermore, other materials can be included to promote fluorescence including for example MgO and Ag.

In various embodiments of the invention, the following luminescent polymers are also suitable as conversion materials: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

In the embodiments shown in FIGS. 12B-1 to 12B-6, the up converting agent is displaced from the plasmonics metal. In one embodiment, the displacement distance effects (and in certain situations enhances) the interaction of the incident radiation with the up converting material. FIG. 12B-7 shows an example of the enhancement (6) of emission as a function of wavelength for a configuration similar to that in FIGS. 12B-1 to 12B-6 where the energy converting molecule is displaced from the metal shell, and where the outer radius of the metal shell is set arbitrarily to 50 nm and b is the value of the inner radius of the shell in units of nanometers.

In concept, the same effect occurs if the molecule were located at different positions inside a metallic shell. The enhancement results are shown in FIG. 12B-8, where the outer radius of the metal shell is set arbitrarily to 50 nm and b is the value of the inner radius of the shell in units of nanometers.

As shown in FIGS. 12A-1 to 12A-7, the up converting agent can be disposed inside a plasmonics metal shell. The maximum enhancement effect will generally occur near a plasmon resonance of the metallic shell, and therefore the enhancement will generally have a strong dependence on wavelength. FIG. 12B-9 shows an example of the dependence of excitation enhancement on wavelength for a configuration similar to that in FIGS. 12A-1 to 12A-7 where the energy converting material is covered with a plasmonics layer, where the outer radius of the shell is set arbitrarily to 50 and b is the value of the inner radius of the shell in units of nanometers.

Once the up converting or down converting molecule is excited by the incident radiation field, its energy is released by emission such as for example fluorescence or phosphorescence. If for the purpose of illustrating this embodiment of the invention, one assumes an intrinsic quantum efficiency of the molecule equal to one, the molecule, in the absence of the shell, will radiate away all its energy due to the exciting field. In the presence of the shell, some of the radiative power will be absorbed the shell. FIG. 12B-10 shows the dependence of the radiation (i.e., emission) on wavelength for the structure and excitation shown in FIG. 12B-9.

Figures 11, 12B:
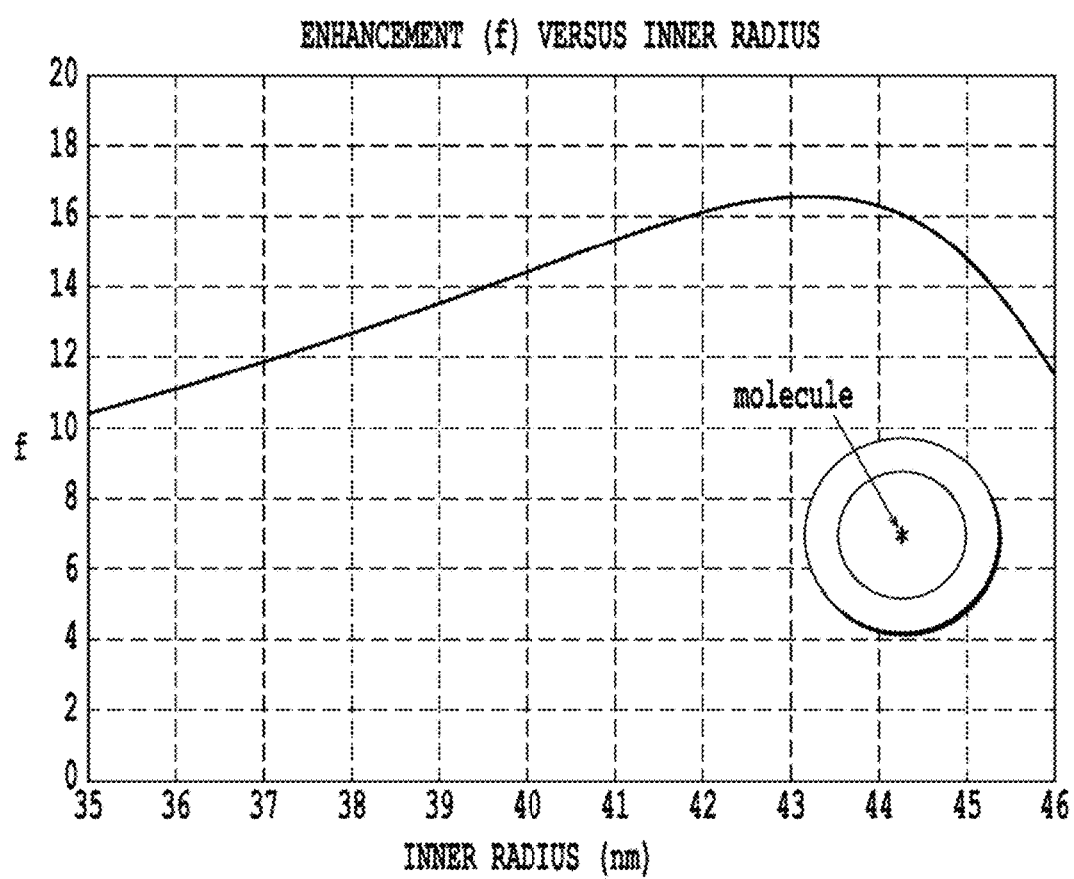

FIG. 12B-11 shows the data of FIG. 12B-10 simplified to show the total enhancement verses the inside diameter of the metal shell.

From the results discussed above, when the molecule is outside the shell, the local field is the incident radiation field plus the field scattered from the shell. When the molecule resides within the shell core, the local field is the radiation field that penetrates the shell. Both the excitation of the molecule and its radiative emission are strongly influenced by plasmon resonances excited within the shell. In one embodiment of the invention, the enhancement for an external molecule is larger for a shell than for a solid sphere of the same diameter.

Both the excitation and the quantum efficiency are larger for a shell than for a solid sphere, although both of these quantities appear to peak at different shell thicknesses. In one embodiment of the invention, the overall enhancement can range as high as 30 for a molecule outside the shell and about 15 for a molecule inside the shell core. In the latter case, however, the enhancement is inhibited by a thick shell and achieves a peak value for a relatively thin shell. Two factors affect the drop off in the enhancement as the shell becomes increasingly thin. The first is the weakening of the plasmon resonance as the volume of metal is reduced and the second is the further damping of the resonance due to electron scattering within a thin shell.

Recent work by Schietinger et al. (*Nano Lett.* 2010, 10, 134-138) demonstrates similar plasmon enhancement of the emission of upconverting nanocrystals. In this work, the group prepared NaYF$_4$ nanocrystals doped with Er and Yb and codeposited 5 nm Au nanoparticles to a thin film. AFM tip manipulation coupled with single particle emission spectroscopy confirmed a 2.7 to 4.8 fold enhancement of the upconverting nanocrystals in a thin film deposition.

The doped yttrium oxide materials described above as well as the other nanocrystalline materials of the invention are upconverters which offer an alternative to more conventional types of techniques for imaging or photo-induced treatment. In some of the cross referenced related patent applications, high energy photons such as X-ray or high energy particles were used in a down conversion manner to generate subsequent ultraviolet light for interaction with drugs introduced to the body or (in other work) for the production of a singlet oxygen in the body or for diagnostics via imaging the secondarily emitted light. In some of the cross referenced related patent applications, high energy photons such as X-ray or high energy particles were used in a down conversion manner to generate secondarily emitted light which activated an agent in the medium. The interaction of X-ray with nanoparticles and the resultant emission is thus a determining event in the down conversion process of the present invention. It has been discovered that the resultant light emission for Y$_2$O$_3$ particles show at least in the range from 120 kV to 320 kV an unexpected increase in emission intensity with decreasing X-ray energy.

In one embodiment of this invention, a more benign radiation source (than X-ray) that of a NIR source can be used. NIR sources are readily available with commercial laser sources that operate, for example at 980 and 808 nm. There are many commercially available NIR diode laser lines; these include 785, 830, 852, 915, 940, 1064, 1310, and 1550 nm in addition to 808 and 980, which depending on the nanoscale agent and application, many of these are suitable for use.

The doped yttrium oxide materials described above as well as the other nanocrystalline materials of the invention are upconverters which offer an alternative to more conventional types of techniques for imaging or photo-induced treatment. In some of the cross referenced related patent applications, high energy photons such as X-ray or high energy particles were used in a down conversion manner to generate subsequent ultraviolet light for interaction with drugs introduced to the body or (in other work) for the production of a singlet oxygen in the body or for diagnostics via imaging the secondarily emitted light. In some of the cross referenced related patent applications, high energy photons such as X-ray or high energy particles were used in a down conversion manner to generate secondarily emitted light which activated an agent in the medium. The interaction of X-ray with nanoparticles and the resultant emission is thus a determining event in the down conversion process of the invention. It has been observed that the resultant light emission for Y$_2$O$_3$ particles show at least in the range from 120 kV to 320 kV an increase in emission intensity with decreasing X-ray energy. Other particles or other energy ranges may well show a different trend.

In one embodiment of this invention, a more benign radiation source, that of a NIR source, can be used. NIR sources are readily available with commercial laser sources that operate, for example at 980 and 808 nm. There are many commercially available NIR diode laser lines; these include 785, 830, 852, 915, 940, 1064, 1310, and 1550 nm in addition to 808 and 980, which depending on the nanoscale agent and application, many of these are suitable for use.

PEGylated-Vectors for PEPST Probes

The synthesis of these particles was first reported by Michael Faraday, who, in 1857, described the chemical process for the production of nanosized particles of Au0 from gold chloride and sodium citrate (Faraday 1857). Initial formulations of the vector, manufactured by binding only TNF to the particles, were less toxic than native TNF and effective in reducing tumor burden in a murine model. Subsequent studies revealed that the safety of this vector was primarily due to its rapid uptake and clearance in the RES. This vector was reformulated to include molecules of thiol-derivatized polyethylene glycol (PEG-THIOL) that were bound with molecules of TNF on the gold nanoparticles surface. The new vector, PT-cAu-TNF, avoids detection and clearance by the RES, and actively and specifically sequesters TNF within a solid tumor. The altered biodistribution correlated to improvements. Similarly one can design PEGylated-Au nanoparticles-PA drug to avoid detection and clearance by the RES.

Disease-Targeted PEPST Probes

Aggregation of metal (such as silver or gold) nanoparticles (nanopsheres, nanorods, etc) is often a problem, especially with citrate-capped gold nanospheres, cetyl trimethylammonium bromide (CTAB)-capped gold nanospheres and nanorods and nanoshells because they have poor stability when they are dispersed in buffer solution due to the aggregating effect of salt ions. The biocompatibility can be improved and nanoparticle aggregation prevented by capping the nanoparticles with polyethylene glycol (PEG) (by conjugation of thiol-functionalized PEG with metal nanoparticles). Furthermore, PEGylated nanoparticles are preferentially accumulated into tumor tissues due to the enhanced permeability and retention effect, known as the "EPR" effect [Maedaa H, Fanga J, Inutsukaa T, Kitamoto Y (2003) *Vascular permeability enhancement in solid tumor: various factors, mechanisms involved and its implications.* Int Immunopharmacol 3:319-328; Paciotti G F, Myer L, Weinreich D, Goia D, Pavel N, McLaughlin R E, Tamarkin L (2004) *Colloidal gold: a novel nanoparticles vector for tumor directed drug delivery.* Drug Deliv 11:169-183]. Blood vessels in tumor tissue are more "leaky" than in normal tissue, and as a result, particles, or large macromolecular species or polymeric species preferentially extravasate into tumor tissue. Particles and large molecules tend to stay a longer time in tumor tissue due to the decreased lymphatic system, whereas they are rapidly cleared out in normal tissue. This tumor targeting strategy is often referred to as passive targeting whereas the antibody-targeting strategy is called active targeting.

To specifically target diseased cells, specific genes or protein markers, the drug systems of the present invention can be bound to a bioreceptor (e.g., antibody, synthetic molecular imprint systems, DNA, proteins, lipids, cell-surface receptors, peptides, saccharides, aptamers, etc.). Immunotargeting modalities to deliver PA agents selectively to the diseased cells and tissue provide efficient strategies to achieving specificity, minimizing nonspecific injury to healthy cells, and reducing the radiation intensity used. Biofunctionalization of metal nanoparticles (e.g., gold, silver) can be performed using commonly developed and widely used procedures. There are several targeting strategies that can be used in the present invention: (a) nanoparticles conjugated to antibodies that recognize biomarkers specific to the diseased cells; (b) nanoparticles passivated by poly (ethylene) glycol (PEG), which is used to increase the biocompatibility and biostability of nanoparticles and impart them an increased blood retention time.

Immobilization of Biomolecules to Metal Nanoparticles

The immobilization of biomolecules (PA molecules, drugs, proteins, peptides, saccharides, enzymes, antibodies, DNA, etc.) to a solid support can use a wide variety of methods published in the literature. Binding can be performed through covalent bonds usually takes advantage of reactive groups such as amine (—$NH_2$) or sulfide (—SH) that naturally are present or can be incorporated into the biomolecule structure. Amines can react with carboxylic acid or ester moieties in high yield to form stable amide bonds. Thiols can participate in maleimide coupling, yielding stable di alkyl sulfides.

A solid support of interest is gold (or silver) nanoparticles. The majority of immobilization schemes involving Au (Ag) surfaces utilize a prior derivatization of the surface with alkylthiols, forming stable linkages. Alkylthiols readily form self-assembled monolayers (SAM) onto silver surfaces in micromolar concentrations. The terminus of the alkylthiol chain can be used to bind biomolecules, or can be easily modified to do so. The length of the alkylthiol chain has been found to be an important parameter, keeping the biomolecules away from the surface. Furthermore, to avoid direct, non-specific DNA adsorption onto the surface, alkylthiols have been used to block further access to the surface, allowing only covalent immobilization through the linker [Steel, A. B.; Herne, T. M.; Tarlov, M. J. Anal. Chem. 1998, 70, 4670-7; Herne, T. M.; Tarlov, M. J. J. Am. Chem. Soc. 1997, 119, 8916-20]

Silver surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold [Burges, J. D.; Hawkridge, F. M. Langmuir 1997, 13, 3781-6]. After SAM formation on gold/silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. As a general rule, a more active intermediate (labile ester) is first formed with the carboxylic acid moiety and in a later stage reacted with the free amine, increasing the coupling yield. Successful coupling procedures include:

Binding Procedure Using N-Hydroxysuccinimide (NHS) and its Derivatives

The coupling approach involves the esterification under mild conditions of a carboxylic acid with a labile group, an N-hydroxysuccinimide (NHS) derivative, and further reaction with free amine groups in a polypeptide (enzymes, antibodies, antigens, etc) or amine-labeled DNA, producing a stable amide [Boncheva, M.; Scheibler, L.; Lincoln, P.; Vogel, H.; Akerman, B. Langmuir 1999, 15, 4317-20]. NHS reacts almost exclusively with primary amine groups. Covalent immobilization can be achieved in as little as 30 minutes. Since $H_2O$ competes with —$NH_2$ in reactions involving these very labile esters, it is important to consider the hydrolysis kinetics of the available esters used in this type of coupling. The derivative of NHS used in FIG. 1, O—(N-succinimidyl)-N,N,N',N'-tetramethyluronium tetrafluoroborate, increases the coupling yield by utilizing a leaving group that is converted to urea during the carboxylic acid activation, hence favorably increasing the negative enthalpy of the reaction.

Binding Procedure Using Maleimide

Maleimide can be used to immobilize biomolecules through available —SH moieties (FIG. 3). Coupling schemes with maleimide have been proven useful for the site-specific immobilization of antibodies, Fab fragments, peptides, and SH-modified DNA strands. Sample preparation for the maleimide coupling of a protein involves the simple reduction of disulfide bonds between two cysteine residues with a mild reducing agent, such as dithiothreitol, 2-mercaptoethanol or tris(2-carboxyethyl)phosphine hydrochloride. However, disulfide reduction will usually lead to the protein losing its natural conformation, and might impair enzymatic activity or antibody recognition. The modification of primary amine groups with 2-iminothiolane hydrochloride (Traut's reagent) to introduce sulfydryl groups is an alternative for biomolecules lacking them. Free sulfhydryls are immobilized to the maleimide surface by an addition reaction to unsaturated carbon-carbon bonds [Jordan, C. E., et al., 1997].

Binding Procedure Using Carbodiimide.

Surfaces modified with mercaptoalkyldiols can be activated with 1,1'-carbonyldiimidazole (CDI) to form a carbonylimidazole intermediate. A biomolecule with an available amine group displaces the imidazole to form a carbamate linkage to the alkylthiol tethered to the surface [Potyrailo, R. A., et al., 1998].

Other Experimental Procedures to Conjugate Biomolecules to Metal (e.g., Silver, Gold) Nanoparticles.

Nanoparticles of metal colloid hydrosols are generally prepared by rapidly mixing a solution of $AgNO_3$ with ice-cold $NaBH_4$. To develop a SMP probes, one needs to bind a DNA segment to a nanoparticle of silver or gold. The immobilization of biomolecules (e.g., DNA, antibodies, enzymes, etc.) to a solid support through covalent bonds usually takes advantage of reactive groups such as amine (—$NH_2$) or sulfide (—SH) that naturally are present or can be incorporated into the biomolecule structure. Amines can react with carboxylic acid or ester moieties in high yield to form stable amide bonds. Thiols can participate in maleimide coupling yielding stable dialkylsulfides.

In the present invention, we use silver nanoparticles. The majority of immobilization schemes involving Ag surfaces utilize a prior derivatization of the surface with alkylthiols, forming stable linkages. Alkylthiols readily form self-assembled monolayers (SAM) onto silver surfaces in micromolar concentrations. The terminus of the alkylthiol chain can be directly used to bind biomolecules, or can be easily modified to do so. The length of the alkylthiol chain was found to be an important parameter, keeping the biomolecules away from the surface. Furthermore, to avoid direct, non-specific DNA adsorption onto the surface, alkylthiols were used to block further access to the surface, allowing only covalent immobilization through the linker.

Silver/gold surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold.

After SAM formation on silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. As a general rule, a more active intermediate (labile ester) is first formed with the carboxylic acid moiety and in a later stage reacted with the free amine, increasing the coupling yield. Successful coupling procedures include:

The coupling approach used to bind DNA to a silver nanoparticle involves the esterification under mild conditions of a carboxylic acid with a labile group, an N-hydroxysuccinimide (NHS) derivative, and further reaction with free amine groups in a polypeptide (enzymes, antibodies, antigens, etc) or amine-labeled DNA, producing a stable amide [4]. NHS reacts almost exclusively with primary amine groups. Covalent immobilization can be achieved in as little as 30 minutes. Since $H_2O$ competes with —$NH_2$ in reactions involving these very labile esters, it is important to consider the hydrolysis kinetics of the available esters used in this type of coupling. The derivative of NHS used, O—(N-succinimidyl)-N,N,N',N'-tetramethyluronium tetrafluoroborate, increases the coupling yield by utilizing a leaving group that is converted to urea during the carboxylic acid activation, hence favorably increasing the negative enthalpy of the reaction.

PEPST UC-PA Probe with Detachable PA.

For some photoactive drug requiring that the PA molecule to enter the nucleus. FIGS. 13A-13C show an embodiment of a PEPST-UC probe where the PA drug molecule is bound to the metal nanoparticles via a linker (FIG. 13A) that can be cut by a photon radiation (FIG. 13B). Such a probe is useful for therapy modalities where the PA molecules have to enter the nucleus, e.g., psoralen molecules need to enter the nucleus of cells and intercalate onto DNA (FIG. 13C). Since it is more difficult for metal nanoparticles to enter the cell nucleus than for smaller molecules, it is desirable to PEPST-UC probes that have releasable PA molecules.

The novel materials and upconverter structures of the invention include in various embodiments nanoparticles of neodymium and ytterbium doped yttrium oxide, europium and ytterbium doped yttrium oxide, and any combination of rare earth trivalent ions doped into a neodymium oxide nanocrystal. The dual doped yttrium oxide of composition neodymium and ytterbium and also the dual doped europium and ytterbium are new for the yttrium oxide host lattice, although such dual doped systems have been shown to work in other host lattices such as YAG.

These dual doped lanthanide glasses have been shown to upconvert efficiently on bulk materials, and thereby can provide new upconverter structures at the nanoscale. There are a number of advantages offered by these yttrium oxide nanostructures of the invention. The small scale synthetic methodology for creating nanoscale yttrium oxide is easier to control and produce in yttrium oxide than in YAG. The host structure of yttrium oxide scintillates (by down conversion) at a valuable emission wavelength to excite known pharmaceutical materials as the recipients. Finally, these combinations of dopants in yttrium oxide provide new emission colors for the yttrium oxide nanocrystal in an imaging format.

In one embodiment of the invention, a dual dopant permits excitation of either ion in the host glass. For instance, excitation by 980 nm light excites a ytterbium ion, where through transfer of energy from one excited state of the ytterbium ion to another dopant provides a mechanism for upconversion emission of light in the ultraviolet, visible, and NIR spectral regions.

Neodymium oxide is a novel dielectric nanostructural material that can also be synthesized by the same polyalcohol method described above with regard to yttrium oxide nanocrystal preparation. Doped neodymium oxide is expected to also show upconversion processes. Neodymium oxide as a host structure possesses lower optical phonon modes than all other oxide based materials. Lower frequency of phonon may be best suited for electronic transfer between ions. In general, phonon modes are vibrations in a crystal lattice whose frequencies are dependent on the crystal lattice structure and materials. Energy released by upconversion (effectively atomic emission) is transmitted through the photons. With photons, energy can be transferred via Forster, Dexter, or photon capture pathways. Meanwhile, for holes and electrons, charge tunneling is one mechanism for energy transfer. For photons, lower phonon modes typically exhibit less destructive interference, thereby being more suitable for upconverted emission. Accordingly, in one embodiment of the invention, the lower energy phonon modes for neodymium oxide are expected to provide for a stronger electron phonon coupling transfer to occur between the dopants inside of the neodymium oxide. Neodymium oxide has also shown the same low toxic effects as yttrium oxide and therefore is suitable for insertion in living biological tissue.

Accordingly, the novel upconversion emitters of this invention involve a number of configurable structures and materials which will permit their use in a variety of applications. Further, many of the dielectric cores described in the invention exhibit down conversion properties. The invention in several applications described below utilizes both the upconversion and down conversion properties of a particular nanoparticle material system. In some of the application described below, particles designed for down conversion can be used in conjunction with separate particles designed for upconversion.

Accordingly, the invention can use a wide variety of down conversion materials. These down conversion materials can include quantum dots, semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties.

Further, the down conversion materials for the invention described here can be coated with insulator materials such as for example silica which will reduce the likelihood of any chemical interaction between the luminescing particles and the medium. For biological applications of inorganic nanoparticles, one of the major limiting factors is their toxicity. Generally speaking, all semiconductor nanoparticles are more or less toxic. For biomedical applications, nanoparticles with toxicity as low as possible are desirable or else the nanoparticles have to remain separated from the medium. Pure $TiO_2$, $ZnO$, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$. Other suitable down conversion materials which would seem the most biocompatible are zinc sulfide, $ZnS:Mn^{2+}$, ferric oxide, titanium oxide, zinc oxide, zinc oxide containing small amounts of $Al_2O_3$ and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, Cesium Iodine, Bismuth Germanate, Cadmium Tungstate, and CsBr doped with divalent Eu.

In various embodiments of the invention, the following luminescent polymers are also suitable as conversion materials: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

The doped yttrium oxide materials described above as well as the other nanocrystalline materials of the invention are upconverters which offer an alternative to more conventional types of techniques for imaging or photo-induced treatment. In the cross referenced related patent applications and in other work, high energy photons such as X-ray or high energy particles were used in a down conversion manner to generate subsequent ultraviolet light for interaction with drugs introduced to the body or for the production of a singlet oxygen in the body or for diagnostics via imaging the secondarily emitted light. In this invention, a more benign radiation source that of a NIR source can be used. NIR sources are readily available with commercial laser sources that operate, for example at 980 and 808 nm. There are many commercially available NIR diode laser lines; these include 785, 830, 852, 915, 940, 1064, 1310, and 1550 nm in addition to 808 and 980, which depending on the nanoscale agent and application, many of these are suitable for use.

These IR frequencies have significant penetration into the human body and permit the primary excitation $\lambda_1$ to penetrate subcutaneously into the body tissue. Upon their penetration into the body tissue, the dielectric core of the invention interacts with the incident radiation $\lambda_1$ to generate the secondary light $\lambda_2$ as described above. Therefore, permitting the generation in situ to the body of a wavelength $\lambda_2$ which may be in the UV or visible range is appropriate for activations of psoralen or other types of drugs known to be activated by a UV or visible light source.

Since the dielectric cores of this invention have the ability to be selectively stimulated by discrete wavelengths of $\lambda_1$ and produce discrete emission wavelengths at $\lambda_2$, the medial applications can be manipulated so that a number of dual purpose diagnostic/treatment tools can be produced.

For example, in one embodiment of the invention, a material such as the above-described co-doped yttrium oxide is introduced into the body. Yttrium oxide as a host is known to be a down converter from X-ray radiation. In this particular example, X-ray incident radiation on the yttrium oxide will produce UV light which would in turn be used to activate drugs such as psoralen for the treatment of cancer. Meanwhile, the co-doped yttrium oxide as a upconverter could be used where the NIR excitation could produce an emission at a wavelength that was different than that produced from the X-ray down conversion radiation. In this manner, the progression of the yttrium oxide (with drug attached as the recipient 4) into a target organ to be treated could be monitored using the NIR light as the excitation source and collecting the visible light in some type of CCD camera. Once the yttrium oxide particles were absorbed into the respective tumor cells for treatment, at that point in time, X-ray radiation could be initiated and thereby activating the psoralen tagged yttrium oxide and providing an effective means for treating the tumor cell.

Alternatively, in another dual purpose diagnostic/treatment example, one can choose a system where the NIR wavelength is specifically tuned for diagnostics as explained above while excitation with a separate wavelength of NIR can be used to produce UV light (through another upconversion channel) that would itself activate a recipient molecule (e.g. psoralen for cancer treatment) without the necessity of X-ray and down conversion activation. This feature then permits one to use a drug which either would be acceptable for deep body penetration through X-ray radiation or would be acceptable for more shallow body penetration through NIR radiation to treat cancer cells that were located in different parts of the body relative to the surface of the body. Moreover, fiber optics could be used to direct the NIR light (through a surgical incision for example) directly to a target. By locally activating the psoralen and by the known autovaccine effect, this initially local NIR activated treatment may be effective at treating cancer outside the NIR irradiated area.

Examples of such dual use drugs which all exhibit NIR activation and upconversion for the purpose of imaging and/or to excite psoralen would include the dual dopants of yttrium oxide, the dual dopants of neodymium oxide, triply doped ytterbium thulium neodymium oxides, the dual dopants of sodium yttrium fluoride, and the dual dopants of lanthanum fluoride. For example, by providing a ytterbium-thulium doped yttrium oxide containing 95% verses 5% dopant concentration with another lanthanide, one will produce diagnostic/treatment functions through pure NIR excitation, having the drug treatment excitable at 980 nanometers verses the diagnostic imaging process excitable at 808 nanometers with different emissions coming from each excitation process.

Nanoparticle Chain for Dual Plasmonics Effect

As discussed previously, there is the need to develop nanoparticle systems that can have dual (or multi) plasmonics resonance modes. FIG. 14 illustrates an embodiment of the present invention PEPST probe having a chain of metal particles having different sizes and coupled to each other, which could exhibit such dual plasmonics-based enhancement. For example the parameters (size, metal type, structure, etc) of the larger nanoparticle (FIG. 14, left) can be tuned to NIR, VIS or UV light while the smaller particle (FIG. 14, right) can be tuned to X ray. There is also a coupling effect between these particles.

These nanoparticle chains are useful in providing plasmonics enhancement of both the incident radiation used (for example, x-ray activation of CdS) as well as plasmonics enhancement of the emitted radiation that will then activate the PA. Similar nanoparticles systems have been used as nanolens [*Self-Similar Chain of Metal Nanospheres as an Efficient Nanolens*, Kuiru Li, Mark I. Stockman, and David J. Bergman, *Physical Review Letter*, VOLUME 91, NUMBER 22, 227402-1, 2003].

Drug Delivery Platforms

Liposome Delivery of Energy Modulation Agent-PA Systems

The field of particle-based drug delivery is currently focused on two chemically distinct colloidal particles, liposomes and biodegradable polymers. Both delivery systems encapsulate the active drug. The drug is released from the particle as it lyses, in the case of lipsomes, or disintegrates, as described for biodegradable polymers. One embodiment of the present invention uses liposomal delivery of energy modulation agent-PA systems (e.g., gold nanoshells) for therapy. An exemplary embodiment is described below, but is not intended to be limiting to the specific lipids, nanoparticles or other components recited, but is merely for exemplary purposes:

Preparation of Liposomes. The liposome preparation method is adapted from Hölig et. al Hölig, P., Bach, M., Völkel, T., Nande, T., Hoffmann, S., Müller, R., and Kontermann, R. E., *Novel RGD lipopeptides for the targeting of liposomes to integrin-expressing endothelial and melanoma cells*. Protein Engineering Design and Selection, 2004. 17(5): p. 433-441]. Briefly, the lipids PEG-DPPE, PC, and Rh-DPPE are mixed in chloroform in a round bottom flask and evaporated (Hieroglyph Rotary Evaporator, Rose Scientific Ltd., Edmonton, Alberta, Canada) to eliminate chloroform. The dry film is dehydrated into aqueous phase with using PBS solution. A dry lipid film is prepared by rotary evaporation from a mixture of PC, cholesterol, and PEG-DPPE and then hydrated into aqueous phase using PBS. The mixture is vigorously mixed by overtaxing and bath solicited (Instrument, Company) and the suspension extruded through polycarbonate filter using Liposofast apparatus (Avestin Inc., Ottawa, ON, Canada) (pore-size 0.8 μm). Preparation of liposomes is performed as follows; 0.1 mmol of PC is dispersed in 8 ml of chloroform and supplemented with 0.5 mol of PEG-DPPE in 20 ml of chloroform. 0.3 mmol rhodamine-labeled phosphatidylethanolamine (Rh-DPPE) is then incorporated into the liposomes. The organic solvents are then removed by rotary evaporation at 35° C. for 2 h leaving a dry lipid film. Gold nanoshells are encapsulated into liposomes by adding them to the PBS hydration buffer and successively into the dry lipid film. This mixture is emulsified in a temperature controlled sonicator for 30 minutes at 35° C. followed by vortexing for 5 min. Encapsulated gold nanoshells are separated from unencapsulated gold nanoshells by gentle centrifugation for 5 minutes at 2400 r.p.m (1200 g). The resulting multilamellar vesicles suspension is extruded through polycarbonate filter using Liposofast apparatus (Avestin Inc., Ottawa, ON, Canada) (pore-size 0.8 μm). The aqueous mixture is obtained and stored at 4° C.

Fabrication of Gold Nanoparticles: The Frens method [Frens, G., *Controlled nucleation for the regulation of the particle size in monodisperse gold solutions*. Nature (London) Phys Sci, 1973. 241: p. 20-22] can be used in the present invention to synthesize a solution of gold nanoparticles ranging in diameter from 8-10 nm. Briefly, $5.0 \times 10^{-6}$ mol of $HAuCl_4$ is dissolved in 19 ml of deionized water producing a faint yellowish solution. This solution is heated with vigorous stirring in a rotary evaporator for 45 minutes. 1 ml of 0.5% sodium citrate solution is added and the solution is stirred for an additional 30 minutes. The color of the solution gradually changed from the initial faint yellowish to clear, grey, purple and finally a tantalizing wine-red color similar to merlot. The sodium citrate used serves in a dual capacity, first acting as a reducing agent, and second, producing negative citrate ions that are adsorbed onto the gold nanoparticles introducing surface charge that repels the particles and preventing nanocluster formation.

Preparation and Internalization of Liposome-encapsulated Gold Nanoshells: Liposome-encapsulated gold nanoshells are incubated with MCF-7 cells grown on partitioned cover-slips for intracellular delivery. This is done by adding 10 μl of liposome-encapsulated gold nanoshells per 1 ml of cell culture medium. This is incubated for 30 minutes in a humidified (86% RH) incubator at 37° C. and 5% $CO_2$. This cell is used for localization studies; to track the rhodamine-DPPE-labeled liposomes into the cytoplasm of the MCF-7 cell. After incubation, the cells grown on cover-slips are washed three times in cold PBS and fixed using 3.7% formaldehyde in PBS. Rhodamine staining by rhodamine-DPPE-labeled liposomes is analyzed using a Nikon Diaphot 300 inverted microscope (Nikon, Inc., Melville, N.Y.).

Non-Invasive Cleavage of the Drug System In Vivo

After delivery of the drug system into the cell, there is sometimes the need to have the PA system (e.g. psoralen) in the nucleus in order to interact with DNA. If the PA is still linked to the energy modulation agent, both of them have to be transported into the nucleus. In the case with gold nanoparticles as the energy modulation agent system, there are several methods to incubate cells in vitro. For in vivo applications, one can link the PA to the gold nanoparticles using a chemical linkage that can be released (or cut) using non-invasive methods such as infrared, microwave, or ultrasound waves. An example of linkage is through a chemical bond or through a bioreceptor, such as an antibody. In this case, the PA is the antigen molecule bound to the energy modulation agent system that has an antibody targeted to the PA.

When the energy modulation agent-Ab-PA enters the cell, the PA molecules can be released from the energy modulation agent Ab system. To release the PA molecule from the antibody, chemical reagents can be used to cleave the binding between antibody and antigen, thus regenerating the biosensor [Vo-Dinh et al, 1988]. This chemical procedure is simple but is not practical inside a cell due to possible denaturation of the cell by the chemical. In previous studies, it has been demonstrated that the gentle but effective MHz-range ultrasound has the capability to release antigen molecules from the antibody-energy modulation agent system [Moreno-Bondi, M., Mobley, J., and Vo-Dinh, T., "Regenerable Antibody-based Biosensor for Breast Cancer," J. Biomedical Optics, 5, 350-354 (2000)]. Thus, an alternative embodiment is to use gentle ultrasonic radiation (non-invasively) to remove the PA (antigen) from the antibody at the energy modulation agent system.

In a preferred embodiment, the PA molecule is bound to the energy modulation agent by a chemically labile bond [Jon A. Wolff, and David B. Rozema, Breaking the Bonds: Non-viral Vectors Become Chemically Dynamic, *Molecular Therapy* (2007) 16(1), 8-15]. A promising method of improving the efficacy of this approach is to create synthetic vehicles (SVs) that are chemically dynamic, so that delivery is enabled by the cleavage of chemical bonds upon exposure to various physiological environments or external stimuli. An example of this approach is the use of masked endosomolytic agents (MEAs) that improve the release of nucleic acids from endosomes, a key step during transport. When the MEA enters the acidic environment of the endosome, a pH-labile bond is broken, releasing the agent's endosomolytic capability.

Use of Ferritin and Apoferritin as Targeted Drug Delivery

Another embodiment to deliver the energy modulation agent-PA drugs involves the use of ferritin and apoferritin compounds. There is increasing interest in ligand-receptor-mediated delivery systems due to their non-immunogenic and site-specific targeting potential to the ligand-specific bio-sites. Platinum anticancer drug have been encapsulated in apoferritin [Zhen Yang, Xiaoyong Wang, Huajia Diao, Junfeng Zhang, Hongyan Li, Hongzhe Sun and Zijian Guo, Encapsulation of platinum anticancer drugs by apoferritin, *Chem. Commun.* 33, 2007, 3453-3455]. Ferritin, the principal iron storage molecule in a wide variety of organisms, can also be used as a vehicle for targeted drug delivery. It contains a hollow protein shell, apoferritin, which can contain up to its own weight of hydrous ferric oxide-phosphate as a microcrystalline micelle. The 24 subunits of ferritin assemble automatically to form a hollow protein cage with internal and external diameters of 8 and 12 nm, respectively. Eight hydrophilic channels of about 0.4 nm, formed at the intersections of subunits, penetrate the protein shell and lead to the protein cavity. A variety of species such as gadolinium ($Gd^{3+}$) contrast agents, desferrioxamine B, metal ions, and nanoparticles of iron salts can be accommodated in the cage of apoferritin. Various metals such as iron, nickel, chromium and other materials have been incorporated into apoferritin [Iron incorporation into apoferritin. The role of apoferritin as a ferroxidase, The Journal of Biological Chemistry [0021-9258] Bakker yr: 1986 vol: 261 iss: 28 pg: 13182-5; Mitsuhiro Okuda[1], Kenji Iwahori[2], Ichiro Yamashita[2], Hideyuki Yoshimura[1]*, Fabrication of nickel and chromium nanoparticles using the protein cage of apoferritin, Biotechnology Bioengineering, Volume 84, Issue 2, Pages 187-194]. Zinc selenide nanoparticles (ZnSe NPs) were synthesized in the cavity of the cage-shaped protein apoferritin by designing a slow chemical reaction system, which employs tetraaminezinc ion and selenourea. The chemical synthesis of ZnSe NPs was realized in a spatially selective manner from an aqueous solution, and ZnSe cores were formed in almost all apoferritin cavities with little bulk precipitation [Kenji Iwahori, Keiko Yoshizawa, Masahiro Muraoka, and Ichiro Yamashita, Fabrication of ZnSe Nanoparticles in the Apoferritin Cavity by Designing a Slow Chemical Reaction System, Inorg. Chem., 44 (18), 6393-6400, 2005].

A simple method for synthesizing gold nanoparticles stabilized by horse spleen apoferritin (HSAF) is reported using $NaBH_4$ or 3-(N-morpholino)propanesulfonic acid (MOPS) as the reducing agent [Lei Zhang, Joe Swift, Christopher A. Butts, Vijay Yerubandi and Ivan J. Dmochowski, Structure and activity of apoferritin-stabilized gold nanoparticles, Journal of Inorganic Biochemistry, Vol. 101, 1719-1729, 2007]. Gold sulfite ($Au_2S$) nanoparticles were prepared in the cavity of the cage-shaped protein, apoferritin. Apoferritin has a cavity, 7 nm in diameter, and the diameter of fabricated $Au_2S$ nanoparticles is about the same size with the cavity and size dispersion was small. [Keiko Yoshizawa, Kenji Iwahori, Kenji Sugimoto and Ichiro Yamashita, Fabrication of Gold Sulfide Nanoparticles Using the Protein Cage of Apoferritin, Chemistry Letters, Vol. 35 (2006), No. 10 p. 1192]. Thus, in a preferred embodiment, the PA or energy modulation agent-PA compounds are encapsulated inside the apoferrtin shells.

Use of Ferritin and Apoferritin as Enhanced Targeting Agents

It was reported that ferritin could be internalized by some tumor tissues, and the internalization was associated with the membrane-specific receptors [S. Fargion, P. Arosio, A. L. Fracanzoni, V. Cislaghi, S. Levi, A. Cozzi, A Piperno and A. G. Firelli, *Blood*, 1988, 71, 753-757; P. C. Adams, L. W. Powell and J. W. Halliday, *Hepatology*, 1988, 8, 719-721]. Previous studies have shown that ferritin-binding sites and the endocytosis of ferritin have been identified in neoplastic cells [M. S. Bretscher and J. N. Thomson, *EMBO J.*, 1983, 2, 599-603]. Ferritin receptors have the potential for use in the delivery of anticancer drugs into the brain [S. W. Hulet, S. Powers and J. R. Connor, *J. Neurol. Set.*, 1999, 165, 48-55]. In one embodiment, the present invention uses ferritin or apoferritin to both encapsulate PA and energy modulation agent-PA systems and also target tumor cells selectively for enhanced drug delivery and subsequent phototherapy. In this case no additional bioreactors are needed.

FIGS. 15A to 15D schematically illustrate the use of encapsulated photoactive agents (FIG. 15A) for delivery into tissue and subsequent release of the photoactive drugs after the encapsulated systems enter the cell. Note the encapsulated system can have a bioreceptor for selective tumor targeting (FIG. 15B). Once inside the cell, the capsule shell (e.g., liposomes, apoferritin, etc.) can be broken (FIG. 15C) using non-invasive excitation (e.g., ultrasound, RF, microwave, IR, etc) in order to release the photoactive molecules that can get into the nucleus and bind to DNA (FIG. 15D).

Non-Invasive Phototherapy Using PEPST Modality

Figure 16B:
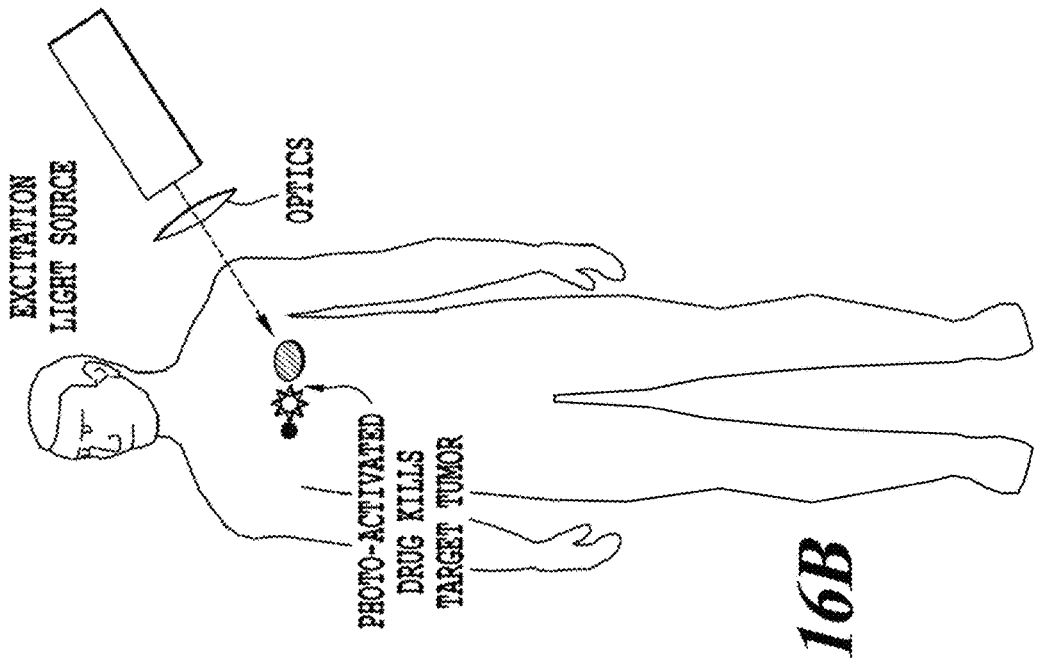
FIGS. 16A and 16 B are simplified graphical representations of the use of the present invention principle of non-invasive PEPST modality.
Figure 16A:
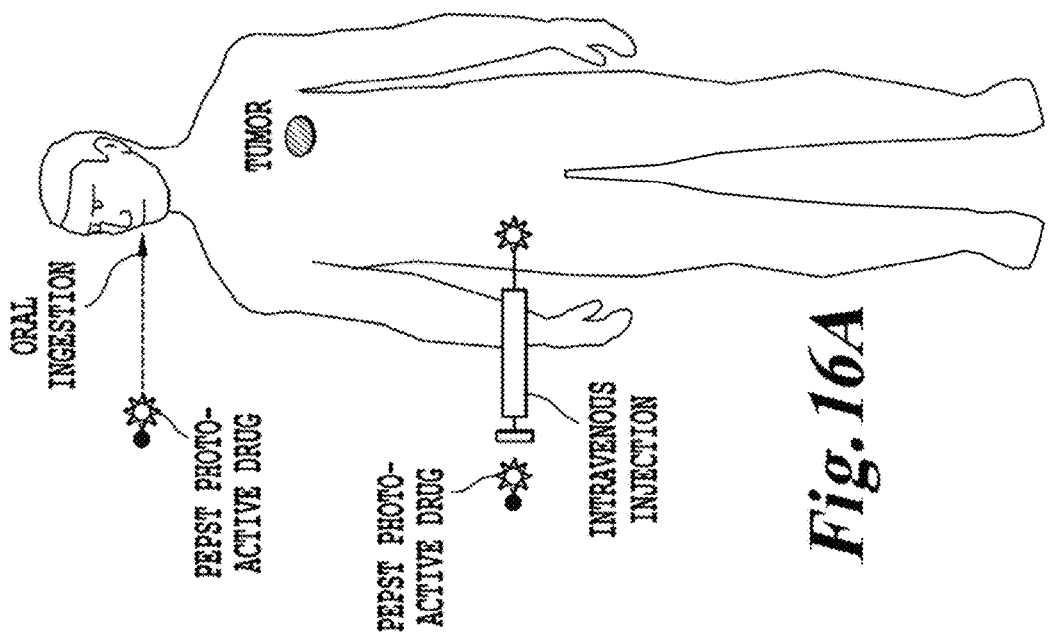

FIGS. 16A and 16B illustrate the basic operating principle of the PEPST modality. The PEPST photoactive drug molecules are given to a patient by oral ingestion, skin application, or by intravenous injection. The PEPST drugs travel through the blood stream inside the body towards the targeted tumor (either via passive or active targeting strategies). If the disease is systematic in nature a photon radiation at suitable wavelengths is used to irradiate the skin of the patient, the light being selected to penetrate deep inside tissue (e.g., NIR or X ray). For solid tumors, the radiation light source is directed at the tumor. Subsequently a treatment procedure can be initiated using delivery of energy into the tumor site. One or several light sources may be used as described in the previous sections. One embodiment of therapy comprises sending NIR radiation using an NIR laser through focusing optics. Focused beams of other radiation types, including but not limited to X ray, microwave, radio waves, etc. can also be used and will depend upon the treatment modalities used.

The present invention treatment may also be used for inducing an auto vaccine effect for malignant cells, including those in solid tumors. To the extent that any rapidly dividing cells or stem cells may be damaged by a systemic treatment, then it may be preferable to direct the stimulating energy directly toward the tumor, preventing damage to most normal, healthy cells or stem cells by avoiding photoactivation or resonant energy transfer of the photoactivatable agent.

Exciton-Plasmon Enhanced Phototherapy (EPEP)
Basic Principle of Exciton-Induced Phototherapy
Excitons in Solid Materials Excitons are often defined as "quasiparticles" inside a solid material. In solid materials, such as semiconductors, molecular crystals and conjugated organic materials, light excitation at suitable wavelength (such as X ray, UV and visible radiation, etc) can excite electrons from the valence band to the conduction band. Through the Coulomb interaction, this newly formed conduction electron is attracted, to the positively charged hole it left behind in the valence band. As a result, the electron and hole together form a bound state called an exciton. (Note that this neutral bound complex is a "quasiparticle" that can behave as a boson—a particle with integer spin which obeys Bose-Einstein statistics; when the temperature of a boson gas drops below a certain value, a large number of bosons 'condense' into a single quantum state—this is a Bose-Einstein condensate (BEC). Exciton production is involved in X-ray excitation of a solid material. Wide band-gap materials are often employed for transformation of the x-ray to ultraviolet/visible photons in the fabrication of scintillators and phosphors [Martin Nikl, *Scintillation detectors for x-rays, Meas. Sci. Technol.* 17 (2006) R37-R54]. The theory of excitons is well known in materials research and in the fabrication and applications of semiconductors and other materials. However, to the present inventors' knowledge, the use of excitons and the design of energy modulation agent materials based on exciton tunability for phototherapy have not been reported.

During the initial conversion a multi-step interaction of a high-energy X-ray photon with the lattice of the scintillator material occurs through the photoelectric effect and Compton scattering effect; for X-ray excitation below 100 keV photon energy the photoelectric effect is the main process. Many excitons (i.e., electron-hole pairs) are produced and thermally distributed in the conduction bands (electrons) and valence bands (holes). This first process occurs within less than 1 ps. In the subsequent transport process, the excitons migrate through the material where repeated trapping at defects may occur, leading to energy losses due to nonradiative recombination, etc. The final stage, luminescence, consists in consecutive trapping of the electron-hole pairs at the luminescent centers and their radiative recombination. The electron-hole pairs can be trapped at the defects and recombine, producing luminescent. Luminescent dopants can also be used as traps for exciton.

Exciton Traps

Figure 17A:
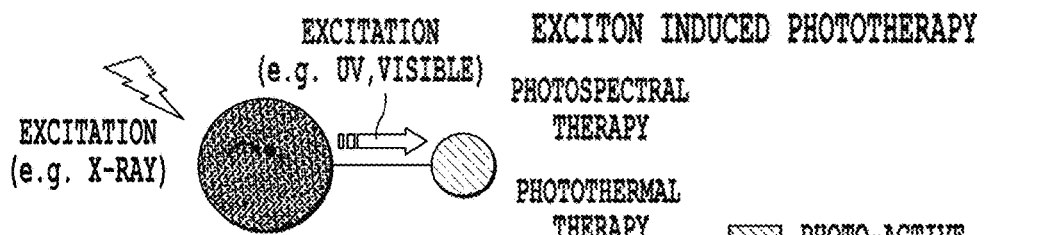
FIGS. 17A and 17B show various schematic embodiments of basic EIP probes.
Figure 17B:
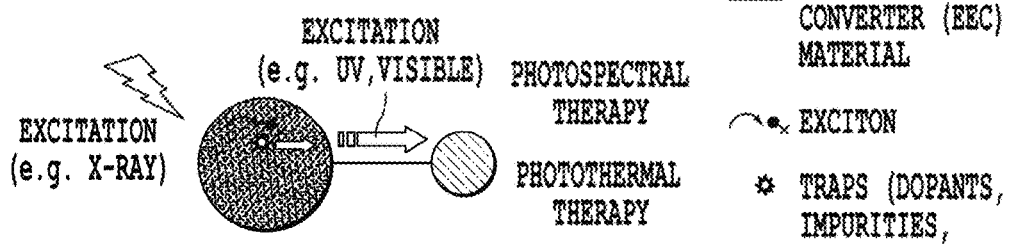

Exciton traps can be produced using impurities in the crystal host matrix. In impure crystals with dipolar guest molecules the electron trap states may arise when electron is localized on a neighbor of the impurity molecule. Such traps have been observed in anthracene doped with carbazole [Kadshchuk, A. K, Ostapenko, N. I, Skryshevskii, Yu. A., Sugakov, V. I. and Susokolova, T. O., *Mol. Cryst. and Liq. Cryst.,* 201, 167 (1991)]. The formation of these traps is due to the interaction of the dipole moment of the impurity with charge carrier. When the concentration of the dopant (or impurities) is increased, spectra exhibit additional structure of spectrum due to the trapping of carriers on clusters of impurity molecules. Sometimes, impurities and dopants are not required: the electron or exciton can also be trapped on a structural defect in such crystals due to the electrostatic interaction with reoriented dipole moment of disturbed crystal molecules [S. V. Izvekov, V. I. Sugakov, *Exciton and Electron Traps on Structural Defects in Molecular Crystals with Dipolar Molecules, Physica Scripta.* Vol. T66, 255-257, 1996]. One can design structural defects in molecular crystals that serve as exiton traps. The development of GaAs/AlGaAs nanostructures and use of nanofabrication technologies can design engineered exciton traps with novel quantum mechanical properties in materials Design, Fabrication and Operation of EIP Probes FIGS. 17A and 17B show various embodiments of EIP probes that can be designed:

(A) probe comprising PA molecules bound (through a linker, which can be fixed or detachable) to an energy modulation agent particle that can produce excitons under radiative excitation at a suitable wavelength (e.g., X-ray). In this preferred embodiment, the energy modulation agent materials have structural defects that serve as traps for excitons.

(B) probe comprising PA molecules bound (through a linker, which can be fixed or detachable) to an energy modulation agent particle that can produce excitons under radiative excitation at a suitable wavelength (e.g., X-ray). In this preferred embodiment, the energy modulation agent materials have impurities or dopant molecules that serve as traps for excitons.

EIP Probes with Tunable Emission:

The embodiment in probes B provide the capability to tune the energy conversion from an X ray excitation source into a wavelength of interest to excite the PA molecules. In 1976, D' Silva et al demonstrated that polynuclear aromatic hydrocarbons (PAH) molecules doped in a frozen n-alkane solids could be excited by X-ray and produce luminescence at visible wavelengths characteristics of their luminescence spectra. [A. P. D'Silva, G. J. Oestreich, and V. A. Fassel, X-ray excited optical luminescence of polynuclear aromatic hydrocarbons, Anal. Chem.; 1976; 48(6) pp 915-917]. Tunable EIP probes can be designed to contain such luminescent dopants such as highly luminescent PAHs exhibiting luminescence emission in the range of 300-400 nm suitable to activate psoralen. A preferred embodiment of the EIP with tunable emission comprises a solid matrix (semiconductors, glass, quartz, conjugated polymers, etc) doped with naphthalene, phenanthrene, pyrene or other compounds exhibiting luminescence (fluorescence) in the 300-400 nm range [T. Vo-Dinh, *Multicomponent analysis by synchronous luminescence spectrometry, Anal. Chem.;* 1978; 50(3) pp 396-401]. The EEC matrix could be a semiconductor material, preferably transparent at optical wavelength of interest (excitation and emission).

Other dopant species such as rare earth materials can also be used as dopants. FIG. 27 shows the X ray excitation optical luminescence (XEOL) of Europium doped in a matrix of BaFBr, emitting at 370-420 nm. U.S. Patent Application Publication No. 2007/0063154 (hereby incorporated by reference) describes these and other nanocomposite materials (and methods of making them) suitable for XEOL.

Various EIP probes can be designed:

(A) A probe comprising PA molecules bound around the energy modulation agent particle or embedded in a shell around an energy modulation agent particle that can produce excitons under radiative excitation at a suitable wavelength (e.g., X-ray). In this preferred embodiment, the energy modulation agent materials has structural defects that serve as traps for excitons.

(B) A probe comprising PA molecules bound around the energy modulation agent particle or embedded in a shell around an energy modulation agent particle that can produce excitons under radiative excitation at a suitable wavelength (e.g., X-ray). In this preferred embodiment, the energy modulation agent materials have impurities or dopant molecules that serve as traps for excitons.

Principle of Exciton-Plasmon Enhanced Phototherapy (EPEP)

There is recent interest in an advanced photophysical concept involving quantum optical coupling between electronic states (excitons), photons and enhanced electromagnetic fields (plasmons). Such a concept involving coupling between excitons and plasmons can be used to enhance a phototherapy modality, referred to as Exciton-Plasmon Enhanced Phototherapy (EPEP).

A fundamental key concept in photophysics is the formation of new quasiparticles from admixtures of strongly-coupled states. Such mixed states can have unusual properties possessed by neither original particle. The coupling between excitons and plasmons can be either weak or strong. When the light-matter interaction cannot be considered as a perturbation, the system is in the strong coupling regime. Bellesa et al showed a strong coupling between a surface plasmon (SP) mode and organic excitons occurs; the organic semiconductor used is a concentrated cyanine dye in a polymer matrix deposited on a silver film [Ref. J. Bellessa, * C. Bonnand, and J. C. Plenet, J. Mugnier, *Strong Coupling between Surface Plasmons and Excitons in an Organic Semiconductor*, Phys. Rev. Lett, 93 (3), 036404-1, 2004]. Govorov et al describe the photophysical properties of excitons in hybrid complexes consisting of semiconductor and metal nanoparticles. The interaction between individual nanoparticles can produce an enhancement or suppression of emission. Enhanced emission comes from electric field amplified by the plasmon resonance, whereas emission suppression is a result of energy transfer from semiconductor to metal nanoparticles. [Alexander O. Govorov, *, † Garnett W. Bryant, ‡ Wei Zhang, † Timur Skeini, † Jaebeom Lee, § Nicholas A. Kotov, § Joseph M. Slocik, | and Rajesh R. Naik|, *Exciton-Plasmon Interaction and Hybrid Excitons in Semiconductor-Metal Nanoparticle Assemblies*, Nano Lett., Vol. 6, No. 5, 984, 2006]. Bondarev et al also described a theory for the interactions between excitonic states and surface electromagnetic modes in small-diameter (<1 nm) semiconducting single-walled carbon nanotubes (CNs). [I. V. Bondarev, K. Tatur and L. M. Woods, *Strong exciton-plasmon coupling in semiconducting carbon nanotubes*].

Fedutik et al reported about the synthesis and optical properties of a composite metal-insulator-semiconductor nanowire system which consists of a wet-chemically grown silver wire core surrounded by a $SiO_2$ shell of controlled thickness, followed by an outer shell of highly luminescent CdSe nanocrystals [Yuri Fedutik, † Vasily Temnov, † Ulrike Woggon, † Elena Ustinovich, ‡ and Mikhail Artemyev*‡, *Exciton-Plasmon Interaction in a Composite Metal-Insulator-Semiconductor Nanowire System*, J. Am. Chem. Soc., 129 (48), 14939-14945, 2007]. For a $SiO_2$ spacer thickness of ~15 nm, they observed an efficient excitation of surface plasmons by excitonic emission of CdSe nanocrystals. For small d, well below 10 nm, the emission is strongly suppressed (PL quenching), in agreement with the expected dominance of the dipole-dipole interaction with the damped mirror dipole [G. W. Ford and W. H. Weber, *Electromagnetic interactions of molecules with metal surfaces,"* Phys. Rep. 113, 195-287 (1984)]. For nanowire lengths up to ~10 μm, the composite metal-insulator-semiconductor nanowires ((Ag)$SiO_2$)CdSe act as a waveguide for 1D-surface plasmons at optical frequencies with efficient photon out coupling at the nanowire tips, which is promising for efficient exciton-plasmon-photon conversion and surface plasmon guiding on a submicron scale in the visible spectral range.

Experiments on colloidal solutions of Ag nanoparticles covered with J-aggregates demonstrated the possibility of using the strong scattering cross section and the enhanced field associated with surface plasmon to generate stimulated emission from J-aggregate excitons with very low excitation powers. [Gregory A. Wurtz, * Paul R. Evans, William Hendren, Ronald Atkinson, Wayne Dickson, Robert J. Pollard, and Anatoly V. Zayats, Molecular Plasmonics with Tunable *Exciton-Plasmon Coupling Strength in J-Aggregate Hybridized Au Nanorod Assemblies*, Nano Lett., Vol. 7, No. 5, 1297, 2007]. Their coupling to surface plasmons excitations therefore provides a particularly attractive approach for creating low-powered optical devices. This process can lead to efficient X-ray coupling for phototherapy. In addition, the coupling of J-aggregates with plasmonics structures presents genuine fundamental interest in the creation of mixed plasmon-exciton states.

Design, Fabrication and Operation of EPEP Probes

Figure 18A:
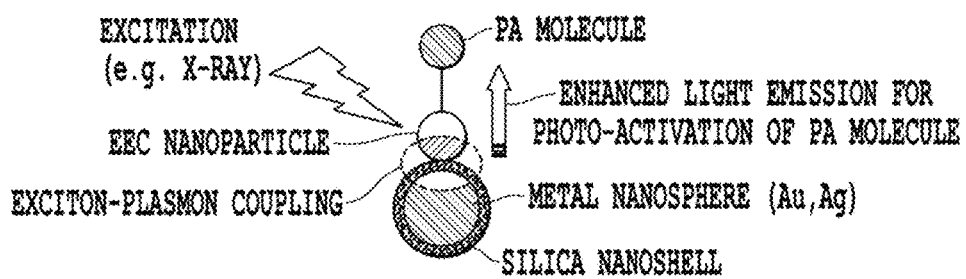
FIGS. 18A and 18B are graphical representations of various embodiments of basic EPEP probes.
Figure 18B:
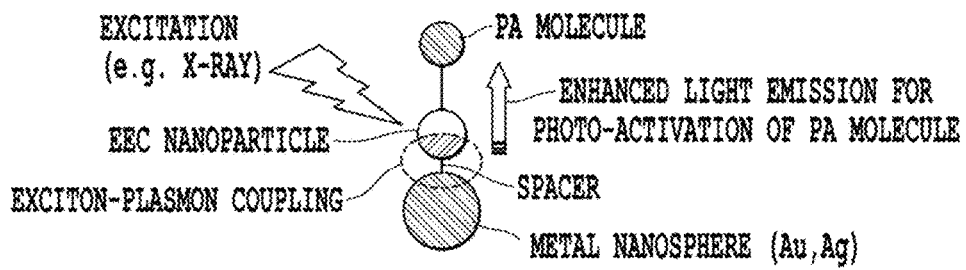

FIGS. 18A and 18B show various embodiments of EPEP probes of the present invention showing the exciton-plasmon coupling:

(A) a probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticle covered with a nanoshell of silica (or other dielectric material). The silica layer (or nanoshell) is designed to prevent quenching of the luminescence light emitted by the energy modulation agent particle excited by X-ray. The metal nanoparticle (Au, Ag, etc) is designed to induce plasmons that enhance the X ray excitation that subsequently leads to an increase in the energy modulation agent light emission, ultimately enhancing the efficiency of photoactivation, i.e. phototherapy. The structure of the nanoparticle can also be designed such that the plasmonics effect also enhances the energy modulation agent emission light. These processes are due to strong coupling between excitons (in the energy modulation agent materials and plasmons in the metal nanoparticles; and (B) a probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticle via a spacer (linker). The spacer is designed to prevent quenching of the luminescence light emitted by the energy modulation agent particle excited by X-ray.

Figure 19A:
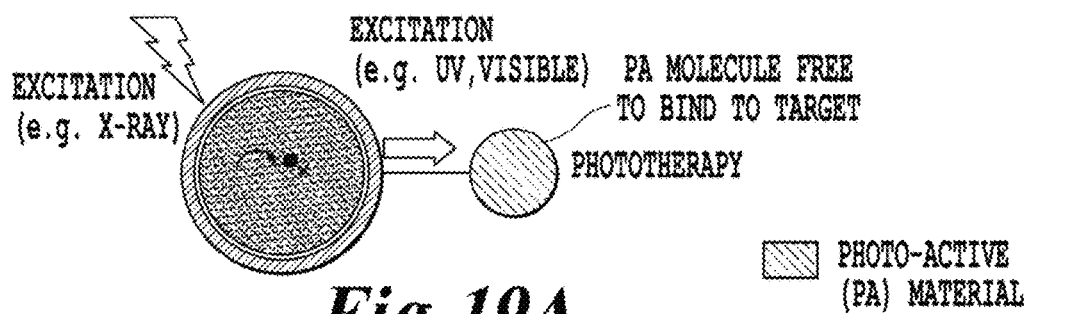
FIGS. 19A to 19C are graphical representations of various embodiments of basic EPEP probes.
Figure 19B:
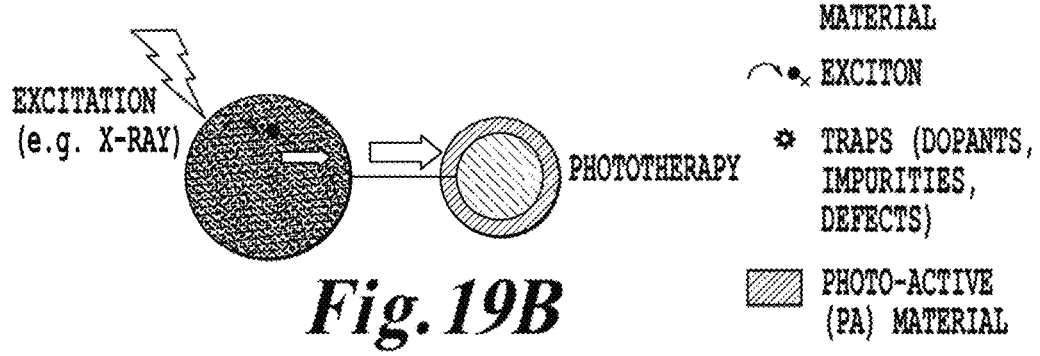
Figure 19C:
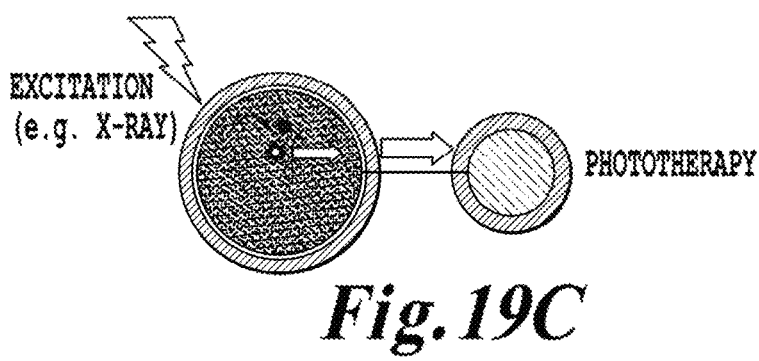

FIGS. 19A to 19C show yet further embodiments of EPEP probes of the present invention:

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is covered with a nanoshell of silica (or other dielectric material), which is covered by a layer of separate nanostructures (nano islands, nanorods, nanocubes, etc. . . . ) of metal (Au, Ag). The silica layer (or other dielectric material) is designed to prevent quenching of the luminescence light emitted by the EEC (also referred to as energy modulation agent) particle excited by X-ray. The metal nanostructures (Au, Ag, etc) are designed to induce plasmons that enhance the X ray excitation that subsequently leads to an increase in the EEC light emission, ultimately enhancing the efficiency of photoactivation, i.e. phototherapy. The structure of the nanoparticle can also be designed such that the plasmonics effect also enhance the energy modulation agent emission light. These processes are due to strong coupling between excitons (in the energy modulation agent materials and plasmons in the metal nanostructures).

(B) a probe comprising a group of PA molecules in a particle bound (through a linker, which can be fixed or detachable) to an energy modulation agent particle that can produce excitons under radiative excitation at a suitable wavelength (e.g., X-ray). The PA-containing particle is covered with a layer of metallic nanostructures (Au, Ag). The metal nanostructures (Au, Ag, etc) are designed to induce plasmons that enhance the energy modulation agent light emission, ultimately enhancing the efficiency of photoactivation, i.e. phototherapy.

(C) a probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is covered with a nanoshell of silica (or other dielectric material), which is covered by a layer of metallic nanostructures (Au, Ag). The silica layer (or other dielectric material) is designed to prevent quenching of the luminescence light emitted by the energy modulation agent particle excited by X-ray. The metal nanostructures (Au, Ag, etc) are designed to induce plasmons that enhance the X ray excitation that subsequently leads to an increase in the energy modulation agent light emission, ultimately enhancing the efficiency of photoactivation, i.e. phototherapy. In addition. the PA-containing to particle is covered with a layer of metallic nanostructures (Au, Ag). The metal nanostructures (Au, Ag, etc) are designed to induce plasmons that enhance the EEC light emission, ultimately enhancing the efficiency of photoactivation, i.e. phototherapy.

Hybrid EPEP Nano-Superstructures

EPEP probes can also comprise hybrid self-assembled superstructures made of biological and abiotic nanoscale components, which can offer versatile molecular constructs with a spectrum of unique electronic, surface properties and photospectral properties for use in phototherapy.

Biopolymers and nanoparticles can be integrated in superstructures, which offer unique functionalities because the physical properties of inorganic nanomaterials and the chemical flexibility/specificity of polymers can be used. Noteworthy are complex systems combining two types of excitations common in nanomaterials, such as excitons and plasmons leading to coupled excitations. Molecular constructs comprising building blocks including metal, semiconductor nanoparticles (NPs), nanorods (NRs) or nanowires (NWs) can produce EPEP probes with an assortment of photonic properties and enhancement interactions that are fundamentally important for the field of phototherapy. Some examples of assemblies of some NW nanostructures and NPs have been reported in biosensing. Nanoscale superstructures made from CdTe nanowires (NWs) and metal nanoparticles (NPs) are prepared via bioconjugation reactions. Prototypical biomolecules, such as D-biotin and streptavidin pair, were utilized to connect NPs and NWs in solution. It was found that Au NPs form a dense shell around a CdTe NW. The superstructure demonstrated unusual optical effects related to the long-distance interaction of the semiconductor and noble metal nanocolloids. The NW☐NP complex showed 5-fold enhancement of luminescence intensity and a blue shift of the emission peak as compared to unconjugated NW. [Jaebeom Lee, † Alexander O. Govorov, ‡ John Dulka, ‡ and Nicholas A. Kotov*, †, *Bioconjugates of CdTe Nanowires and Au Nanoparticles: Plasmon-Exciton Interactions, Luminescence Enhancement, and Collective Effects, Nano Lett.*, Vol. 4, No. 12, 2323, 2004].

To the present inventors' knowledge, these advanced concepts have not been applied to phototherapy and EPEP probes comprising superstructures from NPs, NRs and NWs are still a new unexplored territory of phototherapy.

Figure 20A:
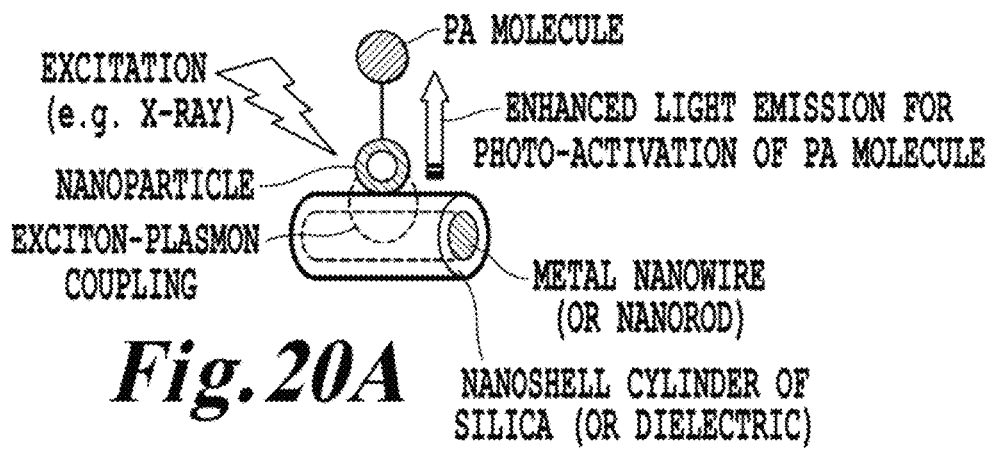
FIGS. 20A and 20B are graphical representations various embodiments of EPEP probes having NPs, NWs and NRs.
Figure 20B:
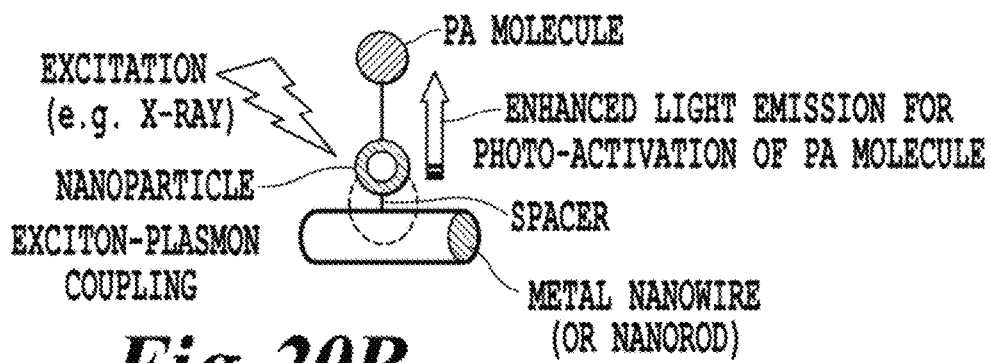

FIGS. 20A and 20B various embodiments of EPEP probes of the present invention comprising superstructures of NPs, NWs and NRs.:

(A) a probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanowire (or nanorod) covered with a nanoshell cylinder of silica (or other dielectric material). The silica nanoshells cylinder is designed to prevent quenching of the luminescence light emitted by the energy modulation agent particle excited by X-ray. The metal nanoparticle (Au, Ag, etc) is designed to induce plasmons that enhance the X ray excitation that subsequently leads to an increase in the energy modulation agent light emission, ultimately enhancing the efficiency of photoactivation, i.e. phototherapy. The structure of the nanoparticle can also be designed such that the plasmonics effect and/or the exciton-plasmon coupling (EPC) effect also enhances the energy modulation agent emission light. These processes are due to strong coupling between excitons (in the energy modulation agent materials and plasmons in the metal nanoparticles; and (B) a probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticles via a spacer (linker). The spacer is designed to prevent quenching of the luminescence light emitted by the energy modulation agent particle excited by X-ray. Same effect as above in (A)

Figure 21A:
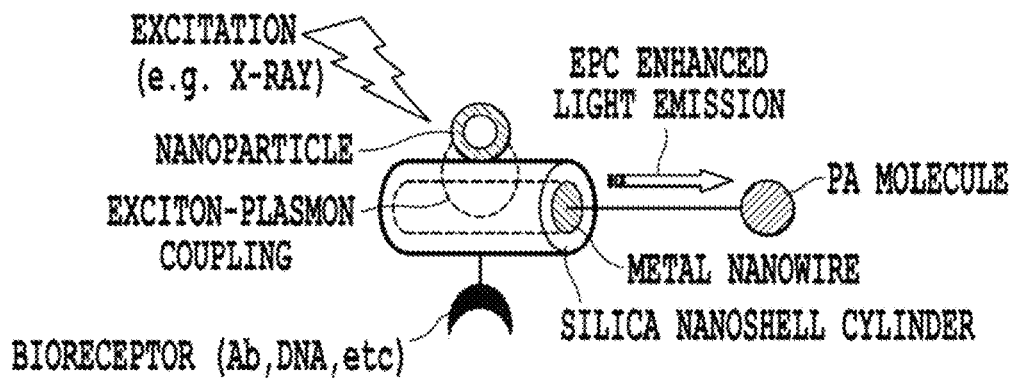
FIGS. 21A and 21B are graphical representations of various embodiments of EPEP probes having NPs, NWs, NRs and bioreceptors.
Figure 21B:
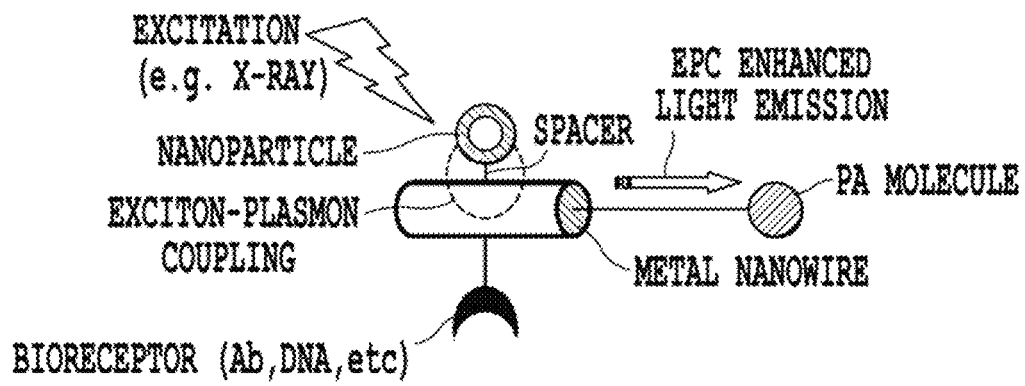

FIGS. 21A and 21B show another set of embodiments of EPEP probes of the present invention comprising superstructures of NPs, NWs and NRs and bioreceptors (antibodies, DNA, surface cell receptors, etc.). The use of bioreceptors to target tumor cells has been discussed previously above in relation to PEPST probes. Note that in this embodiment the PA molecules are attached along the NW axis in order to be excited by the emitting light form the NWs.

Figure 22:
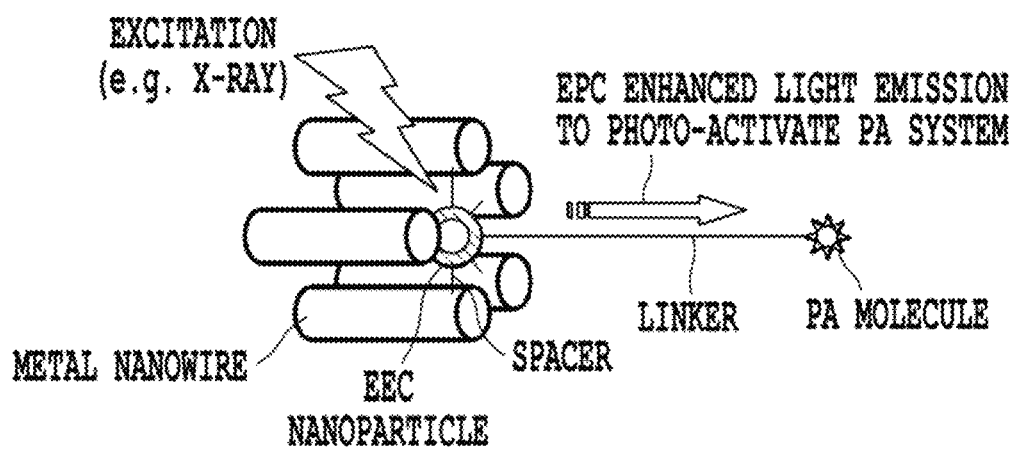
FIG. 22 is a graphical representation of an embodiment of EPEP probes having NPs and multiple NWs.

FIG. 22 shows another embodiment of EPEP probes of the present invention comprising superstructures of NPs linked to multiple NWs.

For some embodiments, by adding metal nanostructures designed to interact specifically with the excitons in the energy modulation agent system, there are significant improvements:

(1) an additional radiative pathway from exciton to photon conversion is introduced (2) the metal nanostructures can be designed to amplify (due to the plasmonics effect) the excitation radiation (e.g., X-ray) and/or the emission radiation (e.g, UV or visible) to excite the photo-active (PA) molecule, thereby enhancing the PA effectiveness.

Various metallic nanostructures that can be used in EPEP probe embodiments of the present invention are the same as those illustrated in FIG. 9A for the PEPST probes.

EPEP Probes with Microresonators

In a preferred embodiment the energy modulation agent system can be designed to serve also as a microresonator having micron or submicron size. Lipson et al described a resonant microcavity and, more particularly, to a resonant microcavity which produces a strong light-matter interaction [M. Lipson; L. C. Kimerling; Lionel C, *Resonant microcavities*, U.S. Pat. No. 6,627,923, 2000]. A resonant microcavity, typically, is formed in a substrate, such as silicon, and has dimensions that are on the order of microns or fractions of microns. The resonant microcavity contains optically-active matter (i.e., luminescent material) and reflectors which confine light in the optically-active matter. The confined light interacts with the optically-active matter to produce a light-matter interaction. The light-matter interaction in a microcavity can be characterized as strong or weak. Weak interactions do not alter energy levels in the matter, whereas strong interactions alter energy levels in the matter. In strong light-matter interaction arrangements, the confined light can be made to resonate with these energy level transitions to change properties of the microcavity.

Experimental Methods

Preparation of Nanoparticles (Ag, Au)

There many methods to prepare metal nanoparticles for EPEP or PEPST probes. Procedures for preparing gold and silver colloids include electroexplosion, electrodeposition, gas phase condensation, electrochemical methods, and solution-phase chemical methods. Although the methodologies for preparing homogeneous-sized spherical colloidal gold populations 2-40 nm in diameter are well known [N. R. Jana, L. Gearheart and C. J. Murphy, *Seeding growth for size control of 5-40 nm diameter gold nanoparticles. Langmuir* 17 (2001), pp. 6782-6786], and particles of this size are commercially available. An effective chemical reduction method for preparing populations of silver particles (with homogeneous optical scattering properties) or gold particles (with improved control of size and shape monodispersity) is based on the use of small-diameter uniform-sized gold particles as nucleation centers for the further growth of silver or gold layers.

A widely used approach involves citrate reduction of a gold salt to produce 12-20 nm size gold particles with a relatively narrow size distribution. The commonly used method for producing smaller gold particles was developed by Brust et al [Brust, M; Walker, M; Bethell, D.; Schiffrin, D. J.; Whyman, R. *Chem. Commun.* 1994, 801]. This method is based on borohydride reduction of gold salt in the presence of an alkanethiol capping agent to produce 1-3 nm particles. Nanoparticle sizes can be controlled between 2 and 5 nm by varying the thiol concentration, [Hostetler, M. J.; Wingate, J. E.; Zhong, C. J.; Harris, J. E.; Vachet, R. W.; Clark, M. R.; Londono, J. D.; Green, S. J; Stokes, J. J; Wignall, G. D.; Glish, G. L.; Porter, M. D.; Evans, N. D.; Murray, R. W. *Langmuir* 1998, 14, 17]. Phosphine-stabilized gold clusters have also been produced and subsequently converted to thiol-capped clusters by ligand exchange in order to improve their stability [Schmid, G.; Pfeil, R.; Boese, R.; Bandrmann, F.; Meyer, S.; Calis, G. H. M.; van der Velden, J. W. A. *Chem. Ber.* 1981, 114, 3634; Warner, M. G.; Reed, S. M.; Hutchison, J. E. *Chem. Mater.* 2000, 12, 3316.] and phosphine-stabilized monodispersed gold particles were prepared using a similar protocol to the Brust method [Weare, W. W.; Reed, S. M.; Warner, M. G.; Hutchison, J. E. *J. Am. Chem. Soc.* 2000, 122, 12890]. See also recent review: Ziyi Zhong, Benoit[1] Male, Keith B.[1] Luong, John H. T., *More Recent Progress in the Preparation of Au Nanostructures, Properties, and Applications, Analytical Letters;* 2003, Vol. 36 Issue 15, p 3097-3118]

Fabrication of Nanoparticle of Metal Coated with Nanoshells of Dyes

The fabrication of metal nanoparticles coated with nanoshells of dye molecules can be performed using the method described by Masuhara et al [AKITO MASUHARA_, SATOSHI OHHASHIy, HITOSHI KASAI; SHUJI OKADA, FABRICATION AND OPTICAL PROPERTIES OF NANOCOMPLEXES COMPOSED OF METAL NANOPARTICLES AND ORGANIC DYES, *Journal of Nonlinear Optical Physics & Materials* Vol. 13, Nos. 3 & 4 (2004) 587-592]. Nanocomplexes composed of Ag or Au as a core and 3-carboxlymethyl-5-[2-(3-octadecyl-2-benzoselenazolinylidene) ethylidene]rhodanine (MCSe) or copper (II) phthalocyanine (CuPc) as a shell are prepared by the co-reprecipitation method. In the case of Ag-MCSe nanocomplexes, 0.5 mM acetone solution of MCSe are injected into 10 ml of Ag nanoparticle water dispersion, prepared by the reduc-tion of $AgNO_3$ using $NaBH_4$: Au-MCSe nanocomplexes are also fabricated in a similar manner. A water dispersion of Au nanoparticles was prepared by the reduction of $HAuCl_4$ using sodium citrate. Subsequently, 2 M $NH_4OH$ (50 µl) was added and the mixture was thermally treated at 50° C. This amine treatment often stimulates the J-aggregate formation of MCSe.6 Ag—CuPc and Au—CuPc nanocomplexes were also fabricated in the same manner: 1 mM 1-methyl-2-pyrrolidinone (NMP) solution of CuPc (200 µl) was injected into a water dispersion (10 ml) of Ag or Au nanoparticles.

Having generally described this invention, a further understanding can be obtained by reference to certain specific examples which are provided herein for purposes of illustration only and are not intended to be limiting unless otherwise specified.

Gold Nanoshell Preparations with Dielectric Cores:

Materials:

Yttrium oxide nanoparticles (e.g., 99.9% purity, 32-36 nm average diameter, cubic crystal structure) were obtained from Nanostructured and Amorphous Materials, Inc. (Houston, Tex.). Tri-arginine (H-Arg-Arg-Arg-OH) acetate was obtained from Bachem (Torrance, Calif.), and gold tribromide ($AuBr_3$) was obtained from Alfa Aesar (Ward Hill, Mass.). Dimethyl sulfoxide (DMSO) was purchased from CalBioChem (La Jolla, Calif.) and was used as received. A cysteine-modified version of the TAT peptide (residues 49-57, sequence Arg-Lys-Lys-Arg-Arg-Arg-Gln-Arg-Arg-Cys-CONH2, molecular weight 1442 g/mol, hereafter referred to as "TAT") was obtained from SynBioSci (Livermore, Calif.). Succinimidyl-[4-(psoralen-8-yloxy)]butyrate (SPB) was obtained from Pierce (Rockford, Ill.), and Marina Blue, Alexa 350 and Alexa 546 NHS esters were obtained from Invitrogen (Carlsbad, Calif.). Ultrapure 18.2 MΩ deionized (DI) water purified with a Millipore Synergy filtration system (Millipore, Billerica, Mass.) was used to make all solutions.

Yttrium Oxide Dispersion:

Tip sonication was used to disperse autoclaved $Y_2O_3$ nanoparticles at 10 mg/mL in 10 mM tri-arginine solution which had been pre-filtered at 0.22 microns. Following moderate mixing in a sealed, sterile container on a stir plate for 24 hours to allow tri-arginine attachment and improved $Y_2O_3$ dispersion, the solution was centrifuged at 8200 relative centrifugal force (RCF) to remove fused particles and large aggregates.

Gold Shell Formation:

Supernatant from the initial $Y_2O_3$ dispersion was diluted 1:1 (v/v) with 5.7 mM $AuBr_3$ dissolved in sterile DI water and pre-filtered at 0.22 microns, then exposed to high-intensity fluorescent light (Commercial Electric, Model 926) for 16 hours in a sealed, sterile glass container with moderate mixing. During the time course of this photochemical process, the reddish-brown $AuBr_3$ solution turned yellow immediately after addition of the $Y_2O_3$ in tri-arginine; became clear and visually colorless; then developed an intense purple color as Au shells formed on the $Y_2O_3$ cores. In the absence of the $Y_2O_3$ cores, neither the intense purple color associated with plasmonic absorption by gold nanoshells nor the deep red color associated with solid gold nanoparticles appears. Use of heat rather than light in the presence of $Y_2O_3$ particles tends to produce a large number of solid gold nanoparticles rather than or in addition to core-shell structures, as evidenced by strong absorption at ~530 nm.

Particle Functionalization with TAT:

Gold-coated $Y_2O_3$ nanoparticles were centrifuged at 16 k RCF for 15 minutes, and the pellet was re-dispersed in a 50% volume of sterile DI water by a short tip sonication. The particles were further purified by two additional centrifugations at 16 k RCF for 15 minutes each, with redispersion in a 100% volume of sterile DI water following the second centrifugation and final redispersion in a 100% volume of 1 mg/mL (0.7 mM) TAT peptide dissolved in sterile DI water and pre-filtered at 0.22 microns.

This solution was vigorously mixed at room temperature for one hour to allow thiol anchoring to the gold shell via the c-terminal cysteine residue. Variations in the TAT concentration, temperature and reaction time can all affect the extent of surface coverage and the potential for further functionalization.

Peptide Functionalization with Dye Molecules:

The TAT-functionalized, gold-coated $Y_2O_3$ particles were purified by triplicate centrifugation at 16 k RCF, with the first two re-dispersions in sterile DI water and the final re-dispersion in sterile 100 mM bicarbonate buffer at pH 9.0. Each NHS ester (SPB, Alexa 350, Marina Blue and Alexa 546) was dissolved at 10 mg/mL in dimethyl sulfoxide (DMSO), and 100 microliters of a given NHS-functionalized dye were added to a 1 mL aliquot of TAT-functionalized, gold-coated $Y_2O_3$. The solutions were reacted for one hour at room temperature in the dark with vigorous mixing to allow attachment of dye molecules to primary amines along the TAT peptide (such as the attachment of N terminus and the lysine side chains).

The psoralen-functionalized nanoparticles were centrifugally cleaned using a 1:1 volume of DMSO in water to remove any residual SPB crystals, then all dye-functionalized core-shell nanoparticles were purified by triplicate centrifugation at 16 k RCF for 15 minutes. Each centrifugation step was followed by re-dispersion in a 100% volume of sterile DI water. Presuming removal of 95+% of non-attached dye molecules during each centrifugation step, no more than 0.01% of the unbound dye is estimated to remain in the final solution.

Nanoparticle Characterization:

Transmission electron microscopy (TEM) provides additional evidence for the presence of gold-coated $Y_2O_3$ particles. FIG. 10E, for example, shows a representative TEM image of as purchased $Y_2O_3$ nanoparticles. The particles are quite polydisperse, but exhibit an average diameter of approximately 35 nm. FIG. 10F shows similar images for $Y_2O_3$ particles coated with a gold shell using the synthetic procedure described above. Like the underlying $Y_2O_3$ cores, the gold-coated yttrium oxide particles are somewhat polydisperse with an average diameter of approximately 50 nm.

Perhaps the most conclusive demonstration that these nanoparticles are in fact gold-coated $Y_2O_3$ comes from comparison of X-ray diffraction data (XRD). FIG. 10G shows diffractograms for both the initial cubic $Y_2O_3$ nanoparticles (lower trace) and the final gold-coated core-shell particles (upper trace). Strong peaks at $2\theta=29$, 33.7, 48.5 and 57.5 degrees in the lower trace are indicative of cubic $Y_2O_3$. The most pronounced features in the upper trace are two gold-associated peaks at $2\theta=38.2$ and 44.4 degrees. In addition, the four strongest cubic $Y_2O_3$ peaks at $2\theta=29$, 33.7, 48.5 and 57.5 degrees are also visibly superimposed on the baseline diffractogram from the gold nanoshells. The reason for the broadening of the $Y_2O_3$ peak at $2\theta=29$ degrees is not definite, but may be a result of gold-$Y_2O_3$ interactions or, alternatively, the preferential size-selection of small $Y_2O_3$ particles during the 8200 RCF centrifugation used to remove large $Y_2O_3$ particles and aggregates.

Gold Colloidal Nanoparticles:

a. Synthesis of Gold Nanoparticles

The Frens method (see G. Frens, Nat. Phys. Sci. 241 (1973) 20, the entire contents of which are incorporated herein by reference) can be used to synthesize gold nanoparticles. In this process, $5.0\times10^{-6}$ mol of $HAuCl_4$ was dissolved in 19 mL of deionized water. The resulting solution was faintly yellow. The solution was heated and vigorously stirred in a rotary evaporator for 45 minutes. One mL of 0.5% sodium citrate was added, and the solution was stirred for an additional 30 minutes. Addition of sodium citrate has multiple purposes. First, citrate acts as a reducing agent. Second, citrate ions that adsorb onto the gold nanoparticles introduce surface charge that stabilizes the particles through charge repulsion, thus preventing nanocluster formation.

b. Synthesis of Gold Nanoparticles Having 15-nm Diameter

Two mL of 1% gold chloride in 90 mL DI water was heated to 80° C. for 15 minutes, then 80 mg sodium citrate in 10 ml DI water was added. The solution was boiled and vigorously stirred for 30 minutes. FIG. 10H shows pictures of ~15-nm gold nanoparticles prepared using citrate reduction.

c. Synthesis of 30-nm Gold Nanoparticles

Two mL of 1% $HAuCl_4$ solution in a 100-mL round-bottom flask were mixed with 20 mg of sodium citrate, then boiled and vigorously stirred for 30 minutes. FIG. 10I shows TEM images of 30-nm gold nanoparticles prepared using the citrate reduction technique.

d. Synthesis of 60-nm Gold Nanoparticles

Two mL of 1% HAuCl4 in 100 mL of water were mixed with 10 mg of sodium citrate. The solution was boiled and vigorously stirred for 30 minutes. FIG. 10J shows TEM pictures of 60-nm gold nanoparticles prepared using the citrate reduction technique.

e. Use of Hydrazine Monohydrate as a Reducing Agent:

100 microliters (0.1 mL) of 12 millimolar gold chloride solution was diluted with 80 ml $H_2O$ in a beaker. The initial pH of the gold solution was 3.67. The temperature of the solution was increased to 80° C. for 30 minutes, at which point 0.3 mL hydrazine monohydrate was added to the gold solution. The solution pH shifted to 7.64. Over time, gold solution changed to a very light pink color. FIG. 10K shows TEM pictures of ~30-nm gold nanoparticles prepared using the hydrazine monohydrate reduction technique.

Colloidal Silver Nanoparticles:

Use of Sodium Citrate as a Reducing Agent: In this method, 50 mL of a $10^{-3}$ M $AgNO_3$ aqueous solution was heated to boiling. Then, 1 mL of a 1% trisodium citrate ($C_6H_5O_7Na_3$) was added to the solution, and the solution was maintained at boiling for 1 hour before being allowed to cool. The resultant colloidal mixture exhibited a dark grey color.

Use of Hydroxylamine Hydrochloride as a Reducing Agent:

A colloidal solution was formed by dissolving 0.017 g of silver nitrate ($AgNO_3$) in 90 mL water. 21 mg of hydroxylamine hydrochloride ($NH_2OH.HCl$) was dissolved in 5 mL water and 4.5 ml of 0.1 M sodium hydroxide was added. This mixture was added to the $AgNO_3$ solution. Very rapidly, (e.g., just in a few seconds), a grey-brown solution appeared.

Use of Sodium Borohydride as a Reducing Agent:

Aqueous solutions containing 10 mL $10^{-3}$ M $AgNO_3$ and 30 mL $10^{-3}$ M $NaBH_4$ were mixed under ice-cooled conditions. The $AgNO_3$ solution was added dropwise to the $NaBH_4$ solution with vigorous stirring. The resultant mixture was allowed to age 1 hour before stirring the resultant mixture again for 10 minutes.

Metallic/Dielectric, Multi-Layer, Core-Shell Nanoparticles:

Au Nanoparticles Coated with Ag or Ag Nanoparticles Coated with Au:

Core-shell nanoparticles such as gold-coated silver nanoparticles and silver-coated gold nanoparticles have been synthesized in an aqueous medium using CTAB as a surfactant and ascorbic acid as a reducing agent. Core nanoparticles (i.e. Au or Ag) were prepared using the above procedures, then coated with secondary, tertiary, etc. shells.

For example, spherical gold nanoparticles (~15 nm) were prepared by boiling $HAuCl_4$ in the presence of sodium citrate. For coating gold with a layer of silver, 1 mL of 0.1 M ascorbic acid solution, 0.5 mL of 10 mM $AgNO_3$ solution, and 0.5 mL of the previously formed Au colloid were sequentially added to 20 mL of a 50 mM CTAB solution. Subsequently, 0.1 mL of 1.0 M NaOH was added dropwise, which led to a fast color change (from red to yellow). FIG. 10M shows TEM images of Au nanoparticles coated with Ag.

A similar procedure was used to prepare Ag nanoparticles coated with Au.

Au@Ag@Au@Ag Multi Shell Nanoparticles:

Multishell nanoparticles such as Au@Ag@Au@Ag were prepared using CTAB as a surfactant, and ascorbic acid and NaOH as reducing agents. Spherical gold nanoparticles (~15 nm) were prepared by boiling $HAuCl_4$ in the presence of sodium citrate. To coat gold cores with a layer of silver, 20 mL of a 50 mM CTAB, 1 mL of 0.1 M ascorbic acid, 0.5 mL of 10 mM $AgNO_3$, and 0.5 mL of the Au colloid were sequentially mixed. Subsequently, 0.1 mL of 1.0 M NaOH was added in a dropwise manner, which led to a fast color change from red to yellow.

Then, another gold layer was coated by mixing 20 mL of the Ag-coated Au colloid in water with 1 mL of the ascorbic acid solution. The resulting mixture was then added to 0.05 mL of 0.10 M $HAuCl_4$ in a dropwise manner. The solution color changed to deep blue at this stage. Subsequently, an outer silver shell was formed on the previously formed Au@Ag@Au nanoparticles by mixing 20 mL of colloid with 0.5 mL 10 mM $AgNO_3$ followed by drop wise addition of 0.2 mL of 1.0 M NaOH. The solution then showed a color change to orange. FIG. 10N shows TEM images of Au@Ag@Au@Ag multi-shell nanoparticles.

All of the above core-shell nanoparticle solutions were stable in solution.

Chemical Synthesis of Multi-Layer Core-Shell Structures Using $Y_2O_3$

To deposit multiple shells on $Y_2O_3$ nanoparticles, $Y_2O_3$ nanoparticles were initially coated with Ag via UV photoreduction in a procedure similar to that discussed above for gold shells. In the present invention, a number of approaches can be utilized for the addition of a gold shell. These include 1) a sodium citrate process, 2) a sodium borohydride reduction, 3) a hydrazine monohydrate reduction, 4) a solution containing hydroxyl amine and NaOH, and 5) a mixture of CTAB, ascorbic acid, and NaOH.

Use of Sodium Citrate as a Reducing Agent:

A typical experiment used 0.1 to 1 mL of $Y_2O_3$ coated with Ag (~50 nm), 1 to 3 mL of 2.5 $H10^{-3}$ M $HAuCl_4$, and 50 mL distilled water in a 100 ml round bottom flask. This solution was boiled with constant stirring, and 3 mL of 1 wt % sodium citrate was added. The resultant colloidal solution color became black with a pH of approximately pH 6.5. The solution was stirred for another 15 min and then allowed to stand.

Use of Sodium Borohydride as Reducing Agent:

A typical experiment used 0.1 to 1 mL of $Y_2O_3$ coated with Ag (~50 nm), 1 to 3 mL of 2.5 $H10^{-3}$ M $HAuCl_4$, and 50 mL distilled water in a 100 mL round bottom flask. Under constant stirring this solution was boiled prior to addition of 0.1 to 1 mL of 0.1 M $NaBH_4$ solution. The resultant colloidal solution became black and aggregated within a few minutes.

Probe for Measurement of Apoptosis with the PDT Drug ALA

A method has been developed using nanosensors that can be used to evaluate the effectiveness of PEPST probes. Although one can use conventional methods (not requiring nanosensors), we describe the nanosensor method previously developed [P. M. Kasili, J. M. Song, and T. Vo-Dinh, "*Optical Sensor for the Detection of Caspase-9 Activity in a Single Cell*", *J. Am. Chem. Soc.*, 126, 2799-2806 (2004)]. The method comprises measuring caspases activated by apoptosis induced by the photoactive drugs. In this experiment, we measure two sets of cells I and II. Set I is treated with the drug ALA and set II is treated by the drug ALA conjugated to a PEPST probe described in the previous section. By comparing the results (amount of Caspases detected), one can evaluate the efficiency of the PEPST-ALA drug compared to ALA alone.

In the classical model of apoptosis, caspases are divided into initiator caspases and effector caspases according to their function and their sequence of activation. Initiator caspases include caspase-8, -9, while effector caspases include, caspases-3, -6 and -7. The activation of caspases is one of the earliest biomarkers of apoptosis making caspases an early and ideal target for measuring apoptosis. Apoptosis, or programmed cell death, is a mode of cell death characterized by specific morphological and biochemical features. The results obtained in these experiments can be used to evaluate the effectiveness of phototherapeutic drugs that induce apoptosis (e.g. PDT drugs). Since caspases play a central role in the induction of apoptosis, tetrapeptide-based optical nanosensors were used to determine their role in response to a photodynamic therapy (PDT) agent, δ-aminolevulinic acid (ALA) in the well-characterized human breast carcinoma cell line, MCF-7. MCF-7 cells were exposed to the photosensitizer ALA to explore ALA-PDT induced apoptosis by monitoring caspase-9 and caspase-7 activity. Caspase-9 and caspase-7 protease activity was assessed in single living MCF-7 cells with the known caspase-9 and caspase-7 substrates, Leucine-aspartic-histidine-glutamic acid 7-amino-4-methylcoumarin (LEHD-AMC) and aspartic-glutamic acid-valine-aspartic acid 7-amino-4-methylcoumarin (DEVD-AMC) respectively, covalently immobilized to the nanotips of optical nanosensors. Upon the induction of apoptosis, activated target caspases recognize the tetrapeptide sequence and specifically cleaves it. The recognition of substrate by caspases is immediately followed by a cleavage reaction yielding the fluorescent AMC which can be excited with a Helium-Cadmium (HeCd) laser to generate a measurable fluorescence signal. By comparing the fluorescence signal generated from AMC within cells with activated caspases and from those with inactive caspases, we are able to successfully detect caspase activity within a single living MCF-7 cell.

Chemicals and Reagents

δ-aminolevulinic acid (ALA), phosphate buffered saline (PBS), hydrochloric acid (HCl), nitric acid ($HNO_3$), Glycidoxypropyltrimethoxysilane (GOPS), 1,1'-Carbonyldiimidazole (CDI), and anhydrous acetonitrile were purchased from Sigma-Aldrich, St. Louis, Mo. Caspase-9 substrate, LEHD-7-amino-4-methylcoumarin (AMC), Caspase-7 substrate, DEVD-7-amino-4-methylcoumarin (AMC), 2× reaction buffer, dithiothreitol (DTT), and dimethylsulfoxide (DMSO) were purchased from BD Biosciences, Palo Alto. Calif.

Cell Lines

Human breast cancer cell line, MCF-7, was obtained from American Type Culture Collection (Rockville, Md., USA, Cat-no. HTB22). MCF-7 cells were grown in Dulbecco's Modified Eagle's Medium ((DMEM) (Mediatech, Inc., Herndon, Va.)) supplemented with 1 mM L-glutamine (Gibco, Grand Island, N.Y.) and 10% fetal bovine serum (Gibco, Grand Island, N.Y.). Cell culture was established in growth medium (described above) in standard T25 tissue culture flasks (Corning, Corning, N.Y.). The flasks were incubated in a humidified incubator at 37° C., 5% $CO_2$ and 86% humidity. Cell growth was monitored daily by microscopic observation until a 60-70% state of confluence was achieved. The growth conditions were chosen so that the cells would be in log phase growth during photosensitizer treatment with ALA, but would not be so close to confluence that a confluent monolayer would form by the termination of the chemical exposure. In preparation for experiments, cells were harvested from the T25 flasks and 0.1 ml ($10^5$ cells/ml) aliquots were seeded into 60 mm tissue culture dishes (Corning Costar Corp., Corning, N.Y.) for overnight attachment. The MCF-7 cells were studied as four separate groups with the first group, Group I, being the experimental, exposed to 0.5 mM ALA for 3 h followed by photoactivation ([+]ALA[+]PDT). This involved incubating the cells at 37° C. in 5% $CO_2$ for 3 h with 0.5 mM ALA. Following incubation the MCF-7 cells were exposed to red light from a HeNe laser (λ 632.8 nm, <15 mW, Melles Griot, Carlsbad, Calif.) positioned about 5.0 cm above the cells for five minutes at a fluence of 5.0 mJ/$cm^2$ to photoactivate ALA and subsequently induce apoptosis. The second and third groups, Group II and III respectively, served as the "treated control" and were exposed to 0.5 mM ALA for 3 hours without photoactivation ([+]ALA[−]PDT) and photoactivation without 0.5 mM ALA ([−]ALA[+]PDT]) respectively. The fourth group, Group IV was the "untreated control," which received neither ALA nor photoactivation ([−]ALA[−]PDT Preparation of Enzyme Substrate-Based Optical Nanosensors Briefly, this process involved cutting and polishing plastic clad silica (PCS) fibers with a 600-µm-size core (Fiberguide Industries, Stirling, N.J.). The fibers were pulled to a final tip diameter of 50 nm and then coated with ~100 nm of silver metal (99.999% pure) using a thermal evaporation deposition system (Cooke Vacuum Products, South Norwalk, Conn.) achieving a final diameter of 150 nm. The fused silica nanotips were acid-cleaned ($HNO_3$) followed by several rinses with distilled water. Finally, the optical nanofibers were allowed to air dry at room temperature in a dust free environment. The nanotips were then silanized and treated with an organic coupling agent, 10% Glycidoxypropyltrimethoxysilane (GOPS) in distilled water. The silanization agent covalently binds to the silica surface of the nanotips modifying the hydroxyl group to a terminus that is compatible with the organic cross-linking reagent, 1'1, Carbonyldiimidazole (CDI). The use of CDI for activation introducing an imidazole-terminal group was particularly attractive since the protein to be immobilized could be used without chemical modification. Proteins bound using this procedure remained securely immobilized during washing or subsequent manipulations in immunoassay procedures, as opposed to procedures that use adsorption to attach proteins. The silanized and activated nanotips for measuring caspase-9 activity were immersed in a solution containing DMSO, 2× reaction buffer, PBS, and LEHD-AMC, and allowed to incubate for 3 h at 37° C., while those for measuring caspase-7 activity were immersed in a solution containing DMSO, 2× reaction buffer, PBS, and DEVD-AMC, and allowed to incubate for 3 h at 37° C.

Measurement System and Procedure

A schematic representation of the experimental setup used in this work is described in a previous work [[P. M. Kasai, J. M. Song, and T. Vo-Dinh, "*Optical Sensor for the Detection of Caspase-9 Activity in a Single Cell*", J. Am. Chem. Soc., 126, 2799-2806 (2004)]. The components included a HeCd laser (Omnichrome, <5 mW laser power) for excitation, an optical fiber for delivery of excitation light to the optical nanosensor, a Nikon Diaphot 300 inverted fluorescence microscope (Nikon, Inc., Melville, N.Y.), a photon counting photomultiplier tube (PMT) and a PC for data acquisition and processing. This experimental set-up, used to probe single cells, was adapted for this purpose from a standard micromanipulation and microinjection apparatus. The Nikon Diaphot 300 inverted microscope was equipped with a Diaphot 300/Diaphot 200 Incubator to maintain the cell cultures at 37° C. on the microscope stage, during these experiments. The micromanipulation equipment consisted of MN-2 (Narishige Co. Ltd., Tokyo, Japan) Narishige three-dimensional manipulators for coarse adjustment, and Narishige MMW-23 three-dimensional hydraulic micromanipulators for fine adjustments. The optical nanosensor was mounted on a micropipette holder (World Precision Instruments, Inc., Sarasota, Fla.). The 325 nm laser line of a HeCd laser was focused onto a 600-µm-delivery fiber that is terminated with a subminiature A (SMA) connector. The enzyme substrate-based optical nanosensor was coupled to the delivery fiber through the SMA connector and secured to the Nikon inverted microscope with micromanipulators. To record the fluorescence generated by AMC molecules at the nanotips, a Hamamatsu PMT detector assembly (HC125-2) was mounted in the front port of the Diaphot 300 microscope. The fluorescence emitted by AMC from the measurement made using single live cells was collected by the microscope objective and passed through a 330-380 nm filter set and then focused onto a PMT for detection. The output from the PMT was recorded using a universal counter interfaced to a personal computer (PC) for data treatment and processing.

In Vitro Determination of Caspase Activity

After incubation using the following treatment groups, group (I)—[+]ALA[+]PDT, group II—[+]ALA[−]PDT, group III—[−]ALA[+]PDT, and group IV—[−]ALA[−]PDT, MCF-7 cells were washed with PBS solution, pH 7.4, and then resuspended in lysis buffer (100 mM HEPES, pH 7.4, 10% sucrose, 0.1% 3-[(3-cholamidopropyl)-dimethylammonio]-1-propanesulfonate (CHAPS), 1 mM EDTA, 10 mill dithiothreitol (DTT), 1 mM phenylmethylsulphonyl fluoride (PMSF), 10 mg/ml pepstatin, 10 mg/ml leupeptin) and left on ice for 45 minutes. The cells were then repeatedly passed through a syringe with a 25-gauge needle until most of the cell membrane was disrupted, and centrifuged at 1500 RPM for 10 min. Activity of caspases was measured using the fluorogenic substrate peptides; LEHD-AMC for caspase-9 and DEVD-AMC for caspase-7. The release of AMC was measured after incubating optical nanosensors in picofuge tubes containing the cell lysates from the various treatment groups and using a HeCd laser (excitation 325 nm) to excite AMC. Caspase activity was expressed as fluorescence intensity of AMC as a function of equivalent nanomoles of LEHD-AMC and DEVD-AMC respectively.

The results of the in vitro measurement of caspase-9 and caspase-7 activity were plotted. The curves for each fluorescent measurement of AMC were plotted for each as a function of AMC concentration. Caspase-9 activity was determined by incubation of optical nanosensors with the substrate LEHD-7-amino-4-methylcoumarin (AMC) in cell lysate ($\sim 10^5$ cells) obtained from the following treatment groups; group I, II, III and IV, described earlier in the article. The release of AMC was measured after excitation using HeCd laser (325 nm) and collecting the fluorescence signal using a 380 nm longpass filter. The peak emission wavelength of AMC is about 440 nm. Likewise, Caspase-7 activity was determined by incubation in cell lysate ($\sim 10^5$ cells) obtained from the following treatment groups I, II, III, and IV. The release of AMC was measured after excitation using a HeCd laser (325 nm) and collecting the fluorescence signal using a 380 nm longpass filter.

In this experiment, we measure two sets of cells I and II: (1) Set I is treated with the drug ALA and (2) set 11 is treated by the drug ALA conjugated to a PEPST probe described in the previous section. By comparing the results (amount of caspase detected), one can evaluate the efficiency of the PEPST-ALA drug compared to ALA alone.

Obviously, additional modifications and variations of the present invention are possible in light of the above teachings. It is therefore to be understood that within the scope of the appended claims, the invention may be practiced otherwise than as specifically described herein.

The invention claimed is:

1. A method for modifying a target structure which mediates or is associated with a biological activity, the method comprising:
   placing a nanoparticle in a vicinity of a target structure in a subject; and
   applying an initiation energy including a first wavelength $\lambda 1$ from an initiation energy source to the subject such that the nanoparticle upon exposure to the first wavelength $\lambda_1$ emits light including a second wavelength $\lambda_2$, in the vicinity of or into the target structure, wherein the second wavelength $\lambda_2$ has a higher energy than the first wavelength $\lambda_1$,
   wherein the emitted light including the second wavelength $\lambda 2$ directly or indirectly contacts the target structure and induces a predetermined change in the target structure in situ,
   wherein said predetermined change modifies the target structure and modulates the biological activity of the target structure.

2. The method of claim 1, wherein:
   the nanoparticle comprises a metallic structure deposited in relation to the nanoparticle, and
   a physical characteristic of the metallic structure is set to a value so that a surface plasmon resonance in the metallic structure resonates at a frequency which provides spectral overlap with at least one the first wavelength $\lambda 1$ and the second wavelength $\lambda 2$.

3. The method of claim 2, wherein the nanoparticle comprises a dielectric core.

4. The method of claim 3, wherein the metallic structure comprises at least one of a spherical or elliptical shell covering at least a part of said dielectric core.

5. The method of claim 2, wherein the metallic structure comprises at least one of shell selected from the group consisting of a spherical shell, an oblate shell, a crescent shell, and a multilayer shell.

6. The method of claim 2, wherein the metallic structure comprises at least one element selected from the group consisting of Au, Ag, Cu, Ni, Pt, Pd, Co, Ru, Rh, Al, Ga, and alloys or layers thereof.

7. The method of claim 2, wherein the nanoparticle has at least one of:
   a dielectric or semiconductor configured to generated said wavelength $\lambda_2$; or
   multiple dielectrics or semiconductors respectively configured to emit at different wavelengths for $\lambda_2$.

8. The method of claim 7, wherein the metallic structure comprises at least one of a spherical and elliptical shell covering at least a part of said dielectric or semiconductor.

9. The method of claim 2, wherein the metallic structure comprises a metallic shell encapsulating at least a fraction of the nanoparticle.

10. The method of claim 2, wherein the metallic structure comprises at least one structure selected from the group consisting of a conducting material including at least one metal, a doped glass, and a doped semiconductor.

11. The method of claim 10, wherein the conducting material comprises at least one elemental metal, an alloy of the element metal, or layers of the conducting materials.

12. The method of claim 2, wherein:
   the nanoparticle comprises a sub 1000 nm dielectric particle;
   the dielectric particle comprises at least one compound selected from the group consisting of $Y_2O_3$, $Y_2O_2S$, $NaYF_4$, $NaYbF_4$, YAG, YAP, $Nd_2O_3$, $LaF_3$, $LaCl_3$, La$_2$O$_3$, TiO$_2$, LuPO$_4$, YVO$_4$, YbF$_3$, YF$_3$, Na-doped YbF$_3$, SiO$_2$ and alloys or layers thereof;

the dielectric particle comprises a dopant comprising Er, Eu, Yb, Tm, Nd, Tb, Ce, Y, U, Pr, La, Gd or other rare-earth species or a combination thereof;

the dopant has a concentration of 0.01%-50% by mole; and the metallic structure includes at least one element selected from the group consisting of Au, Ag, Cu, Ni, Pt, Pd, Co, Ru, Rh, Al, Ga, and alloys or layers thereof.

13. The method of claim 2, wherein the metallic structure comprises at least one of:

a metallic shell encapsulating at least a fraction of the nanoparticle in the metallic shell and wherein a conductivity, a radial dimension, a crystalline state, or a shape of the metallic shell sets said surface plasmon resonance in the metallic structure to resonate at a frequency which provides spectral overlap with either the first wavelength $\lambda_1$ or the second wavelength $\lambda_2$;

at least one of a metallic particle sphere, spheroid, rod, cube, triangle, pyramid, pillar, crescent, tetrahedral shape, star or combination thereof disposed adjacent said nanoparticle and wherein a conductivity, a dimension, or a crystalline state of the metallic particle or rod sets said surface plasmon resonance in the metallic particle or rod to resonate at a frequency which provides spectral overlap with either the first wavelength $\lambda_1$ or the second wavelength $\lambda 2$; or at least one of a metallic particle, sphere, spheroid, rod, cube, triangle, pyramid, pillar, crescent, tetrahedral shape, star or combination thereof disposed interior to said nanoparticle and wherein a conductivity or a dimension of the metallic particle or rod sets said surface plasmon resonance in the metallic particle or rod to resonate at a frequency which provides spectral overlap with either the first wavelength $\lambda_1$ or the second wavelength $\lambda_2$.

14. The method of claim 2, wherein the metallic structure comprises at least one of:

a metallic shell encapsulating at least a fraction of the nanoparticle in the metallic shell and wherein a conductivity, a radial dimension, a crystalline state, or a shape of the metallic shell sets said surface plasmon resonance in the metallic structure to resonate at a frequency which provides spectral overlap with both the first wavelength $\lambda_1$ and the second wavelength $\lambda_2$;

at least one of a metallic particle sphere, spheroid, rod, cube, triangle, pyramid, pillar, crescent, tetrahedral shape, star or combination thereof disposed adjacent said nanoparticle and wherein a conductivity, a dimension, a crystalline state of the metallic particle or rod or sets said surface plasmon resonance in the metallic particle or rod to resonate at a frequency which provides spectral overlap with both the first wavelength $\lambda_1$ and the second wavelength $\lambda_2$; or at least one of a metallic particle, sphere, spheroid, rod, cube, triangle, pyramid, pillar, crescent, tetrahedral shape, star or combination thereof disposed interior to said nanoparticle and wherein a conductivity or a dimension of the metallic particle or rod sets said surface plasmon resonance in the metallic particle or rod to resonate at a frequency which provides spectral overlap with both the first wavelength $\lambda_1$ and the second wavelength $\lambda_2$.

15. The method of claim 2, wherein the metallic structure comprises an alloy of two or more metals.

16. The method of claim 15, wherein the alloy has a composition between the two or more metals set to a compositional value where said surface plasmon resonance in the metallic alloy structure spectrally overlaps the second wavelength $\lambda_2$.

17. The method of claim 15, wherein the metallic structure comprises at least one of an Au:Ag alloy, an Pt:Ag alloy, and an Pt:Au alloy.

18. The method of claim 15, wherein the metallic structure has an alloy content set to provide said surface plasmon resonance at 365 nm.

19. The method of claim 18, wherein the Au:Ag alloy has a silver concentration of from 65 to 75%.

20. The method of claim 19, wherein the silver concentration is 67%.

21. The method of claim 2, wherein the nanoparticle comprises a dielectric material having energetic states for absorption of the first wavelength $\lambda_1$ and recombination states for emission of the second wavelength $\lambda_2$.

22. The method of claim 21, wherein the metallic structure comprises a plasmonic shell configured to enhance at least one of said absorption or said emission.

23. The method of claim 22, wherein the surface plasmon resonance is in the NIR frequency band and the emission is in the visible frequency band.

24. The method of claim 22, wherein the surface plasmon resonance is in the NIR frequency band and the emission is in the ultraviolet frequency band.

25. The method of claim 22, wherein the absorption is in the NIR frequency band and the surface plasmon resonance is in the visible frequency band or the NIR frequency band.

26. The method of claim 22, wherein the absorption band is in the NIR frequency band and the surface plasmon resonance is in the ultraviolet frequency band or the NIR frequency band.

27. The method of claim 2, further comprising detecting Raman scattered light from at least one of the nanoparticle, the metal shell, or a recipient attached to one of the nanoparticle and/or the metal shell for identification of at least one of the nanoparticle, the metal shell, or the recipient.

28. The method of claim 2, wherein:
the nanoparticle is disposed outside the metallic structure;
the metallic structure comprises a metallic shell; and
at least one of a separation distance between the nanoparticle and the metallic shell or a shell thickness of the metallic shell sets said surface plasmon resonance in the metallic structure to resonate at a frequency which provides spectral overlap with either of the first wavelength $\lambda_1$ or the second wavelength $\lambda_2$ or which provides spectral overlap with both of the first wavelength $\lambda_1$ and the second wavelength $\lambda_2$.

29. The method of claim 2, wherein said initiation energy produces plasmonics and/or exciton coupling enhanced light generation that is capable of inducing the predetermined change in the target structure with or without an energy modulator agent and/or a photoactive agent.

30. The method of claim 1, wherein the nanoparticle comprises a dielectric core.

31. The method of claim 30, wherein the dielectric core has a diameter of from 2 nm to 100 nm.

32. The method of claim 1, wherein the nanoparticle comprises at least one compound selected from the group consisting of Y$_2$O$_3$, Y$_2$O$_2$S, NaYF$_4$, NaYbF$_4$, YAG, YAP, Nd$_2$O$_3$, LaF$_3$, LaCl$_3$, La$_2$O$_3$, TiO$_2$, LuPO$_4$, YVO$_4$, YbF$_3$, YF$_3$, Na-doped YbF$_3$, SiO$_2$, and alloys or layers thereof.

33. The method of claim 1, wherein the nanoparticle comprises a dopant including at least one element selected from the group consisting of Er, Eu, Yb, Tm, Nd, Tb, Ce, Y, U, Pr, La, Gd, other rare-earth species and a combination thereof.

34. The method of claim 33, wherein the dopant is present in an amount of from 0.01% to 50 mol. %.

35. The method of claim 1, wherein the initiation energy is capable of penetrating completely through said subject.

36. The method of claim 1, wherein the nanoparticle is provided in the vicinity of the target structure at a local concentration sufficient that under the irradiation conditions a photon is absorbed by the target structure with a finite probability.

37. The method of claim 1, wherein applying comprises:
applying the initiation energy from (i) an initiation energy source that is external to the subject; or (ii) an initiation energy source that is internal to the subject, which is placed or delivered internally into the subject and/or the target structure.

38. The method of claim 1, wherein applying comprises applying said initiation energy from a source emitting at least one energy selected from the group consisting of visible light, infrared radiation, microwaves, and radio waves.

39. The method of claim 1, wherein said initiation energy is energy emitted by at least one cell excited by one or more metabolic processes and said applying is conducted via a cell-to-cell energy transfer.

40. The method of claim 39, wherein said initiation energy is in a wavelength range of from 100 GHz to 10 THz.

41. The method of claim 1, wherein said initiation energy is energy emitted by at least one cell and said applying is conducted via cell-to-cell energy transfer.

42. The method of claim 41, wherein said initiation energy is in a wavelength range of from 100 GHz to 10 THz.

43. The method of claim 1, in which said predetermined change enhances an activity of the target structure.

44. The method of claim 43, wherein the activity enhanced is energy emission from the target, which then mediates, initiates or enhances a biological activity of other target structures in the subject, or of a second target structure.

45. The method of claim 1, wherein the nanoparticle comprises a dielectric, a glass, a semiconductor, or a combination thereof.

46. The method of claim 1, wherein:
the nanoparticle comprises a sub 1000 nm dielectric particle; and
the dielectric particle comprises at least one compound selected from the group consisting of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, $SiO_2$ and alloys or layers thereof.

47. The method of claim 46, wherein the dielectric particle has a diameter ranging from at least one of 2-1000 nm, 2-100 nm, 2-50 nm, 2-20 nm, or 2-10 nm.

48. The method of claim 46, wherein the dielectric particle is configured to exhibit at least one of ultraviolet or visible emission upon interaction with NIR light.

49. The method of claim 1, wherein the nanoparticle comprises an alloy of two or more dielectric materials, an alloy of two or more glasses, or an alloy of two or more semiconductors.

50. The method of claim 1, wherein the nanoparticle comprises an alloy of two or more materials, wherein the alloy has a composition between the two or materials set to a compositional value where excitation of the alloy at the first wavelength $\lambda_1$ produces emission at the second wavelength $\lambda_2$.

51. The method of claim 50, wherein the alloy comprises at least one of:
a zinc sulfide and zinc selenide alloy; or
a zinc sulfide and cadmium sulfide alloy.

52. The method of claim 51, wherein the alloy comprises at least one of:
said zinc sulfide and zinc selenide alloy having a zinc sulfide concentration from 65 to 75%; or
said zinc sulfide and cadmium sulfide nanoparticle alloy having a zinc sulfide concentration from 65 to 75%.

53. The method of claim 50, wherein the alloy has said emission of the second wavelength $\lambda_2$ at 365 nm.

54. The method of claim 53, wherein the alloy comprises said zinc sulfide and zinc selenide alloy having a zinc sulfide concentration of 67%.

55. The method of claim 53, wherein the alloy comprises said zinc sulfide and cadmium sulfide nanoparticle alloy having a zinc sulfide concentration of 67%.

56. The method of claim 1, wherein the nanoparticle is configured to exhibit ultraviolet emission upon interaction with the first wavelength $\lambda_1$.

57. The method of claim 1, wherein the nanoparticle is configured to exhibit at least one of infrared, visual, and ultraviolet emission upon interaction with the first wavelength $\lambda_1$.

58. The method of claim 57, wherein the nanoparticle comprises a plurality of nanoparticles including at least one of a first group which exhibits a visible emission upon interaction with the first wavelength $\lambda_1$ and a second group which exhibits ultraviolet emission upon interaction with the first wavelength $\lambda_1$.

59. The method of claim 58, where the first group comprises a diagnostic group for producing imaging light showing a position of the first group in said subject and/or target structure, and the second group comprises a reaction-stimulating group producing a photostimulated reaction.

60. The method of claim 1, wherein
said nanoparticle has an upconversion capability to produce, from first said wavelength $\lambda_1$ of radiation, an up-converted light of said second wavelength $\lambda_2$, and the method further comprising administering an X-ray down-converter particle having a down conversion capability to produce down converted light and application of X-rays to the subject.

61. The method of claim 60, wherein
the down converted light comprises X-ray stimulated emission in the ultraviolet frequency band, and
the up-converted light comprises emitted light in the visible or near-infrared or infrared frequency band.

62. The method of claim 60, wherein
the down converted light comprises X-ray stimulated emission in the ultraviolet frequency band, and
the up-converted light comprises emitted light in the ultraviolet or visible frequency band.

63. The method of claim 62, wherein either one of the down converted light or the upconverted ultraviolet or visible light is generated in proximity of an activatable pharmaceutical agent applied to the subject and the activatable pharmaceutical agent is activated by the ultraviolet or visible light.

64. The method of claim 63, wherein the activatable pharmaceutical agent is disposed in or nearby a tumor.

65. The method of claim 64, further comprising:
a fiber optic inserted into the subject, wherein light from a laser diode is transmitted through the fiber optic to the tumor.

66. The method of claim 60, wherein the X-ray downconverter particle includes at least one compound selected from the group consisting of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, Er3+; ZnS:$Mn^{2+}$; ZnS:Mn,$Er^{3+}$, alkali lead silicate including compostions of $SiO_2$, $B_2O_3$, $Na_2O$, $K_2O$, PbO, MgO, Ag, and combinations or alloys or layers thereof.

67. The method of claim 1, further comprising a recipient linked to the nanoparticle by a chemical moiety.

68. The method of claim 67, wherein a length of the chemical moiety is selected to increase a reactivity of the second wavelength λ2 with the recipient compared to the unlinked recipient.

69. The method of claim 67, wherein the recipient comprises an activatable pharmaceutical agent.

70. The method of claim 69, wherein the activatable pharmaceutical agent is a photoactivatable agent comprising at least one of agent selected from the group consisting of psoralen, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones, and porphycene, rubyrin, rosarin, hexaphyrin, sapphyrin, chlorophyl, chlorin, phthalocynine, porphyrazine, bacteriochlorophyl, pheophytin, texaphyrin macrocyclic-based component, and a metalated derivative thereof.

71. The method of claim 67, wherein the recipient comprises at least one of a laser dye, a fluorophore, a lumophore, or a phosphor.

72. The method of claim 71, wherein the recipient comprises at least one laser dye, wherein the at least one laser dye comprises at least one agent selected from the group consisting of p-terphenyl, sulforhodamine B, p-quaterphenyl, Rhodamine 101, curbostyryl 124, cresyl violet perchlorate, popop, DODC iodide, coumarin 120, sulforhodamine 101, coumarin 2, oxozine 4 perchlorate, coumarin 339, PCM, coumarin 1, oxazine 170 perchlorate, coumarin 138, nile blue A perchlorate, coumarin 106, oxatine 1 perchlorate, coumarin 102, pyridine 1, coumarin 314T, styryl 7, coumarin 338, HIDC iodide, coumarin 151, PTPC iodide, coumarin 4, cryptocyanine, coumarin 314, DOTC iodide, coumarin 30, HITC iodide, coumarin 500, HITC perchlorate, coumarin 307, PTTC iodide, coumarin 334, DTTC perchlorate, coumarin 7, IR-144, coumarin 343, HDITC perchlorate, coumarin 337, IR-NO, coumarin 6, IR-132, coumarin 152, IR-125, coumarin 153, boron-dipyrromethere, HPTS, flourescein, rhodamine 110, 2, 7-dichlorofluorescein, rhodamine 65, and rhodamin 19 perchlorate, rhodamine b, and derivatives thereof.

73. The method of claim 1, wherein the nanoparticle further comprises a bioreceptor linked to the nanoparticle, and wherein the bioreceptor is at least one probe selected from the group consisting of an antibody probe, a DNA probe, a saccharide probe, a peptide probe, and an enzyme probe.

74. The method of claim 1, wherein the nanoparticle further comprises a secondary agent linked to the nanoparticle, and wherein the secondary agent is at least one agent selected from the group consisting of a secondary emitter, cytotoxic agent, magnetic resonance imaging (MRI) agent, positron emission tomography (PET) agent, radiological imaging agent, and photodynamic therapy (PDT) agent.

75. The method of claim 1, wherein the initiation energy source is an infrared source which produces, for said first wavelength $\lambda_1$, at least one frequency selected from the group consisting of 785 nm, 808 nm, 830 nm, 852 nm, 915 nm, 940 nm, 980 nm, 1064 nm, 1310 nm, and 1550 nm.

76. The method of claim 75, wherein the nanoparticle converts said first wavelength $\lambda_1$ of 785 nm, 808 nm, 830 nm, 852 nm, 915 nm, 940 nm, 980 nm, 1064 nm, 1310 nm, and/or 1550 nm into visible light.

77. The method of claim 75, wherein light from a laser diode is transmitted through the subject into the tumor.

78. The method of claim 1, wherein the nanoparticle converts said first wavelength $\lambda_1$ into ultraviolet light.

79. The method of claim 1, wherein said first wavelength $\lambda_1$ is in the range of 700-1100 nanometers.

80. The method of claim 1, wherein said first wavelength $\lambda_1$ is in the range of 1300-1550 nm.

81. The method of claim 1, further comprising at least one down converter nanoparticle including at least one compound selected from the groups consisting of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, Er3+; ZnS:$Mn^{2+}$; ZnS:Mn,$Er^{3+}$, alkali lead silicate including compositions of $SiO_2$, $B_2O_3$, $Na_2O$, $K_2O$, PbO, MgO, Ag, and combinations or alloys or layers thereof.

82. The method of claim 1, wherein said initiation energy is applied to the subject directly or indirectly.

83. The method of claim 1, wherein said initiation energy is applied from a single source.

84. The method of claim 1, wherein said initiation energy is applied from more than one source.

85. The method of claim 1, further comprising administering to said subject at least one energy modulation agent.

86. The method of claim 85, wherein the at least one energy modulation agent converts the initiation energy into an energy in the range of the first wavelength $\lambda_1$ that cause the nanoparticle to emit energy in the range of said second wavelength $\lambda_2$ that is capable of inducing the predetermined change in the target structure.

87. The method of claim 86, wherein the energy modulation agent is specifically located around, on, or in the target structure.

88. The method of claim 86, wherein the energy modulation agent transforms the initiation electromagnetic energy into a photonic or another electromagnetic energy in the range of the first wavelength $\lambda_1$ that cause the nanoparticle to emit energy in the range of said second wavelength λ2 that induces the predetermined change in the target structure.

89. The method of claim 86, wherein the energy modulation agent downconverts the initiation energy.

90. The method of claim 86, wherein the energy modulation agent upconverts the initiation energy.

91. The method of claim 85, wherein the initiation energy is up-converted by the nanoparticle and is further converted by the at least modulation agent prior to contacting the target structure.

92. The method of claim 85, wherein the at least one energy modulation agent is one or more members selected from the group consisting of a biocompatible fluorescing metal nanoparticle, fluorescing metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

93. The method of claim 85, wherein the initiation energy is generated in-situ in the subject.

94. The method of claim 1, in which the predetermined change results in destruction, lysis or inactivation of the target structure.

95. The method of claim 1, in which the predetermined change does not result in destruction or inactivation of the target structure.

96. The method of claim 1, in which the predetermined change enhances an activity of the target structure.

97. The method of claim 1, wherein the target structure is a eukaryotic cell.

98. The method of claim 1, wherein the target structure is a prokaryotic cell.

99. The method of claim 1, wherein the target structure is a subcellular structure.

100. The method of claim 99, wherein the subcellular structure is a cell membrane, a nuclear membrane, cell nucleus, nucleic acid, mitochondria, ribosome, or other cellular organelle or component.

101. The method of claim 1, wherein the target structure is an extracellular structure.

102. The method of claim 1, wherein the target structure is a virus or prion.

103. The method of claim 1, wherein the predetermined change results in treatment of a condition, disease, or disorder in said subject.

104. The method of claim 103, wherein said condition, disease, or disorder is cancer.

105. The method of claim 103, wherein said condition, disease, or disorder occurs in a soft tissue and/or cartilage.

106. The method of claim 103, wherein said condition, disease, or disorder occurs in bone tissue.

107. The method of claim 103, wherein said condition, disease, or disorder is chronic pain.

108. The method of claim 103, wherein said condition, disease, or disorder is at least one autoimmune disease.

109. The method of claim 103, wherein said condition, disease, or disorder is a prion, viral, bacterial, fungal, or parasitic infection.

110. The method of claim 103, wherein said condition, disease, or disorder is varicose veins.

111. The method of claim 103, wherein said condition, disease, or disorder is an enlarged prostate, colon cancer, breast cancer, or lung cancer.

112. The method of claim 103, wherein said condition, disease, or disorder is retinal injury or an ocular disease.

113. The method of claim 103, wherein said condition, disease, or disorder is Parkinson's disease.

114. The method of claim 103, wherein said condition, disease, or disorder is behavioral, perceptional and/or cognitive disorders.

115. The method of claim 103, wherein said condition, disease, or disorder is mediated by abnormal cellular proliferation and said predetermined change ameliorates the abnormal cellular proliferation.

116. The method of claim 115, wherein said abnormal cellular proliferation is higher than that of cells from a subject not having said condition, disorder or disease.

117. The method of claim 115, wherein said abnormal cellular proliferation is lower than that of cells from a subject not having said condition, disorder or disease.

118. The method of claim 103, wherein said condition, disease, or disorder is not significantly mediated by abnormal cellular proliferation and said predetermined change does not substantially affect cellular proliferation.

119. The method of claim 1, wherein said predetermined change comprises wound healing.

120. The method of claim 1, wherein said predetermined change comprises enhancement of tissue growth, nerve regeneration or sensory regeneration/restoration.

121. The method of claim 1, wherein said predetermined change comprises reduction or removal of fat deposits (liposuction).

122. The method of claim 1, wherein said predetermined change comprises nerve (brain) imaging and stimulation or direct control of brain cell activity with light.

123. The method of claim 1, wherein said predetermined change comprises modulation of cell death (apoptosis).

124. The method of claim 1, wherein said predetermined change comprises modulating cell growth and division.

125. The method of claim 1, wherein said predetermined change comprises modulation of an activity, quantity, or number of intracellular components in a cell.

126. The method of claim 1, wherein said predetermined change comprises modulation of an activity, quantity, or number of extracellular components produced by, excreted by, or associated with a cell.

127. The method of claim 1, wherein the initiation energy is generated in-situ in the subject.

128. The method of claim 1, further comprising applying a heat producing energy source to the target structure to generate heat in the target structure and enhance the induction of the predetermined change.

129. The method of claim 128, wherein the heat producing energy source and the initiation energy source are the same.

130. The method of claim 128, wherein the heat producing energy source and the initiation energy source are different from one another.

131. The method of claim 1, further comprising administering an initiation energy source to the subject.

132. The method according to claim 131, wherein said initiation energy source is a chemical energy source.

133. The method according to claim 132, wherein the chemical energy source is a member selected from the group consisting of a phosphorescent compound, chemiluminescent compound, bioluminescent compound, and light emitting enzyme.

134. The method of claim 1, further comprising applying a plasmonic-active agent.

135. The method of claim 134, wherein an electromagnetic field enhancement produced near nanostructured metal surfaces of the plasmonic-active agent is from $10^6$ to $10^{15}$ fold.

136. The method of claim 134, wherein the plasmonics-active agent is a plasmonics enhanced photospectral therapy (PEPST) probe, comprising:
 a) at least one metal nanoparticle,
 b) at least one activatable pharmaceutical agent, and
 c) optionally, at least one energy modulation agent.

137. The method of claim 136, wherein at least two of components a)-c) are coupled one to another.

138. The method of claim 136, wherein the plasmonics-active agent comprises a) and b).

139. The method of claim 136, wherein the plasmonics-active agent comprises a), b), and c).

140. The method of claim 136, wherein the at least one metal nanoparticle is bound to the at least one energy modulation agent via a linker.

141. The method of claim 136, wherein the energy modulation agent is at least one selected from the group consisting of a metal, quantum dot, semiconductor material, scintillation and phosphor material, material that exhibit X-ray excited luminescence (XEOL), organic solid, metal complex, inorganic solid, crystal, rare earth material (lanthanidees), polymer, scintillator, phosphor material, and material that exhibit excitonic properties.

142. The method of claim 134, wherein the plasmonics-active agent is a PEPST probe possessing plasmonics photospectral properties, biocompatibility, an improved drug payload delivery and passive targeting of metal nanoparticles.

143. The method of claim 136, wherein the plasmonics-active agent enhances or modifies an X ray energy applied to the subject to excite the energy modulation agent which converts the enhanced or modified X ray energy.

144. The method of claim 136, wherein the plasmonics-active agent is a PEPST probe comprising a chain of metal particles having the same or different size and coupled to one another, wherein the chain of the metal particles exhibits dual or multi plasmonics resonance modes.

145. The method of claim 144, wherein the chain of particles is used for providing a plasmonics enhancement of the initiation energy and/or an energy emitted by the modulation agent.

146. The method of claim 136, wherein the activatable pharmaceutical agent is delivered to a target and is released from the plasmonics-active agent by photon radiation or ultrasound, and wherein the plasmonics-active agent is a PEPST probe.

147. The method of claim 146, wherein the activatable pharmaceutical agent is released from the plasmonics-active agent comprising an antibody or antigen system coupled with the activatable pharmaceutical agent.

148. The method of claim 136, wherein the activatable pharmaceutical agent is delivered to a cell and is released from the energy modulation agent coupled with the plasmonics-active agent by photon radiation or ultrasound, and wherein the plasmonics-active agent is the PEPST probe.

149. The method of claim 134, wherein the plasmonics-active agent is a PEPST probe having a multi plasmonics resonance mode.

150. The method of claim 134, wherein the plasmonics-active agent is a PEPST probe comprising plasmonics-active metal nanostructures.

151. The method of claim 150, wherein the metal nanostructure is at least one selected from the group consisting of a nanosphere, nanorod, nanocube, nanopyramid, nanoshell, nanoshell cylinder, and a nanoshell or a multi-layer nanoshell.

152. The method of claim 134, wherein the plasmonics-active agent is a PEPST probe comprising multiple structures for different plasmonics activation regimes.

153. The method of claim 152, wherein said regime is at least one selected from the group consisting of NIR and X ray.

154. The method of claim 134, wherein the plasmonics-active agent is a PEPST probe comprising at least one metal nanosystem coupled with the activatable pharmaceutical agent, or with an energy modulation agent coupled with the activatable pharmaceutical agent.

155. The method of claim 154, wherein the nanosystem is bound to the activatable pharmaceutical agent or the energy modulation agent by a bond selected from the group consisting of a biochemical bond, a DNA bond, and an antigen-antibody bond.

156. The method of claim 154, wherein the bond is a photo-labile bond.

157. The method of claim 154, wherein the activatable pharmaceutical agent is released from the nanosystem inside a cell by photon radiation or ultrasound.

158. The method of claim 134, wherein the plasmonics-active agent is a PEPST probe comprising at least one metal nanostructure selected from the group consisting of a metal nanoparticle, a dielectric nanoparticle core covered with a metal nanocap, a spherical metal nanoshell covering a dielectric spheroid core, an oblate metal nanoshell covering a dielectric spheroid core, a metal nanoparticle core covered with a dielectric nanoshell, a metal nanoshell with a protective coating layer, multi layer metal nanoshells covering a dielectric spheroid core, multi-nanoparticle structures, a metal nanocube and a nanotriangle/nanoprism, and a metal cylinder.

159. The method of claim 134, wherein the plasmonics-active agent is a PEPST probe comprising a combination of metal nanoparticles, covered by a layer of a dielectric material comprising the activatable pharmaceutical agent, with an energy modulation agent which is bound to the activatable pharmaceutical agent.

160. The method of claim 134, wherein the plasmonics-active agent is a PEPST probe, and the components of the PEPST probe are bound using conjugates, metals binding to organic and inorganic compounds, and biomolecules.

161. The method of claim 134, wherein the plasmonics-active agent comprises a plasmonic-active metal nanoparticle bound to an excitation energy converter (EEC) material which is bound to the activatable pharmaceutical agent, wherein the EEC material for exciton induced phototherapy (EIP) probes is optimized based on exciton properties.

162. The method of claim 134, wherein the plasmonics-active agent comprises an excitation energy converter (EEC) material, said method tunes an emission of the EEC material in exciton induced phototherapy (EIP) probes to a wavelength capable of exciting the activatable pharmaceutical agent using specific materials with specific exciton properties, wherein said EEC material can produce excitons under a radiative excitation.

163. The method of claim 162, wherein the EEC material is a modulation agent, and the activatable pharmaceutical agent is embedded in a shell around said EEC material.

164. The method of claim 162, wherein the EEC material has structural defects that serve as traps for the excitation.

165. The method of claim 162, wherein the EEC material comprises impurities or dopant molecules that serve as traps for the excitation.

166. The method of claim 162, wherein the initiation energy is X ray which is transformed to UV or visible photons by the EEC material.

167. The method of claim 162, wherein the EEC material is a modulation agent, said EEC material is bound via a linker to the activatable pharmaceutical agent.

168. The method of claim 134, wherein the plasmonics-active agent is an exciton-plasmon enhanced phototherapy (EPEP) probe which comprises at least one plasmonics-active metal nanostructure, at least one exciton-generating energy modulation agent material, and the at least one activatable pharmaceutical agent, wherein said metal nanostructure and said material produce exciton-plasmon (EPC) coupling.

169. The method of claim 168, wherein the plasmonics-active metal nanostructure and the exciton-generating energy modulation agent material are coupled via a spacer.

170. The method of claim 168 or 169, wherein exciton-generating energy modulation agent material is coupled with the activatable pharmaceutical agent via a linker.

171. The method of claim 168 or 169, wherein the activatable pharmaceutical agent and the plasmonics-active metal nanostructure are coupled via a linker.

172. The method of claim 168, wherein the EPEP probe comprises a bioreceptor.

173. The method of claim 172, wherein the bioreceptor is bound to the plasmonics-active metal nanostructure or to the plasmonics-active metal nanostructure covered with a nanoshell or a nanoshell cylinder made of a dielectic material.

174. The method of claim 172, wherein the EPEP probe enhances a XEOL light emitted by the exciton-generating energy modulation agent material irradiated by an X ray.

175. The method of claim 168 or 169, wherein the plasmonics-active metal nanostructure is covered with a nanoshell made of a dielectric material.

176. The method of claim 168, wherein the EPEP probe comprises multiple metal nanowires coupled with the exciton-generating energy modulation agent material with or without spacers which can be the same or different, said exciton-generating energy modulation agent material is bound to the activatable pharmaceutical agent via a linker.

177. The method of claim 168, wherein the exciton-generating energy modulation agent material is a microresonator.

178. The method of claim 168, wherein the exciton-generating energy modulation agent material is at least one selected from the group consisting of a metal, quantum dot, semiconductor material, scintillation and phosphor material, material that exhibit X-ray excited luminescence (XEOL), organic solid, metal complex, inorganic solid, crystal, rare earth material (lanthanides), polymer, scintillator, phosphor material, and material that exhibit excitonic properties.

179. The method of claim 168, wherein the EPEP probe comprises multiple structures for different plasmonics activation regimes.

180. The method of claim 179, wherein said regime is at least one selected from the group consisting of NIR and an X ray.

181. The method of claim 168, wherein the EPEP probe comprises at least one metal nanostructure selected from the group consisting of a metal nanoparticle, a dielectric nanoparticle core covered with a metal nanocap, a spherical metal nanoshell covering a dielectric spheroid core, a oblate metal nanoshell covering a dielectric spheroid core, a metal nanoparticle core covered with a dielectric nanoshell, a metal nanoshell with a protective coating layer, multi layer metal nanoshells covering a dielectric spheroid core, multi-nanoparticle structures, a metal nanocube and a nanotriangle/nanoprism, and a metal cylinder.

182. The method of claim 168, wherein the EPEP probe comprises a combination of metal nanoparticles with an energy modulation agent which is bound to the activatable pharmaceutical agent, wherein the metal nanoparticles are covered by a layer of a dielectric material comprising the activatable pharmaceutical agent.

183. The method of claim 168, wherein the EPEP probe possesses plasmonics photospectral properties, biocompatibility, an improved drug payload delivery and passive targeting of metal nanoparticles.

184. The method of claim 168, wherein at least one biomolecule is immobilized on the metal nanostrucutre.

185. The method of claim 168, wherein the at least one biomolecule is at least one selected from the group consisting of the activatable pharmaceutical agent, the energy modulation agent, a drug, a protein, an enzyme, an antibody, a saccharide, a peptide, and a nucleic acid.

186. The method of claim 168, wherein (a) the exciton-generating energy modulation agent, (b) the activatable pharmaceutical agent, or (c) the exciton-generating energy modulation agent and the activatable pharmaceutical agent, are covered with a layer comprising the plasmonics-active metal nanostrucutre.

187. The method of claim 168, wherein the EPEP probe comprises a chain of metal particles having the same of different size and coupled to one another, wherein the chain of the metal particles exhibit dual or multi plasmonics resonance modes.

188. The method of claim 187, wherein the chain of the particles is used for providing a plasmonics enhancement of the initiation energy and/or an energy emitted by the exciton-generating energy modulation agent material.

\* \* \* \* \*

UNITED STATES PATENT AND TRADEMARK OFFICE
CERTIFICATE OF CORRECTION

| | |
|---|---|
| PATENT NO. | : 10,493,296 B2 |
| APPLICATION NO. | : 15/045524 |
| DATED | : December 3, 2019 |
| INVENTOR(S) | : Tuan Vo-Dinh et al. |

It is certified that error appears in the above-identified patent and that said Letters Patent is hereby corrected as shown below:

On the Title Page

Page 3, in Column 1, item (56), Line 25, "en.wikipeda." should read -- en.wikipedia. --;
    Line 26, "Themal_" should read -- Thermal_ --; and
    Line 27, "-Wkipedia" should read -- Wikipedia --.

Page 3, Column 2, item (56), Line 11, "http:en." should read -- http://en. --.

In the Specification

Column 7, Line 58, "Os and is" should read -- 0s and 1s --.

Column 11, Line 58, "Corner" should read -- Comer --.

Column 12, Line 38, "corner" should read -- Comer --.

Column 32, Line 57, "Cercid" should read -- Ceroid --.

Column 42, Line 32, "constant," should read -- constant, $K_i$, --.

Column 53, Line 67, "Calif.)" should read -- Calif.). --.

Column 54, Line 8 (approx.), "PEP ST" should read -- PEPST --; and
    Line 31 (approx.), after "From the" insert -- $S_n$ --.

Column 56, Line 36, "$Yb^{3+}$ion" should read -- $Yb^{3+}$ ion --.

Column 57, Line 17, "PEP ST" should read -- PEPST --; and
    Line 54, "λ," should read -- λ --.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,493,296 B2

Column 58, Line 34, "Hiromolo," should read -- Hiromoto, --.

Column 61, Line 45, "$Yb^+$" should read -- $Yb^{3+}$ --.

Column 63, Line 42, "$\lambda_2$" should read -- $\lambda_1$ and $\lambda_2$ --.

Column 64, Line 12 (approx.), "$\lambda 2$." should read -- $\lambda_2$. --; and
 Line 62, "at" should read -- al --.

Column 67, Line 22, "Ss and Sp" should read -- 5s and 5p --.

Column 72, Line 46, "nm+/-5" should read -- mn +/-5 --.

Column 79, Lines 14-15, "aminopropyltrimethoxy silane" should read -- aminopropyl trimethoxy silane --; and
 Lines 16-17, "oleic_acid," should read -- oleic acid, --.

Column 81, Line 26, "Liz-Marzám," should read -- Liz-Marzán, --.

Column 84, Line 24, "NTR" should read -- NIR --; and
 Line 26, "NTR" should read -- NIR --.

Column 91, Line 67, "di alkyl sulfides." should read -- dialkylsulfides. --.

Column 100, Line 37, "Set.," should read -- Sci., --.

Column 105, Line 50, "Pa-containing to" should read -- Pa-containing --.

Column 114, Line 47, "Kasai," should read -- Kasili, --.

Column 115, Line 26, "mill" should read -- mM --.

In the Claims

Column 117, Line 29, Claim 13, "$\lambda 2$;" should read -- $\lambda_2$; --.